US012671088B2

(12) United States Patent
Miljanic et al.

(10) Patent No.: US 12,671,088 B2
(45) Date of Patent: Jun. 30, 2026

(54) MATERIALS AND METHODS FOR IODINE CAPTURE

(71) Applicant: UNIVERSITY OF HOUSTON SYSTEM, Houston, TX (US)

(72) Inventors: Ognjen Miljanic, Houston, TX (US); Alexandra Robles, San Francisco, CA (US)

(73) Assignee: University of Houston System, Houston, TX (US)

( * ) Notice: Subject to any disclaimer, the term of this patent is extended or adjusted under 35 U.S.C. 154(b) by 373 days.

(21) Appl. No.: 18/216,181

(22) Filed: Jun. 29, 2023

(65) Prior Publication Data

US 2024/0300889 A1 Sep. 12, 2024

Related U.S. Application Data

(60) Provisional application No. 63/444,456, filed on Feb. 9, 2023.

(51) Int. Cl.

| | |
|---|---|
| ***H01M 4/60*** | (2006.01) |
| ***B01D 53/02*** | (2006.01) |
| ***C02F 1/26*** | (2023.01) |
| ***C07C 49/792*** | (2006.01) |
| ***C07C 249/16*** | (2006.01) |
| ***C07C 251/86*** | (2006.01) |
| ***C07D 213/76*** | (2006.01) |
| ***C30B 29/54*** | (2006.01) |
| ***G21F 9/02*** | (2006.01) |
| ***H01M 10/0525*** | (2010.01) |
| *C02F 101/00* | (2006.01) |

(Continued)

(52) U.S. Cl.

CPC .............. *H01M 4/60* (2013.01); *B01D 53/02* (2013.01); *C02F 1/26* (2013.01); *C07C 49/792* (2013.01); *C07C 249/16* (2013.01); *C07C 251/86* (2013.01); *C07D 213/76* (2013.01); *C30B 29/54* (2013.01); *G21F 9/02* (2013.01); *H01M 10/0525* (2013.01); *B01D 2253/20* (2013.01); *B01D 2257/202* (2013.01); *C02F 2101/006* (2013.01); *C02F 2101/12* (2013.01); *C02F 2305/00* (2013.01); *C07B 2200/13* (2013.01); *C07C 2603/92* (2017.05); *H01M 2004/028* (2013.01)

(58) Field of Classification Search

CPC ............... H01M 4/60; H01M 10/0525; H01M 2004/028; H01M 10/0567; B01D 53/02; B01D 2253/20; B01D 2257/202; C02F 1/26; C02F 2101/006; C02F 2101/12; C02F 2305/00; C02F 1/285; C07C 49/792; C07C 249/16; C07C 251/86; C07C 2603/92; C07B 2200/13; C07D 213/76; C30B 29/54; G21F 9/02; Y02E 60/10

See application file for complete search history.

(56) References Cited

U.S. PATENT DOCUMENTS

2024/0290976 A1 8/2024 Miljanic et al.

OTHER PUBLICATIONS

3rd International Symposium on Porous Organic Polymers (POPs 2022), Cyclobenzoins as Precursors for Porous Materials and Lithium-Ion Batteries, Abstract, Aug. 28-Sep. 1, 2022, Boulder, Colorado, 1 page.

(Continued)

*Primary Examiner* — Thuan D Dang
(74) *Attorney, Agent, or Firm* — Nixon Peabody LLP

(57) ABSTRACT

This invention relates to materials and methods for iodine capture from a variety of sources and media, and at water/organic solvent interfaces.

20 Claims, 37 Drawing Sheets

1a / 2a 1b / 2b 1c / 2c 1d / 2d 1e / 2e

(51) Int. Cl.
*C02F 101/12* (2006.01)
*H01M 4/02* (2006.01)

(56) References Cited

OTHER PUBLICATIONS

3rd International Symposium on Porous Organic Polymers (POPs 2022), Cyclobenzoins as Precursors to Porous Materials and Lithium-Ion Batteries, Presentation, Aug. 28-Sep. 1, 2022, Boulder, Colorado, 35 pages.
3rd International Symposium on Porous Organic Polymers (POPs 2022), Program, Aug. 28-Sep. 1, 2022, Boulder, Colorado, 69 pages.
1st North American Supramolecular Chemistry Meeting (NASC 2022), Cyclobenzoin Precursors to Porous Materials and Lithium-Ion Batteries, Abstract, Dec. 19-20, 2022, New Orleans, Louisiana, 1 page.
1st North American Supramolecular Chemistry Meeting (NASC 2022), Cyclobenzoins as Materials for Energy Industries: Iodine Capture and Lithium-Ion Batteries, Presentation, Dec. 19-20, 2022, New Orleans, Louisiana, 41 pages.
1st North American Supramolecular Chemistry Meeting (NASC 2022), Program, Dec. 19-20, 2022, New Orleans, Louisiana, 83 pages.
Luo et al., Reversible lodine Capture by Nonporous Adaptive Crystals of a Bipyridine Cage, J. Am. Chem. Soc. 2022, 144, 1, 113-117.
Luo et al., Reversible lodine Capture by Nonporous Adaptive Crystals of a Bipyridine Cage, J. Am. Chem. Soc. 2022, 144, 1, 113-117, Supporting Information, S1-S21.
Robles et al., Cyclobenzil hydrazones with high iodine capture capacities in solutions and on interfaces, Cell Reports Physical Science, vol. 4, Issue 8, 12 pages.
Meng et al., Cyclotetrabenzil Derivatives for Electrochemical Lithium-Ion Storage, Angew. Chem. Int. Ed. 2023, 62, 29, e202300892, 5 pages.
Meng et al., Cyclotetrabenzil Derivatives for Electrochemical Lithium-Ion Storage, Angew. Chem. Int. Ed. 2023, 62, 29, e202300892, Supporting Information, 44 pages.
Ji et al., Cyclotetrabenzoin: Facile Synthesis of a Shape-Persistent Molecular Square and Its Assembly into Hydrogen-Bonded Nanotubes, Chem. Eur. J. 2015, 21, 48, 17205-17209.
Eisterhold et al., Expanded Cyclotetrabenzoins, Org. Lett. Mar. 23, 2021, 781-785.
McHale et al., Porosity and Guest Inclusion in Cyclobenzoin Esters, Cryst. Growth Des. Feb. 19, 2019, 562-567.
Wang et al., Cyclotetrabenzoin Acetate: A Macrocyclic Porous Molecular Crystal for CO2 Separations by Pressure Swing Adsorption, Angew. Chem. Ind. Ed. 2021, 60, 27, 14931-14937.
Wang et al., Efficient CO2/CO Separation by Pressure Swing Adsorption Using an Intristically Nanoporous Molecular Crystal, ACS Appl. Nano Mater. May 10, 2022, 14021-14026.
Tietze et al., Formation of organic iodides from containment paint ingredients caused by gamma irradiation, J. Nucl. Sci. Technol. 2013, 50, 7, 689-694.
Tietze et al., Identification of the chemical inventory of different paint types applied in nuclear facilities, J. Radioanal. Nucl. Chem. 2013, 295, 1981-1999.
Lu et al., Prospects of organic electrode materials for practical lithium batteries, Nat. Rev. Chem. Apr. 2020, 127-142.
Lu et al., Prospects of organic electrode materials for practical lithium batteries, Nat. Rev. Chem. Apr. 2020, 127-142, Supplemental, 14 pages.
Dabbagh et al., The stereoselective synthesis and the nitrogen interconversion studies of 2-(tert-butoxymethyl)-1-[N'-(4-methylbnzenesulfonyl) (4-methylphenoxy)imidoyl] aziridine, J. Chem. Research (S), 2000, 190-192.
Choi et al., Promise and reality of post-lithium-ion batteries with high energy densities, Nat. Rev. Mater. Jan. 2016, 16013.
Choi et al., Promise and reality of post-lithium-ion batteries with high energy densities, Nat. Rev. Mater. Jan. 2016, 16013, Supplemental, 29 pages.
Ren et al., Advanced gel polymer electrolytes for safe and durable lithium metal batteries: Challenges, strategies, and perspectives, Energy Stor. Mater. 2021, 34, 515-535.
Cordell et al., Towards global phosphorus security: A systems framework for phosphorus recovery and reuse options, Chemosphere, 2011, 84, 6, 747-758.
Spears et al., Concerns about global phosphorus demand for lithium-iron-phosphate batteries in the light electric vehicle sector, Commun. Mater. Mar. 2022, pp. 1-2.
Ji et al., Cyclotribenzoin, Synlett, Nov. 26, 2015, 1625-1627.
McHale et al., Cyclobenzoin Esters as Hosts for Thin Guests, Org. Lett. Jun. 23, 2021, 2253-2257.

3

Ar =

1a / 2a

1b / 2b

1c / 2c

1d / 2d

1e / 2e

Ia Ib Ic Id Ie

Ia: 25.3% void volume

Ib: 33.3% void volume

Ic: 38.1% void volume

Id: 53.1% void volume

Ie: 79.1% void volume

MATERIALS AND METHODS FOR IODINE CAPTURE

CROSS-REFERENCE TO RELATED APPLICATIONS

This application claims the benefit of priority under 35 U.S.C. § 119(e) to U.S. Provisional Patent Application No. 63/444,456 filed Feb. 9, 2023, the contents of which is incorporated herein by reference in its entirety.

STATEMENT REGARDING FEDERALLY SPONSORED RESEARCH OR DEVELOPMENT

This invention was made with government support under Grant No. DMR-1904998 awarded by the National Science Foundation. The government has certain rights in the invention.

FIELD OF THE INVENTION

In various embodiments, the present invention relates to materials and methods for iodine capture from a variety of sources and media, and at water/organic solvent interfaces.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

With the ever-increasing environmental and geopolitical concerns about fossil fuel use, nuclear energy is a subject of renewed interest as the only currently scalable and geographically unrestricted way of producing electricity without greenhouse gas emissions. To alleviate public concerns about safety, comprehensive strategies for the management of nuclear waste must be developed. Radioactive iodine isotopes I-131 (half-life, $\tau_{1/2}$=8 days) and I-132 ($\tau_{1/2}$=3 days) are common products of nuclear fission and have been implicated in spreading the radioactivity following the Chernobyl accident. Iodine's volatility, solubility in organic and aqueous media, and tendency to concentrate in the human thyroid gland all make it a problematic pollutant Radioactive iodine additionally damages the nuclear paint used to coat the insides of nuclear reactors and waste containment vessels. Through incompletely understood mechanisms which involve radical formation and iodination of residual solvents in paint formulations and, radioactive irradiation of these paints yields small and volatile organic alkyl iodides, more difficult to capture than the iodine itself. As nuclear paints are hydrophobic, stopping iodine transfer from the aqueous to the organic layer can be a viable strategy for preventing this significant contamination problem.

Therefore, there is a need in the art for materials and methods for iodine capture. The embodiments of the present invention address that need.

SUMMARY OF THE INVENTION

The following embodiments and aspects thereof are described and illustrated in conjunction with compositions, methods, and articles of manufacture which are meant to be exemplary and illustrative, not limiting in scope.

In various embodiments, the present invention provides compound of Formula (II):

Formula (II)

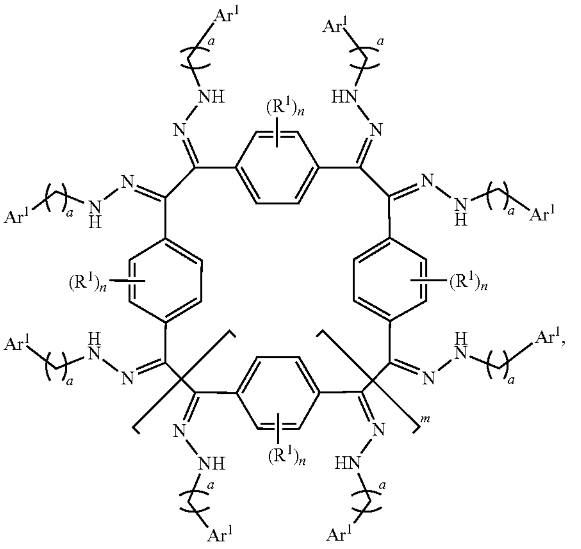

wherein: m is 0, 1, 2, 3, or 4; n is 0, 1, 2, 3 or 4; a is 0, 1 or 2, $Ar^1$ is optionally substituted aryl, or optionally substituted heteroaryl, and $R^1$ is an electron withdrawing group, or an electron donating group. In some embodiments. $Ar^1$ is selected from the group consisting of:

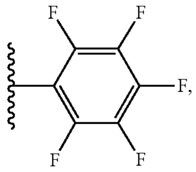,
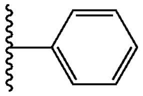,

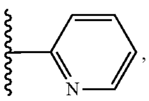,
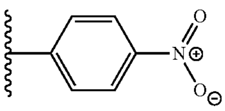, and

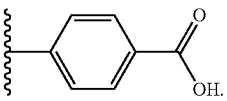

In various embodiments of the present invention, the compound of Formula (II) is a compound of Formula (II-a):

Formula (II-a)

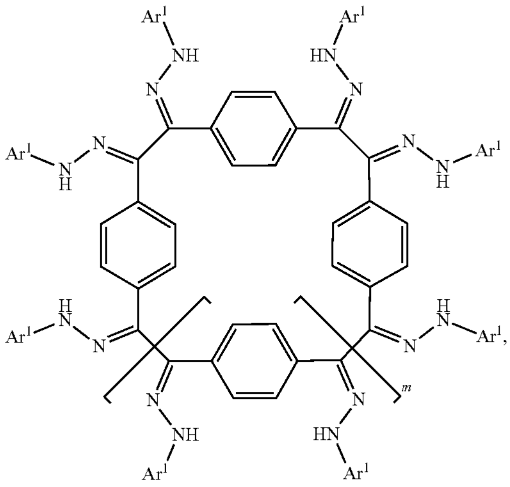

wherein: m is 0, 1, 2, 3, or 4; and $Ar^1$ is optionally substituted aryl, or optionally substituted heteroaryl. In some embodiments, $Ar^1$ is selected from the group consisting of:

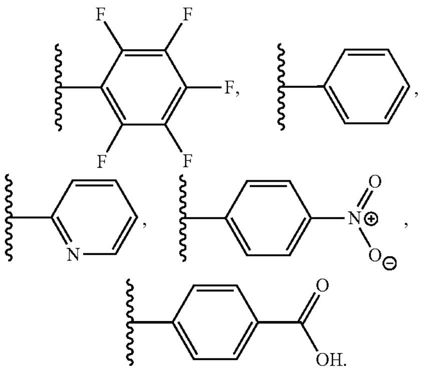

and

In various embodiments of the present invention, the compound of Formula (II) is a compound of Formula (II-b):

Formula (II-b)

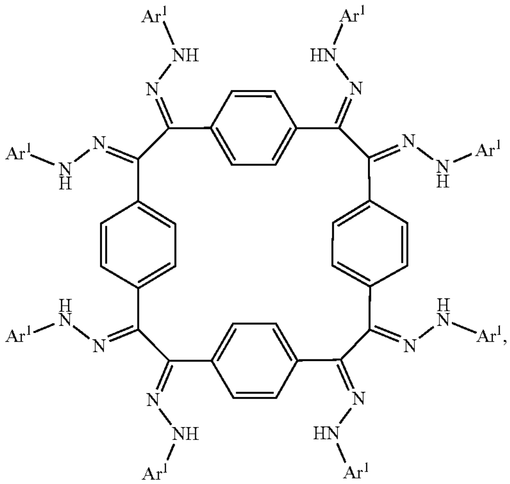

wherein: $Ar^1$ is optionally substituted aryl, or optionally substituted heteroaryl. In some embodiments, $Ar^1$ is selected from the group consisting of:

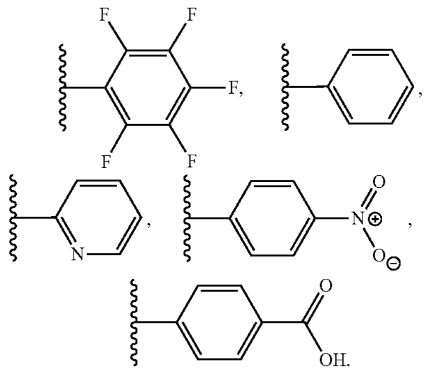

and

In some embodiments, the compound of Formula (II) is selected from the group consisting of:

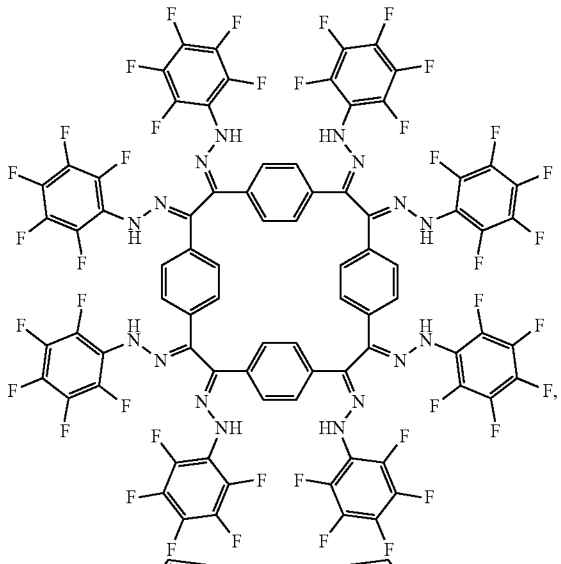

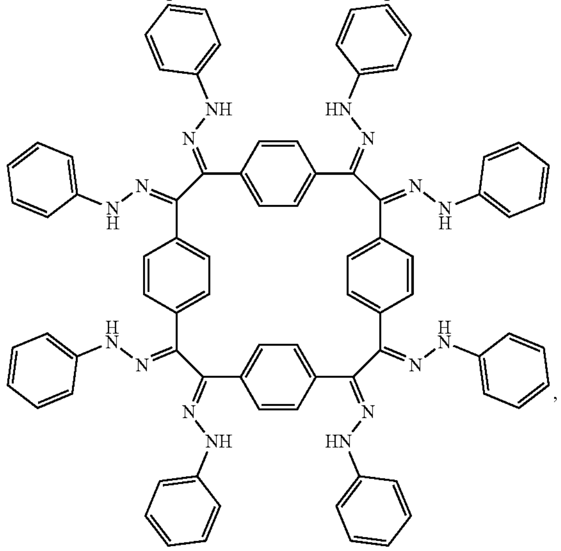

-continued

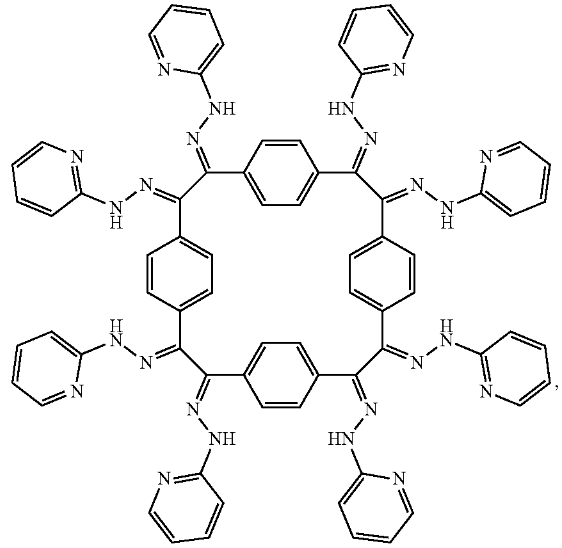

,

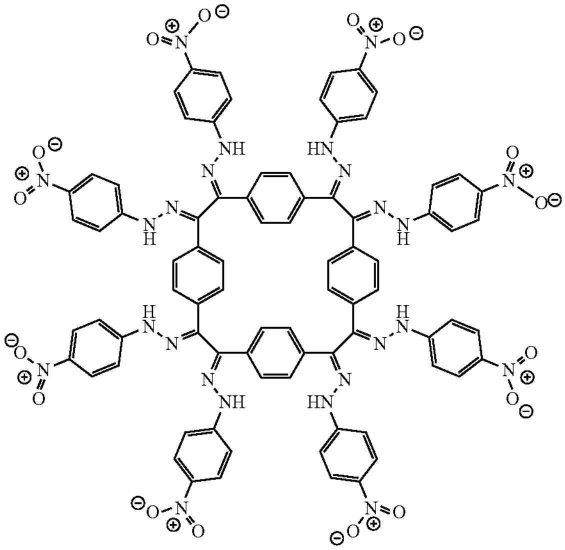

, and

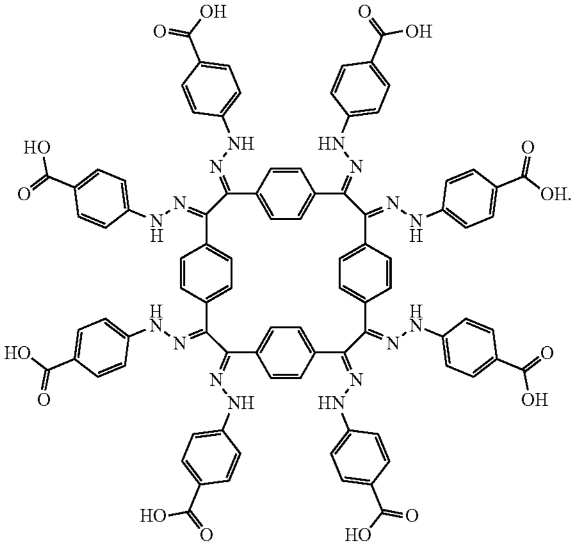

.

In various embodiments, the present invention provides a method for removing a material from a medium, the method comprising: providing a medium comprising a material; contacting the medium with a compound of Formula (II); capturing the material with the compound; and removing the compound that contains the captured material from the medium. In some embodiments, the method further comprises removing the captured material from the compound. In some embodiments, the material is non-radioactive molecular iodine ($I_2$), radioactive molecular iodine ($I_2$), or combination thereof. In some embodiments, the medium is aqueous medium, organic medium, or combination thereof.

In various embodiments, the present invention provides a method for removing a material from a medium, the method comprising: providing a medium comprising a material; contacting the medium with a compound; capturing the material with the compound; and removing the compound that contains the captured material from the medium, wherein the compound is selected from the group consisting of:

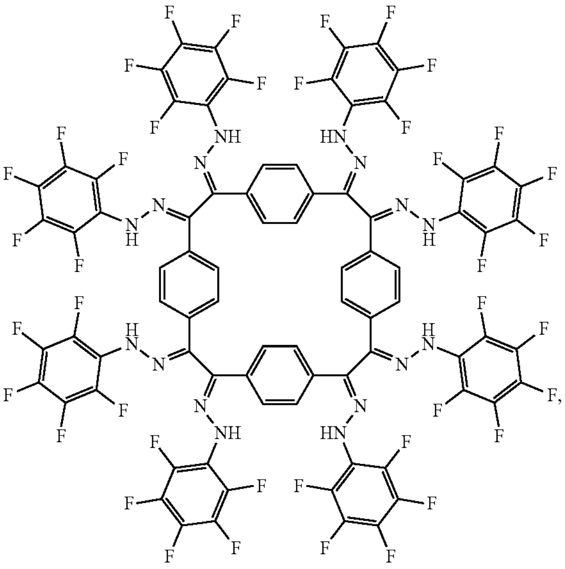

,

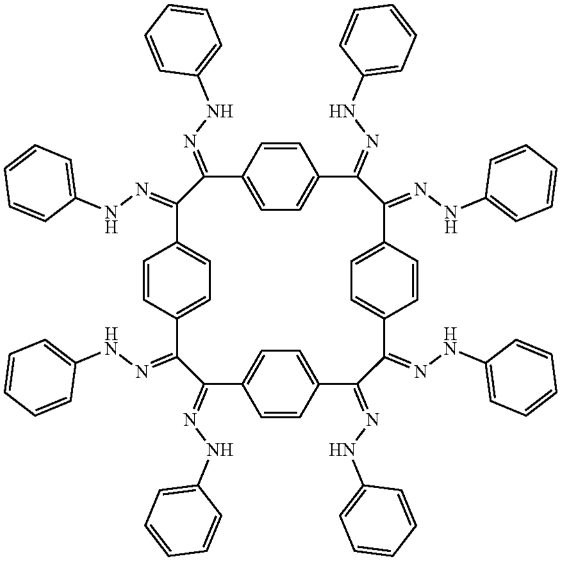

,

-continued

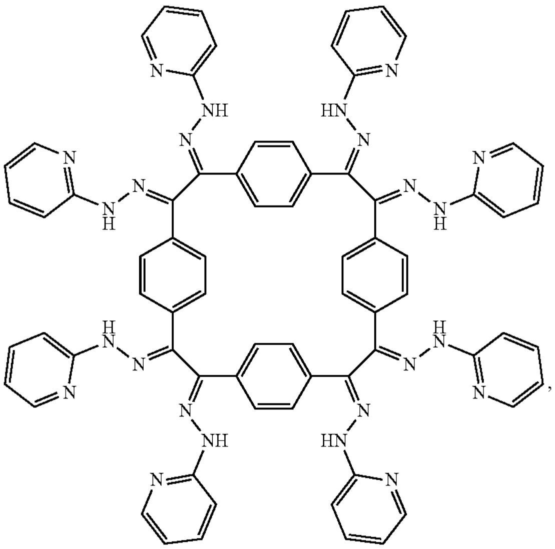

,

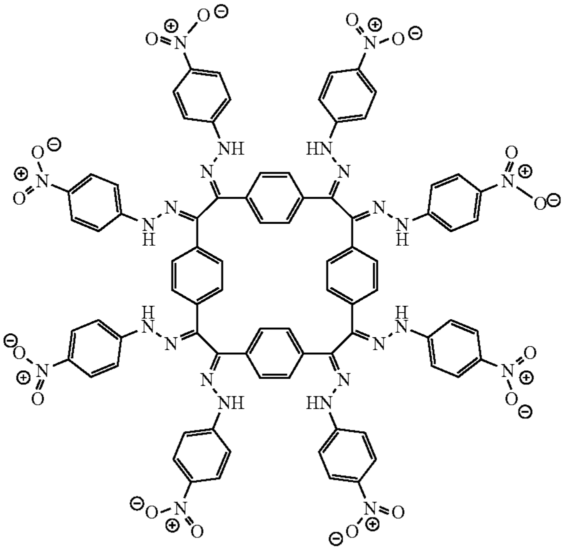

, and

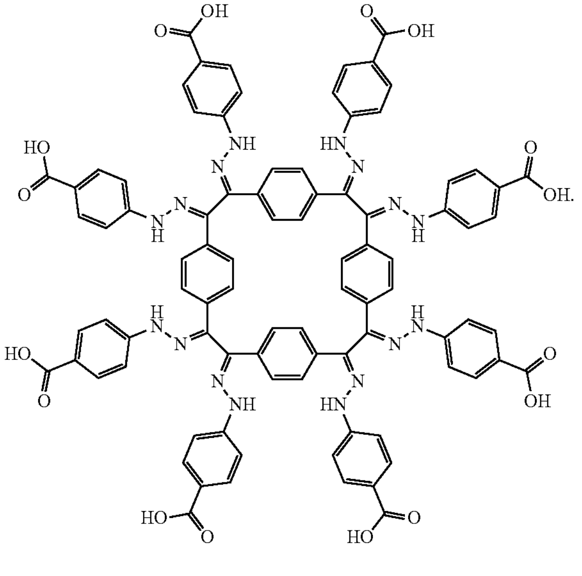

In some embodiments, the method further comprises removing the captured material from the compound. In some embodiments, the material is non-radioactive molecular iodine ($I_2$), radioactive molecular iodine ($I_2$), or combination thereof. In some embodiments, the medium is aqueous medium, organic medium, or combination thereof.

In various embodiments, the present invention provides a method of making a compound of Formula (II), the method comprising: reacting a compound of Formula (I) with a compound of Formula (VII) to obtain a compound of Formula (II), wherein the compound of Formula (I) is:

Formula (I)

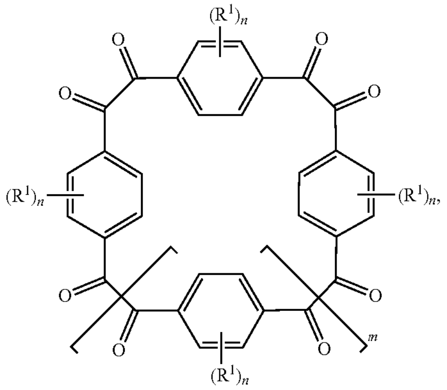

wherein: m is 0, 1, 2, 3, or 4; n is 0, 1, 2, 3 or 4; and $R^1$ is an electron withdrawing group, or an electron donating group; and wherein the compound of Formula (VII) is:

Formula (VII)

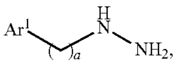

wherein, $Ar^1$ is optionally substituted aryl, or optionally substituted heteroaryl; and a is 0, 1 or 2.

In various embodiments, the present invention provides a composition comprising a compound of Formula (II).

In various embodiments, the present invention provides an article of manufacture comprising a compound of Formula (II). In some embodiments, the article of manufacture is a paint, a primer, a coating, or a coating material.

Exemplary embodiments are illustrated in referenced figures. It is intended that the embodiments and figures disclosed herein are to be considered illustrative rather than restrictive.

BRIEF DESCRIPTION OF THE DRAWINGS

FIG. 5A: plot of iodine vapor uptake by cyclotetra(bisarylhydrazone)benzil compounds 1a-1e, cyclotetrabenzil (3), and cyclotetrabenzoin (6) as a function of adsorption time. FIG. 5B: color changes observed upon exposure of cyclotetra(bisarylhydrazone) benzil compounds 1a-1e, cyclotetrabenzil compound (3), and cyclotetrabenzoin compound (6) to iodine vapor. FIG. 5C: cyclotetra(bisarylhydrazone)benzil compound 1c deposited in the powder form on the organic/aqueous interface prevents iodine migration from hexane to water (top row of photographs) and vice versa (bottom row); two leftmost photos in each row are control experiments without compound 1c.

FIG. 21B: water as Lugol's $I_2$ solution, and FIG. 21C: water upon the addition of cyclotetra(bisarylhydrazone)benzil compound 1c (5 mg); FIG. 21D-FIG. 21F: time dependent $I_2$ removal efficiency curves.

FIG. 22B: water upon the addition of cyclotetra(bisarylhydrazone)benzil compound 1c (5 mg).

FIG. 23B: compound 6 (5 mg). FIG. 23C: Comparison graph of the efficiency of compound 1c, compound 3, and compound 6 in removing $I_2$ from a 1 mM $I_2$ solution in hexane (3 mL).

FIG. 24A: Dark purple $I_2$@1c sample (6.6 mg) to be immersed in 1,4-dioxane (4 mL).

FIG. 24B: Time dependent color change of the 1,4-dioxane solution from light-yellow to a dark orange as $I_2$ was released from compound 1c. FIG. 24C: End color of the remaining compound 1c (1.5 mg) after 85% desorption of $I_2$.

FIG. 25A: Reference 4 mM $I_2$ solution in hexane (5 mL) layered over $H_2O$ (5 mL) after 7 d. FIG. 25B: Time dependent color change of a 4 mM $I_2$ solution in hexane (5 mL) layered over $H_2O$ (5 mL) upon the addition of compound 1c (20 mg). FIG. 25C: Reference 4 mM Lugol's $I_2$ solution in $H_2O$) (5 mL) layered with hexane (5 mL) after 7 d. FIG. 25D: Time dependent color change of a 4 mM Lugol's iodine solution in $H_2O$ (5 mL) layered with hexane (5 mL) upon the addition of compound 1c (20 mg).

FIG. 26B: compound 4, and FIG. 26C: compound 1c on glass captured to measure the contact angle between the solvent and sample.

DETAILED DESCRIPTION OF THE INVENTION

Figure 1:
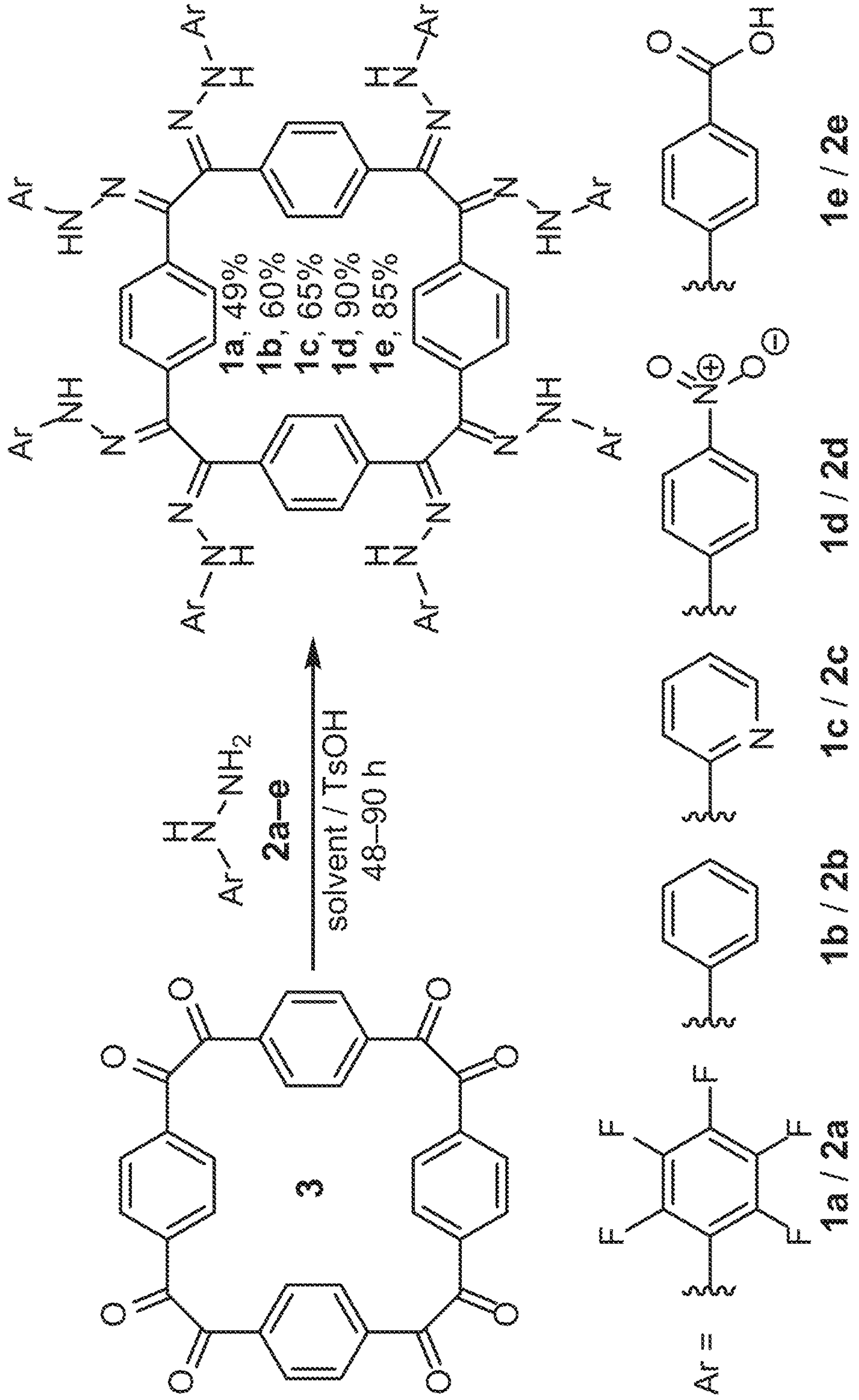
FIG. 1 depicts in accordance with various embodiments of the invention, synthesis of cyclotetra(bisarylhydrazone) benzil compounds 1a-1e.

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term “comprising” or “comprises” is used in reference to compositions, methods, systems, articles of manufacture, apparatus, and respective component(s) thereof, that are useful to an embodiment, yet open to the inclusion of unspecified elements, whether useful or not. It will be understood by those within the art that, in general, terms used herein are generally intended as “open” terms (e.g., the term “including” should be interpreted as “including but not limited to,” the term “having” should be interpreted as “having at least,” the term “includes” should be interpreted as “includes but is not limited to,” etc.). Although the open-ended term “comprising,” as a synonym of terms such as including, containing, or having, is used herein to describe and claim the invention, the present invention, or embodiments thereof, may alternatively be described using alternative terms such as “consisting of” or “consisting essentially of.”

Unless stated otherwise, the terms “a” and “an” and “the” and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, “such as”) provided with respect to certain embodiments herein is intended merely to better illuminate the application and does not pose a limitation on the scope of the application otherwise claimed. The abbreviation, “e.g.” is derived from the Latin exempli gratia, and is used herein to indicate a non-limiting example. Thus, the abbreviation “e.g.” is synonymous with the term “for example.” No language in the specification should be construed as indicating any non-claimed element essential to the practice of the application.

“Optional” or “optionally” means that the subsequently described circumstance may or may not occur, so that the description includes instances where the circumstance occurs and instances where it does not.

In some embodiments, the numbers expressing quantities of reagents, properties such as concentration, reaction conditions, and so forth, used to describe and claim certain embodiments of the invention are to be understood as being modified in some instances by the term “about.” Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

As used herein the terms “virtual porosity” and “virtually porous” are known in the art and generally means porosity/pores that are observable in crystal structure but disappear after solvent or guest removal.

As used herein the term “virtual pore” is known in the art and generally means a pore which is observable in crystal structure but disappears after solvent or guest removal.

As used herein the term “iodine” refers to molecular iodine represented as ($I_2$).

As used herein the term “iodo” refers to the iodine atom (I) when it is used in the context of a halo functional group or halogen functional group or as a halo substituent or halogen substituent.

As used herein the term “bromo” refers to the bromine atom (Br) when it is used in the context of a halo functional group or halogen functional group or as a halo substituent or halogen substituent.

As used herein the term “chloro” refers to the chlorine atom (Cl) when it is used in the context of a halo functional group or halogen functional group or as a halo substituent or halogen substituent.

As used herein the term “fluoro” refers to the fluorine atom (F) when it is used in the context of a halo functional group or halogen functional group or as a halo substituent or halogen substituent.

As used herein the term “electron donating group” is well-known in the art and generally refers to a functional group or atom that pushes electron density away from itself, towards other portions of the molecule, e.g., through resonance and/or inductive effects. Non-limiting examples of electron-donating groups include ORE, $NR^cR^d$, alkyl groups, wherein RE and $R^d$ are each independently H, optionally substituted alkyl, optionally substituted heteroalkyl, optionally substituted aryl, optionally substituted heteroaryl, optionally substituted cyclyl, or optionally substituted heterocyclyl.

As used herein the term "electron withdrawing group" is well-known in the art and generally refers to a functional group or atom that pulls electron density towards itself, away from other portions of the molecule, e.g., through resonance and/or inductive effects. Non-limiting examples of electron withdrawing groups include $NO_2$, F, Cl, Br, I, $CF_3$, CN, $CO_2R^a$, $C(=O)NR^aR^b$, $C(=O)R^a$, $SO_2R^a$, $SO_2OR^a$, $SO_2NR^aR^b$, $PO_3R^aR^b$, or NO, wherein $R^a$ and $R^b$ are each independently H, optionally substituted alkyl, optionally substituted heteroalkyl, optionally substituted aryl, optionally substituted heteroaryl, optionally substituted cycloalkyl, or optionally substituted heterocycloalkyl.

As used herein, the term "alkyl" means a straight or branched, saturated aliphatic radical having a chain of carbon atoms. $C_x$ alkyl and $C_x$-$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., ($C_6$-$C_{10}$)aryl($C_0$-$C_3$)alkyl includes phenyl, benzyl, phenethyl, 1-phenylethyl 3-phenylpropyl, and the like. Backbone of the alkyl can be optionally inserted with one or more heteroatoms, such as N, O, or S.

In preferred embodiments, a straight chain or branched chain alkyl has 30 or fewer carbon atoms in its backbone (e.g., C1-C30 for straight chains, C3-C30 for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths Throughout the application, preferred alkyl groups are lower alkyls. In preferred embodiments, a substituent designated herein as alkyl is a lower alkyl.

Non-limiting examples of substituents of a substituted alkyl can include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), $—CF_3$, —CN and the like.

As used herein, the term "alkenyl" refers to unsaturated straight-chain, branched-chain or cyclic hydrocarbon radicals having at least one carbon-carbon double bond. $C_x$ alkenyl and $C_x$-$C_y$alkenyl are typically used where X and Y indicate the number of carbon atoms in the chain. For example, $C_2$-$C_6$alkenyl includes alkenyls that have a chain of between 2 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$-$C_y$alkynyl are typically used where X and Y indicate the number of carbon atoms in the chain. For example, $C_2$-$C_6$alkynyl includes alkynls that have a chain of between 2 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

The terms "alkylene," "alkenylene," and "alkynylene" refer to divalent alkyl, alkelyne, and alkynylene" radicals. Prefixes $C_x$ and $C_x$-$C_y$ are typically used where X and Y indicate the number of carbon atoms in the chain. For example, $C_1$-$C_6$alkylene includes methylene, ($—CH_2—$), ethylene ($—CH_2CH_2—$), trimethylene ($—CH_2CH_2CH_2—$), tetramethylene ($—CH_2CH_2CH_2CH_2—$), 2-methyltetramethylene ($—CH_2CH(CH_3)CH_2CH_2—$), pentamethylene ($—CH_2CH_2CH_2CH_2CH_2—$) and the like).

As used herein, the term "alkylidene" means a straight or branched unsaturated, aliphatic, divalent radical having a general formula $=CR_aR_b$. Non-limiting examples of $R^a$ and $R_b$ are each independently hydrogen, alkyl, substituted alkyl, alkenyl, or substituted alkenyl. $C_x$ alkylidene and $C_x$-$C_y$alkylidene are typically used where X and Y indicate the number of carbon atoms in the chain. For example, $C_2$-$C_6$alkylidene includes methylidene ($=CH_2$), ethylidene ($=CHCH_3$), isopropylidene ($=C(CH_3)_2$), propylidene ($=CHCH_2CH_3$), allylidene ($=CH—CH=CH_2$), and the like).

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, the term "halogen" or "halo" refers to an atom selected from fluorine (F), chlorine (Cl), bromine (Br) and iodine (I). The term "halogen radioisotope" or "halo radioisotope" refers to a radionuclide of an atom selected from fluorine (F), chlorine (Cl), bromine (Br) and iodine (I).

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl ($—CF_3$), 2,2,2-trifluoroethyl, perfluoroethyl, 2,2,2-trifluoro-1,1-dichloroethyl, and the like).

The term "aryl" refers to monocyclic, bicyclic, or tricyclic fused aromatic ring system. $C_x$ aryl and $C_x$-$C_y$aryl are typically used where X and Y indicate the number of carbon atoms in the ring system. For example, $C_6$-$C_{12}$ aryl includes aryls that have 6 to 12 carbon atoms in the ring system. Exemplary aryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro [2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively. $C_x$ heteroaryl and $C_x$-$C_y$heteroaryl are typically used where X and Y indicate the number of carbon atoms in the ring system. For example, $C_4$-$C_9$ heteroaryl includes heteroaryls that have 4 to 9 carbon atoms in the ring system. Heteroaryls include, but are not limited to, those derived from benzo[b] furan, benzo[b] thiophene, benzimidazole, imidazo[4,5-c] pyridine, quinazoline, thieno[2,3-c]pyridine, thieno[3,2-b] pyridine, thieno[2, 3-b]pyridine, indolizine, imidazo[1,2a] pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a] pyrimidine, imidazo[1,5-c]pyrimidine, pyrrolo[2,3-b] pyridine, pyrrolo[2,3c]pyridine, pyrrolo[3,2-c]pyridine, pyrrolo[3,2-b]pyridine, pyrrolo[2,3-d]pyrimidine, pyrrolo [3,2-d]pyrimidine, pyrrolo[2,3-b]pyrazine, pyrazolo[1,5-a] pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo [3,2,1-hi]indole, indolizine, pyrido[1,2-a]indole, 2(1H)- pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$cyclyl and $C_x$-$C_y$cyclyl are typically used where X and Y indicate the number of carbon atoms in the ring system. For example, $C_3$-$C_8$ cyclyl includes cyclyls that have 3 to 8 carbon atoms in the ring system. The cycloalkyl group additionally can be optionally substituted, e.g., with 1, 2, 3, or 4 substituents. $C_3$-$C_{10}$cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "heterocyclyl" refers to a nonaromatic 4-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. For example, $C_4$-$C_9$ heterocyclyl includes heterocyclyls that have 4-9 carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

The terms "bicyclic" and "tricyclic" refers to fused, bridged, or joined by a single bond polycyclic ring assemblies.

The term "cyclylalkylene" means a divalent aryl, heteroaryl, cyclyl, or heterocyclyl.

As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. The term "carboxyl" means —COOH.

The term "cyano" means the radical —CN.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N=, —$NR^N$—, —$N^+(O^-)$=, —O—, —S— or —$S(O)_2$—, —$OS(O)_2$—, and —SS—, wherein $R^N$ is H or a further substituent.

The term "hydroxy" means the radical —OH.

The term "imine derivative" means a derivative comprising the moiety —C(NR)—, wherein R comprises a hydrogen or carbon atom alpha to the nitrogen.

The term "nitro" means the radical —$NO_2$.

An "oxaaliphatic," "oxaalicyclic", or "oxaaromatic" mean an aliphatic, alicyclic, or aromatic, as defined herein, except where one or more oxygen atoms (—O—) are positioned between carbon atoms of the aliphatic, alicyclic, or aromatic respectively.

An "oxoaliphatic," "oxoalicyclic", or "oxoaromatic" means an aliphatic, alicyclic, or aromatic, as defined herein, substituted with a carbonyl group. The carbonyl group can be an aldehyde, ketone, ester, amide, acid, or acid halide.

As used herein, the term, "aromatic" means a moiety wherein the constituent atoms make up an unsaturated ring system, all atoms in the ring system are $sp^2$ hybridized and the total number of pi electrons is equal to 4n+2. An aromatic ring can be such that the ring atoms are only carbon atoms (e.g., aryl) or can include carbon and non-carbon atoms (e.g., heteroaryl).

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls including ketones, carboxy, carboxylates, $CF_3$, cyano (CN), cycloalkyl, cycloalkylene, ester, ether, haloalkyl, halo, halogen, heteroaryl, heterocyclyl, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

Substituents may be protected as necessary and any of the protecting groups commonly used in the art may be employed. Non-limiting examples of protecting groups may be found, for example, in Greene et al., Protective Groups in Organic Synthesis, 3rd Ed. (New York: Wiley, 1999).

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, isopropyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of—O-alkyl, —O-alkenyl, and —O-alkynyl. Aroxy can be represented by—O-aryl or O-heteroaryl, wherein aryl and heteroaryl are as defined below. The alkoxy and aroxy groups can be substituted as described above for alkyl.

The term "aralkyl", as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S— alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —$SO_2$—. It is noted that the sulfonyl radical can be further substituted with a variety of substituents to form different sulfonyl groups including sulfonic acids (—$SO_3H$), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "amino" means —$NH_2$. The term "alkylamino" means a nitrogen moiety having at least one straight or branched unsaturated aliphatic, cyclyl, or heterocyclyl radicals attached to the nitrogen. For example, representative amino groups include —$NH_2$, —$NHCH_3$, —$N(CH_3)_2$, —NH($C_1$-$C_{10}$alkyl), —N($C_1$-$C_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an ($C_2$-$C_6$) aminoalkyl refers to a chain comprising between 2 and 6 carbons and one or more nitrogen atoms positioned between the carbon atoms.

The term "alkoxyalkoxy" means —O-(alkyl)-O-(alkyl), such as —$OCH_2CH_2OCH_3$, and the like.

The term "alkoxycarbonyl" means —C(O)O-(alkyl), such as —C(═O)$OCH_3$, —C(═O)$OCH_2CH_3$, and the like.

The term "alkoxyalkyl" means -(alkyl)-O-(alkyl), such as —$CH_2OCH_3$, —$CH_2OCH_2CH_3$, and the like.

The term "aryloxy" means —O-(aryl), such as —O-phenyl, —O-pyridinyl, and the like.

The term "arylalkyl" means -(alkyl)-(aryl), such as benzyl (i.e., —$CH_2$phenyl), —$CH_2$-pyrindinyl, and the like.

The term "arylalkyloxy" means —O-(alkyl)-(aryl), such as —O-benzyl, —O—$CH_2$-pyridinyl, and the like.

The term "cycloalkyloxy" means —O-(cycloalkyl), such as —O-cyclohexyl, and the like.

The term "cycloalkylalkyloxy" means —O-(alkyl)-(cycloalkyl, such as —$OCH_2$cyclohexyl, and the like.

The term "aminoalkoxy" means —O-(alkyl)-$NH_2$, such as —$OCH_2NH_2$, —$OCH_2CH_2NH_2$, and the like.

The term "mono- or di-alkylamino" means —NH(alkyl) or —N(alkyl)(alkyl), respectively, such as —$NHCH_3$, —$N(CH_3)_2$, and the like.

The term "mono- or di-alkylaminoalkoxy" means —O-(alkyl)-NH(alkyl) or —O-(alkyl)-N(alkyl)(alkyl), respectively, such as —$OCH_2NHCH_3$, —$OCH_2CH_2N(CH_3)_2$, and the like.

The term "arylamino" means —NH(aryl), such as —NH-phenyl, —NH-pyridinyl, and the like.

The term "arylalkylamino" means —NH-(alkyl)-(aryl), such as —NH-benzyl, —$NHCH_2$-pyridinyl, and the like.

The term "alkylamino" means —NH(alkyl), such as —$NHCH_3$, —$NHCH_2CH_3$, and the like.

The term "cycloalkylamino" means —NH-(cycloalkyl), such as —NH-cyclohexyl, and the like.

The term "cycloalkylalkylamino" —NH-(alkyl)-(cycloalkyl), such as —$NHCH_2$-cyclohexyl, and the like.

It is noted in regard to all of the definitions provided herein that the definitions should be interpreted as being open ended in the sense that further substituents beyond those specified may be included. Hence, a C; alkyl indicates that there is one carbon atom but does not indicate what are the substituents on the carbon atom. Hence, a $C_1$ alkyl comprises methyl (i.e., —$CH_3$) as well as —$CR_aR_bR_c$ where $R_a$, $R_b$, and Re can each independently be hydrogen or any other substituent where the atom alpha to the carbon is a heteroatom or cyano. Hence, $CF_3$, $CH_2OH$ and $CH_2CN$ are all $C_1$ alkyls.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

In various embodiments, compounds of the present invention as disclosed herein may be synthesized using any synthetic method available to one of skill in the art. Non-limiting examples of synthetic methods used to prepare various embodiments of compounds of the present invention are disclosed in the Examples section herein.

Porous molecular crystals (PMCs) are solution processable materials with promising applications in thin films and devices. However, some PMCs are virtually porous, as their pores collapse when desolvated because of the weak interactions that hold the extended structures together. Herein we demonstrate the productive use of virtual porosity when non-volatile $I_2$ guest acts as the probe. We prepared a series of cyclotetrabenzil hydrazone compounds 1a-1e with progressively larger cavities. Their measured surface areas of up to 131 $m^2$ $g^{-1}$ are negligible compared to the values predicted from crystal structures. Nevertheless, the prepared cyclotetrabenzil hydrazone compounds 1a-1e surprisingly capture $I_2$ from aqueous and organic media and at the organic-aqueous interface, with capture capacities generally scaling with virtual void volumes. The pyridine-functionalized cyclotetrabenzil hydrazone, compound 1c, is an unexpected outlier, capable of specifically engaging up to 21 $I_2$ molecules and showing capture capacity of 4.15 g $g^{-1}$, unprecedented among non-polymeric molecular materials. The findings reported herein could impact the management of radioactive $I_2$ and help in ensuring the integrity of protective coatings on nuclear reactors and waste containment vessels.

Herein, we report a set of five molecular crystals based on the readily prepared cyclotetrabenzil hydrazone compounds 1a-1e, their crystal structures, and their use as iodine capture agents in a variety of media and at water/organic solvent interfaces.

-continued
Compound 1a
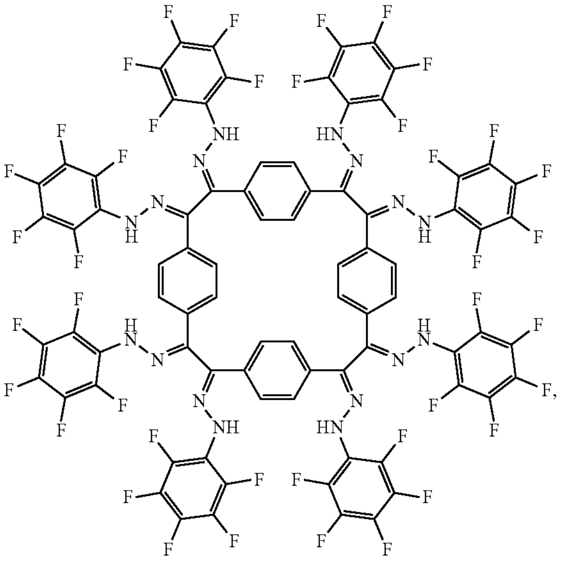
Compound 1c
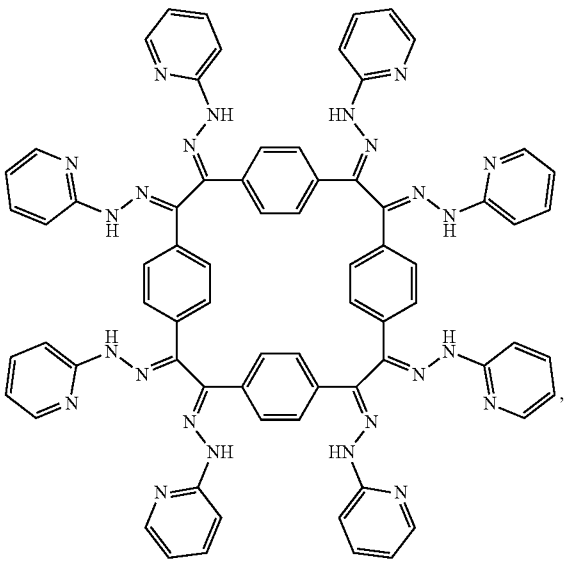
Compound 1b
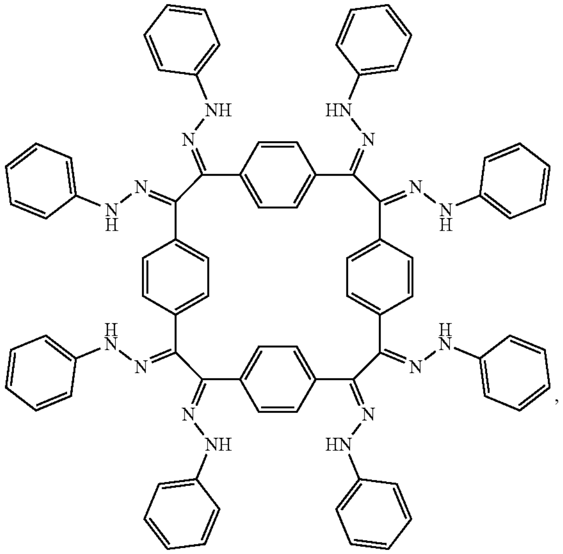
Compound 1d
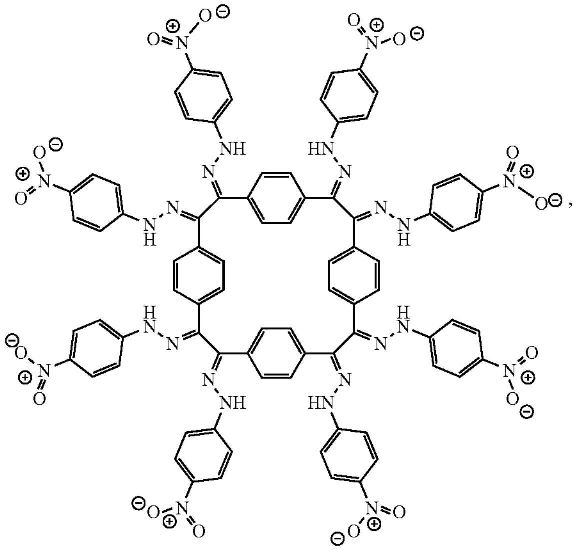

-continued

Compound 1e

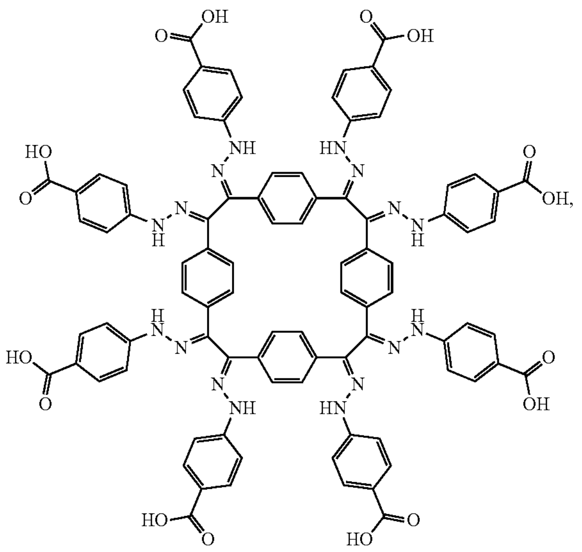

Cmpound 3

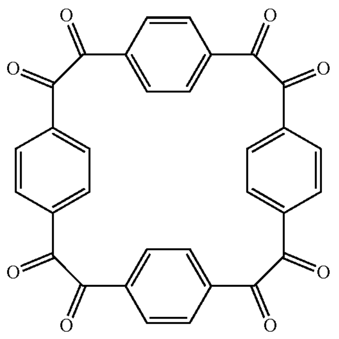

Compound 4

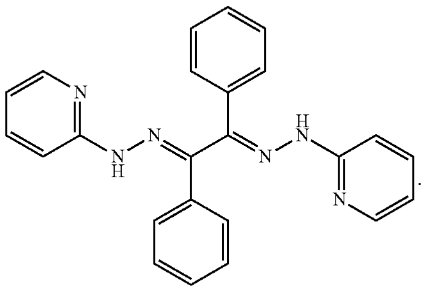

Compound 6

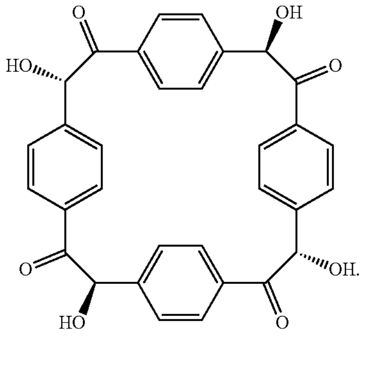

Results

Figure 2:
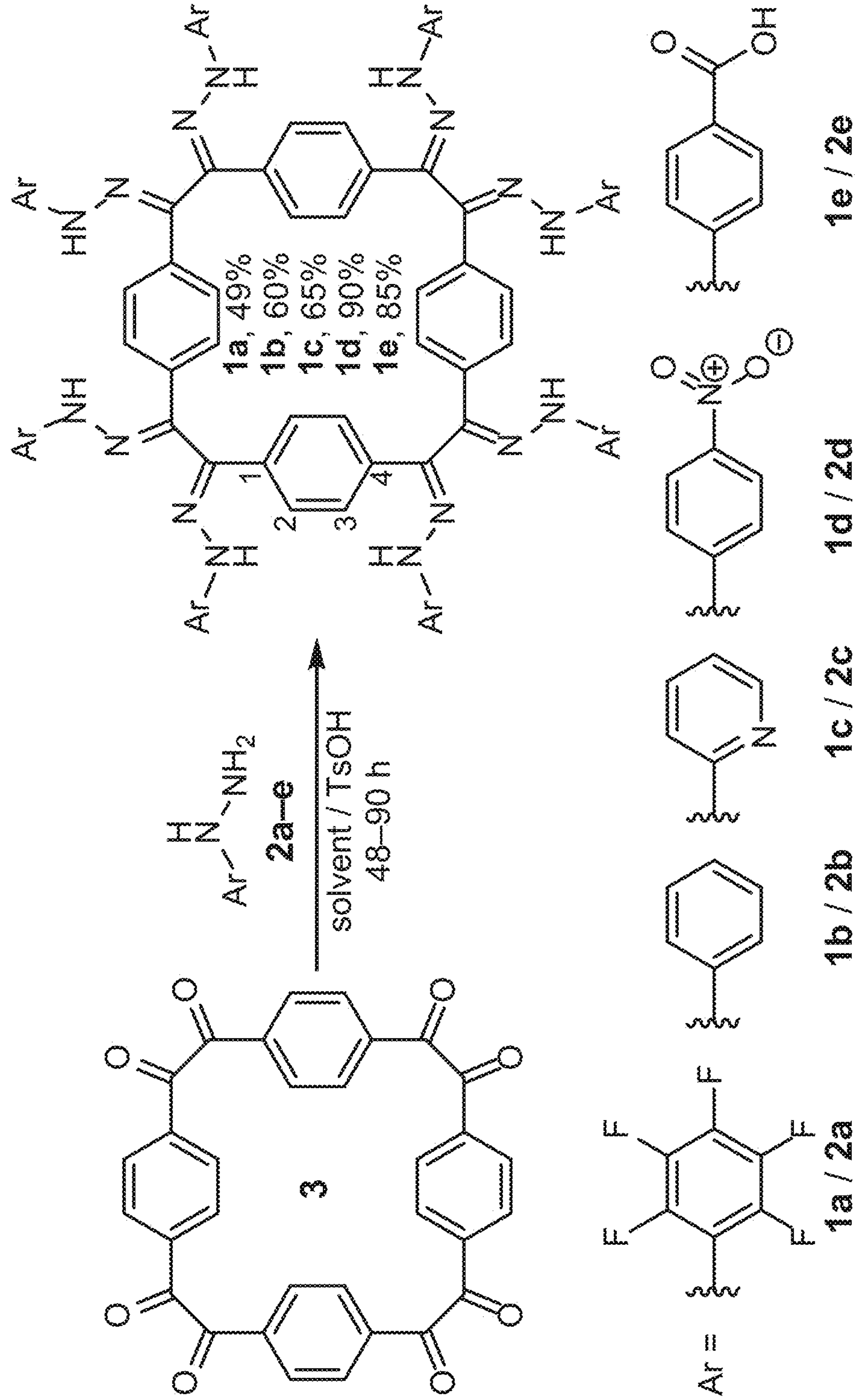
FIG. 2 depicts in accordance with various embodiments of the invention, synthesis of cyclotetra(bisarylhydrazone) benzil compounds 1a-1e.

Cyclotetra(bisarylhydrazone)benzil compounds 1a-1e were synthesized by eightfold hydrazone condensations between cyclotetrabenzil compound (3) and arylhydrazine compounds 2a-2e in EtOH, PhMe, or p-xylene as the solvents, and with p-toluenesulfonic acid as the catalyst (FIG. 1 and FIG. 2). The desired hydrazone products were isolated as crystalline solids in yields between 49% and 90%, corresponding to per-condensation yields ranging from 91.5% (compound 1a) to 98.7% (compound 1d).

Spectroscopic characterization data of compounds 1a-1e is consistent with their molecular structures. The effects of the bulky aryl substituents on the conformational dynamics of compounds 1a-1e in solution were probed by variable-temperature $^1H$ NMR spectroscopy. At ambient conditions, two broad singlets are associated with the phenylene protons of the macrocyclic skeleton in compound 1a and compounds 1c-1e (compound 1b was not studied because of insolubility in all deuterated solvents of sufficiently high boiling point). This doubling up of peaks can be caused either by the slow rotation of the phenylene moieties of the central macrocycle around their $C_1$-$C_4$ axes, or by the slow slipping of the neighboring hydrazine arms by each other. At the coalescence temperatures ($T_c$), the rate constants ($k_c$) for the dynamic processes were calculated using the Gutowsky-Hold equation, $k_c=2.22\Delta_D$, where $\Delta_D$ represents the difference in chemical shifts between the phenyl hydrogens in the macrocylic skeleton. The Gibbs free energies of activation ($\Delta G^+$) were calculated, assuming unity in the transmission coefficient (κ), using the Eyring equation, $\Delta G^+=RT_c[\ln T_c-\ln k_c+23.76]$. The results of the dynamic $^1H$ NMR studies of the conformational dynamics of cyclotetra(bisarylhydrazone)benzil compound 1a, cyclotetra(bisarylhydrazone)benzil compound 1c, cyclotetra(bisarylhydrazone)benzil compound 1d, and cyclotetra(bisarylhydrazone) benzil compound 1e are summarized in Table 1.

TABLE 1

Calculated rate constants ($k_c$) and Gibbs' activation energies ($\Delta G^{\ddagger}$) for conformational equilibration of compounds 1a, 1c, 1d and 1e in DMSO-$d_6$.

| Compound | δ, (Hz)[a] | $T_c$, (K) | $k_c$, ($s^{-1}$) | $\Delta G^{\ddagger}$, (kcal $mol^{-1}$) |
|---|---|---|---|---|
| 1a | 4110, 4730 | 323 | 1376 | 14.35 |
| 1c | 4003, 4925 | 319 | 2048 | 13.91 |
| 1d | 4001, 4996 | 315 | 2209 | 13.68 |
| 1e | 3972, 4966 | 310 | 2223 | 13.45 |

[a]The $^1H$ NMR chemical shifts of the macrocycle skeleton phenyl ring protons are shown in Hz.
Spectrometer frequency: 600 MHz for $^1H$ nuclei.

The inversion barriers for compounds 1a-1e proved minimally sensitive to substitution. This observation suggests that the barriers are largely steric in nature, as the four studied molecules have pendant hydrazone groups of similar sizes. Indirectly, it may also point to the free rotation of the phenylene rings in the central core as the equilibrating process-since the bypassing of the hydrazone arms would involve planarization in the transition state and would thus probably be sensitive to electronic effects.

Single crystals of compounds 1a-1e were grown by slow vapor diffusion and analyzed by X-ray diffraction (Table 2). While the crystals of compounds 1a-1d were grown under routine conditions, hydrazone compound 1e was crystallized by vapor diffusion of a 0.2M solution of $I_2$ in acetone into a 0.05M solution of compound 1e in THF. These unusual crystallization conditions were critical, as numerous prior attempts using various solvent combinations produced crystals of insufficient quality for X-ray diffraction. To our surprise, iodine was not incorporated into the crystal structure of compound 1e when its large yellow prismatic crystals were harvested after 7 d.

TABLE 2

Crystal growth conditions and key parameters for compounds 1a-1e. All crystals were grown by vapor diffusion.

| Compound | Solvent | Crystal description | Time (days) | Space group | Z |
|---|---|---|---|---|---|
| 1a | hexane into $CHCl_3$ | yellow, needle-shaped | 3 | P1 | 2 |
| 1b | EtOH into $CHCl_3$ | yellow, needle-shaped | 5 | $P2_1/n$ | 4 |
| 1c•2AcOH | $Et_2O$ into AcOH | yellow, prismatic | 2 | P2/c | 2 |
| 1d | hexane into THF | red, needle-shape | 3 | $P42_1/c$ | 6 |
| 1e | 0.2M solution of $I_2$ in acetone into THF | yellow, prismatic | 7 | Pmna | 6 |

Figure 3:
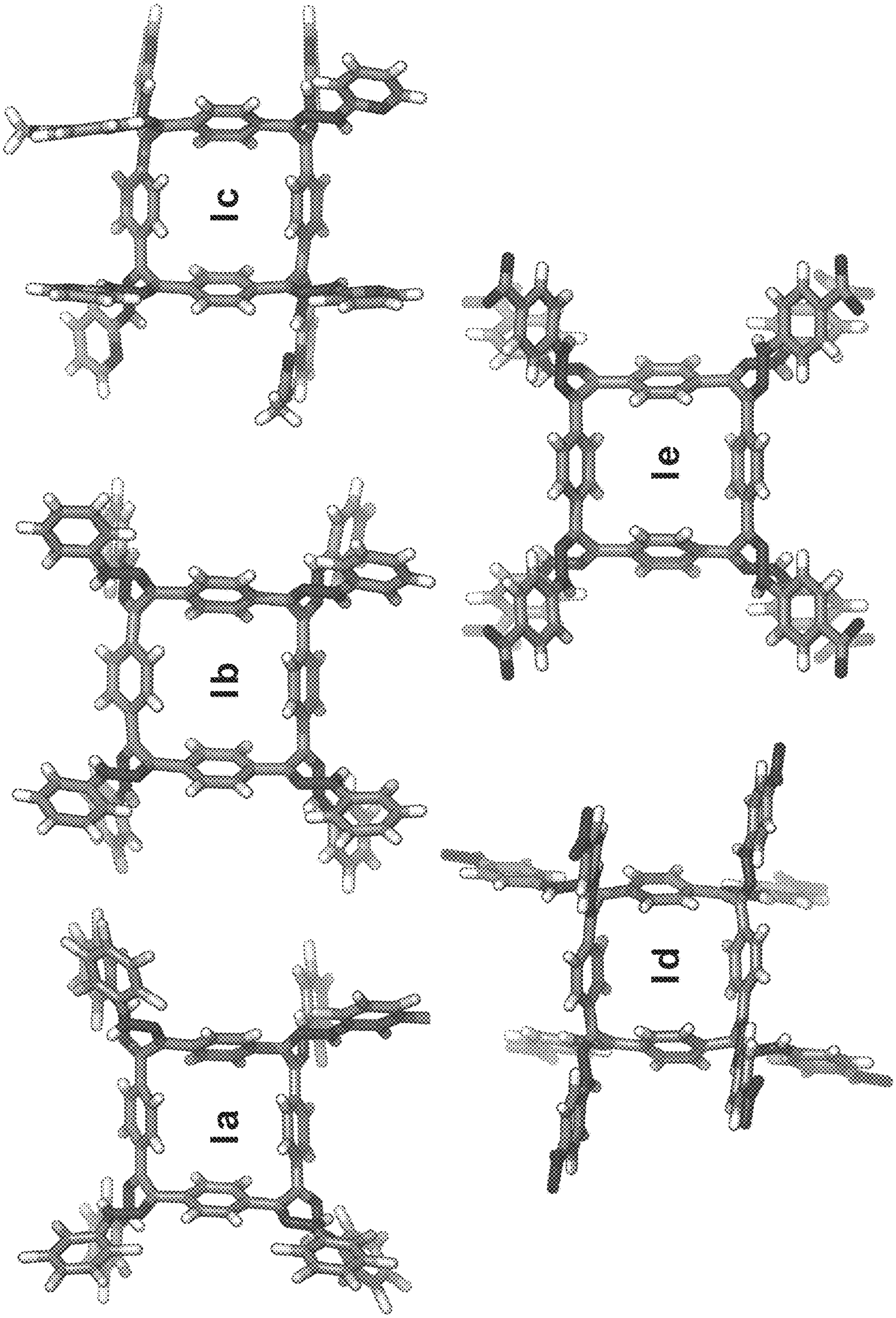
FIG. 3 depicts in accordance with various embodiments of the invention, Crystal structures of cyclotetra(bisarylhydrazone)benzil compounds 1a-1e.

As FIG. 3 shows, all five derivatives maintain the roughly square-shaped central cavity. A closer inspection of their dimensions revealed that the macrocyclic scaffolds adopt boat-like conformations with the directions of opposing dihedral angles being the same (see FIG. 3 and Tables 3-8). In all prepared octahydrazones, the two immediately adjacent arylhydrazone arms point in the opposite directions, while those separated by the phenylene rings point in the same direction, resulting in an overall ab-ba-ab-ba arrangement (where “a” describes units positioned above the plane of the central macrocycle and “b” those positioned below the plane). The C═N bonds are in the (Z)-configuration and the C═N—NH—Ar linkers are in the extended zigzag conformation. In compounds 1a-1d, C═N bonds are shorter (1.28-1.34 Å) than the N—N (1.34-1.37 Å) bonds, consistent with the hydrazone tautomer. However, in compound 1e this trend in bond lengths switches in four out of eight C═N—NH moieties; this observation is counterintuitive as the electron-withdrawing-COOH group should shorten the Ar—N and N═C bonds, lengthening the central N—N bond in hydrazones.

While the molecular structures of compounds 1a-1e appear very similar, their extended crystal structures (FIG. 4) greatly differ, progressively opening up along the series. Compound 1a forms the most tightly packed structure with solvent-accessible void volume of 25.3% of the total unit cell. In compound 1b, this void volume increased to 33.3%. Compound 1c crystallizes with eight AcOH molecules per unit cell. It is the only crystal structure in the series which includes ordered solvent molecules: the AcOH molecule establishes [O—H . . . N] (2.10 Å) and [N—H . . . O] (1.78 Å) hydrogen bonds with the 2-hydrazonopyridine moiety of compound 1c. Its void volume is 38.1%. The final two structures of compound 1d and compound 1e were characterized by the solvent-accessible void volumes of 53.1% and 79.1%, respectively. These large voids are not persistent: exposed to air, the crystals collapsed within minutes. An analysis of such minimally crystalline powders for compound 1c and compound 1e revealed Brunauer-Emmett-Teller (BET) surface areas of just 24.1 and 131 $m^2$ $g^{-1}$, respectively. These values are similar to those measured for the parent cyclotetrabenzoin, but far below the theoretical values which go up to 3531 $m^2$ $g^{-1}$ for compound 1e (calculated using Materials Studio). Thus, structures of compounds 1a-1e are virtually porous.

Iodine Capture Experiments

Figure 5B:
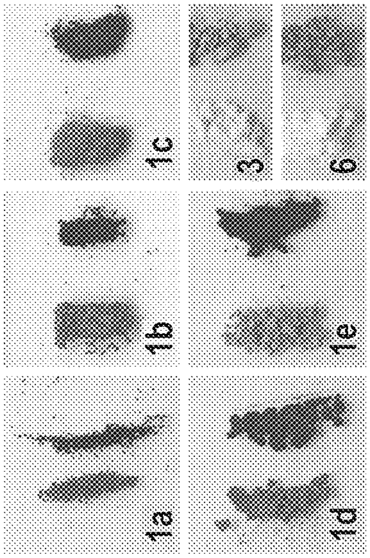
FIG. 5A-FIG. 5C depicts in accordance with various embodiments of the invention.

Inspired by the crucial role iodine played in the successful crystallization of compound 1e, we decided to investigate whether these cyclotetra(bisarylhydrazone)benzil compounds 1a-1e could uptake iodine within their nitrogen-rich structures. Initial experiments to probe their adsorption capabilities were carried out using $I_2$ vapor at room temperature. Exposing all five compounds 1a-1e as well as the parent cyclotetrabenzoin (compound 6) and cyclotetrabenzil (compound 3) to iodine vapor led to an increase in their mass as a function of time (FIG. 5A), and to the darkening of the compounds' colors (FIG. 5B). The non-functionalized parent compound 6 and compound 3 adsorbed little to no $I_2$, having capacities of 0.065 and 0 g $g^{-1}$, respectively. The adsorption profiles of compound 1a, compound 1b, compound 1d, and compound 1e followed an almost linear initial trend, which began to plateau after five days, signaling that equilibrium had been reached. Final uptake capacities correlated with the observed void volumes: the lowest one for compound 1a, slightly higher for compound 1b and compound 1d, and the highest seen for compound 1e. However, the uptake capacity of compound 1c did not reach equilibrium until day 20 and demonstrated an outstandingly high capacity of 4.15 g $g^{-1}$, which equates to ~21 molecules of $I_2$ per molecule of compound 1c (FIG. 5A).

Figure 22B:
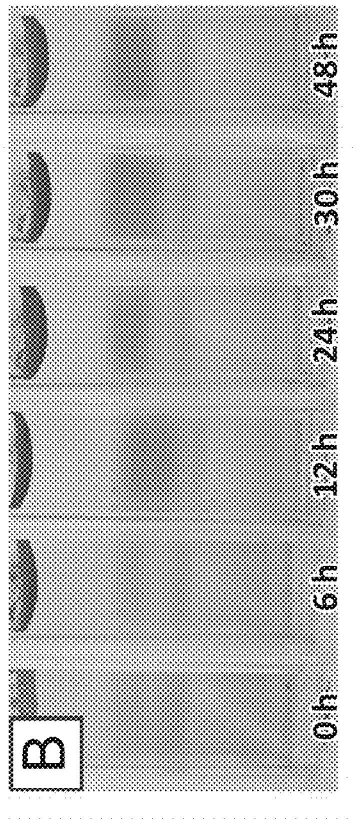
FIG. 22A-FIG. 22B depicts in accordance with various embodiments of the invention, Time dependent color change of 1 mM $I_2$ solutions (3 mL) in FIG. 22A: hexane
Figure 22A:
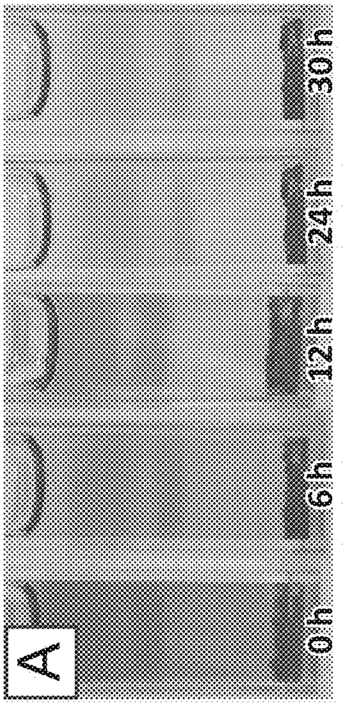
Figure 23A:
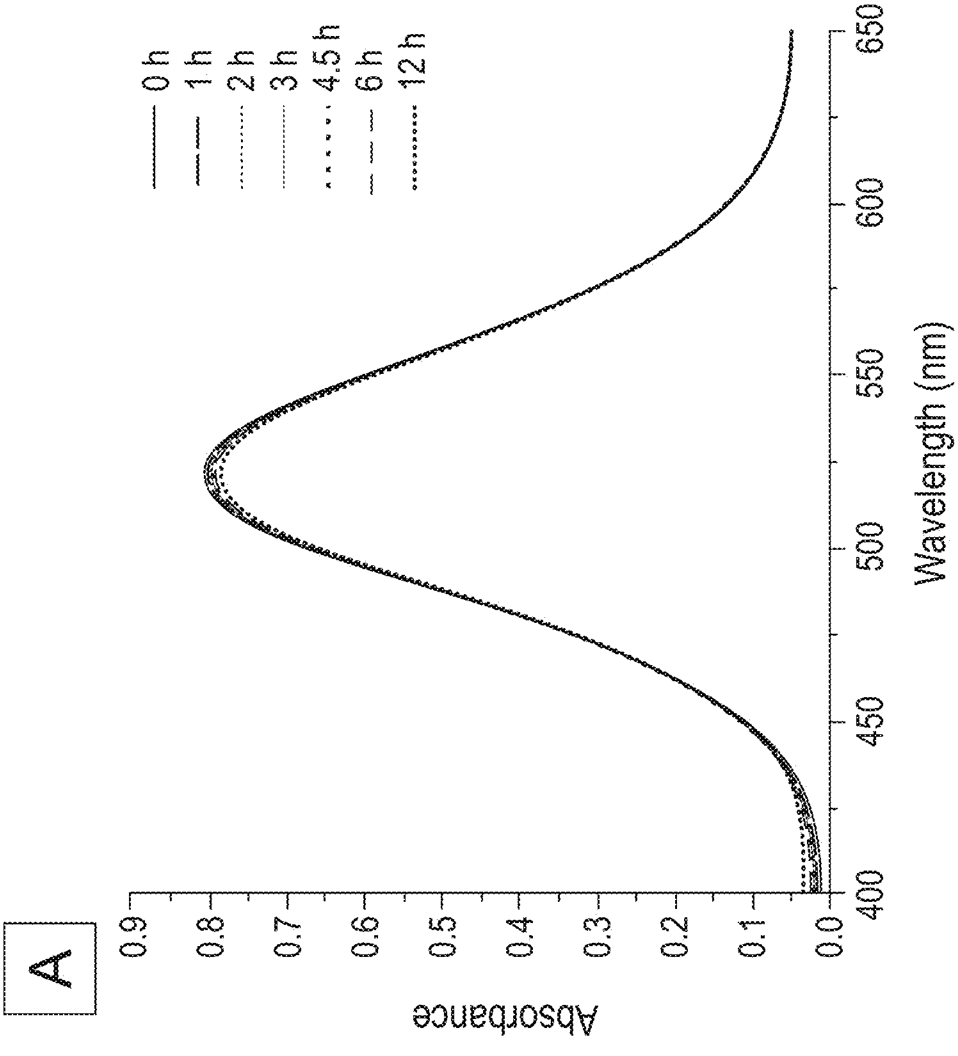
FIG. 23A-FIG. 23C depicts in accordance with various embodiments of the invention, Time dependent UV/Vis adsorption spectra of 1 mM $I_2$ solutions in hexane upon the addition of FIG. 23A: compound 3 (5 mg)
Figure 23B:
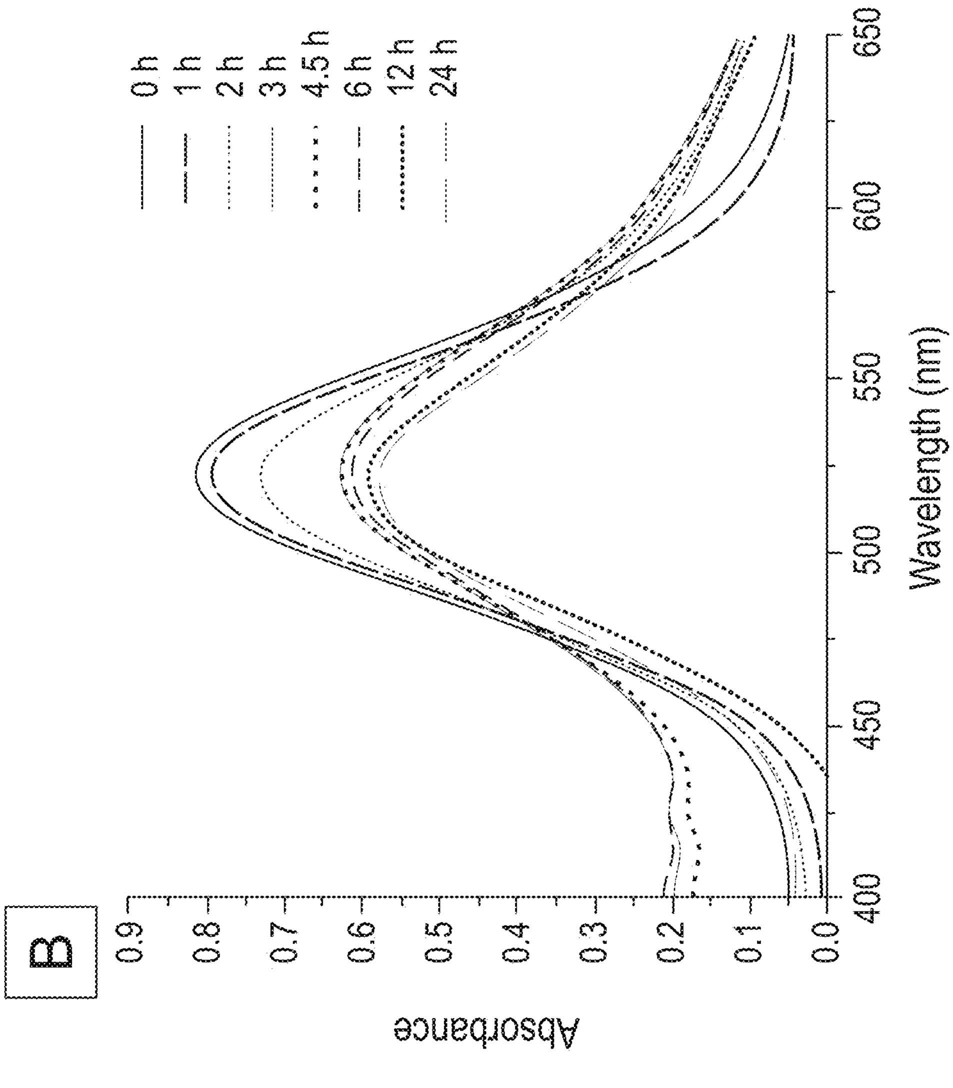
Figure 23C:
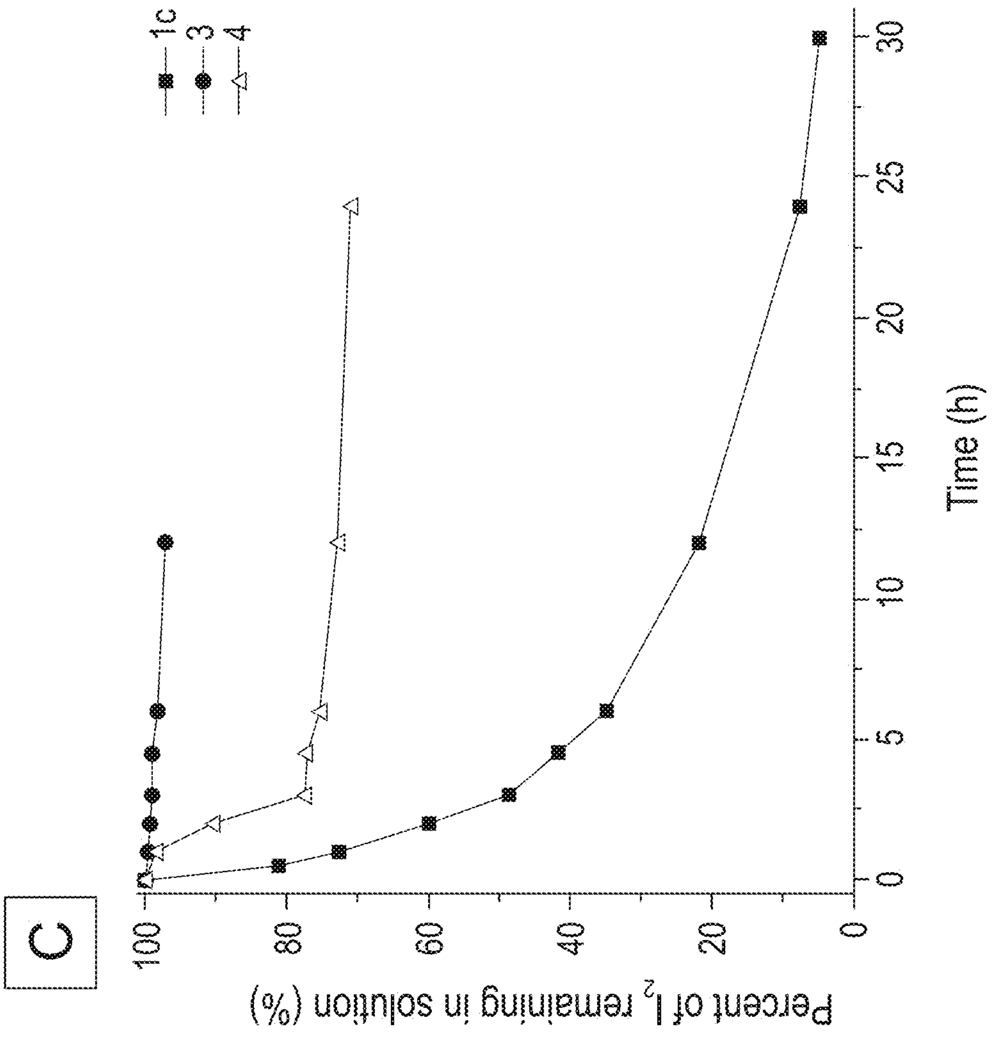
Figure 24A:
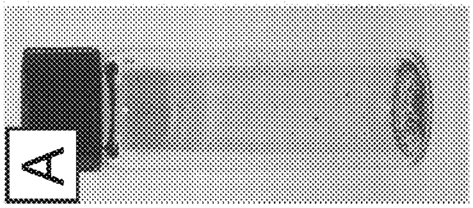
FIG. 24A-FIG. 24C depicts in accordance with various embodiments of the invention.
Figure 24B:
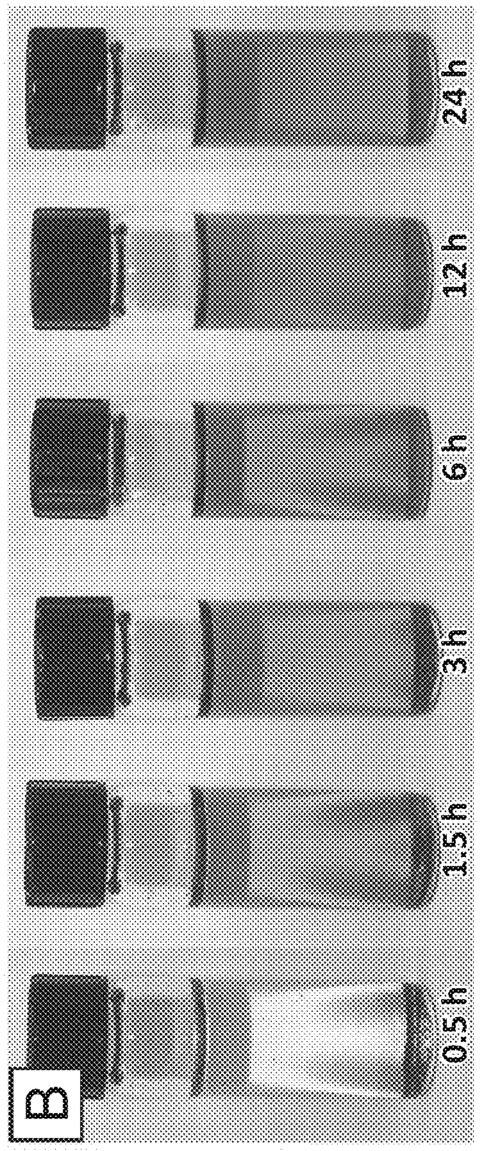
Figure 24C:
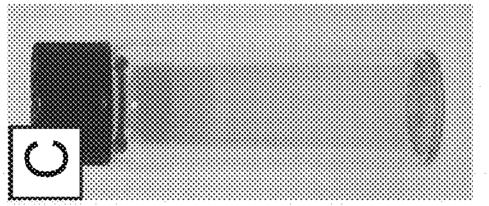
Figures 25A, 25B, 25C, 25D:
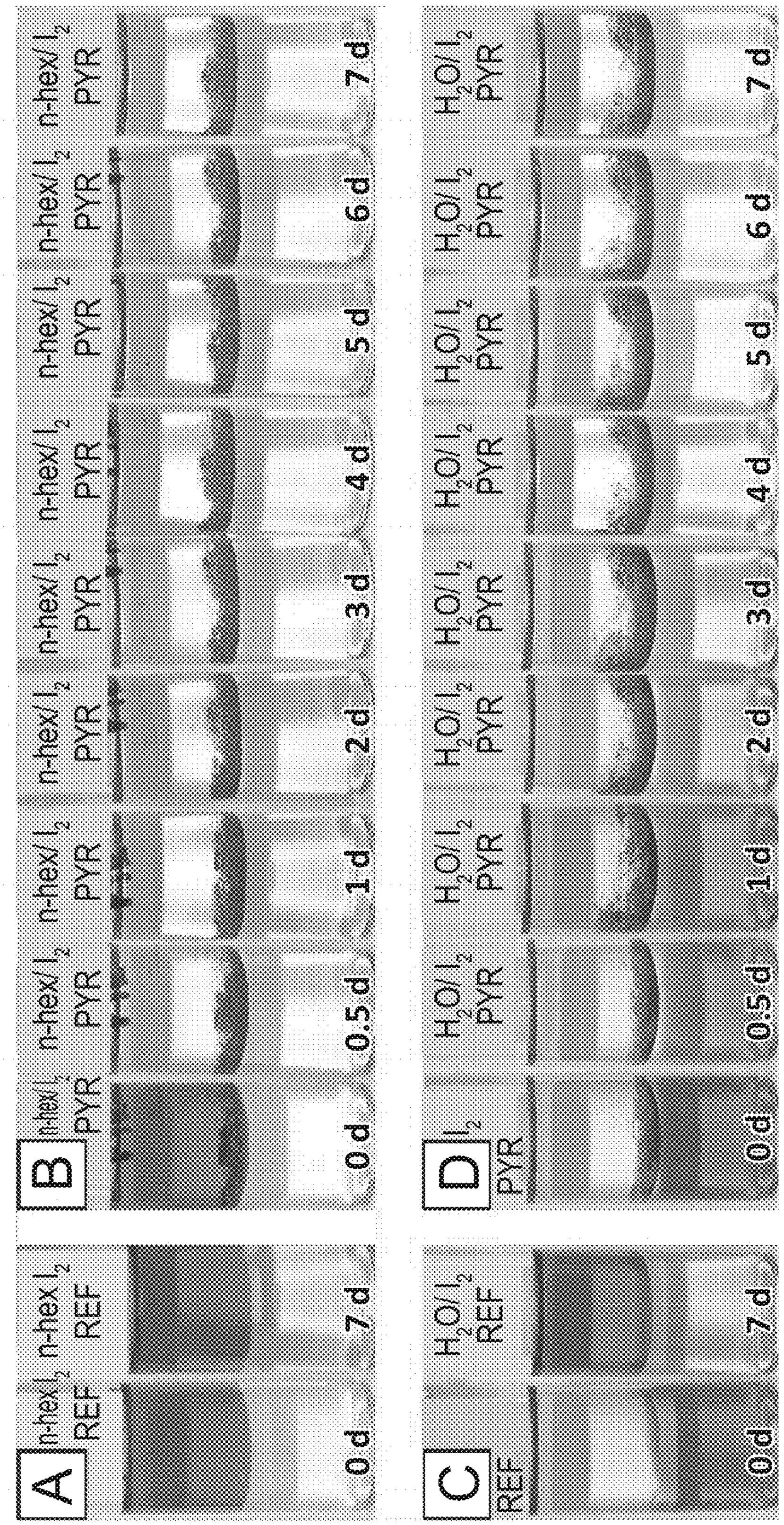
FIG. 25A-FIG. 25D depicts in accordance with various embodiments of the invention.

We extended the study to examine the ability of compound 1c to uptake $I_2$ from solutions in organic solvents and water. When compound 1c was introduced into a 1 mM solution of $I_2$ in hexane, a rapid decrease of ~70% of $I_2$ concentration was observed in the UV/Vis absorption spectrum, and was accompanied by the fading of the purple color of the solution (FIG. 23C and FIG. 22A). The adsorption rate gradually decreased until most of $I_2$ was removed after 30 h. Compound 3 and the monomeric model compound benzil-bis-2-pyridinylhydrazone (compound 4) did not have a significant effect on the concentration of 12, and hydrazone compound 4 begun dissolving in hexane after 2 h (FIG. 23C). In aqueous media, we investigated two different systems: Lugol's triiodide solution prepared using $I_2$ and KI, and a solution of $I_2$ which was allowed to oxidize in water for 3 d to produce hypoiodate. These two solutions are relevant to the photochemical speciation of radioiodine, which produces various iodine species that have been detected in nuclear waste and nuclear accidents. The addition of compound 1e into these two 1 mM aqueous iodine solutions led to approx. 60% and 70% respective decreases in $I_2$ concentration over 6 h (FIG. 21B and FIG. 21E, FIG. 21C and FIG. 21F). From these experiments, we concluded that the adsorption efficiency of compound 1c can be simultaneously attributed to its rigidity, virtual porosity, and hydrazine functionalization. The non-functionalized cyclotetrabenzil (compound 3) adsorbed little to no 12 in solution, while the monomeric compound 4 suffered from high solubility in organic solvents, making it unsuitable for adsorption in such media. Approx. 85% of the iodine adsorbed within compound 1c could be released by submerging 1@1c powder in 1,4-dioxane for 24 h (FIG. 24A-FIG. 24C).

Figure 5C:
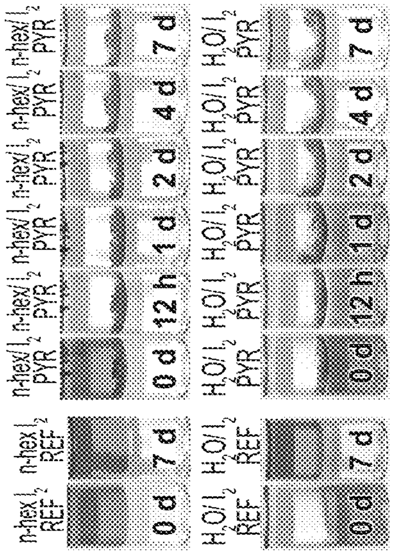
Figure 5A:
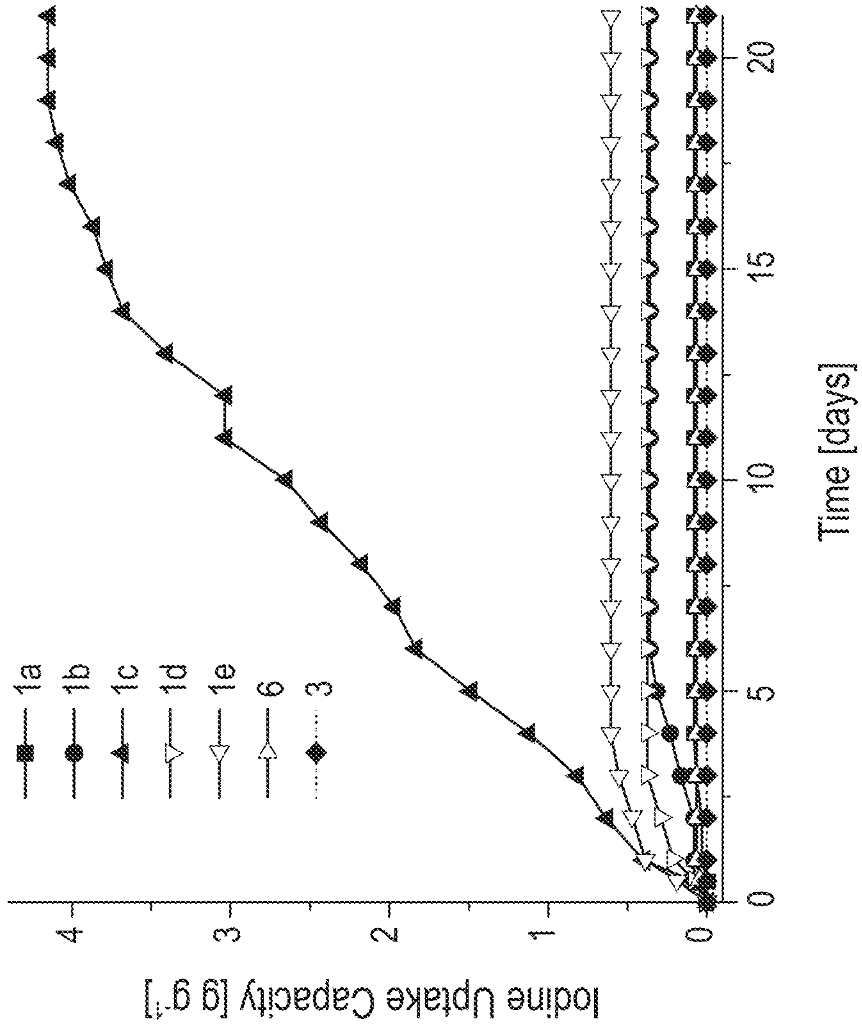
Figure 6:
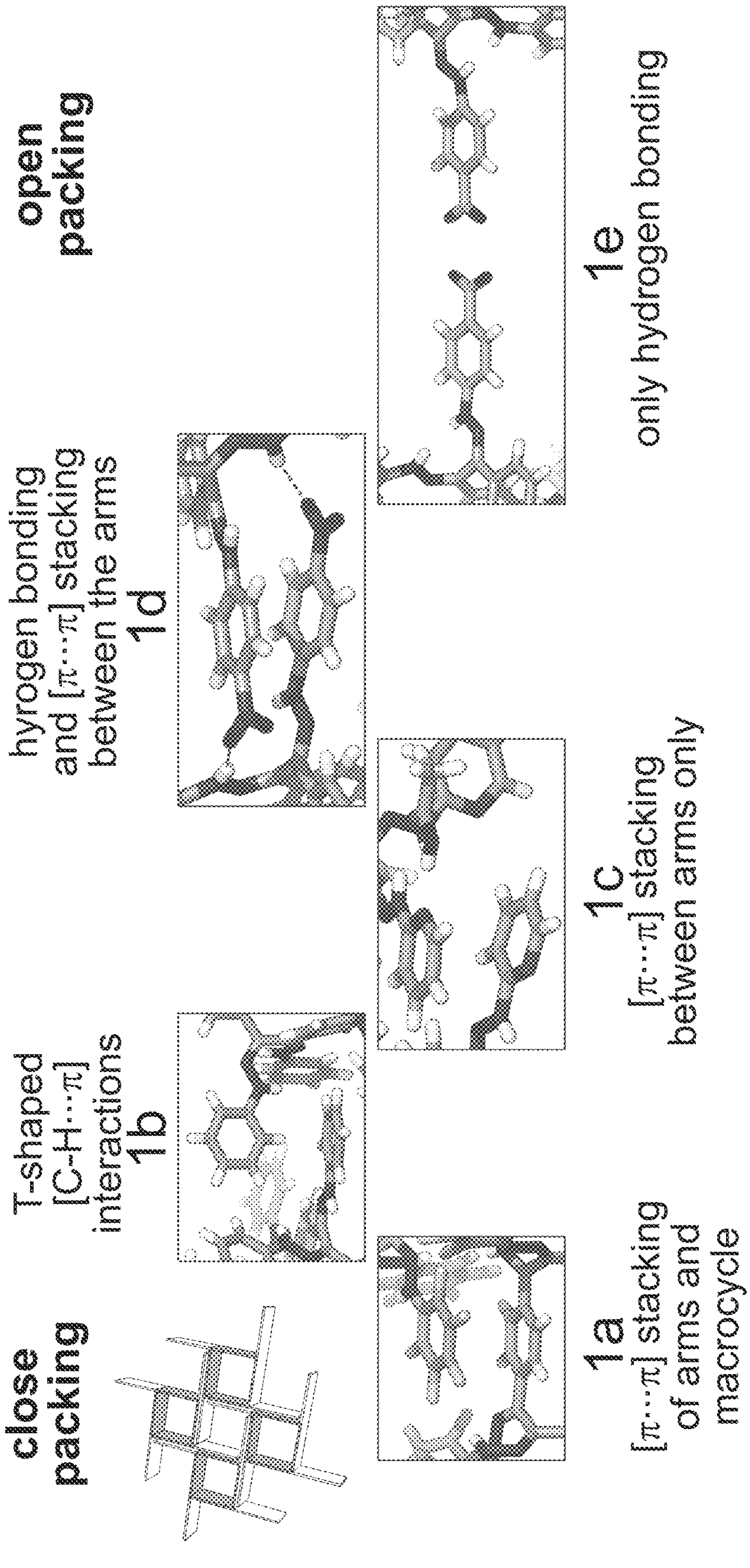
FIG. 6 depicts in accordance with various embodiments of the invention, highlights of key noncovalent interactions stabilizing the extended crystal structures of cyclotetra (bisarylhydrazone)benzil compounds 1a-1e.
Figures 26A, 26B, 26C:
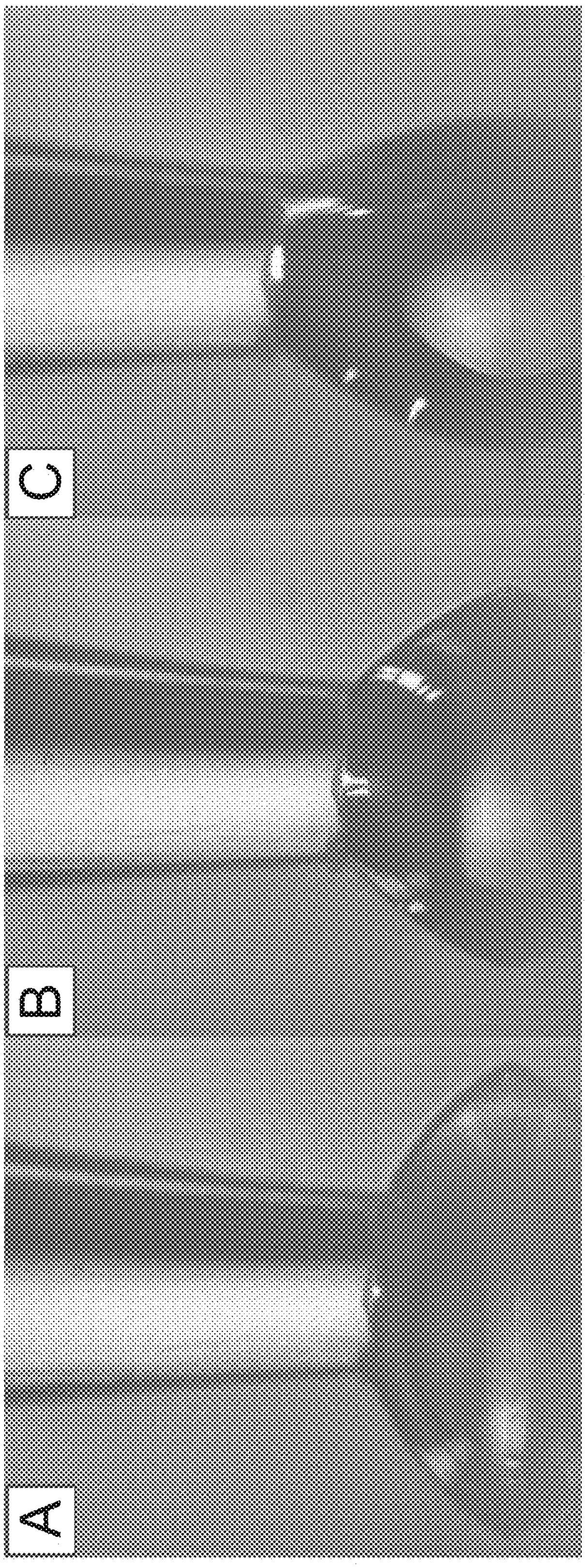
FIG. 26A-FIG. 26C depicts in accordance with various embodiments of the invention, Water droplets atop thin films of FIG. 26A: compound 3.
Figure 27:
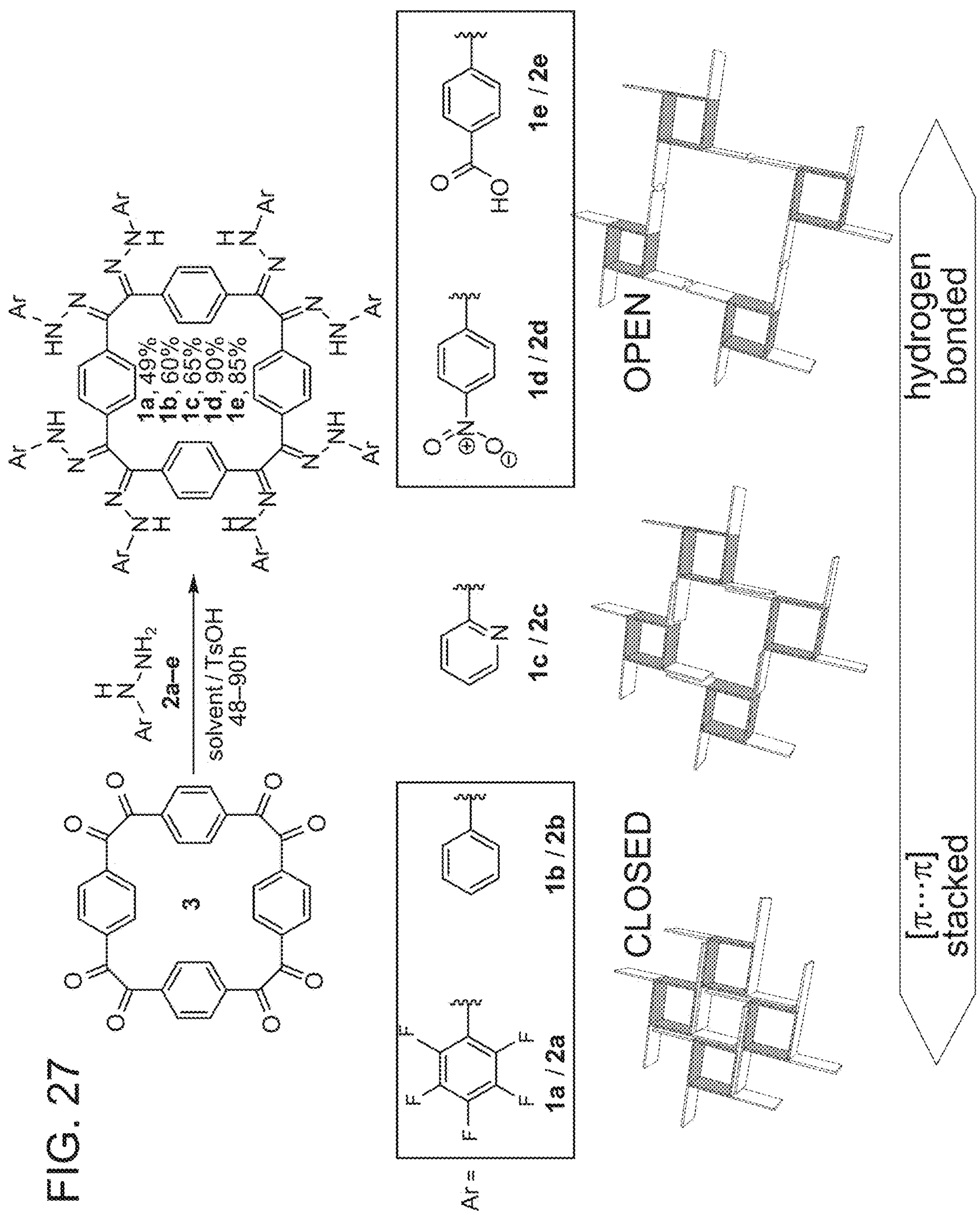
FIG. 27 depicts various embodiments of the invention.
Figure 28:
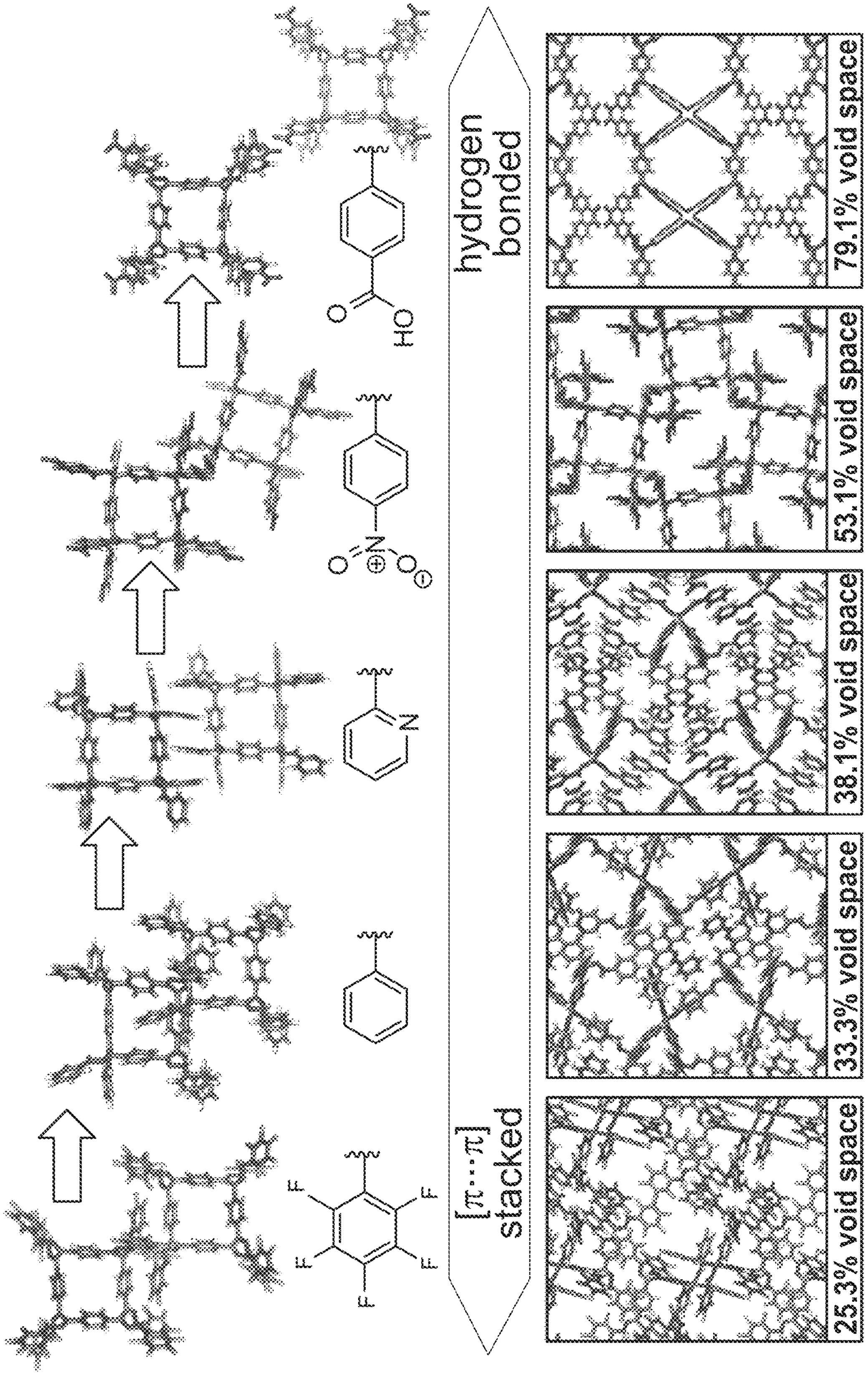
FIG. 28 depicts various embodiments of the invention.
Figure 29:
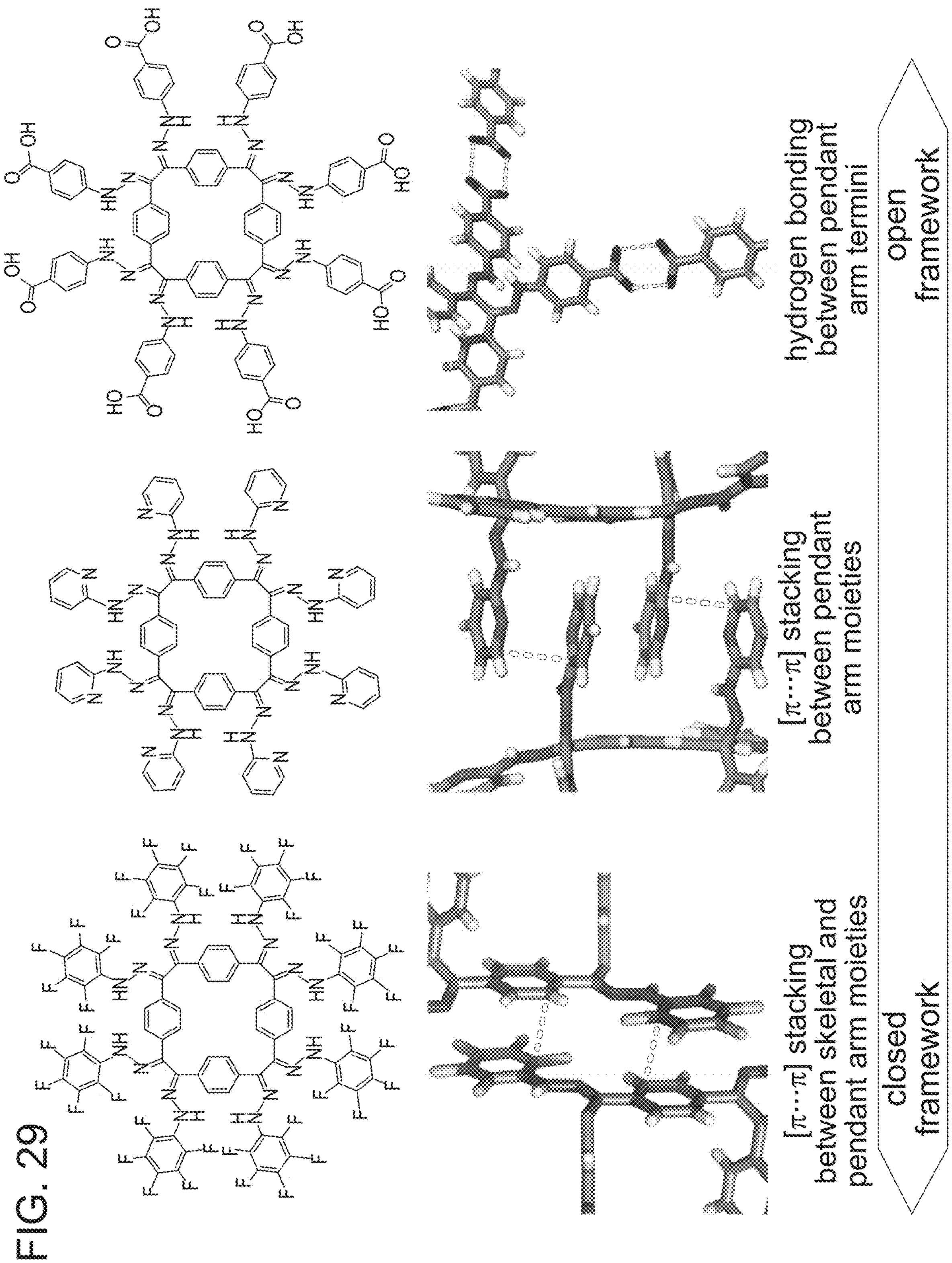
FIG. 29 depicts various embodiments of the invention.
Figure 30:
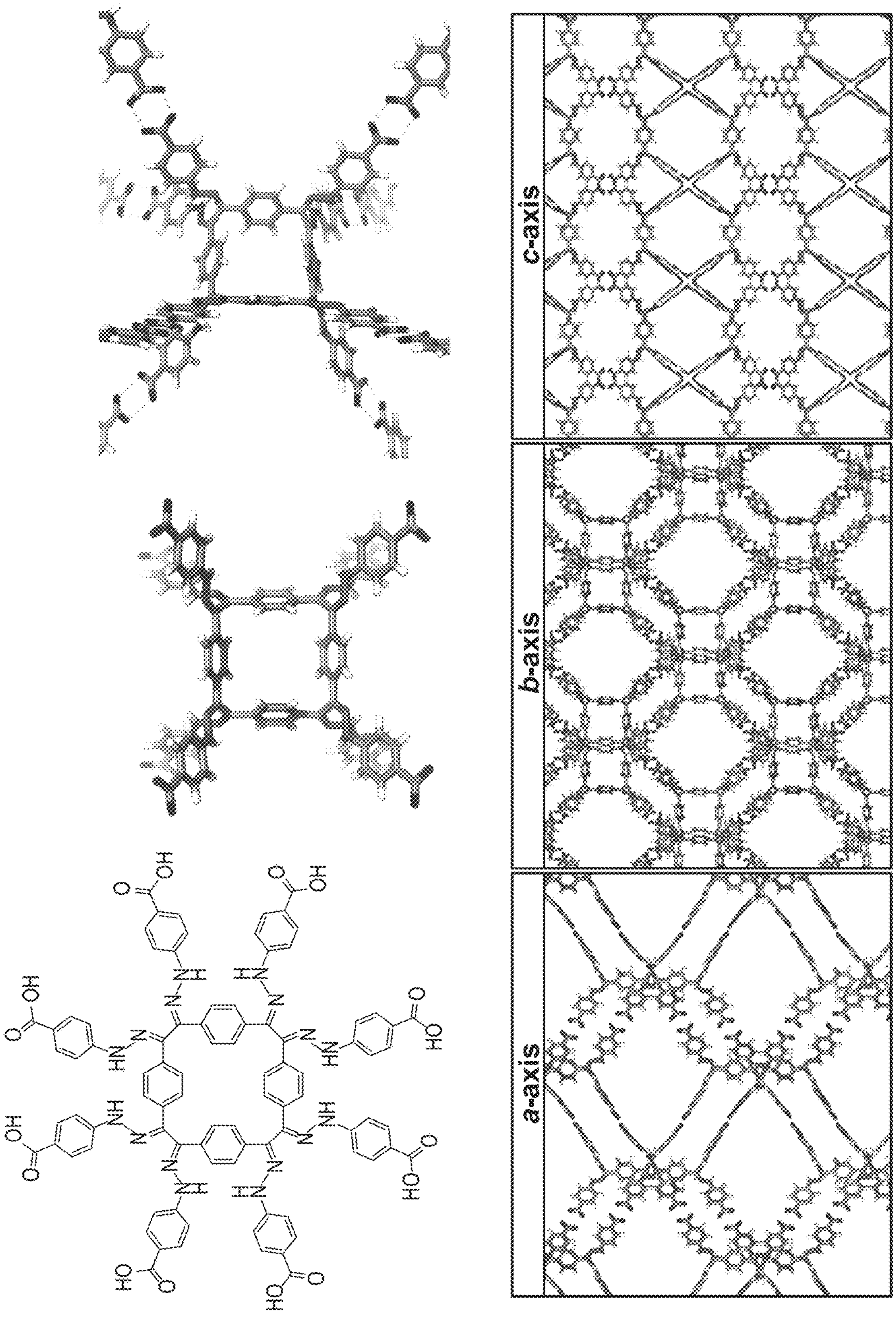
FIG. 30 depicts various embodiments of the invention, Extended structure of compound 1e. Each molecule interacts with 8 neighbors to form a hierarchically porous hydrogen-bonded organic framework.

Finally, we tested whether the $I_2$ adsorption could occur at an organic/aqueous interface as shown in FIG. 5C, bottom right (see also FIG. 25A-FIG. 25D). Compound 1c is hydrophobic—as evidenced by the water contact angle of 87° (FIG. 26C)—and apparently has lower density than water, which results in its deposition on the interface between the organic and aqueous layers. In that interlayer position, compound 1c can successfully adsorb 12 from either the hexane or the water layer. In addition, having compound 1e laid in between the two media creates a protective coating that prevents $I_2$ from diffusing between the organic and aqueous layers. This feature is particularly important for nuclear waste treatment: organic iodides in nuclear waste containment tanks are formed by the interaction of iodine-containing water droplets with the petroleum-based paints covering the inside of these containment tanks. Organic iodides are highly volatile and toxic, and preventing contact between iodine in aqueous media with organic substances could ameliorate the formation of these species. To our knowledge this is the first example of iodine adsorption tested between two immiscible liquid phases.

Discussion

Crystal Structures of Compounds 1a-1e

The crystal structures of compounds 1a-1e show distinct opening along the series, with a marked increase in the solvent-accessible void volume. These changes in the overall packing pattern are consequences of the changes in the dominant noncovalent interaction that stabilizes the extended structures along the series. In the most tightly packed structure of compound 1a, the key stabilizing interaction is the [π . . . π] stacking between the phenyl rings of the macrocycle and the pentafluorophenyl rings (FIG. 7) of four neighboring molecules, with centroid-to-centroid distances between 3.55 and 3.57 Å. These neighbors arrange themselves synclinally around the scaffold with two opposite pairs rotated clockwise with [N—C—C—N] dihedral angles of 58.3 and 60.0° and the other two opposite pairs rotated counterclockwise with dihedral angles of −71.3 and −76.7°. Out of the eight pentafluorophenyl arms on each molecule of compound 1a, only four engage in aromatic stacking with the macrocyclic core. The other four instead establish [C—F . . . F], [F—C . . . C], and [C—H . . . N] short contacts ranging in length from 2.29 to 3.45 Å.

Similar close packing behavior was observed in compound 1b. Four molecules surround each central structure in a synclinal stereochemical arrangement with two opposite pairs rotated clockwise with the [N═C—C═N] dihedral angles measuring 72.1 and 77.1° and the two other opposite pairs rotated counterclockwise with dihedral angles of −78.6 and −89.8°. Notable are T-shaped [C—H . . . π] interactions (FIG. 7) between the pendant phenyl rings and between the phenyl rings of the macrocycle with pendant arms, with [C—H . . . π] distances measuring between 2.56 Å and 2.68 Å, consistent with the previously reported values. Phenyl rings of the hydrazone arms also approach each other in a rather unconvincing [π . . . π] stacking arrangement, characterized by the shortest [C . . . C] contact of 3.21 Å, centroid-centroid distance of 4.66 Å, and an interplanar angle of 14.4°.

Figure 7:
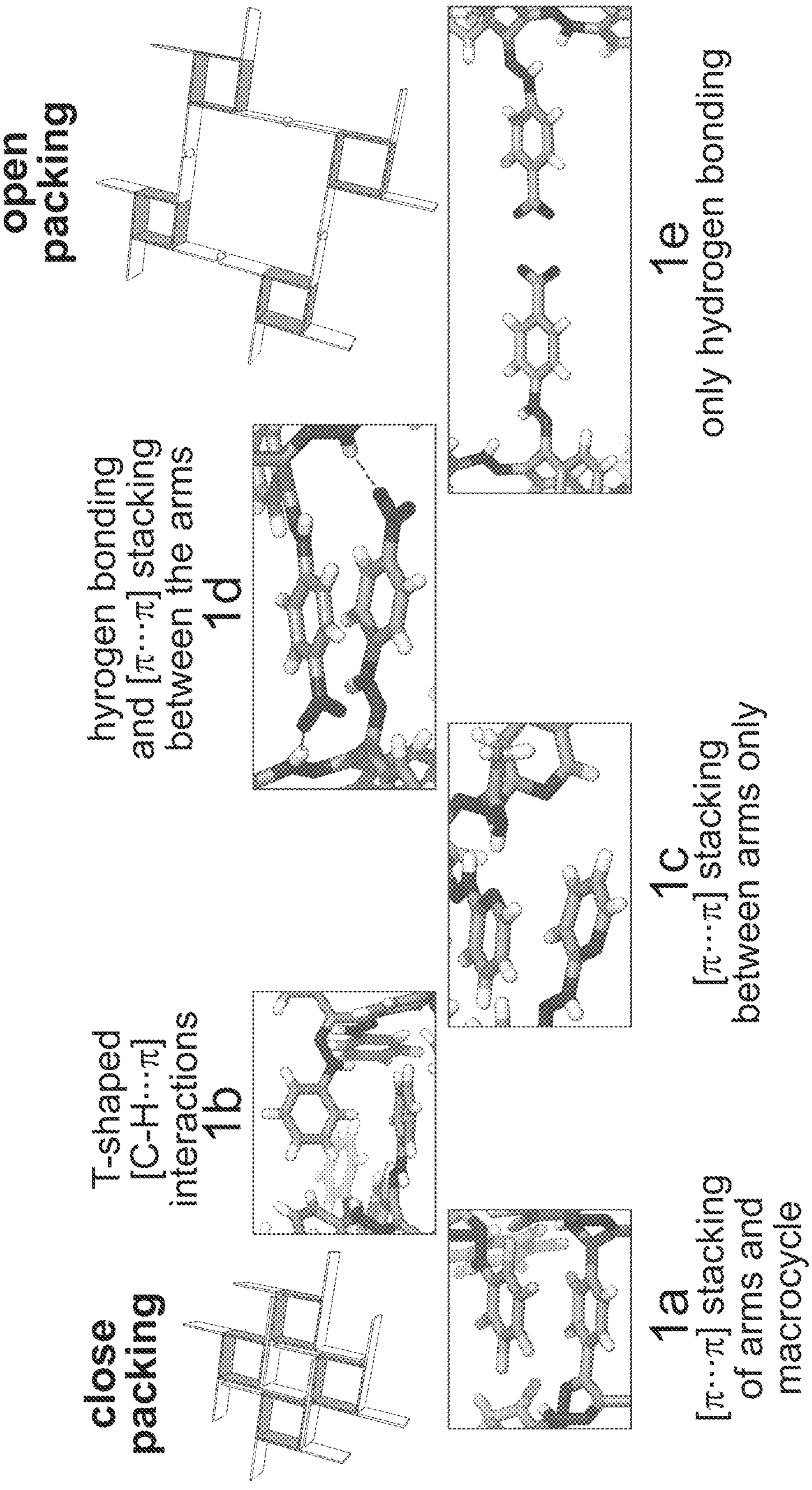
FIG. 7 depicts in accordance with various embodiments of the invention, Highlights of key noncovalent interactions stabilizing the extended crystal structures of cyclotetra (bisarylhydrazone)benzil compounds 1a-1e.

In the extended structure of compound 1c·2AcOH, each molecule is surrounded by four neighbors arranged in an anticlinal fashion with two opposite pairs rotated in a clockwise direction having identical [N═C—C═N] dihedral angles of 90.9° and the other two opposite pairs rotated counterclockwise, with dihedral angles of −110.2 and −107.7°. Once again, the extended crystal structure is dominantly stabilized by [π . . . π] interactions, but now exclusively between the pendant arms bearing pyridyl rings—the aromatic rings of the central core are no longer involved (FIG. 7). The centroid-to-centroid distances in the antiparallel pyridyl [π . . . π] stacks alternate between 3.57 and 3.78 Å, in line with the literature. Several additional short contacts, ranging in length from 2.30 to 3.39 Å, are observed in the extended structure.

Figure 4:
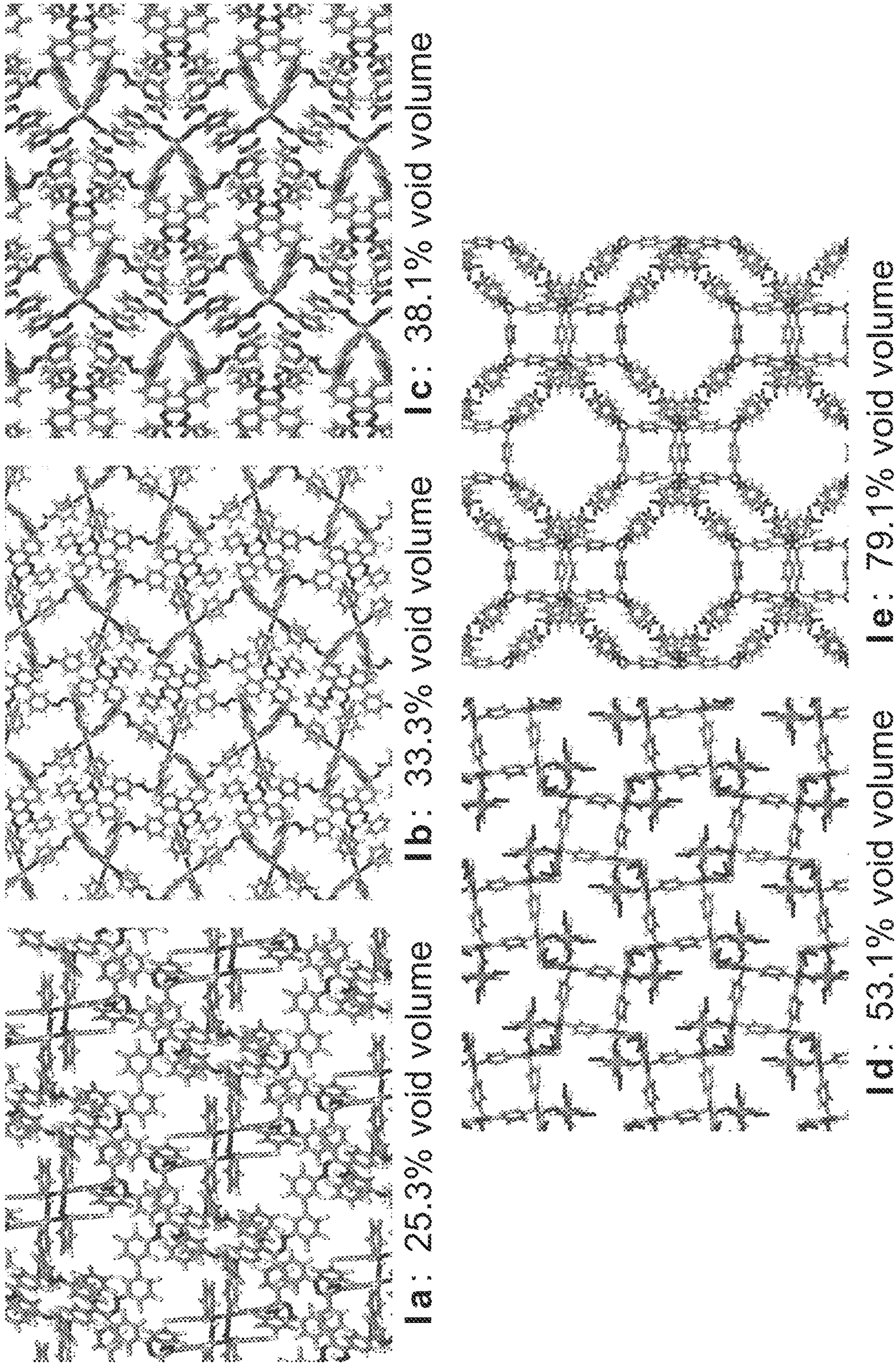
FIG. 4 depicts in accordance with various embodiments of the invention, segments of extended packing diagrams of cyclotetra(bisarylhydrazone)benzil compounds 1a-1e, along with their crystallographically determined void volumes.

In the nitro-functionalized compound 1d, the extended crystal structure is held together by a combination of [π . . . π] stacking and hydrogen bonding. The 4-nitrophenyl moieties from two neighboring molecules of compound 1d engage into slipped [π . . . π] interactions with centroid-to-centroid distances of 3.68 Å (FIG. 7). This interaction brings the—$NO_2$ groups close enough to the hydrazone's NH moieties to allow the establishment of two [N—H . . . O—N] hydrogen bonds characterized by [O . . . . H] distances of 2.16 and 2.17 Å. An additional short contact measuring 2.54 Å is observed between the nitro group and a hydrogen on the central macrocyclic core. The packed structure contains one intrinsic pore created by the cyclotetrabenzil central cavity as well as two extrinsic pores, one of which is shown in FIG. 4. The neighboring molecules are arranged in a synclinal fashion with two opposite pairs rotated clockwise with [N═C—C═N] dihedral angles of 178.18 and 171.07° while the other two opposite pairs are rotated counterclockwise and have identical dihedral angles of −178.18°.

The structure of compound 1e forms a three-dimensional hydrogen-bonded network, within which every 4-carboxyphenylhydrazone moiety interacts with one arm of a neighboring molecule through a head-on carboxylic acid dimer interaction as shown on a fragment in FIG. 7, far right. All heavy atom [O . . . O] contacts within hydrogen bonded dimers measure between 2.58 and 2.66 Å. This association pattern leads to a highly porous structure with several visible pores along all three crystallographic axes, two of which can be seen in FIG. 4. Oligocarboxylic acids such as compound 1e have been used to construct metal-organic frameworks (MOFs) with interesting topologies and excellent performance in gas separation and ion sensing. Compound 1e stands apart from other octacarboxylic acid MOF precursors as the only truly octapodal in nature. The largest virtual pore in the extended structure of compound 1e has a diameter of 30 Å-almost as large as the record for the largest void in a hydrogen-bonded organic framework based on an oligocarboxylic acid, measuring 31.2 Å. Its theoretical surface area rivals some of the highest measured for PMCs.

Iodine Capture Performance of Compounds 1a-1e

Figure 19:
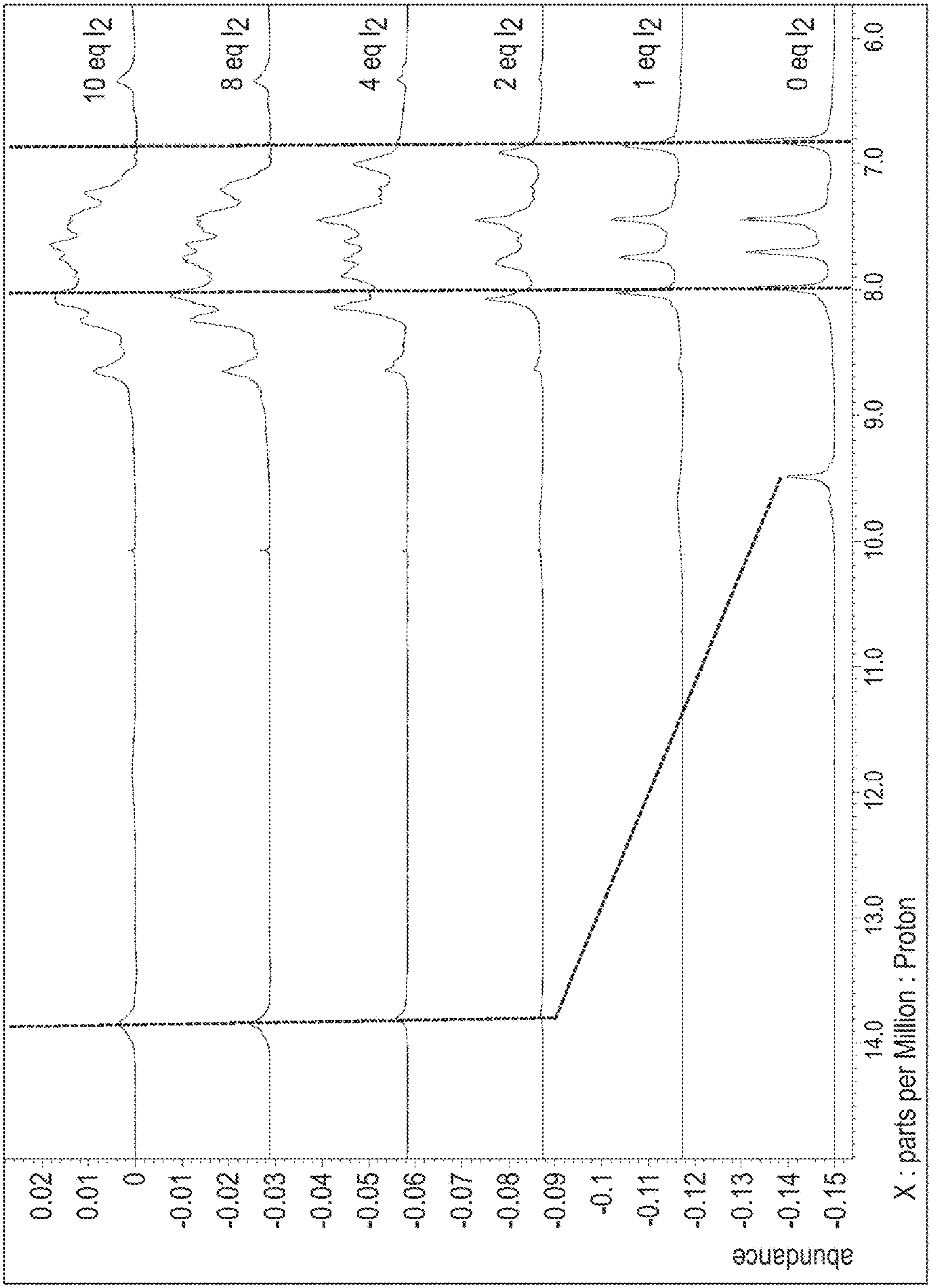
FIG. 19 depicts in accordance with various embodiments of the invention, 1H NMR stepwise spectroscopic titration of 0.6 mL cyclotetra(bisarylhydrazone)benzil compound 1c (1 μM) with $I_2$ (0-10 eq) in DMSO-de. Dashed lines show the changes in shifts of the hydrazone bridge and pyridine aromatic protons as iodine concentration increases.
Figure 20:
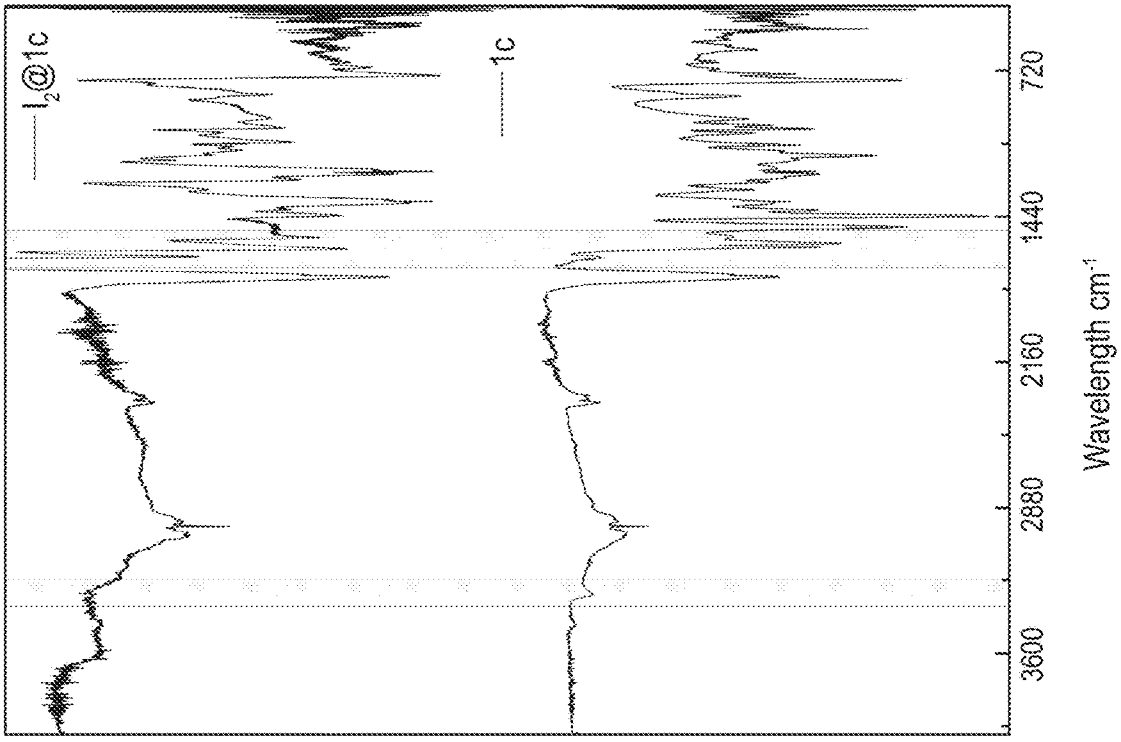
FIG. 20 depicts in accordance with various embodiments of the invention, FT-IR spectra of 12@1c (top) and cyclotetra(bisarylhydrazone)benzil compound 1c following iodine desorption (bottom).
Figure 21A:
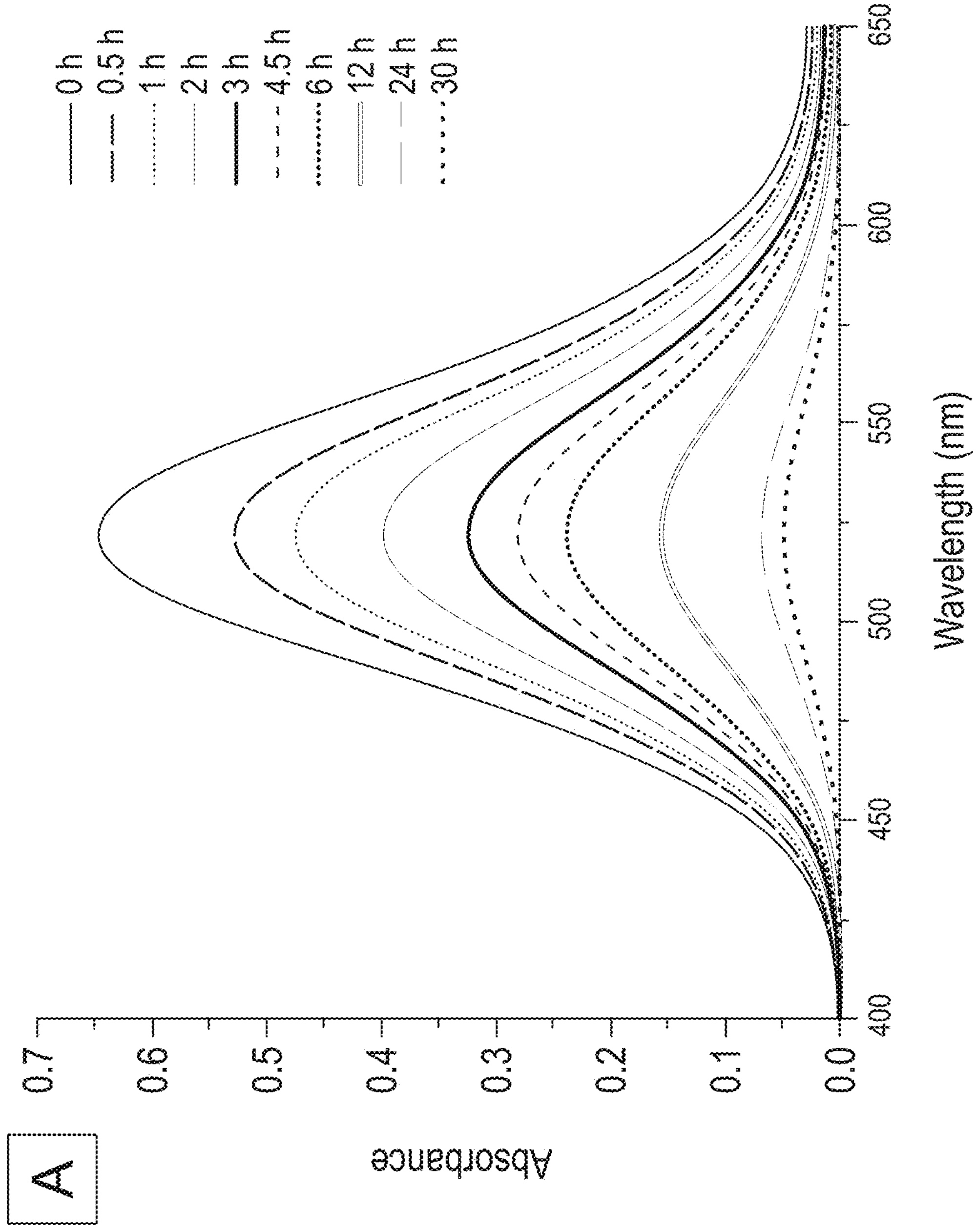
FIG. 21A-FIG. 21F depicts in accordance with various embodiments of the invention, Time dependent UV/Vis adsorption spectra of 1 mM iodine solutions in FIG. 21A: hexane.
Figure 21B:
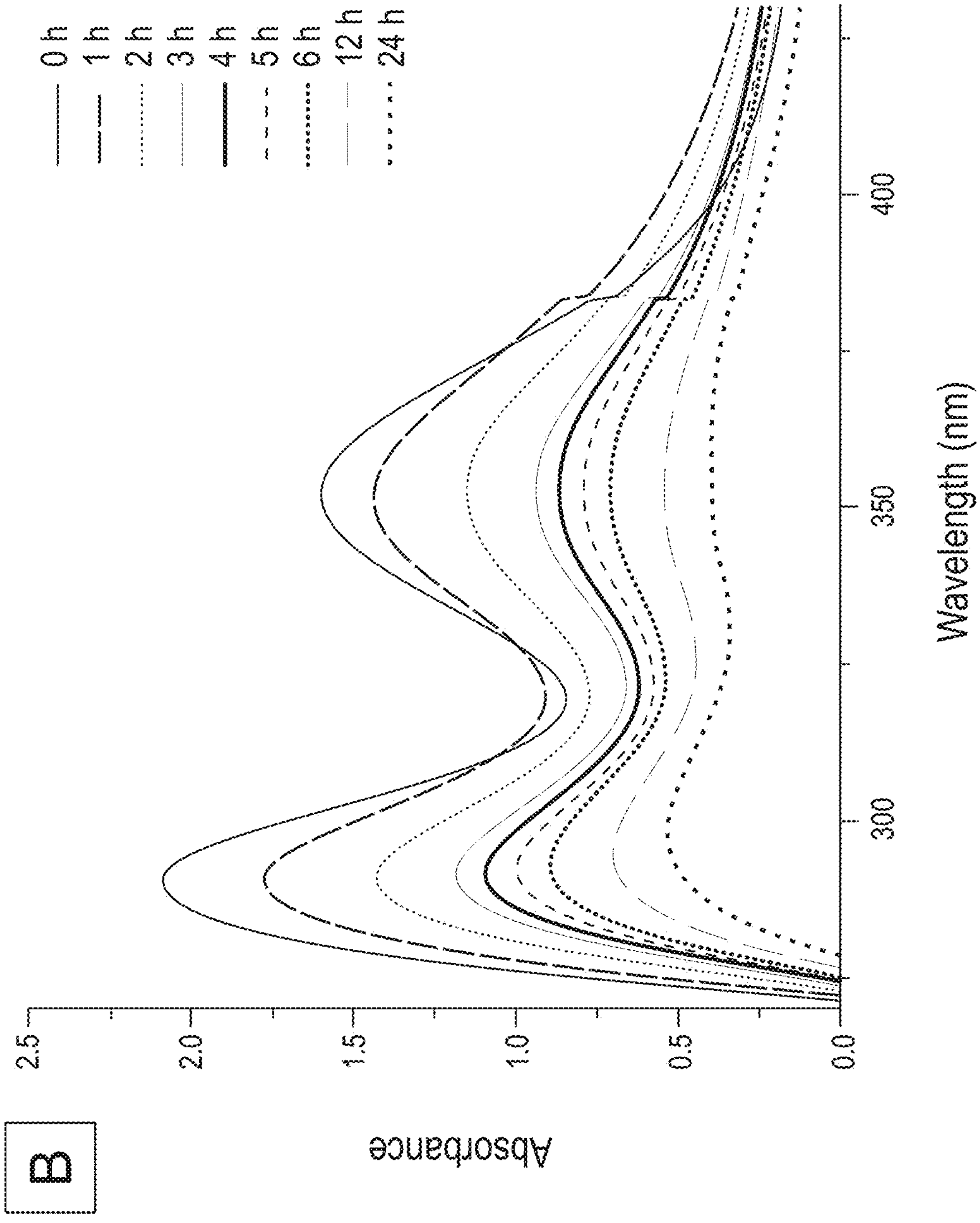
Figure 21C:
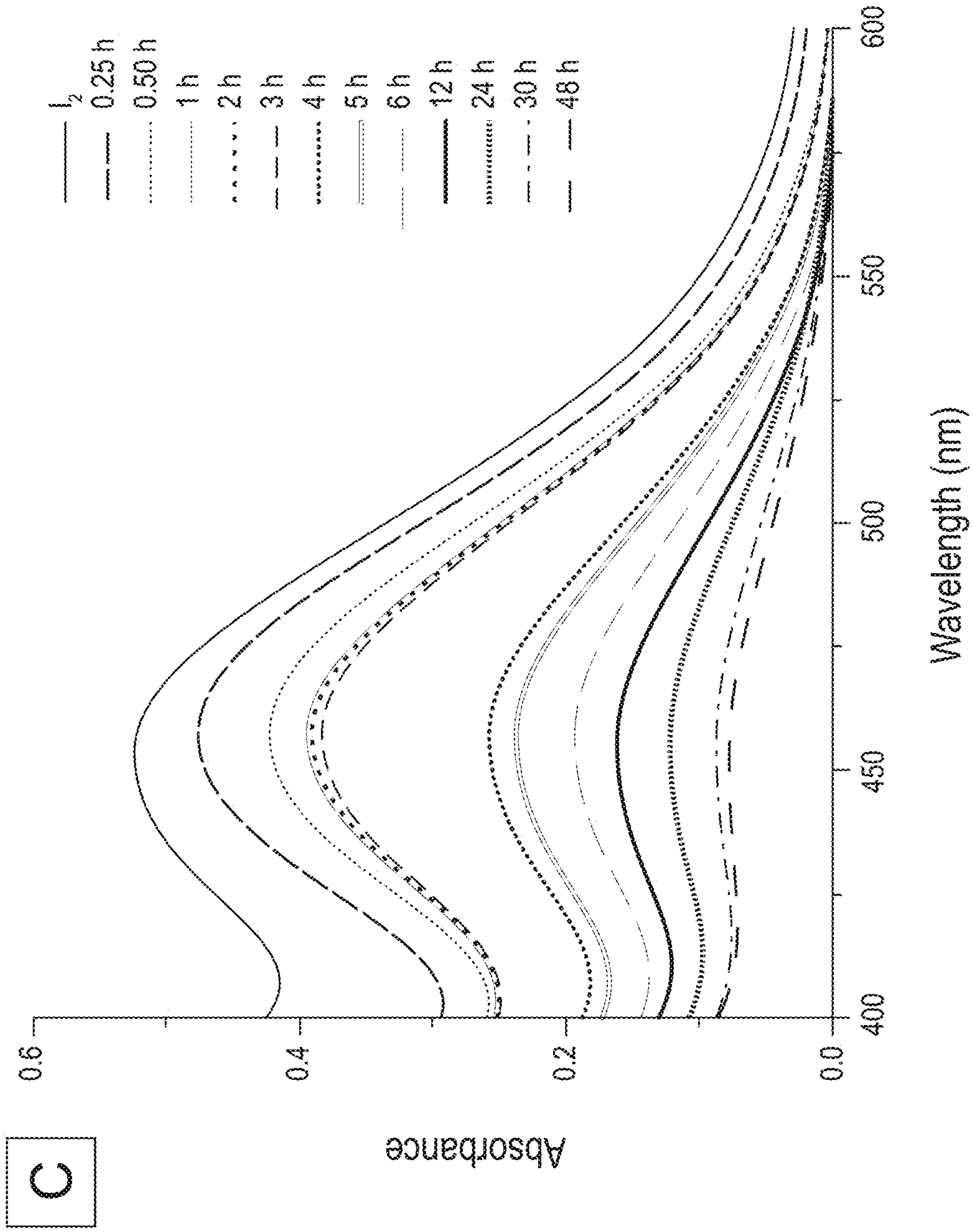
Figure 21D:
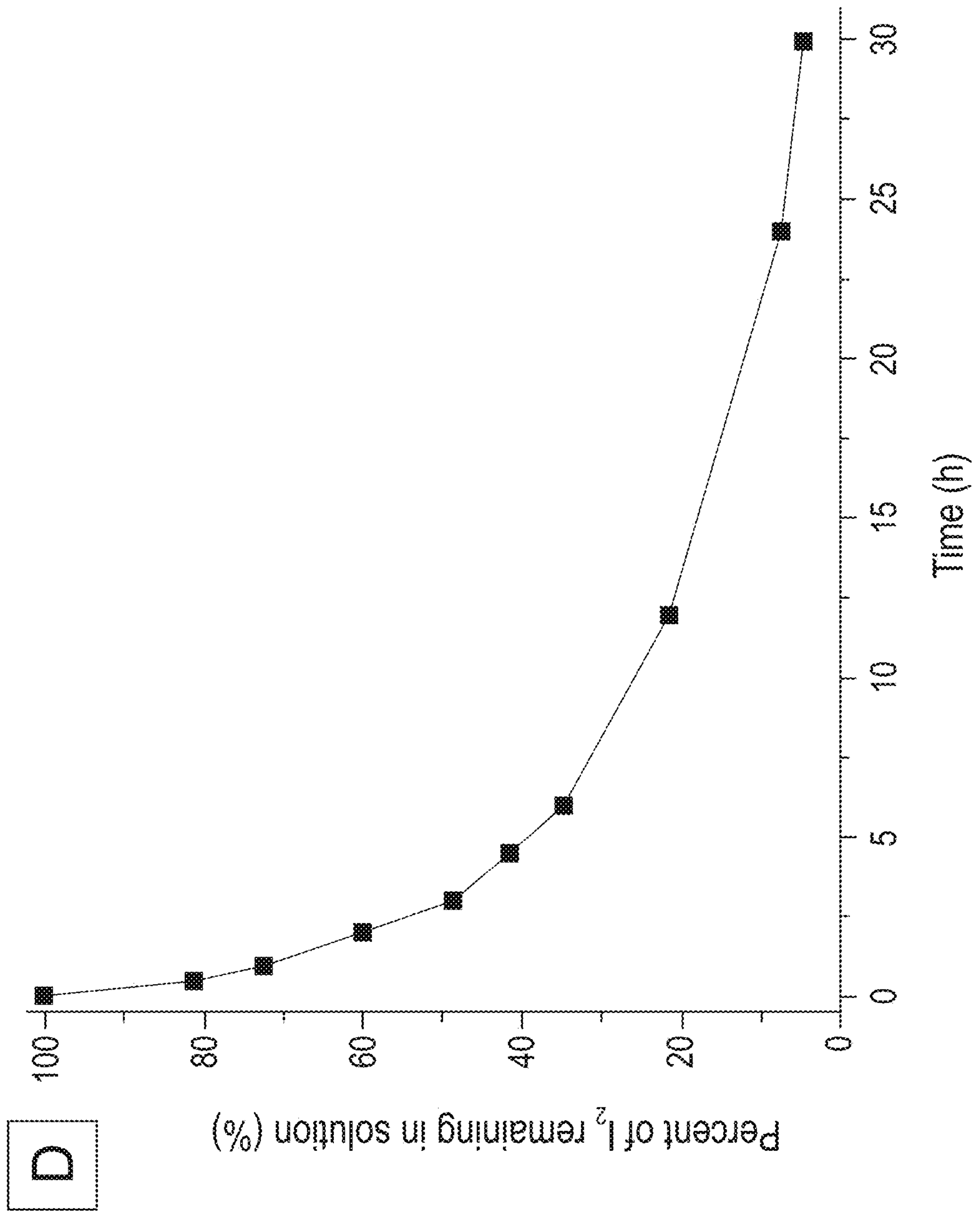
Figure 21E:
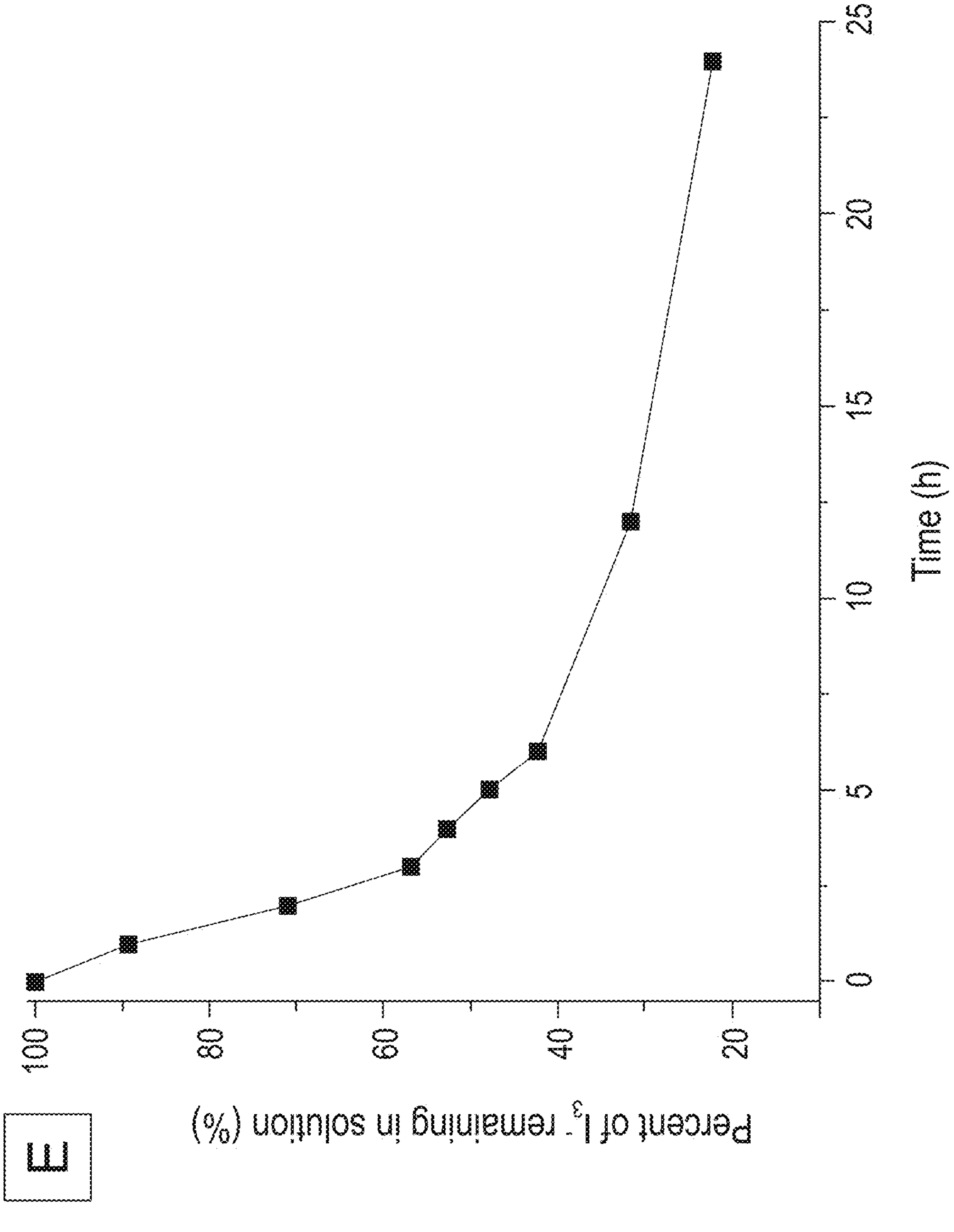
Figure 21F:
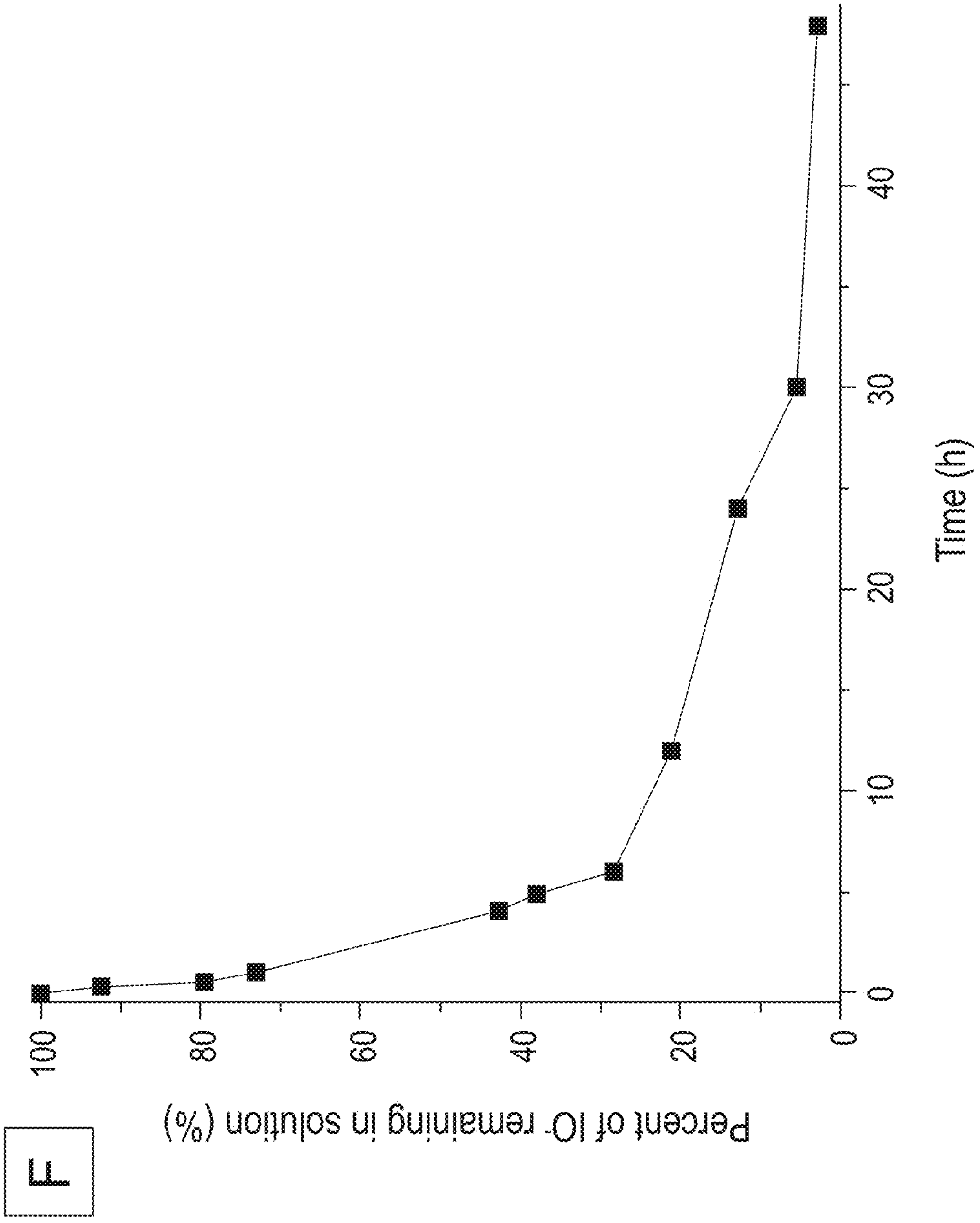

The $I_2$ uptake in compound 1c is 64-fold higher than the capacity exhibited by compound 6, surpasses that of the adaptive bypiridine cage reported by Sessler that previously held the record for $I_2$ uptake in a seemingly non-porous compound, (Table 9) and is comparable to uptakes by polymeric materials. The exposed electron-rich nitrogen-containing groups of the arm moieties play a critical role strengthening the interactions between the host macrocycle compound 1c and $I_2$. $^1$H NMR titration experiments (FIG. 19) support the interactions of the electron-rich pyridine and amine subunit of the hydrazone bridge with $I_2$—as the $I_2$ loading was increased, there was a downfield shift of the aromatic protons corresponding to the pyridine heterocycle and the—NH proton. Furthermore, the FT-IR spectra of compound 1c and 12@1c are consistent with this conclusion as the characteristic peaks of ~1640 cm-1 and ~3312 cm-1 assigned to the C═N and N—H stretches, respectively, decrease in intensity following exposure to 12, but recover after desorption of the guest (FIG. 20).

Conclusions

Starting from the common cyclotetrabenzil precursor, five octahydrazones were prepared and thoroughly studied by crystallography and spectroscopy. The most closely packed structure of compound 1a followed the Kitaigorodskii's principle by dovetailing its electron-poor fluorinated pendant chains with the electron-rich central macrocycle. As the electronic nature of the pendant groups changed to more electron-rich in compound 1b and compound 1c, this interaction became less favorable and the structures started opening. Finally, the introduction of weakly (in compound 1d) and strongly (in compound 1e) hydrogen-bonding groups further weakened the [π . . . π] stacking interactions and eventually led to a completely opened hydrogen-bonded structure of compound 1e. This fine-tuning of crystal packing was easily accomplished: hydrazones are prepared in a single high-yielding step and are famed for their crystallinity.

All five cyclotetra(bisarylhydrazone)benzil compounds 1a-1e exhibit virtual porosity: once exposed to air, they quickly lose their disordered solvents. However, when exposed to iodine guest, this virtual porosity has real consequences: their iodine capture capacities generally scaled with the crystallographically observed void volumes. An exception to this trend was compound 1c, whose nitrogen-based functional groups unexpectedly showed much higher $I_2$ capture affinity that those in other systems. Here too, virtual porosity was effectively turned-on by the presence of the nitrogen-based groups which allowed dramatic increase in the iodine capture capacities. The resulting uptake was the highest among the reported molecular materials with the added benefit of solution processability of compound 1c.

Various Embodiments of the Invention

Embodiments include those listed below.

Embodiment 1. A compound of Formula (I).

Formula (I)

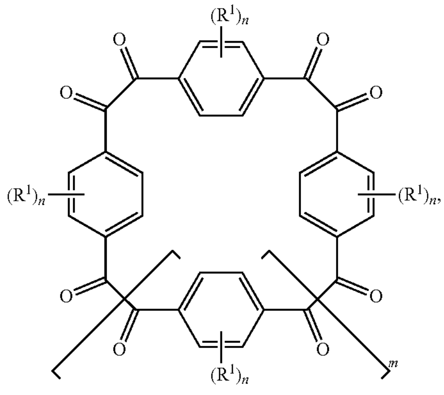

wherein:

m is 0, 1, 2, 3, or 4;

n is 0, 1, 2, 3 or 4; and $R^1$ is an electron withdrawing group, or an electron donating group.

Embodiment 2. A compound of Formula (11):

Formula (II)

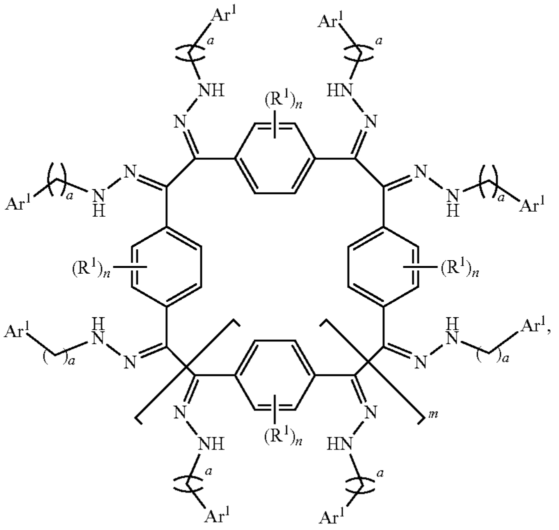

m is 0, 1, 2, 3, or 4, n is 0, 1, 2, 3 or 4;

a is 0, 1 or 2;

$Ar^1$ is optionally substituted aryl, or optionally substituted heteroaryl; and $R^1$ is an electron withdrawing group, or an electron donating group.

Embodiment 3. A method for preparing a compound of embodiment 2, comprising:

reacting a compound of Formula (I) with a compound of Formula (VII) to obtain a compound of Formula (II), wherein the compound of Formula (I) is:

Formula (I)

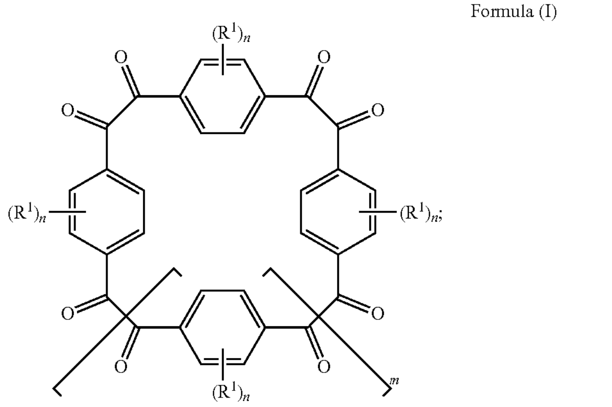

wherein:

m is 0, 1, 2, 3, or 4;

n is 0, 1, 2, 3 or 4; and $R^1$ is an electron withdrawing group, or an electron donating group; and the compound of Formula (VII) is:

Formula (VII)

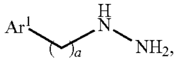

wherein, $Ar^1$ is optionally substituted aryl, or optionally substituted heteroaryl; and a is 0, 1 or 2.

Embodiment 4. A method for removing an amount of a material from a medium, the method comprising: contacting a compound of embodiment 2 with a medium, wherein the medium comprises a material; and removing an amount of the material from the medium.

Embodiment 5. The method of embodiment 4, wherein the material is molecular iodine ($I_2$).

Embodiment 6. The method of embodiment 4, wherein the medium is aqueous medium, organic medium, or combination thereof.

Embodiment 7. A compound of embodiment 1, wherein the compound is a compound of Formula (I-a):

Formula (I-a)

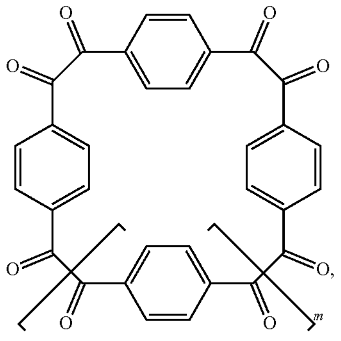

wherein:

m is 0, 1, 2, 3, or 4.

Embodiment 8. A compound of embodiment 2, wherein the compound is a compound of Formula (II-a):

Formula (II-a)

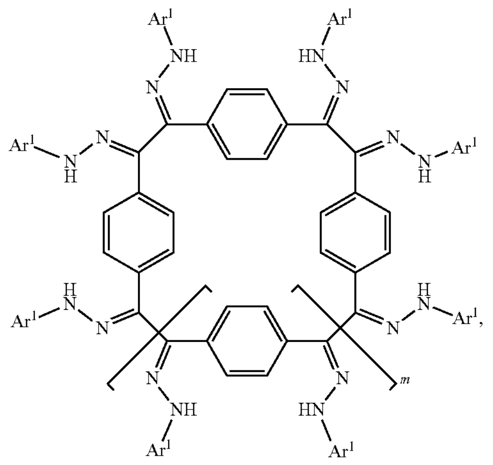

wherein:

m is 0, 1, 2, 3, or 4; and $Ar^1$ is optionally substituted aryl, or optionally substituted heteroaryl.

Embodiment 9. A method for preparing a compound of embodiment 8, comprising:

reacting a compound of Formula (I-a) with a compound of Formula (VII-a) to obtain a compound of Formula (II-a), wherein the compound of Formula (I-a) is:

Formula (I-a)

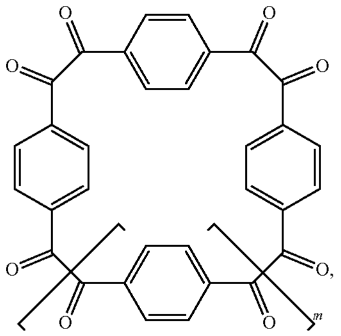

wherein m is 0, 1, 2, 3, or 4; and wherein the compound of Formula (VII-a) is:

Formula (VII-a)

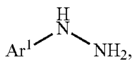

wherein, $Ar^1$ is optionally substituted aryl, or optionally substituted heteroaryl.

Embodiment 10. A method for removing an amount of a material from a medium, the method comprising: contacting a compound of embodiment 8 with a medium, wherein the medium comprises a material; and removing an amount of the material from the medium.

Embodiment 11. The method of embodiment 10, wherein the material is molecular iodine ($I_2$).

Embodiment 12. The method of embodiment 10, wherein the medium is aqueous medium, organic medium, or combination thereof.

Embodiment 13. A compound of embodiment 1, wherein the compound is a compound of Formula (I-b):

Formula (I-b)

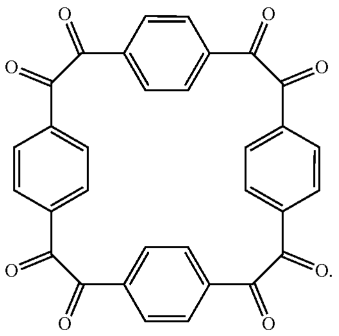

Embodiment 14. A compound of embodiment 2, wherein the compound is a compound of Formula (II-b):

Formula (II-b)

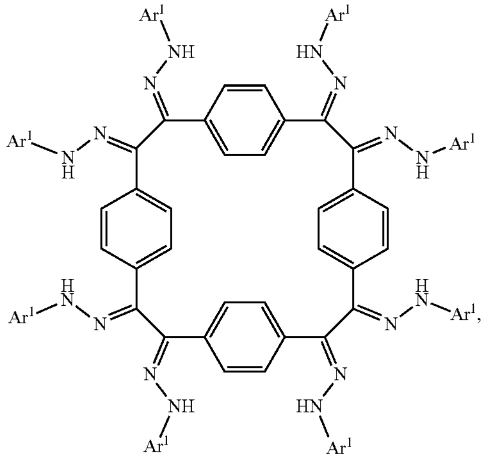

wherein:

$Ar^1$ is optionally substituted aryl, or optionally substituted heteroaryl.

Embodiment 15. A method for preparing a compound of embodiment 14, comprising:

reacting a compound of Formula (I-b) with a compound of Formula (VII-a) to obtain a compound of Formula (II-b), wherein the compound of Formula (I-b) is:

Formula (I-b)

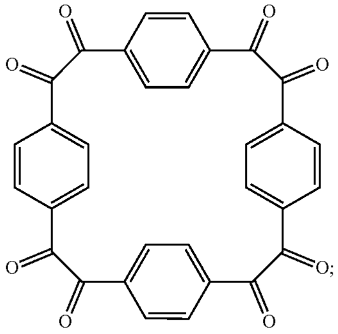

and the compound of Formula (VII-a) is:

Formula (VII-a)

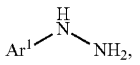

wherein, $Ar^1$ is optionally substituted aryl, or optionally substituted heteroaryl.

Embodiment 16. A method for removing an amount of a material from a medium, the method comprising: contacting a compound of embodiment 14 with a medium, wherein the medium comprises a material; and removing an amount of the material from the medium.

Embodiment 17. The method of embodiment 16, wherein the material is molecular iodine ($I_2$).

Embodiment 18. The method of embodiment 17, wherein the medium is aqueous medium, organic medium, or combination thereof.

Embodiment 19. A compound of Formula (III):

Formula (III)

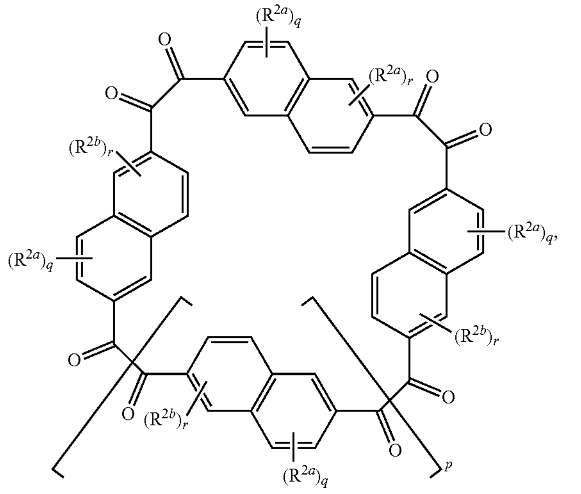

wherein:

p is 0, 1, 2, 3, or 4;

q is 0, 1, 2, or 3, r is 0, 1, 2, or 3, $R^{2a}$ is an electron withdrawing group, or an electron donating group; and $R^{2b}$ is an electron withdrawing group, or an electron donating group.

Embodiment 20. A compound of Formula (IV):

Formula (IV)

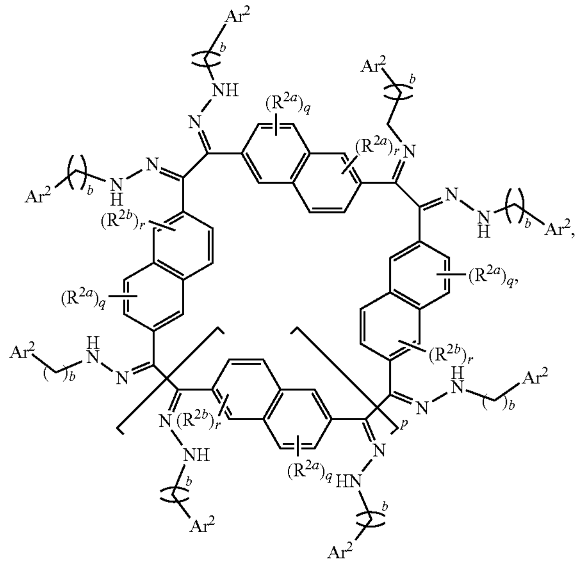

wherein:

p is 0, 1, 2, 3, or 4;

q is 0, 1, 2, or 3, r is 0, 1, 2, or 3, b is 0, 1, or 2;

$Ar^2$ is optionally substituted aryl, or optionally substituted heteroaryl;

$R^{2a}$ is an electron withdrawing group, or an electron donating group; and $R^{2b}$ is an electron withdrawing group, or an electron donating group.

Embodiment 21. A method for preparing a compound of embodiment 20, comprising: reacting a compound of Formula (III) with a compound of Formula (VI) to obtain a compound of Formula (IV), wherein the compound of Formula (II) is:

Formula (III)

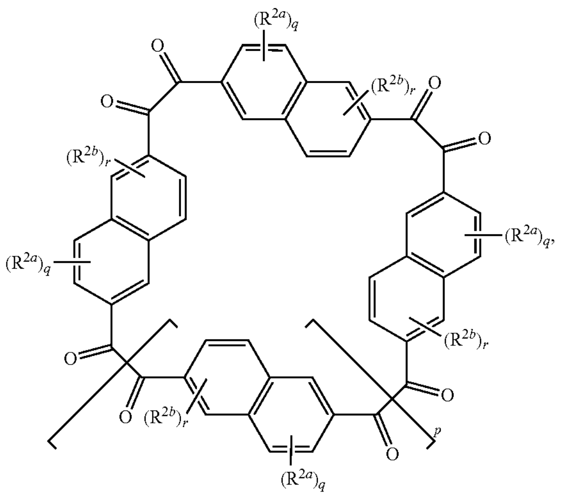

wherein:

p is 0, 1, 2, 3, or 4;

q is 0, 1, 2, or 3;

r is 0, 1, 2, or 3;

$R^{2a}$ is an electron withdrawing group, or an electron donating group; and $R^{2b}$ is an electron withdrawing group, or an electron donating group; and the compound of Formula (VIII) is:

Formula (VIII)

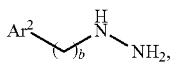

wherein, $Ar^2$ is optionally substituted aryl, or optionally substituted heteroaryl; and b is 0, 1, or 2.

Embodiment 22. A method for removing an amount of a material from a medium, the method comprising: contacting a compound of embodiment 20 with a medium, wherein the medium comprises a material; and removing an amount of the material from the medium.

Embodiment 23. The method of embodiment 22, wherein the material is molecular iodine ($I_2$).

Embodiment 24. The method of embodiment 22, wherein the medium is aqueous medium, organic medium, or combination thereof.

Embodiment 25. A compound of embodiment 19, wherein the compound is a compound of Formula (III-a):

Formula (III-a)

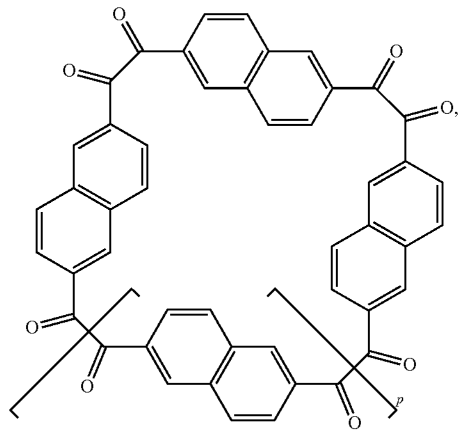

wherein:

p is 0, 1, 2, 3, or 4.

Embodiment 26. A compound of embodiment 20, wherein the compound is a compound of Formula (IV-a):

Formula (IV-a)

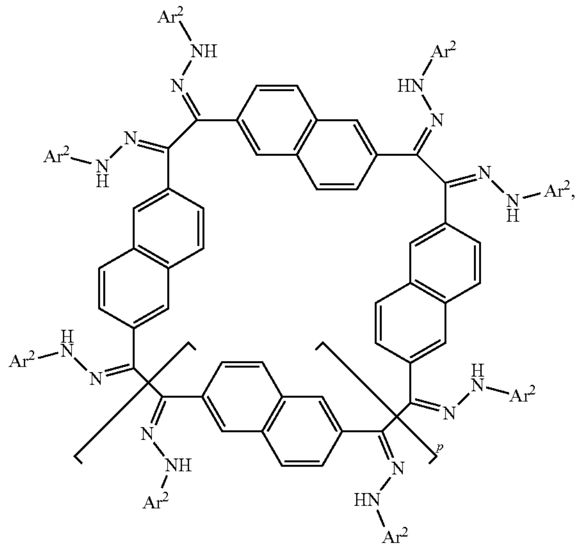

wherein:

p is 0, 1, 2, 3, or 4; and $Ar^2$ is optionally substituted aryl, or optionally substituted heteroaryl.

Embodiment 27. A method for preparing a compound of embodiment 26, comprising:

reacting a compound of Formula (III-a) with a compound of Formula (VIII-a) to obtain a compound of Formula (IV-a), wherein the compound of Formula (III-a) is:

Formula (III-a)

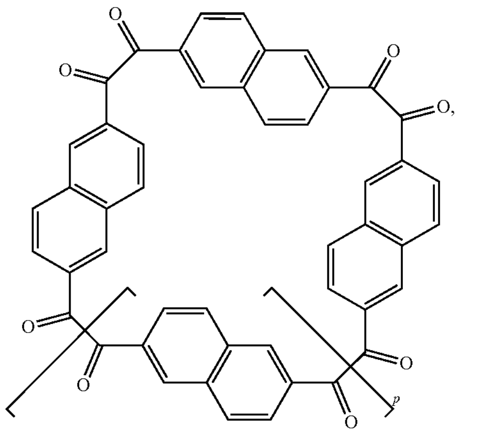

wherein:

p is 0, 1, 2, 3, or 4; and wherein the compound of Formula (VIII-a) is:

Formula (VIII-a)

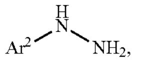

wherein, $Ar^2$ is optionally substituted aryl, or optionally substituted heteroaryl.

Embodiment 28. A method for removing an amount of a material from a medium, the method comprising: contacting a compound of embodiment 26 with a medium, wherein the medium comprises a material; and removing an amount of the material from the medium.

Embodiment 29. The method of embodiment 28, wherein the material is molecular iodine ($I_2$).

Embodiment 30. The method of embodiment 28, wherein the medium is aqueous medium, organic medium, or combination thereof.

Embodiment 31. A compound of embodiment 19, wherein the compound is a compound of Formula (III-b):

Formula (III-b)

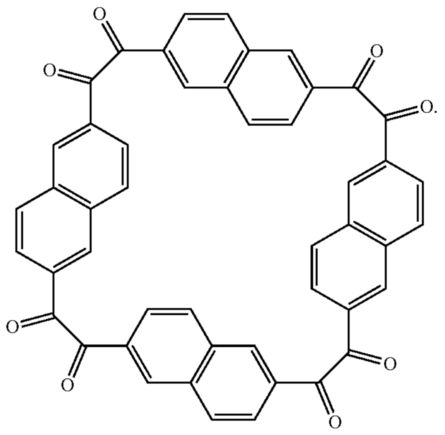

Embodiment 32. A compound of embodiment 20, wherein the compound is a compound of Formula (IV-b):

Formula (IV-b)

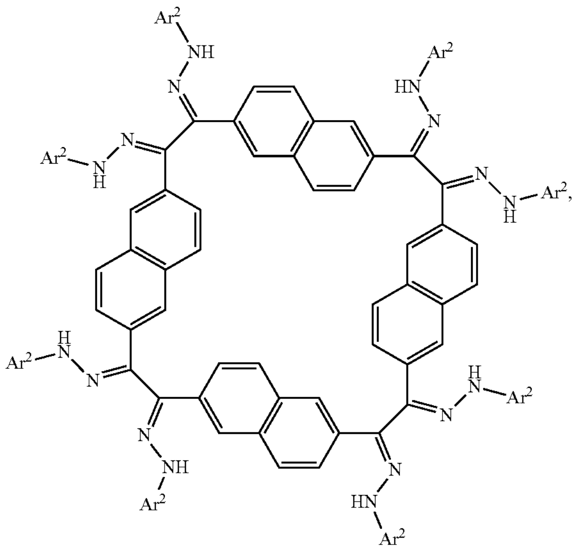

wherein:

$Ar^2$ is optionally substituted aryl, or optionally substituted heteroaryl.

Embodiment 33. A method of making a compound of embodiment 32, comprising:

reacting a compound of Formula (III-b) with a compound of Formula (VIII-a) to obtain a compound of Formula (IV-b), wherein the compound of Formula (III-b) is:

Formula (III-b)

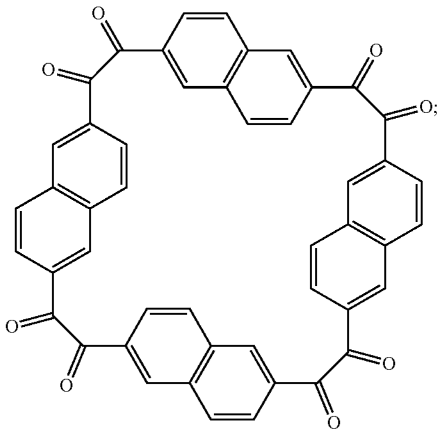

and the compound of Formula (VII-a) is:

Formula (VIII-a)

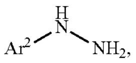

wherein, $Ar^2$ is optionally substituted aryl, or optionally substituted heteroaryl.

Embodiment 34. A method for removing an amount of a material from a medium, the method comprising: contacting a compound of embodiment 32 with a medium, wherein the medium comprises a material; and removing an amount of the material from the medium.

Embodiment 35. The method of embodiment 34, wherein the material is molecular iodine ($I_2$).

Embodiment 36. The method of embodiment 34, wherein the medium is aqueous medium, organic medium, or combination thereof.

Embodiment 37. A compound of Formula (V):

Formula (V)

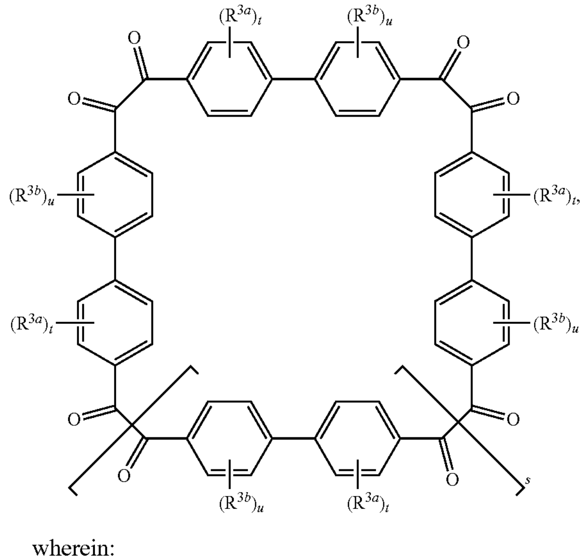

wherein:

s is 0, 1, 2, 3, or 4;

t is 0, 1, 2, 3 or 4;

u is 0, 1, 2, 3, or 4;

$R^{3a}$ is an electron withdrawing group, or an electron donating group; and $R^{3b}$ is an electron withdrawing group, or an electron donating group.

Embodiment 38. A compound of Formula (VI):

Formula (VI)

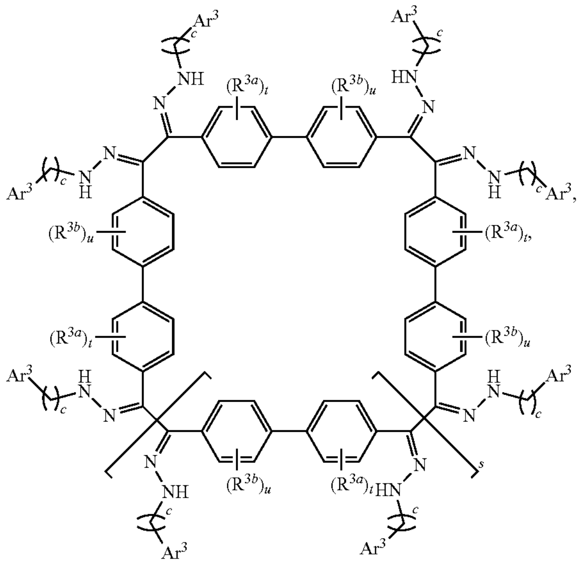

wherein:

s is 0, 1, 2, 3, or 4, t is 0, 1, 2, 3, or 4;

u is 0, 1, 2, 3, or 4;

c is 0, 1, or 2;

$Ar^3$ is optionally substituted aryl, or optionally substituted heteroaryl;

$R^{3a}$ is an electron withdrawing group, or an electron donating group; and $R^{3b}$ is an electron withdrawing group, or an electron donating group.

Embodiment 39. A method for preparing a compound of embodiment 38, comprising:

reacting a compound of Formula (V) with a compound of Formula (IX) to obtain a compound of Formula (VI), wherein the compound of Formula (V) is:

Formula (V)

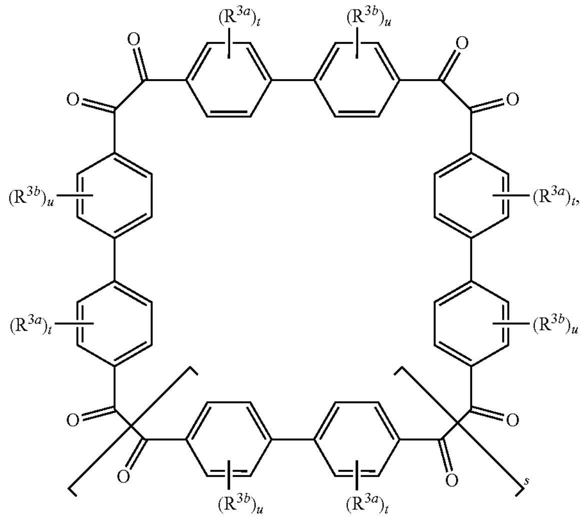

wherein:

s is 0, 1, 2, 3, or 4;

t is 0, 1, 2, 3, or 4;

u is 0, 1, 2, 3, or 4;

$Ar^3$ is optionally substituted aryl, or optionally substituted heteroaryl;

$R^{3a}$ is an electron withdrawing group, or an electron donating group; and $R^{3b}$ is an electron withdrawing group, or an electron donating group; and the compound of Formula (IX) is:

Formula (IX)

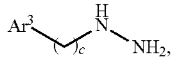

wherein, $Ar^3$ is optionally substituted aryl, or optionally substituted heteroaryl; and c is 0, 1, or 2.

Embodiment 40. A method for removing an amount of a material from a medium, the method comprising: contacting a compound of embodiment 38 with a medium, wherein the medium comprises a material; and removing an amount of the material from the medium.

Embodiment 41. The method of embodiment 40, wherein the material is molecular iodine ($I_2$).

Embodiment 42. The method embodiment 40, wherein the medium is aqueous medium, organic medium, or combination thereof.

Embodiment 43. A compound of Formula (V-a):

Formula (V-a)

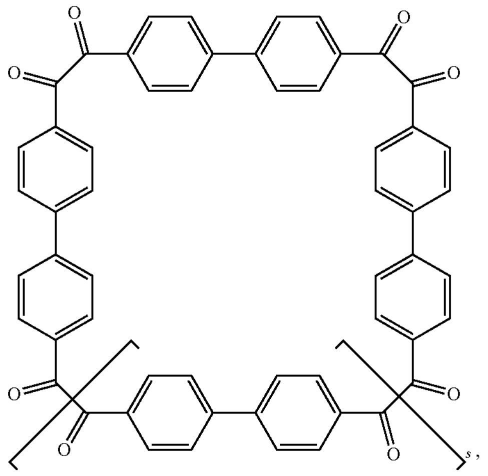

wherein:

s is 0, 1, 2, 3, or 4.

Embodiment 44. A compound of Formula (VI-a):

Formula (VI-a)

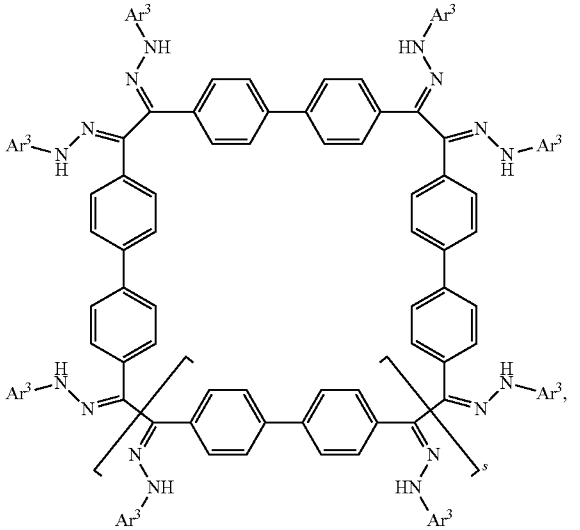

wherein:

s is 0, 1, 2, 3, or 4;

$Ar^3$ is optionally substituted aryl, or optionally substituted heteroaryl.

Embodiment 45. A method for preparing a compound of embodiment 44, comprising:

reacting a compound of Formula (V-a) with a compound of Formula (IX-a) to obtain a compound of Formula (VI-a), wherein the compound of Formula (V-a) is:

Formula (V-a)

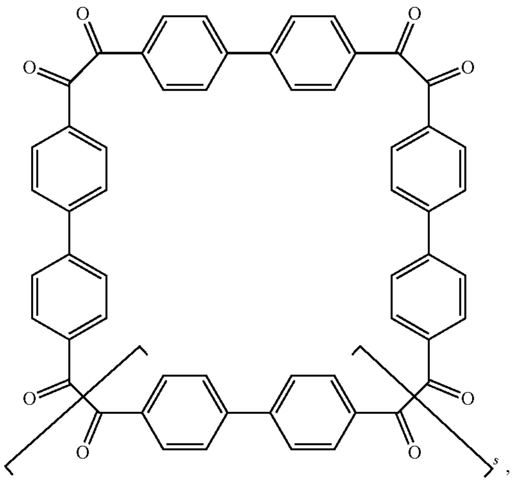

wherein:

s is 0, 1, 2, 3, or 4; and wherein the compound of Formula (IX-a) is:

Formula (IX-a)

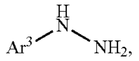

wherein, Ar is optionally substituted aryl, or optionally substituted heteroaryl.

Embodiment 46. A method for removing an amount of a material from a medium, the method comprising: contacting a compound of embodiment 44 with a medium, wherein the medium comprises a material; and removing an amount of the material from the medium.

Embodiment 47. The method of embodiment 46, wherein the material is molecular iodine ($I_2$).

Embodiment 48. The method of embodiment 46, wherein the medium is aqueous medium, organic medium, or combination thereof.

Embodiment 49. A compound of Formula (V-b):

Formula (V-b)

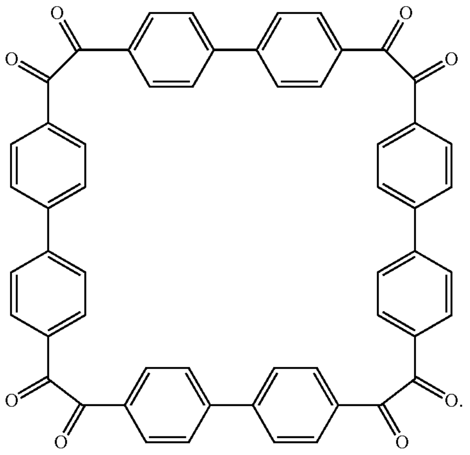

Embodiment 50. A compound of Formula (VI-b):

Formula (VI-b)

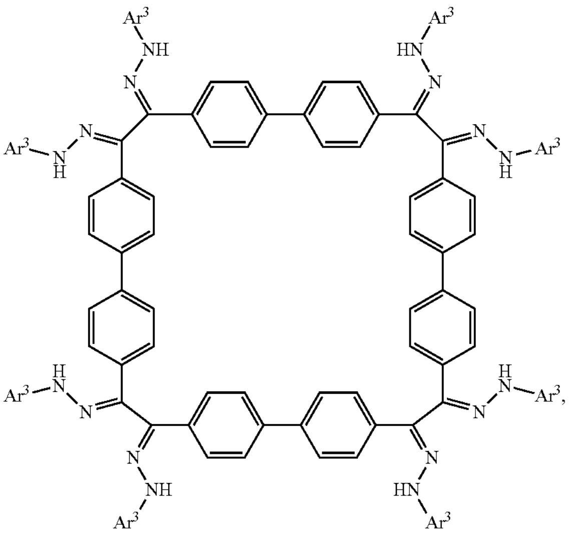

wherein:

$Ar^3$ is optionally substituted aryl, or optionally substituted heteroaryl.

Embodiment 51. A method for preparing a compound of embodiment 50, comprising:

reacting a compound of Formula (V-b) with a compound of Formula (IX-a) to obtain a compound of Formula (VI-b), wherein the compound of Formula (V-b) is:

Formula (V-b)

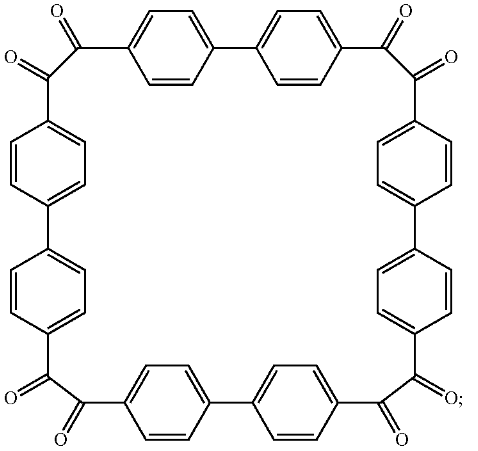

and the compound of Formula (IX-a) is:

Formula (IX-a)

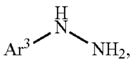

wherein, $Ar^3$ is optionally substituted aryl, or optionally substituted heteroaryl.

Embodiment 52. A method for removing an amount of a material from a medium, the method comprising: contacting a compound of embodiment 50 with a medium, wherein the medium comprises a material; and removing an amount of the material from the medium.

Embodiment 53. The method of embodiment 52, wherein the material is molecular iodine ($I_2$).

Embodiment 54. The method of embodiment 52, wherein the medium is aqueous medium, organic medium, or combination thereof.

Embodiment 55. The compound of embodiment 2, 8, or 14, wherein $Ar^1$ is selected from the group consisting of:

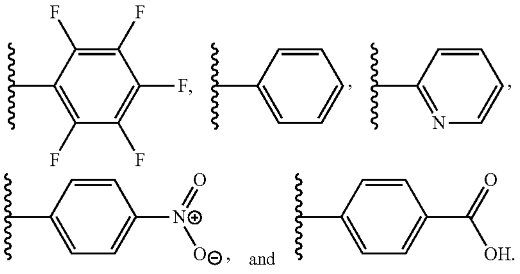

and

Embodiment 56. The method of embodiment 3, 9, or 15, wherein $Ar^1$ is selected from the group consisting of:

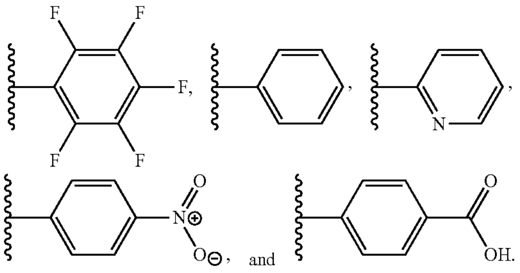

and

Embodiment 57. The compound of embodiment 20, 26, or 32, wherein $Ar^2$ is selected from the group consisting of:

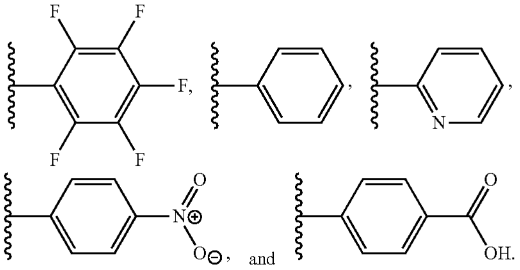

and

Embodiment 58. The method of embodiment 21, 27, or 33, wherein $Ar^2$ is selected from the group consisting of:

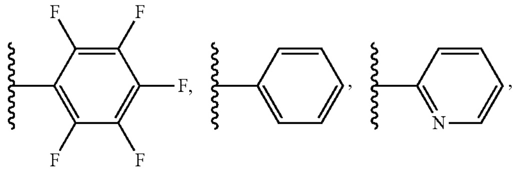

-continued
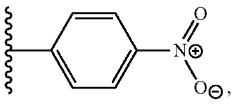
and
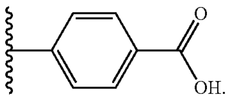
Embodiment 59. The compound of embodiment 38, 44, or 50, wherein $Ar^3$ is selected from the group consisting of:
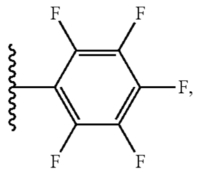
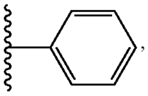
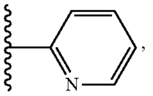
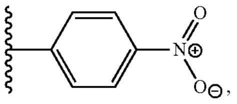
and
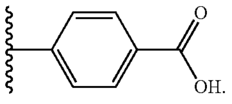
Embodiment 60. The method of embodiment 39, 45, or 51, wherein $Ar^3$ is selected from the group consisting of:
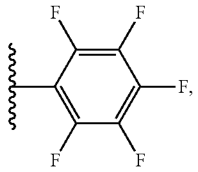
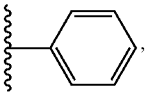
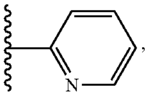
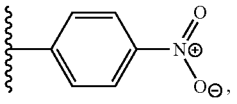
and
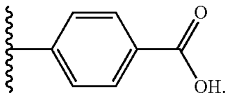
Embodiment 61. A compound selected from the group consisting of:
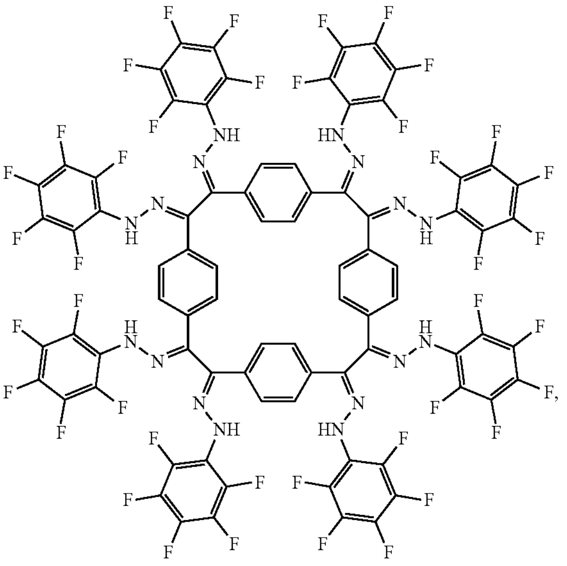
-continued
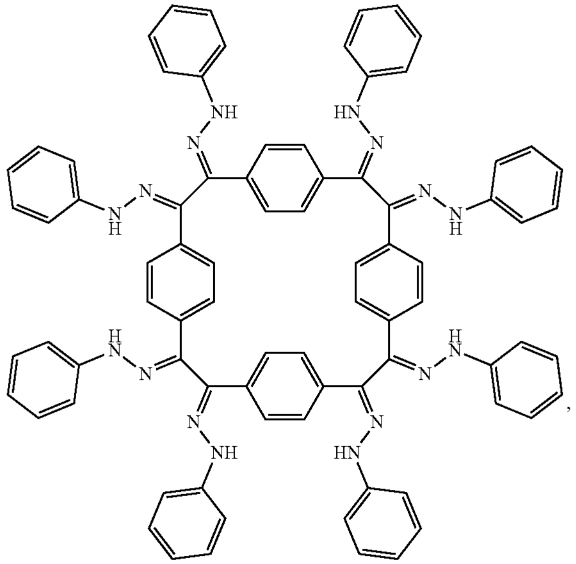
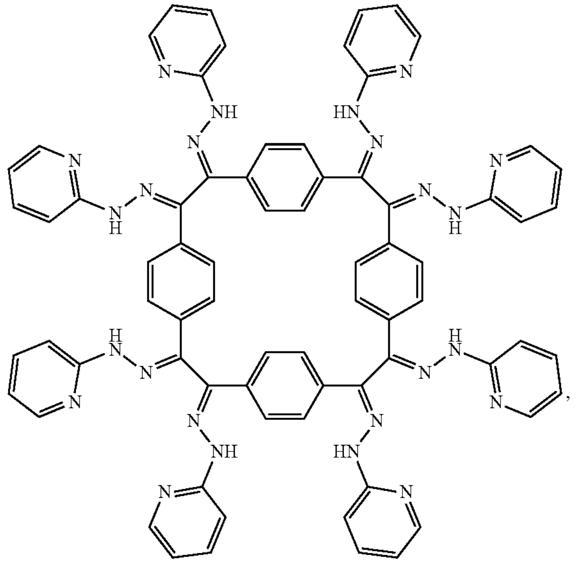
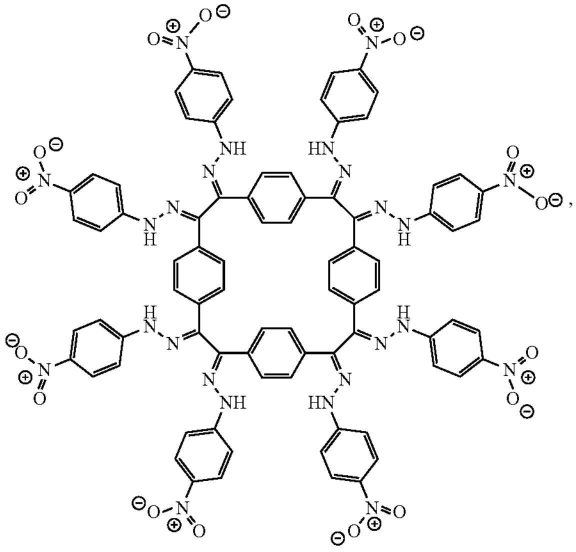
and -continued
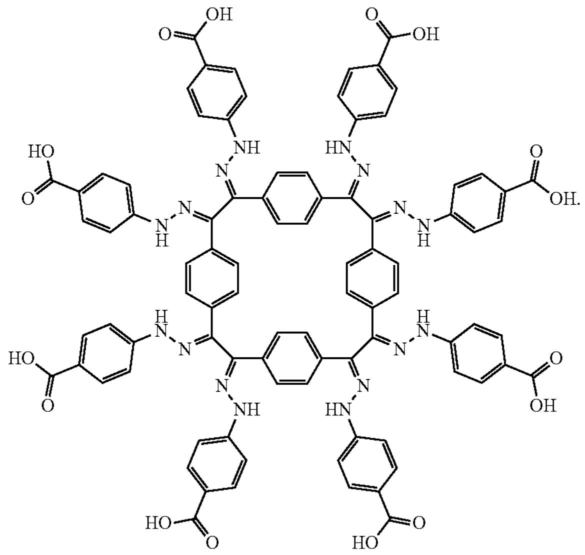
Embodiment 62. A compound:
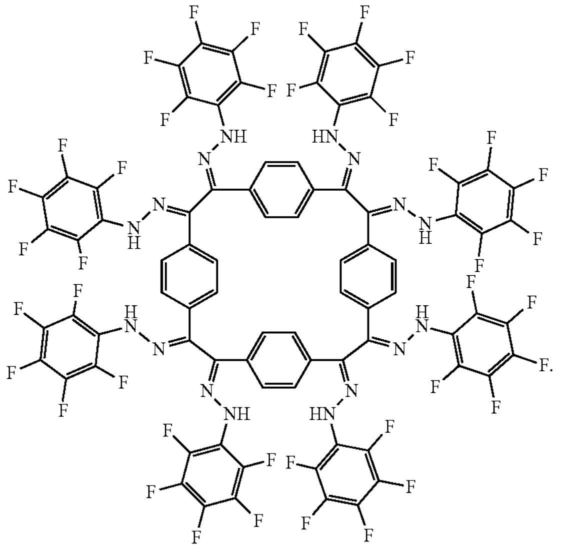 [SMILES: CC(=N\Nc1c(F)c(F)c(F)c(F)c1F)/C(=N/Nc1c(F)c(F)c(F)c(F)c1F)c1ccc(C(=N\Nc2c(F)c(F)c(F)c(F)c2F)/C(=N/Nc2c(F)c(F)c(F)c(F)c2F)c2ccc(C(=N\Nc3c(F)c(F)c(F)c(F)c3F)/C(=N/Nc3c(F)c(F)c(F)c(F)c3F)c3ccc(C(=N\Nc4c(F)c(F)c(F)c(F)c4F)/C(=N/Nc4c(F)c(F)c(F)c(F)c4F)c4ccccc4)cc3)cc2)cc1]
Embodiment 63. A compound
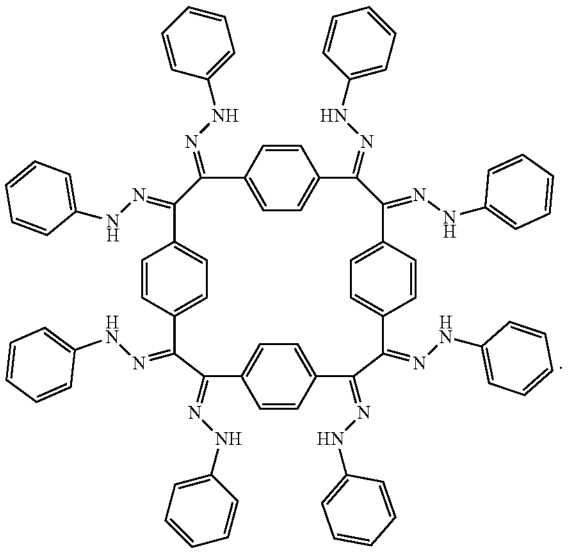 [SMILES: CC(=N\Nc1ccccc1)/C(=N/Nc1ccccc1)c1ccc(C(=N\Nc2ccccc2)/C(=N/Nc2ccccc2)c2ccc(C(=N\Nc3ccccc3)/C(=N/Nc3ccccc3)c3ccc(C(=N\Nc4ccccc4)/C(=N/Nc4ccccc4)c4ccccc4)cc3)cc2)cc1]
Embodiment 64. A compound:
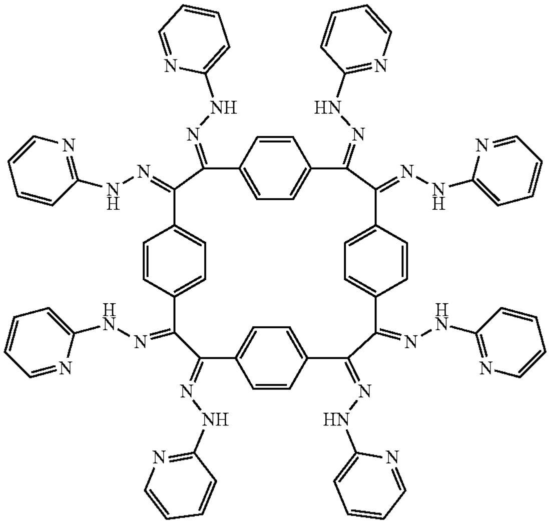 [SMILES: c1ccc(N/N=C2/C(=N/Nc3ccccn3)c3ccc(cc3)C(=N\Nc3ccccn3)/C(=N/Nc3ccccn3)c3ccc(cc3)C(=N\Nc3ccccn3)/C(=N/Nc3ccccn3)c3ccc(cc3)C(=N\Nc3ccccn3)/C(=N/Nc3ccccn3)c3ccc2cc3)nc1]

Embodiment 65. A compound:

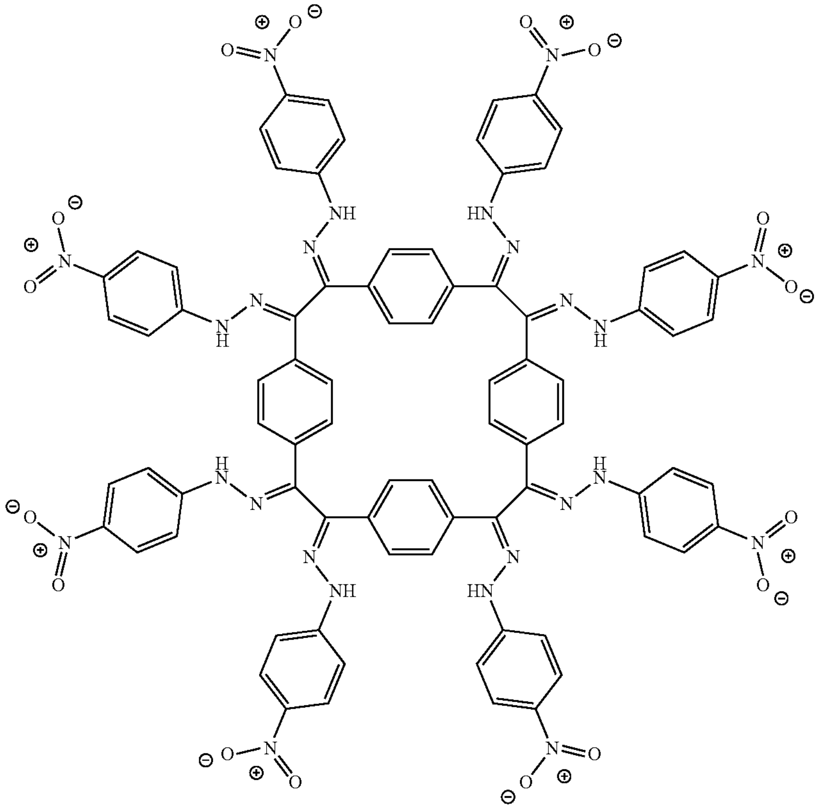

Embodiment 66. A compound:

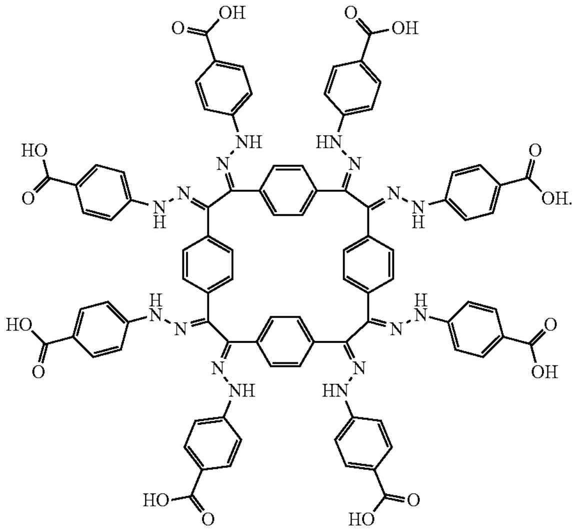 [SMILES: O=C(O)c1ccc(N/N=C2/C(=N/Nc3ccc(C(=O)O)cc3)c3ccc(cc3)C(=N\Nc3ccc(C(=O)O)cc3)/C(=N/Nc3ccc(C(=O)O)cc3)c3ccc(cc3)C(=N\Nc3ccc(C(=O)O)cc3)/C(=N/Nc3ccc(C(=O)O)cc3)c3ccc(cc3)C(=N\Nc3ccc(C(=O)O)cc3)/C(=N/Nc3ccc(C(=O)O)cc3)c3ccc2cc3)cc1]

Embodiment 67. A method for removing an amount of a material from a medium, the method comprising: contacting a compound of any one of embodiments 62-66 with a medium, wherein the medium comprises a material; and removing an amount of the material from the medium.

Embodiment 68. The method of embodiment 67, wherein the material is molecular iodine ($I_2$).

Embodiment 69. The method of embodiment 67, wherein the medium is aqueous medium, organic medium, or combination thereof.

Additional embodiments include those listed below:

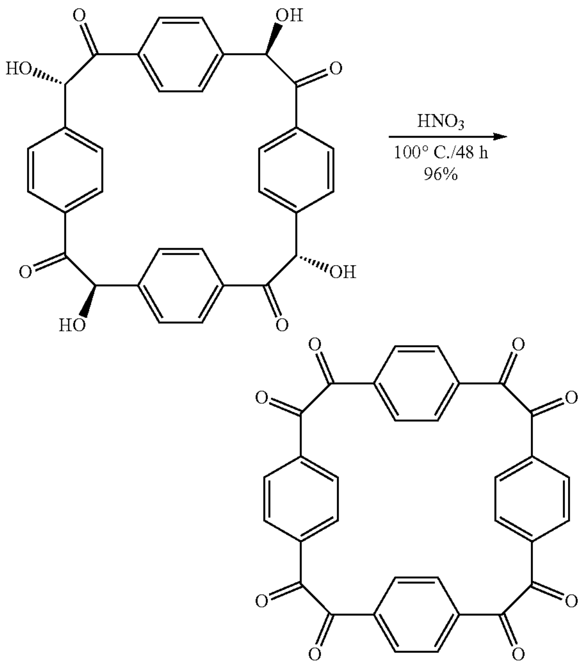

Additional embodiments include those listed below:
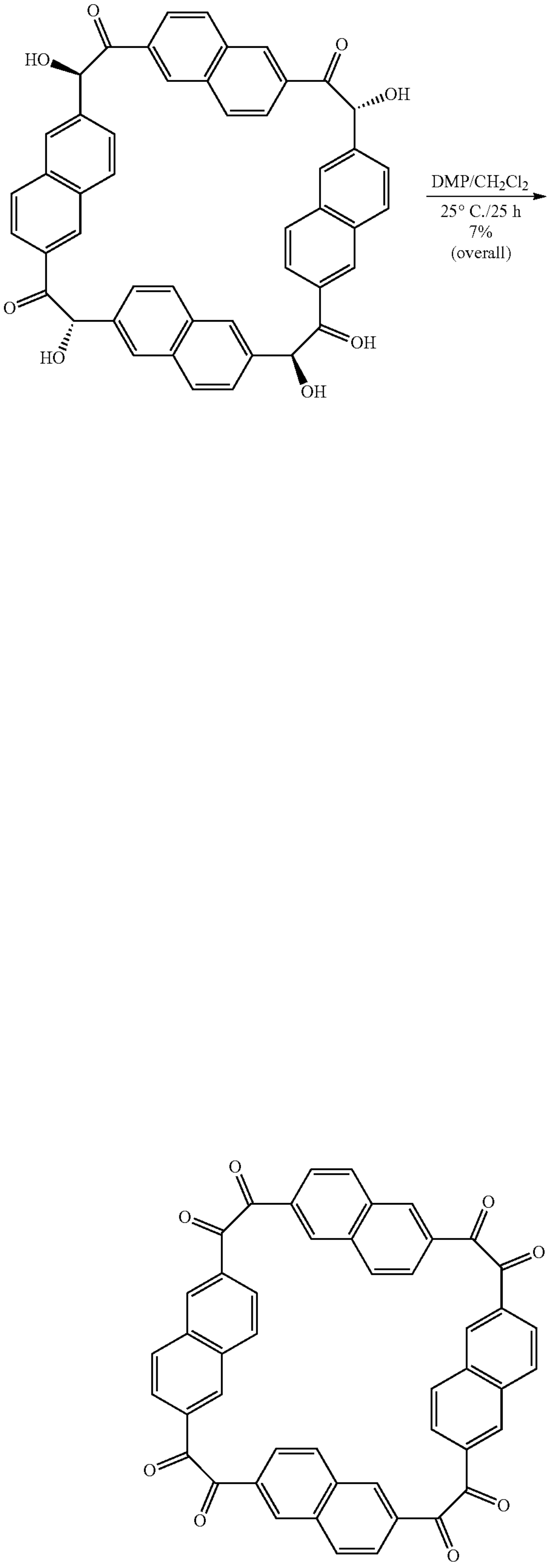
Additional embodiments include those listed below:
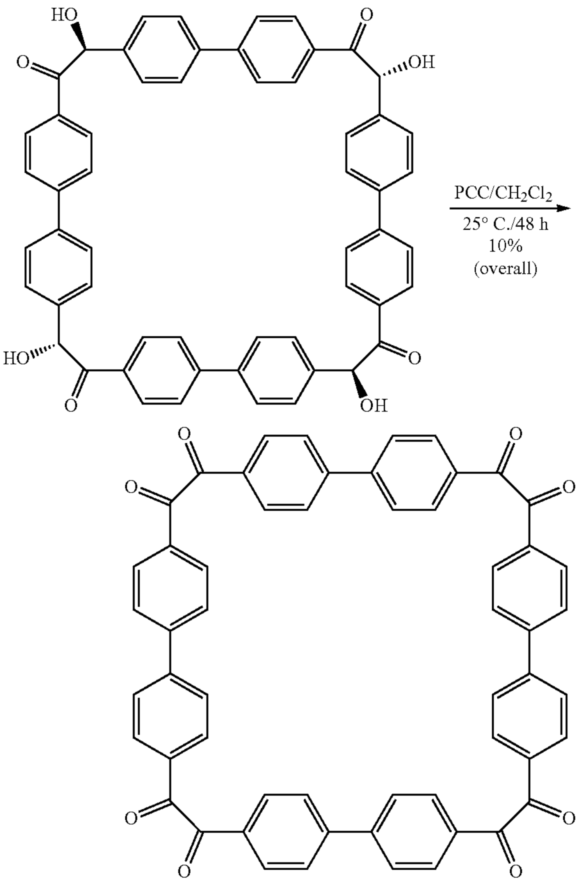
Additional embodiments include those listed below:
In various embodiments, the present invention provides compounds of Formula (II), or Formula (II-a), or Formula (II-b) selected from the group consisting of:
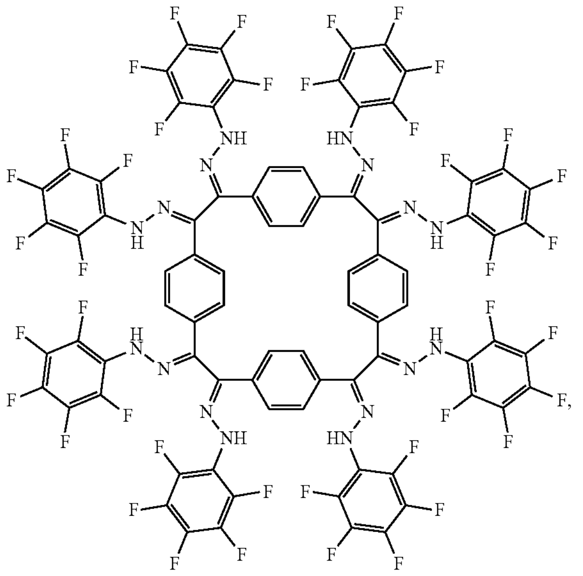

-continued
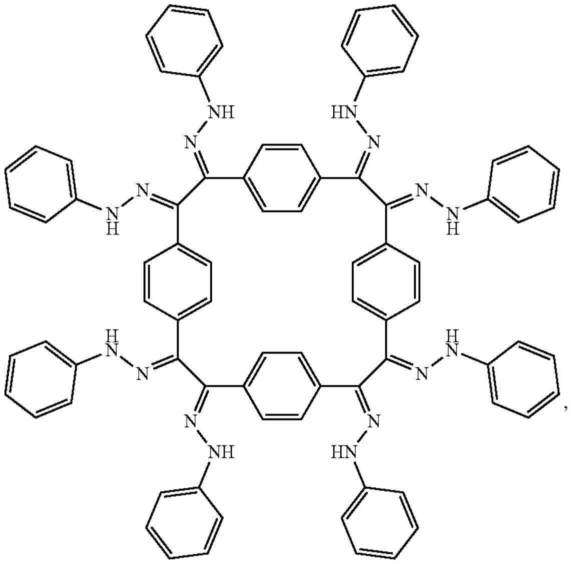
,
-continued
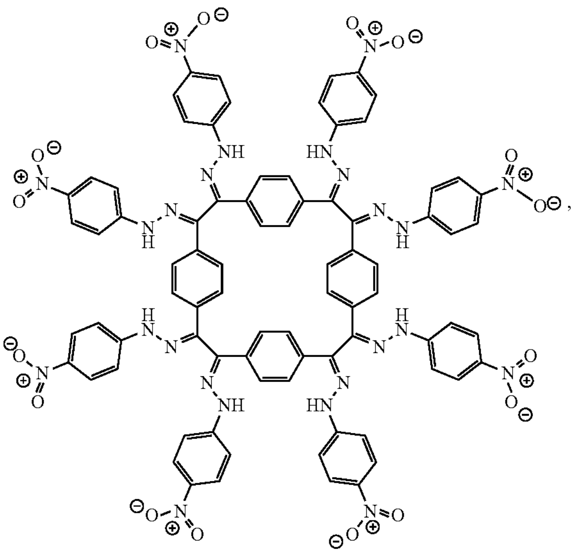
,
and
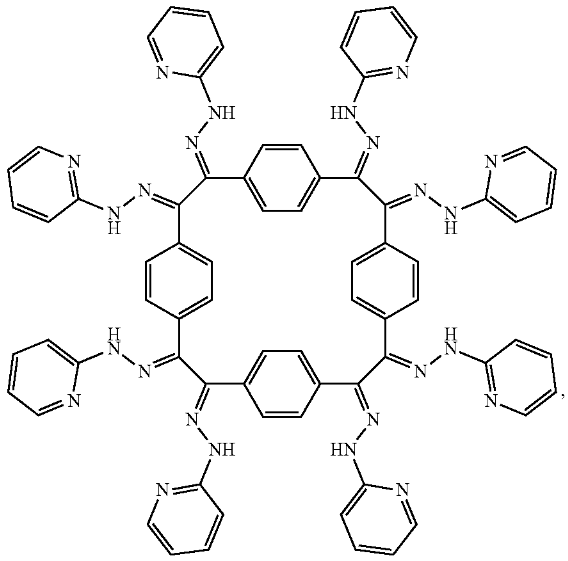
,
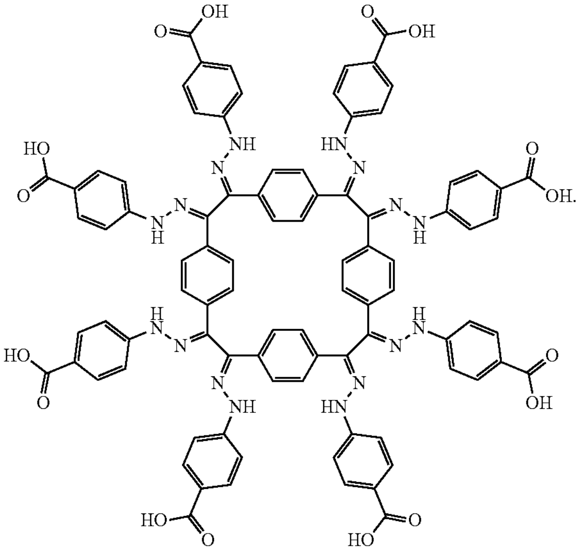 [SMILES: O=C(O)c1ccc(N/N=C2/C(=N/Nc3ccc(C(=O)O)cc3)c3ccc(cc3)C(=N\Nc3ccc(C(=O)O)cc3)/C(=N/Nc3ccc(C(=O)O)cc3)c3ccc(cc3)C(=N\Nc3ccc(C(=O)O)cc3)/C(=N/Nc3ccc(C(=O)O)cc3)c3ccc(cc3)C(=N\Nc3ccc(C(=O)O)cc3)/C(=N/Nc3ccc(C(=O)O)cc3)c3ccc2cc3)cc1]
.

Additional embodiments include those listed below:
In various embodiments, the present invention provides compounds of Formula (IV), or Formula (IV-a), or Formula (IV-b) selected from the group consisting of:
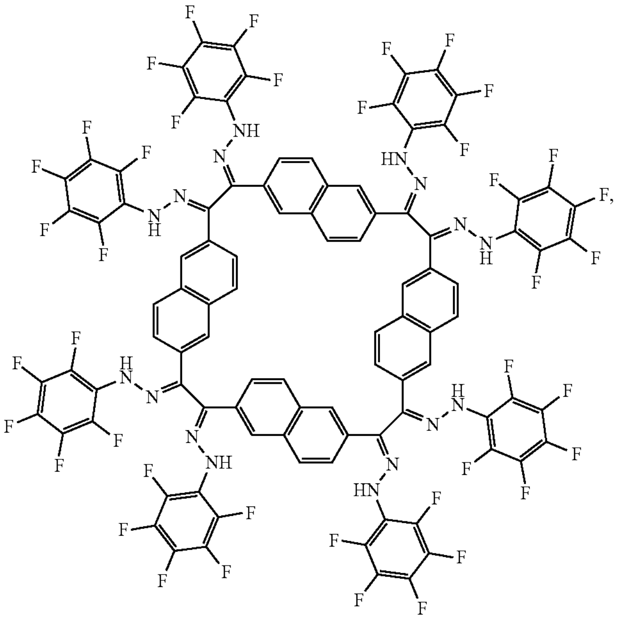
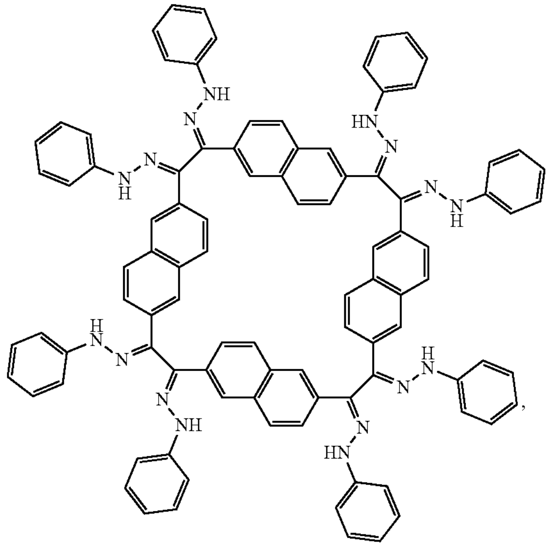
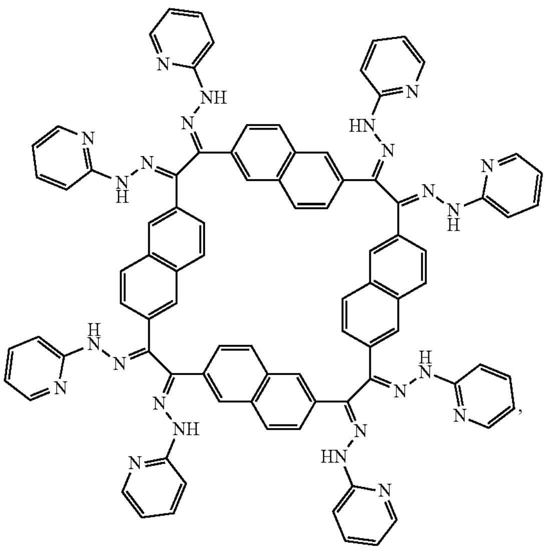

-continued
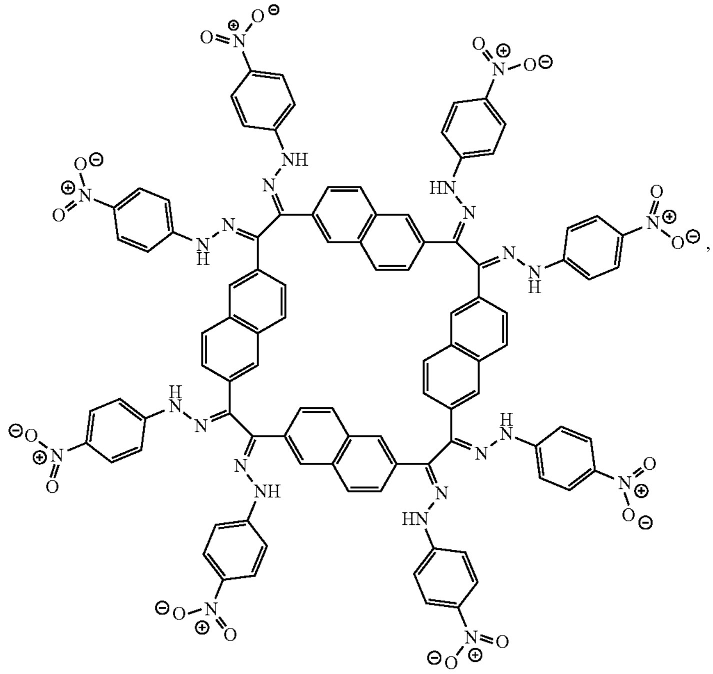
, and
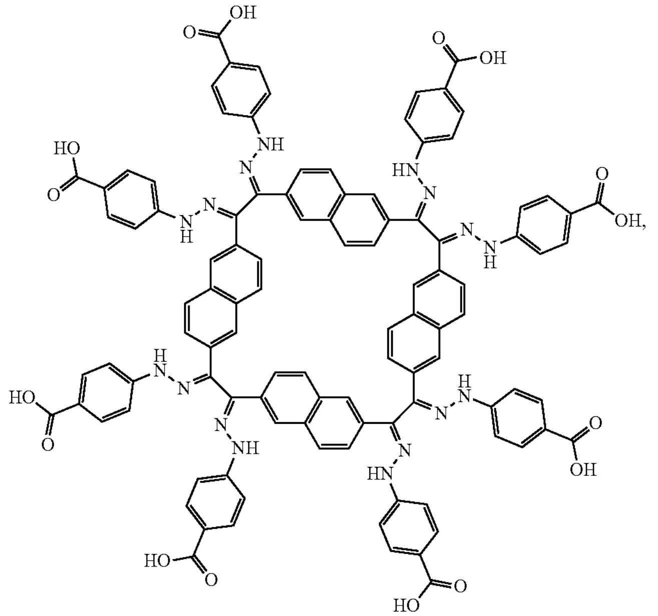
,

Additional embodiments include those listed below:
In various embodiments, the present invention provides compounds of Formula (VI), or Formula (VI-a), or Formula (VI-b) selected from the group consisting of:
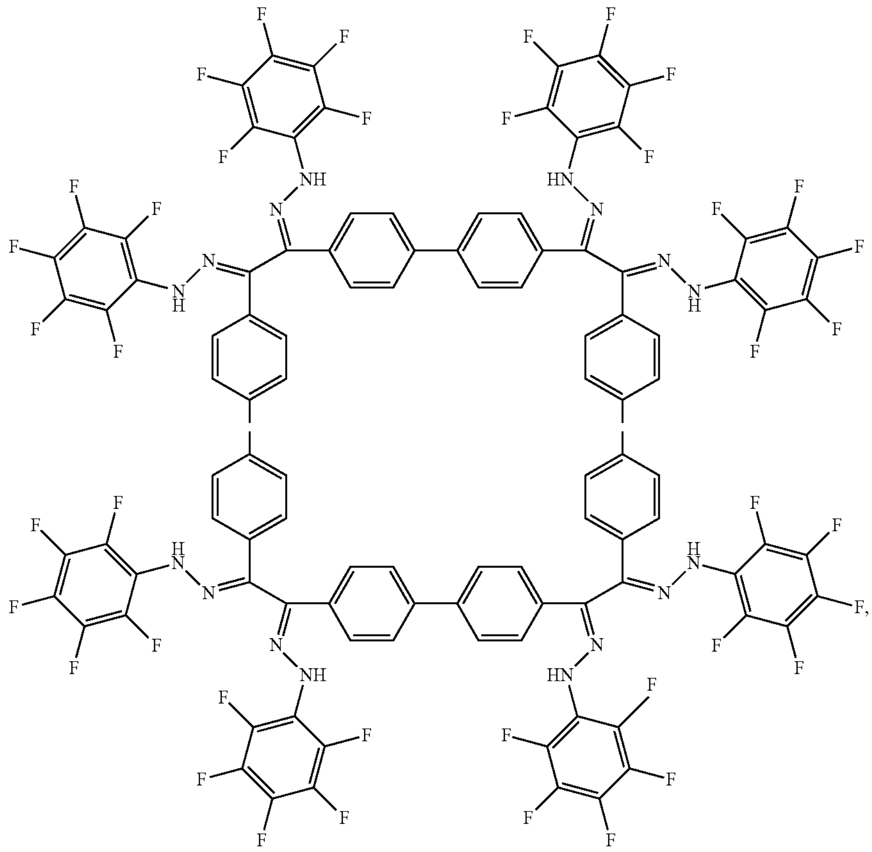
,
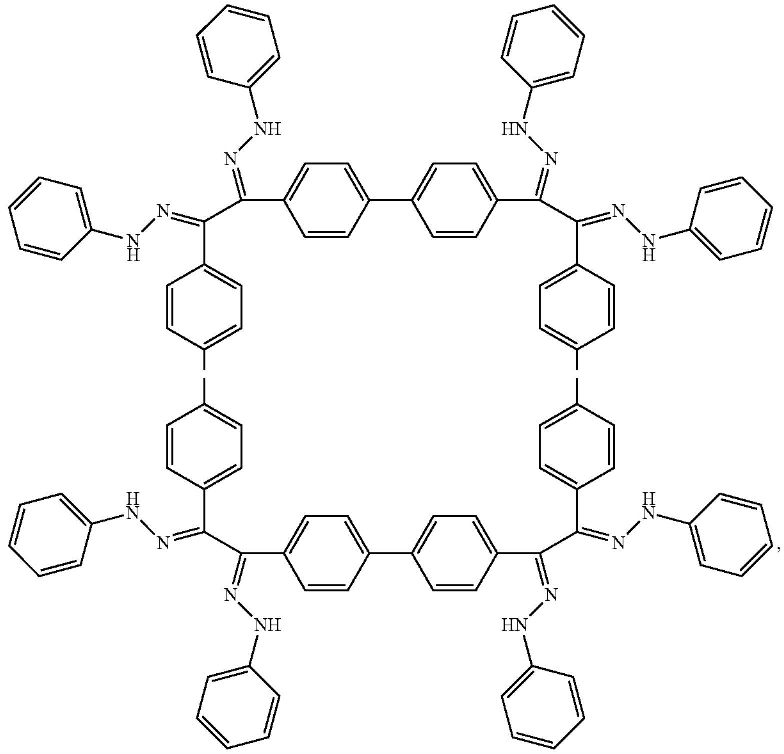
, -continued
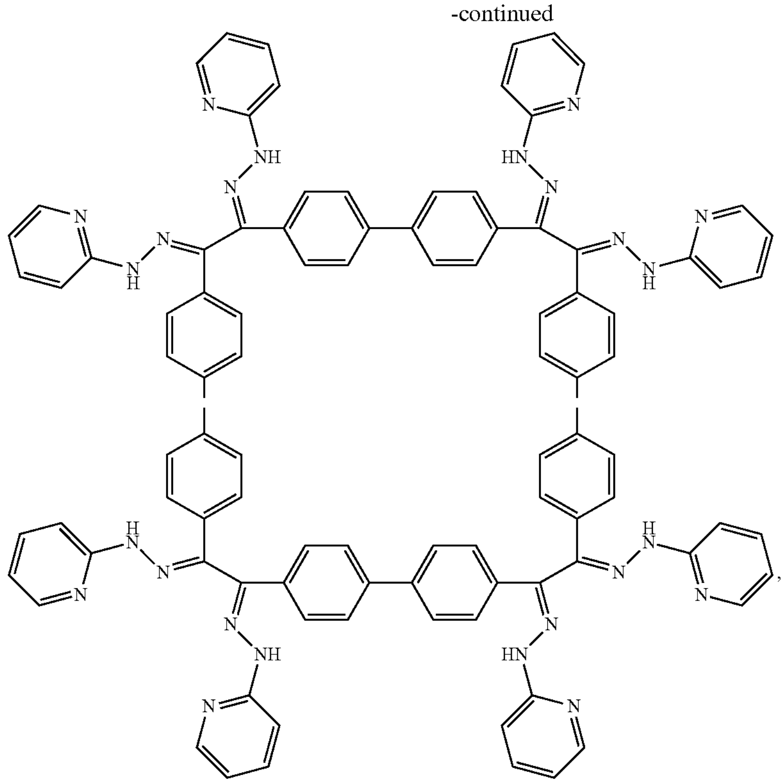
,
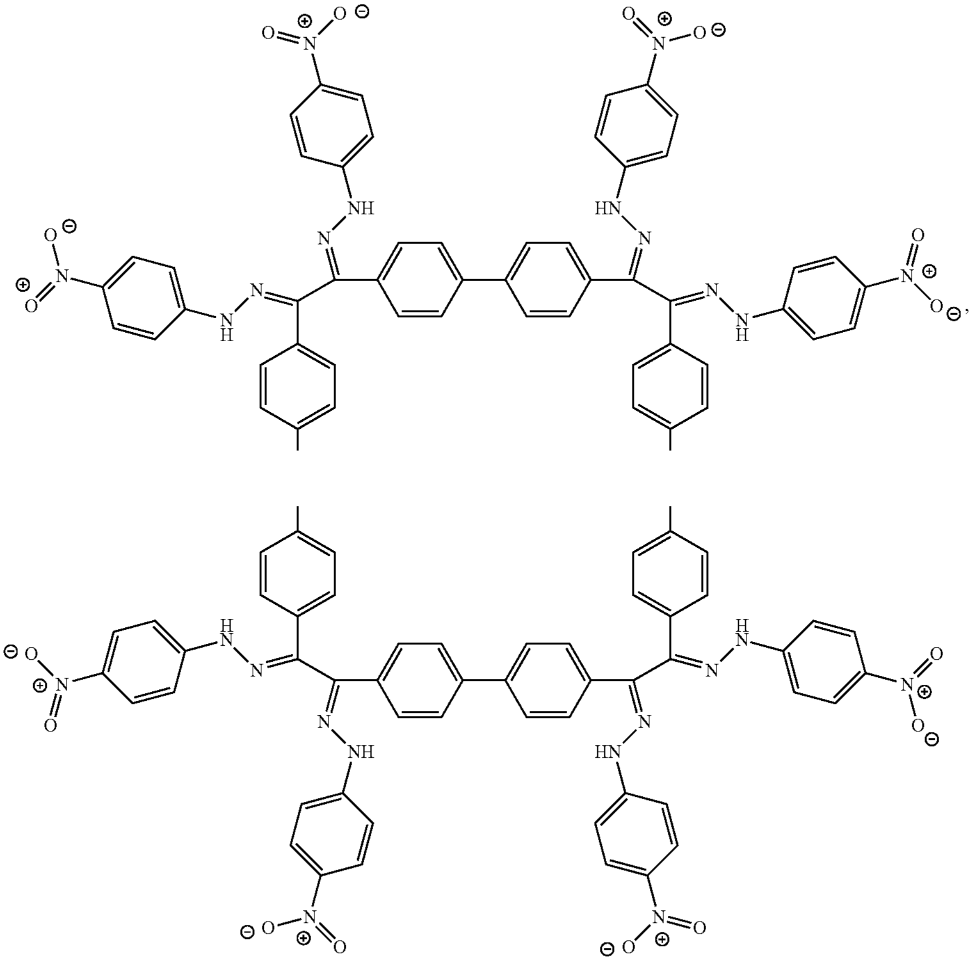
, -continued

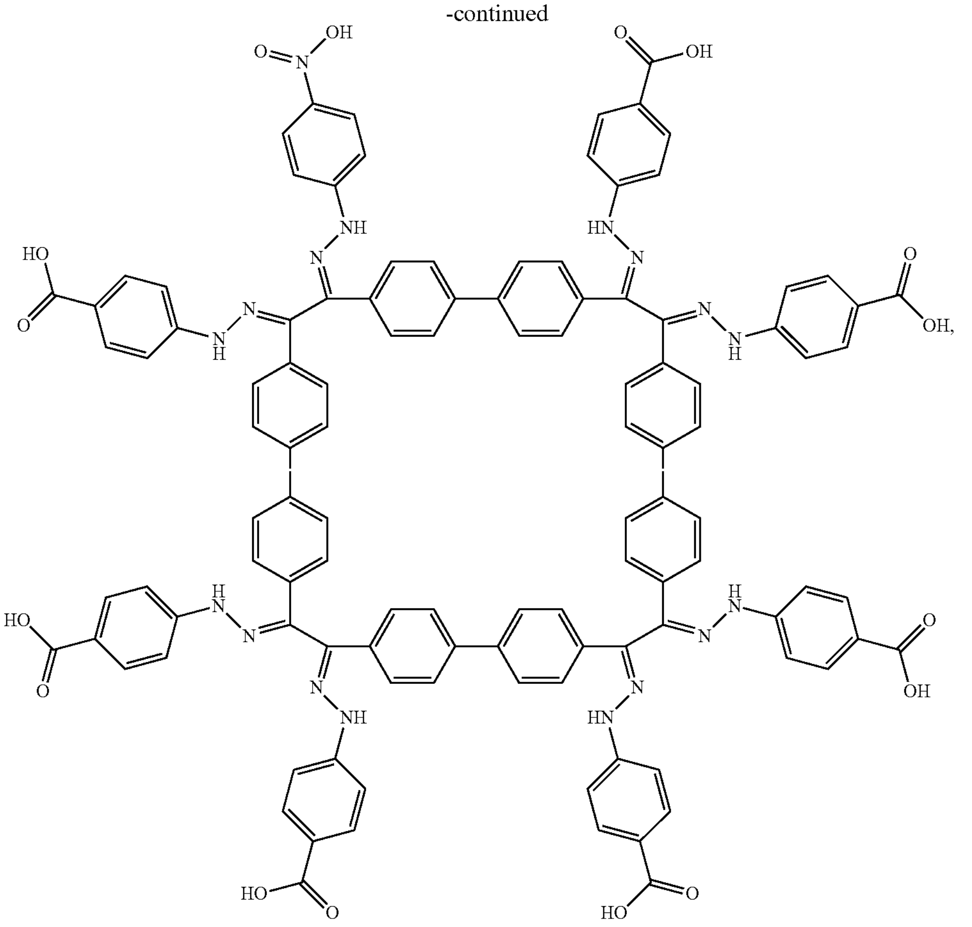

Additional embodiments include those listed below:

In various embodiments, the present invention provides a method for removing an amount of a material from a medium, the method comprising: providing a medium comprising a material; contacting the medium with a compound, wherein the compound is selected from a compound of Formula (II), a compound of Formula (II-a), a compound of Formula (II-b), a compound of Formula (IV), a compound of Formula (IV-a), a compound of Formula (IV-b), a compound of Formula (VI), a compound of Formula (VI-a), a compound of Formula (VI-b), a compound 1a, a compound 1b, a compound 1c, a compound 1d, or a compound 1e, or any combination thereof; and capturing the material with the compound, thereby removing an amount of the material from the medium.

In various embodiments, the present invention provides a method for removing an amount of a material from a medium, the method comprising: providing a medium comprising a material; contacting the medium with a compound, wherein the compound is selected from a compound of Formula (II), a compound of Formula (II-a), a compound of Formula (II-b), a compound of Formula (IV), a compound of Formula (IV-a), a compound of Formula (IV-b), a compound of Formula (VI), a compound of Formula (VI-a), a compound of Formula (VI-b), a compound 1a, a compound 1b, a compound 1e, a compound 1d, or a compound 1e, or any combination thereof; capturing the material with the compound; and removing the compound that contains the captured material from the medium. In some embodiments, the method further comprises treating the compound that contains the captured material to effect release of the captured material from the compound. In some embodiments, the method further comprises removing the captured material from the compound. In some embodiments, the compound that contains the captured material is a compound-material complex.

In some embodiments, the amount of material that is removed or captured from the medium after being contacted with a compound of the present invention is all of the material in the medium. For example, in some embodiments, none of the material or no measurable amount of the material being removed or captured from the medium remains in the medium after being contacted with a compound of the present invention.

In some embodiments, the amount of material that is removed from the medium after being contacted with a compound of the present invention is a portion or fraction of the total amount of material in the medium. For example, in this case a portion or fraction of the total amount of material is removed from the medium after being contacted with a compound of the present invention, and a portion or fraction of the total amount of material remains in the medium.

In various embodiments, the present invention provides a method for removing a material from a medium, the method comprising: providing a medium comprising a material; contacting the medium with a compound, wherein the compound is selected from a compound of Formula (II), a compound of Formula (II-a), a compound of Formula (II-b), a compound of Formula (IV), a compound of Formula (IV-a), a compound of Formula (IV-b), a compound of Formula (VI), a compound of Formula (VI-a), a compound of Formula (VI-b), a compound 1a, a compound 1b, a compound 1c, a compound 1d, or a compound 1e, or any combination thereof; capturing the material with the compound, and removing the compound that contains the captured material from the medium. In some embodiments, the method further comprises treating the compound that contains the captured material to effect release of the captured material from the compound.

In various embodiments, the present invention provides capturing and separating a material from a medium, the method comprising: providing a medium comprising a material; contacting the medium with a compound to effect adsorption of the material by the compound, wherein the compound is selected from a compound of Formula (II), a compound of Formula (II-a), a compound of Formula (II-b), a compound of Formula (IV), a compound of Formula (IV-a), a compound of Formula (IV-b), a compound of Formula (VI), a compound of Formula (VI-a), a compound of Formula (VI-b), a compound 1a, a compound 1b, a compound 1c, a compound 1d, or a compound 1e, or any combination thereof; and treating the compound that contains adsorbed or entrapped material to release the material from the compound.

In some embodiments, the material is a gas, a liquid, or a solid, or combination thereof. In some embodiments, the material comprises a gas, a liquid, or a solid, or combination thereof. In some embodiments, the material is molecular iodine ($I_2$). In some embodiments, the material comprises molecular iodine ($I_2$). In some embodiments, the material is radioactive iodine (e.g., radioactive $I_2$ or radioactive molecular iodine $I_2$). In some embodiments, the material comprises radioactive iodine (e.g., radioactive $I_2$ or radioactive molecular iodine 12). In some embodiments, the molecular iodine ($I_2$) is non-radioactive iodine $I_2$ or non-radioactive molecular iodine ($I_2$). In some embodiments, the molecular iodine ($I_2$) comprises non-radioactive iodine $I_2$ or non-radioactive molecular iodine ($I_2$). In some embodiments, the terms radioactive iodine and radioiodine have the same meaning and may be used interchangeably. In some embodiments, the material is molecular iodine ($I_2$), radioactive iodine (radioactive $I_2$), or combination thereof. In some embodiments, the material comprises molecular iodine ($I_2$), radioactive iodine (radioactive 12), or combination thereof. In some embodiments, the material comprises non-radioactive molecular iodine ($I_2$), radioactive molecular iodine ($I_2$), or combination thereof. In some embodiments, the material is non-radioactive molecular iodine ($I_2$), radioactive molecular iodine ($I_2$), or combination thereof. In some embodiments, the material comprises non-radioactive molecular iodine ($I_2$), radioactive molecular iodine ($I_2$), or combination thereof. In some embodiments the radioactive iodine comprises at least one radioisotope of iodine. Non-limiting examples of radioisotopes of iodine include Iodine-131, Iodine-129, Iodine-123, Iodine-124, Iodine-125, Iodine-135, Iodine-132, Iodine-128, Iodine-137, Iodine-141, Iodine-139. In some embodiments, the molecular iodine ($I_2$) is non-radioactive iodine $I_2$ or non-radioactive molecular iodine ($I_2$) and comprises Iodine-127. In some embodiments, the molecular iodine ($I_2$) is non-radioactive iodine $I_2$ or non-radioactive molecular iodine ($I_2$) and is Iodine-127. In some embodiments, radioactive iodine or radioactive $I_2$ or radioactive molecular iodine $I_2$ is Iodine-131, Iodine-129, Iodine-123, Iodine-124, Iodine-125, Iodine-135, Iodine-132, Iodine-128, Iodine-137, Iodine-141, Iodine-139, or any combination thereof. In some embodiments, radioactive iodine or radioactive $I_2$ or radioactive molecular iodine $I_2$ comprises Iodine-131, Iodine-129, Iodine-123, Iodine-124, Iodine-125, Iodine-135, Iodine-132, Iodine-128, Iodine-137, Iodine-141, Iodine-139, or any combination thereof.

In various embodiments, the present invention provides an article of manufacture, wherein the article of manufacture comprises a compound of Formula (II), a compound of Formula (II-a), a compound of Formula (II-b), a compound of Formula (IV), a compound of Formula (IV-a), a compound of Formula (IV-b), a compound of Formula (VI), a compound of Formula (VI-a), a compound of Formula (VI-b), compound 1a, compound 1b, compound 1c, compound 1d, or compound 1e, or any combination thereof. In some embodiments, the article of manufacture further comprises a carrier. In some embodiments, the carrier is a solvent. In some embodiments, the solvent is water, comprises water, or contains water; or is an organic solvent, comprises an organic solvent, or contains an organic solvent; or is a combination of water and an organic solvent, comprises a combination of water and an organic solvent, or contains a combination of water and an organic solvent.

In some embodiments, the article of manufacture is a coating, a coating material, a material for use as a coating, a primer, a material for use as a primer, a paint, and/or a material for use as a paint. In some embodiments the coating, the coating material, the material for use as a coating, the primer, the material for use as a primer, the paint, and/or the material for use as a paint, further comprises a carrier. In some embodiments, the carrier is a solvent. In some embodiments, the solvent is water, comprises water, or contains water; or is an organic solvent, comprises an organic solvent, or contains an organic solvent; or is a combination of water and an organic solvent, comprises a combination of water and an organic solvent, or contains a combination of water and an organic solvent. In some embodiments, the paint is a nuclear paint. In some embodiments, the primer is a nuclear primer. In some embodiments, the coating material is a nuclear coating material.

In some embodiments, the article of manufacture is a paint, a primer, or coating material for painting, priming, or coating a tank, container, vessel, or pipe, or any component thereof. In some embodiments, the article of manufacture is a paint, a primer, or coating material for coating a waste containment tank, waste containment container, or waste containment vessel. In some embodiments, the waste containment tank, waste containment container, or waste containment vessel is a nuclear waste containment tank, nuclear waste containment container, or nuclear waste containment vessel.

In some embodiments, the present invention provides a method of painting, priming, or coating a tank, container, vessel, pipe, or any component thereof, the method comprising: applying a paint, a primer, coating, and/or coating material to the tank, container, vessel, pipe, or any component thereof, wherein the paint, primer, coating, and/or coating material comprises a compound of Formula (II), a compound of Formula (II-a), a compound of Formula (II-b), a compound of Formula (IV), a compound of Formula (IV-a), a compound of Formula (IV-b), a compound of Formula (VI), a compound of Formula (VI-a), a compound of Formula (VI-b), compound 1a, compound 1b, compound 1c, compound 1d, or compound 1e, or any combination thereof. In some embodiments, the tank, container, vessel, pipe, or any component thereof is used in the containment, handling, and/or transportation of material(s) comprising molecular iodine ($I_2$), non-radioactive molecular iodine ($I_2$), radioactive iodine (radioactive $I_2$), radioactive molecular iodine ($I_2$), or combination thereof.

In some embodiments, the present invention provides a method of applying a compound to a tank, container, vessel, pipe, or any component thereof, the method comprising: applying a compound to the tank, container, vessel, pipe, or any component thereof, wherein the compound is a compound of Formula (II), a compound of Formula (II-a), a compound of Formula (II-b), a compound of Formula (IV), a compound of Formula (IV-a), a compound of Formula (IV-b), a compound of Formula (VI), a compound of Formula (VI-a), a compound of Formula (VI-b), compound 1a, compound 1b, compound 1c, compound 1d, or compound 1e, or any combination thereof. In some embodiments, the tank, container, vessel, pipe, or any component thereof is used in the containment, handling, and/or transportation of material(s) comprising molecular iodine ($I_2$), non-radioactive molecular iodine ($I_2$), radioactive iodine (radioactive $I_2$), radioactive molecular iodine ($I_2$), or combination thereof.

In some embodiments, the present invention provides a method of applying a composition to a tank, container, vessel, pipe, or any component thereof, the method comprising: applying a composition to the tank, container, vessel, pipe, or any component thereof, wherein the composition comprises a compound of Formula (II), a compound of Formula (II-a), a compound of Formula (II-b), a compound of Formula (IV), a compound of Formula (IV-a), a compound of Formula (IV-b), a compound of Formula (VI), a compound of Formula (VI-a), a compound of Formula (VI-b), compound 1a, compound 1b, compound 1c, compound 1d, or compound 1e, or any combination thereof. In some embodiments, the tank, container, vessel, pipe, or any component thereof is used in the containment, handling, and/or transportation of material(s) comprising molecular iodine ($I_2$), non-radioactive molecular iodine ($I_2$), radioactive iodine (radioactive $I_2$), radioactive molecular iodine ($I_2$), or combination thereof.

In some embodiments, the present invention provides a method of applying an article of manufacture to a tank, container, vessel, pipe, or any component thereof, the method comprising: applying an article of manufacture to the tank, container, vessel, pipe, or any component thereof, wherein the article of manufacture comprises a compound of Formula (II), a compound of Formula (II-a), a compound of Formula (II-b), a compound of Formula (IV), a compound of Formula (IV-a), a compound of Formula (IV-b), a compound of Formula (VI), a compound of Formula (VI-a), a compound of Formula (VI-b), compound 1a, compound 1b, compound 1c, compound 1d, or compound 1e, or any combination thereof. In some embodiments, the tank, container, vessel, pipe, or any component thereof is used in the containment, handling, and/or transportation of material(s) comprising molecular iodine ($I_2$), non-radioactive molecular iodine ($I_2$), radioactive iodine (radioactive $I_2$), radioactive molecular iodine ($I_2$), or combination thereof.

In some embodiments, the medium is aqueous medium, organic medium, or combination thereof. In some embodiments, the medium is water. In some embodiments, the aqueous medium is water. In some embodiments, the medium is a gas, a liquid, or a solid, or combination thereof. In some embodiments, the medium is a liquid. In some embodiments, the medium is at least one liquid. In some embodiments, the medium is at least two liquids. In some embodiments, the medium is at least two liquids, wherein each liquid is different from one another. In some embodiments, the at least two liquids are miscible. In some embodiments, the at least two liquids are not miscible. In some embodiments, the medium is an organic solvent. In some embodiments, the organic medium is an organic solvent. Non-limiting examples of an organic medium or an organic solvent include an aromatic organic compound, or a non-aromatic organic compound. Non-limiting examples of an organic medium or an organic solvent include toluene, xylene, benzene, tetrahydrofuran, diethylether, pentane, hexane, hexanes, heptane, octane, methylethylketone, ethylacetate, etc.

In some embodiments, the medium comprises aqueous medium, organic medium, or combination thereof. In some embodiments, the medium comprises water. In some embodiments, the aqueous medium comprises water. In some embodiments, the medium comprises a gas, a liquid, or a solid, or combination thereof. In some embodiments, the medium comprises a liquid. In some embodiments, the medium comprises at least one liquid. In some embodiments, the medium comprises at least two liquids. In some embodiments, the medium comprises at least two liquids, wherein each liquid is different from one another. In some embodiments, the at least two liquids are miscible. In some embodiments, the at least two liquids are not miscible. In some embodiments, the medium comprises an organic solvent. In some embodiments, the organic medium comprises an organic solvent. Non-limiting examples of an organic medium or an organic solvent include an aromatic organic compound, or a non-aromatic organic compound. Non-limiting examples of an organic medium or an organic solvent include toluene, xylene, benzene, tetrahydrofuran, diethylether, pentane, hexane, hexanes, heptane, octane, methylethylketone, ethylacetate, etc.

Additional embodiments include those listed below:

Embodiment 1A. A compound of Formula (II):

Formula (II)

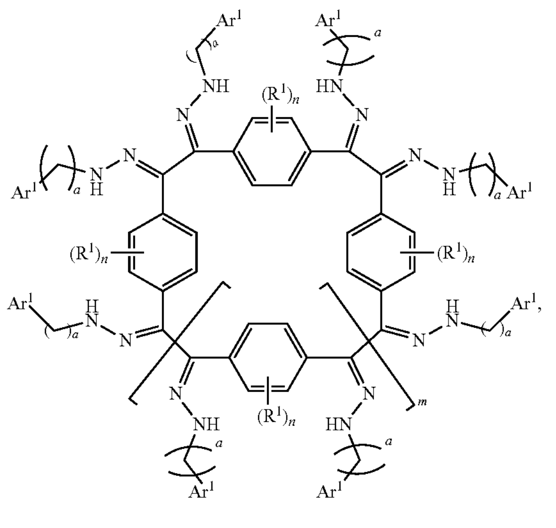

wherein:

m is 0, 1, 2, 3, or 4;

n is 0, 1, 2, 3 or 4;

a is 0, 1 or 2;

$Ar^1$ is optionally substituted aryl, or optionally substituted heteroaryl; and $R^1$ is an electron withdrawing group, or an electron donating group.

Embodiment 2A. The compound of embodiment 1A, wherein $Ar^1$ is selected from the group consisting of:

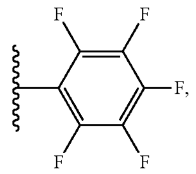 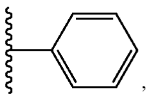, 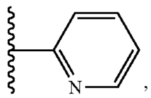, 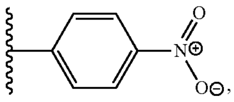, and 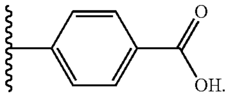

Embodiment 3A. The compound of embodiment 1A, wherein the compound of Formula (II) is a compound of Formula (II-a):

Formula (II-a)

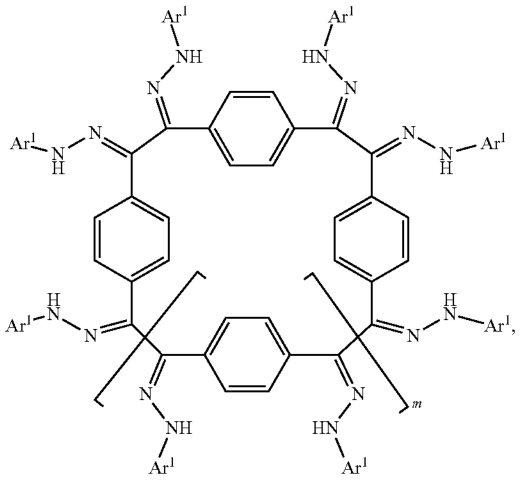

wherein:

m is 0, 1, 2, 3, or 4, and $Ar^1$ is optionally substituted aryl, or optionally substituted heteroaryl.

Embodiment 4A. The compound of embodiment 3A, wherein $Ar^1$ is selected from the group consisting of:

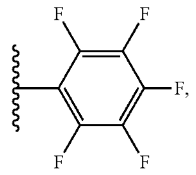 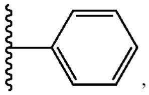, 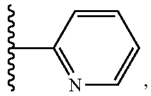, 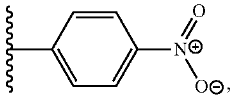, and 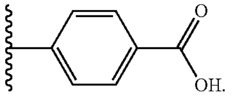

Embodiment 5A. The compound of embodiment 1A, wherein the compound of Formula (II) is a compound of Formula (II-b):

Formula (II-b)

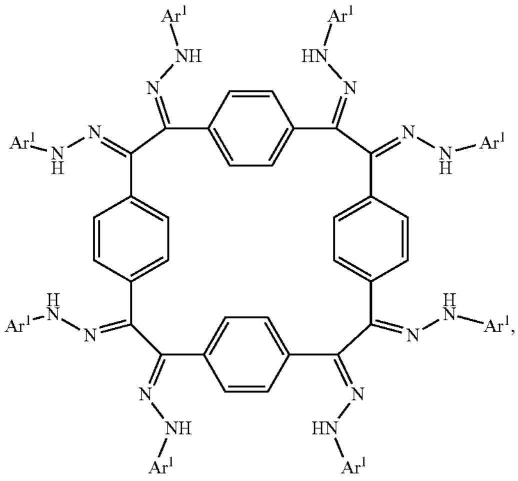

wherein:

$Ar^1$ is optionally substituted aryl, or optionally substituted heteroaryl.

Embodiment 6A. The compound of embodiment 5A, wherein $Ar^1$ is selected from the group consisting of:

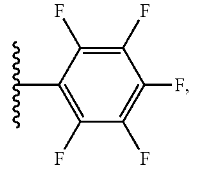 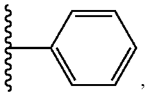, 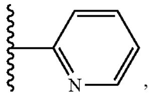, 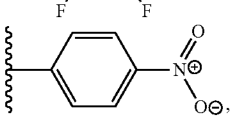, and 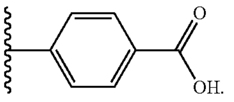

Embodiment 7A. The compound of embodiment 1A, wherein the compound of Formula (II) is selected from the group consisting of:

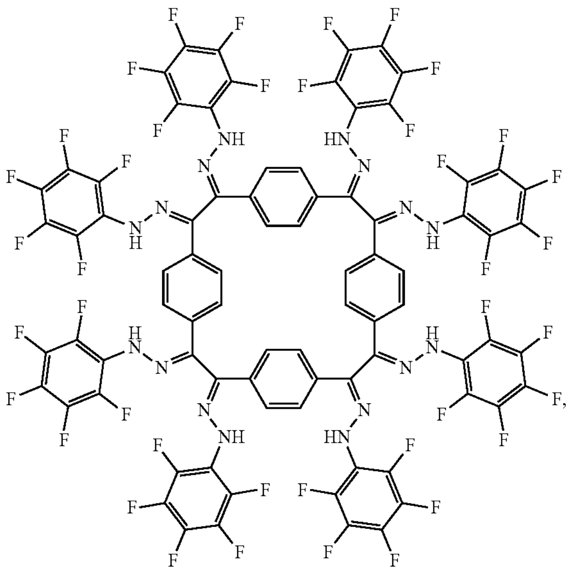

-continued

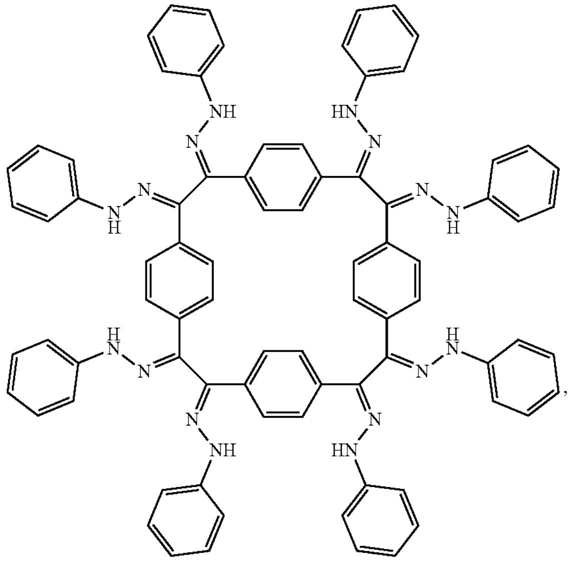

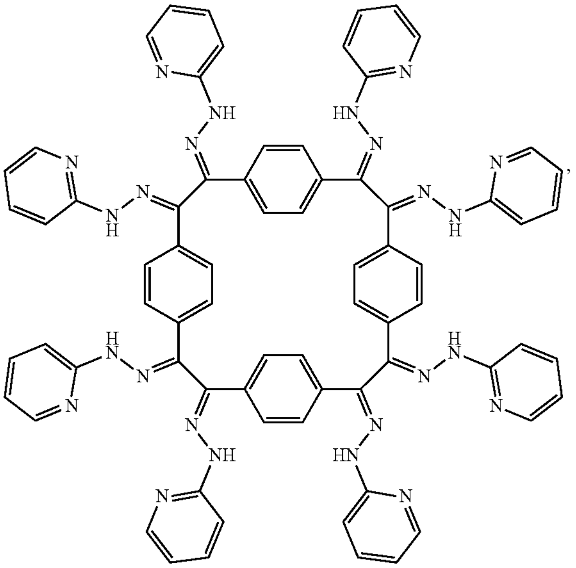

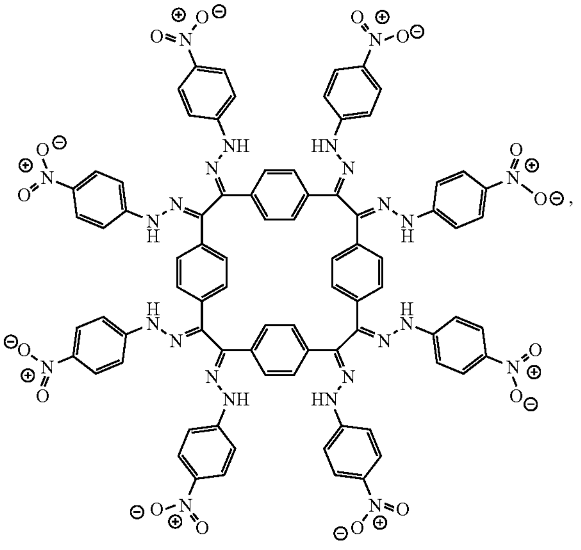

and

-continued

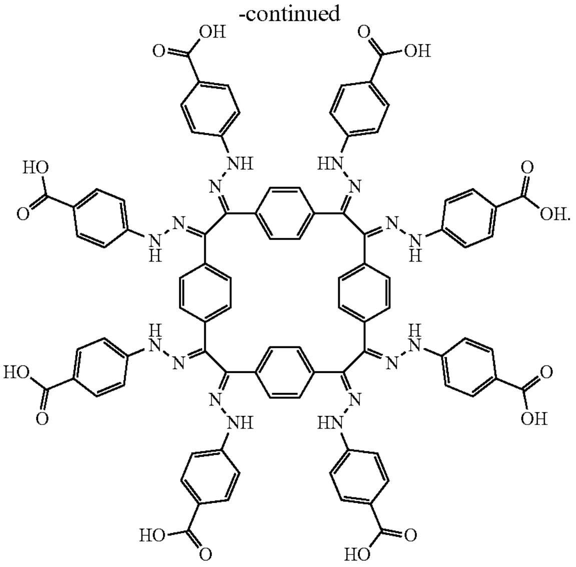

Embodiment 8A. A method for removing a material from a medium, the method comprising:

providing a medium comprising a material;

contacting the medium with a compound of embodiment 1A;

capturing the material with the compound; and removing the compound that contains the captured material from the medium.

Embodiment 9A. The method of embodiment 8A, further comprising removing the captured material from the compound.

Embodiment 10A. The method of embodiment 8A, wherein the material is non-radioactive molecular iodine ($I_2$), radioactive molecular iodine ($I_2$), or combination thereof.

Embodiment 11A. The method of embodiment 8A, wherein the medium is aqueous medium, organic medium, or combination thereof.

Embodiment 12A. A method for removing a material from a medium, the method comprising:

providing a medium comprising a material;

contacting the medium with a compound of embodiment 7A;

capturing the material with the compound; and removing the compound that contains the captured material from the medium.

Embodiment 13A. The method of embodiment 12A, further comprising removing the captured material from the compound.

Embodiment 14A. The method of embodiment 12A, wherein the material is non-radioactive molecular iodine ($I_2$), radioactive molecular iodine ($I_2$), or combination thereof.

Embodiment 15A. The method of embodiment 12A, wherein the medium is aqueous medium, organic medium, or combination thereof.

Embodiment 16A. A method of making a compound of embodiment 1A, the method comprising:

reacting a compound of Formula (I) with a compound of Formula (VII) to obtain a compound of Formula (II) of embodiment 1A, wherein the compound of Formula (I) is:

Formula (I)

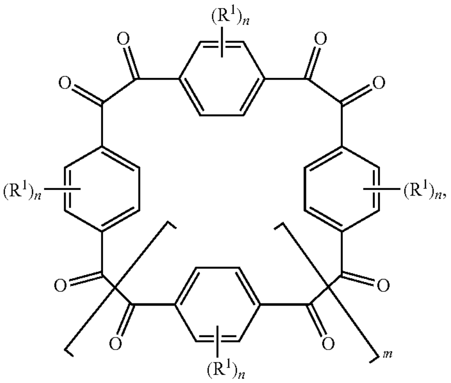

wherein:

m is 0, 1, 2, 3, or 4;

n is 0, 1, 2, 3 or 4; and $R^1$ is an electron withdrawing group, or an electron donating group; and wherein the compound of Formula (VII) is:

Formula (VII)

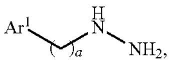

wherein, $Ar^1$ is optionally substituted aryl, or optionally substituted heteroaryl; and a is 0, 1 or 2.

Embodiment 17A. An article of manufacture comprising a compound of embodiment 1A.

Embodiment 18A. The article of manufacture of embodiment 17A, wherein the article of manufacture is a paint, a primer, a coating, or a coating material.

Embodiment 19A. A composition comprising a compound of embodiment 1A.

Embodiment 20A. The composition of embodiment 19A, wherein the compound is selected from the group consisting of:

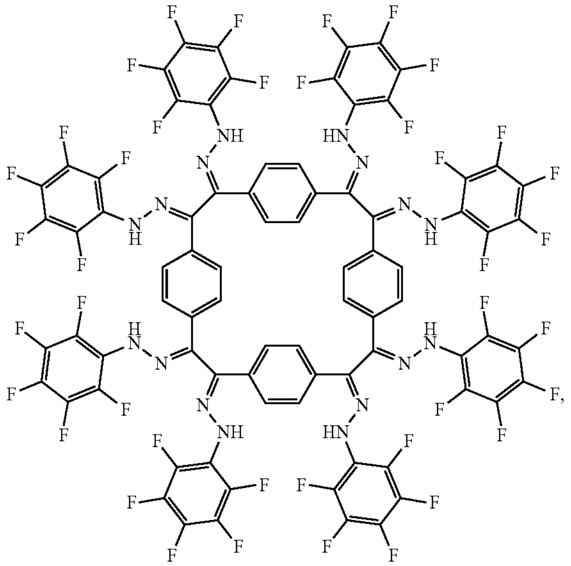

-continued

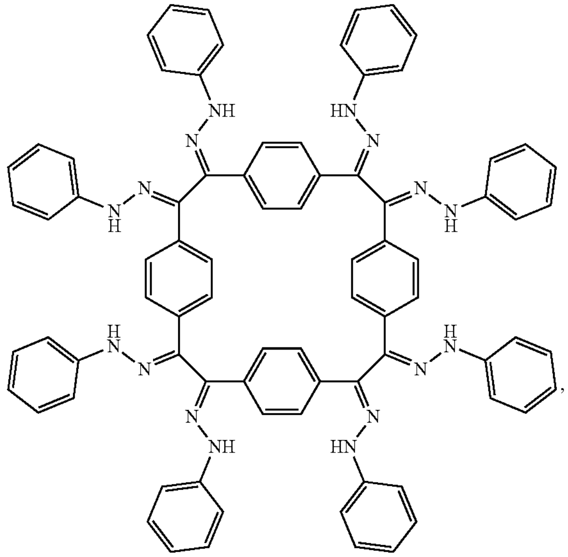

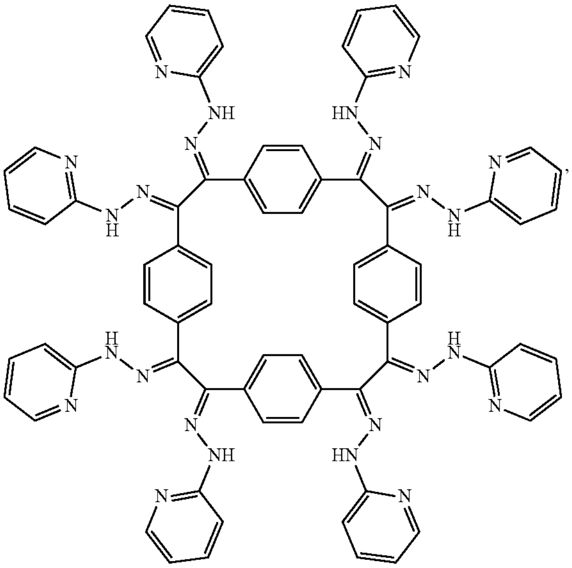

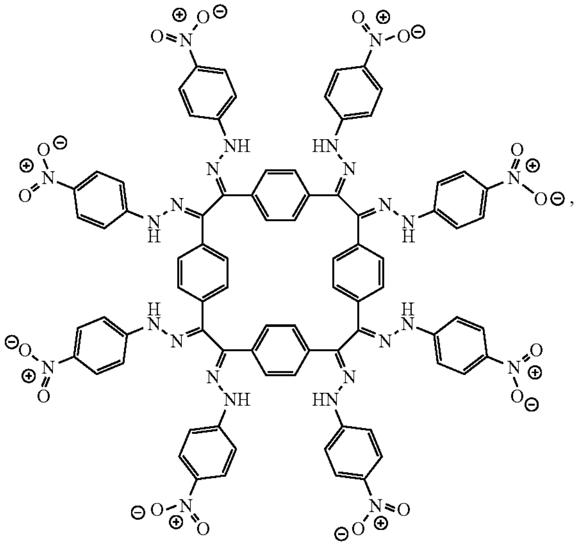

and

-continued

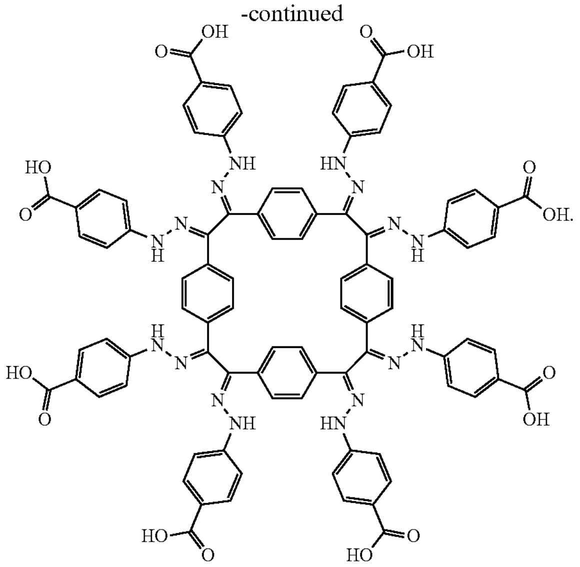

Embodiment 21A. An article of manufacture comprising a compound of embodiment 7A.

Embodiment 22A. The article of manufacture of embodiment 21A, wherein the article of manufacture is a paint, a primer, or a coating material.

Additional embodiments include those listed below:

Embodiment 1B. A compound of Formula (IV):

Formula (IV)

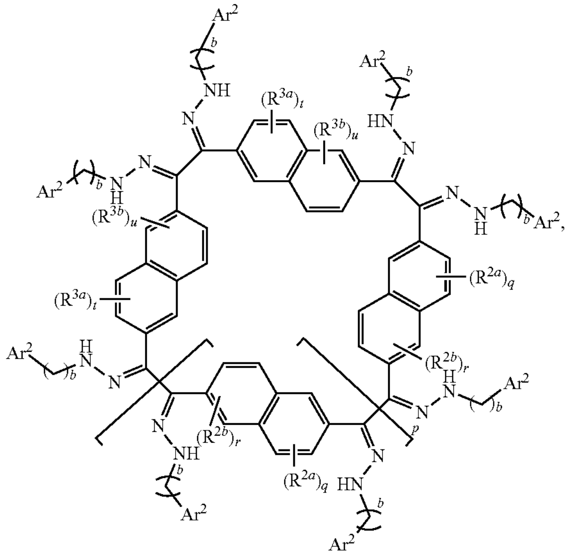

wherein:

p is 0, 1, 2, 3, or 4;

q is 0, 1, 2, or 3;

r is 0, 1, 2, or 3;

b is 0, 1, or 2;

$Ar^2$ is optionally substituted aryl, or optionally substituted heteroaryl;

$R^{2a}$ is an electron withdrawing group, or an electron donating group; and $R^{2b}$ is an electron withdrawing group, or an electron donating group.

Embodiment 2B. The compound of embodiment 1B, wherein $Ar^2$ is selected from the group consisting of:

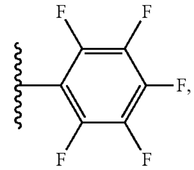 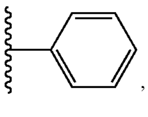, 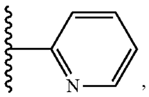,

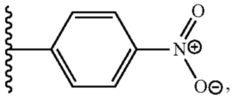, and 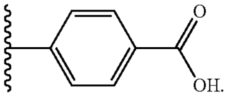

Embodiment 3B. A compound of embodiment 1B, wherein the compound is a compound of Formula (IV-a):

Formula (IV-a)

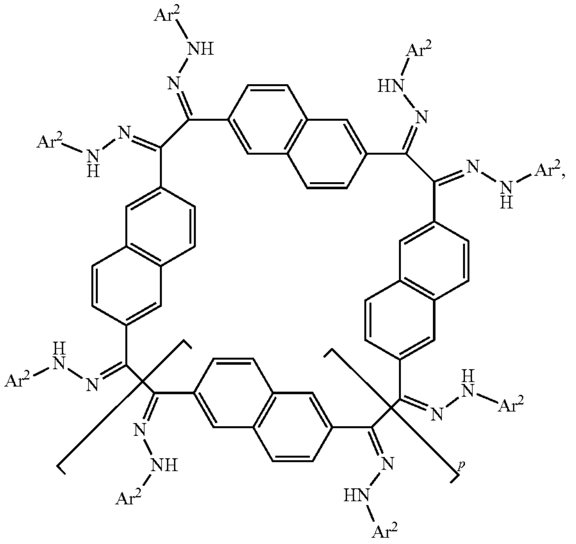

wherein:

p is 0, 1, 2, 3, or 4; and $Ar^2$ is optionally substituted aryl, or optionally substituted heteroaryl Embodiment 4B. The compound of embodiment 3B, wherein $Ar^2$ is selected from the group consisting of:

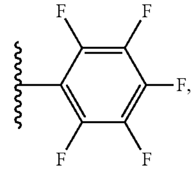 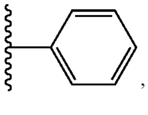, 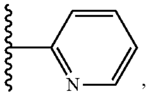,

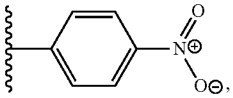, and 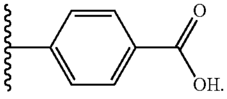

Embodiment 5B. A compound of embodiment 1B, wherein the compound is a compound of Formula (IV-b):

Formula (IV-b)
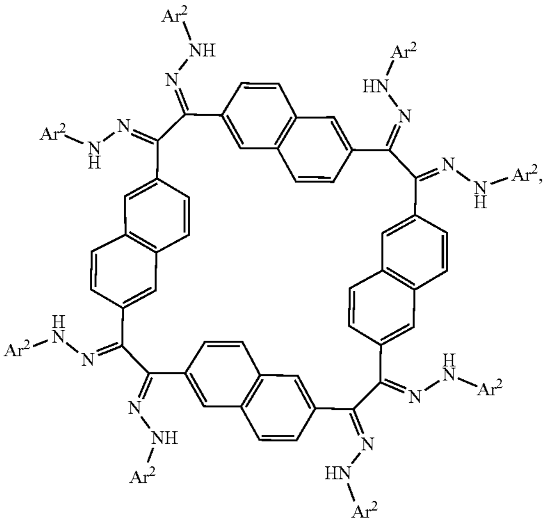
wherein:
$Ar^2$ is optionally substituted aryl, or optionally substituted heteroaryl.
Embodiment 6B. The compound of embodiment 5B, wherein $Ar^2$ is selected from the group consisting of:
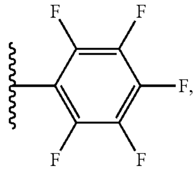,
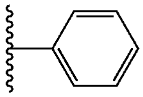,
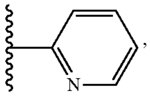,
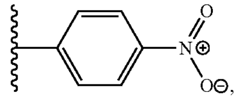,
and
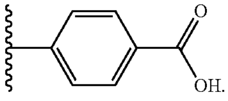.
Embodiment 7B. The compound of embodiment 1B, wherein the compound of Formula (IV) is selected from the group consisting of:
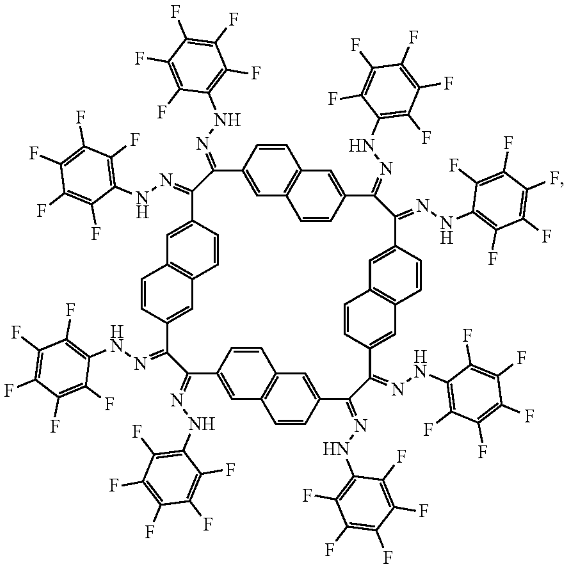
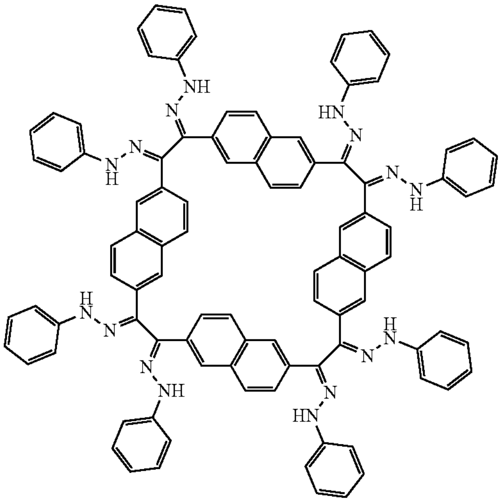, -continued
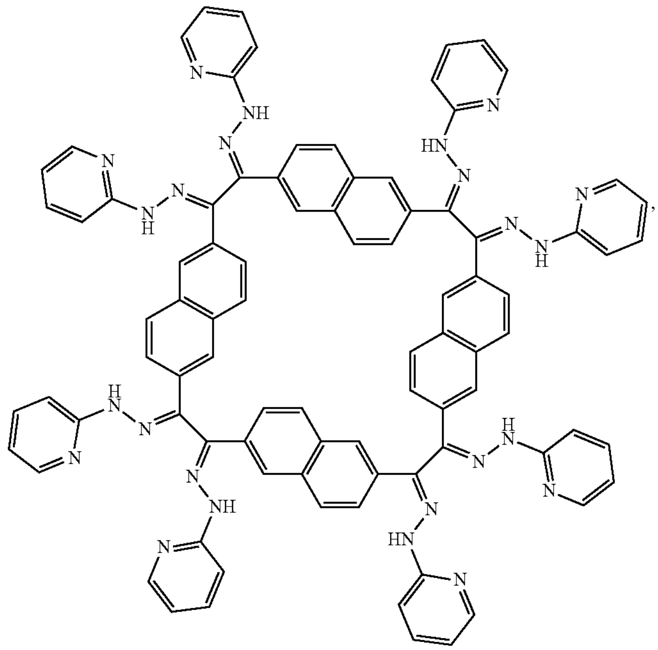
,
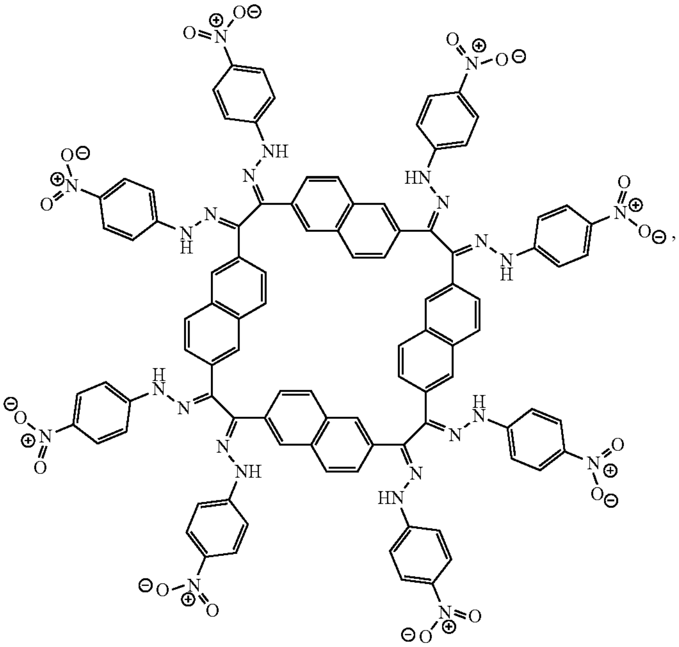
, and -continued

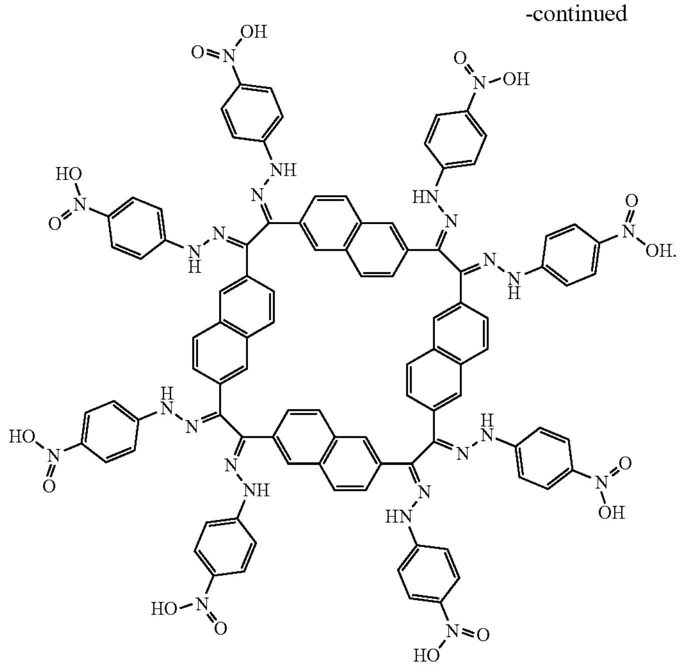

Embodiment 8B. A method for removing a material from a medium, the method comprising:

providing a medium comprising a material;

contacting the medium with a compound of embodiment 1B;

capturing the material with the compound; and removing the compound that contains the captured material from the medium.

Embodiment 9B. The method of embodiment 8B, further comprising removing the captured material from the compound.

Embodiment 10B. The method of embodiment 8B, wherein the material is non-radioactive molecular iodine ($I_2$), radioactive molecular iodine ($I_2$), or combination thereof.

Embodiment 11B. The method of embodiment 8B, wherein the medium is aqueous medium, organic medium, or combination thereof.

Embodiment 12B. A method for removing a material from a medium, the method comprising:

providing a medium comprising a material;

contacting the medium with a compound of embodiment 7B;

capturing the material with the compound; and removing the compound that contains the captured material from the medium.

Embodiment 13B. The method of embodiment 12B, further comprising removing the captured material from the compound.

Embodiment 14B. The method of embodiment 12B, wherein the material is non-radioactive molecular iodine ($I_2$), radioactive molecular iodine ($I_2$), or combination thereof.

Embodiment 15B. The method of embodiment 12B, wherein the medium is aqueous medium, organic medium, or combination thereof.

Embodiment 16B. A method of making a compound of embodiment 1B, the method comprising:

reacting a compound of Formula (II) with a compound of Formula (VII) to obtain a compound of Formula (IV) of embodiment 1B, wherein the compound of Formula (III) is:

Formula (III)

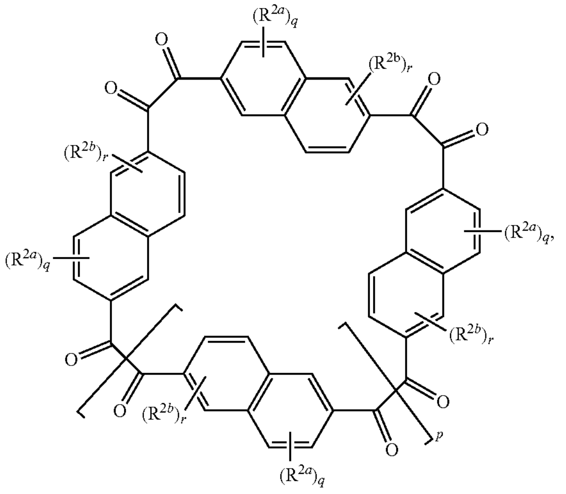

wherein:

p is 0, 1, 2, 3, or 4;

q is 0, 1, 2, or 3;

r is 0, 1, 2, or 3;

$R^{2a}$ is an electron withdrawing group, or an electron donating group; and $R^{2b}$ is an electron withdrawing group, or an electron donating group; and wherein the compound of Formula (VIII) is:

Formula (VIII)

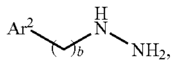

wherein, $Ar^2$ is optionally substituted aryl, or optionally substituted heteroaryl; and b is 0, 1, or 2.

Embodiment 17B. An article of manufacture comprising a compound of Formula (IV) of embodiment 1B.

Embodiment 18B. The article of manufacture of embodiment 17B, wherein the article of manufacture is a paint, a primer, a coating, or a coating material.

Embodiment 19B. A composition comprising a compound of embodiment 1B.

Embodiment 20B. The composition of embodiment 19B, wherein the compound is selected from the group consisting of:

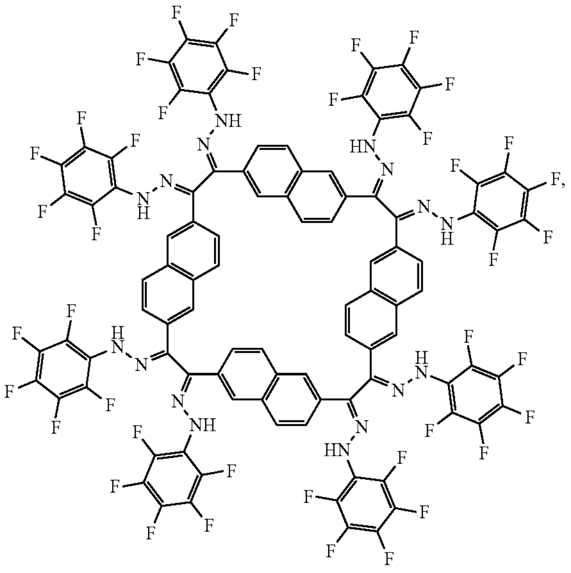

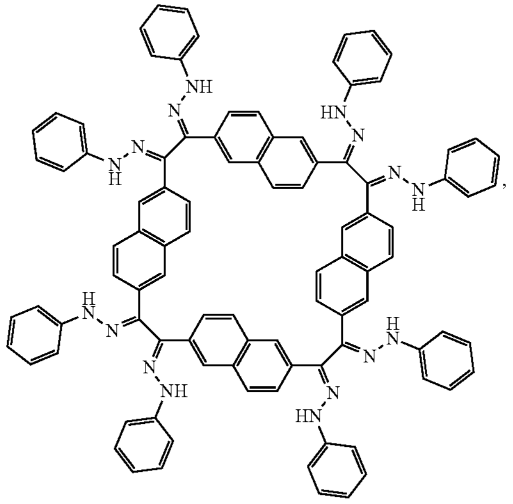

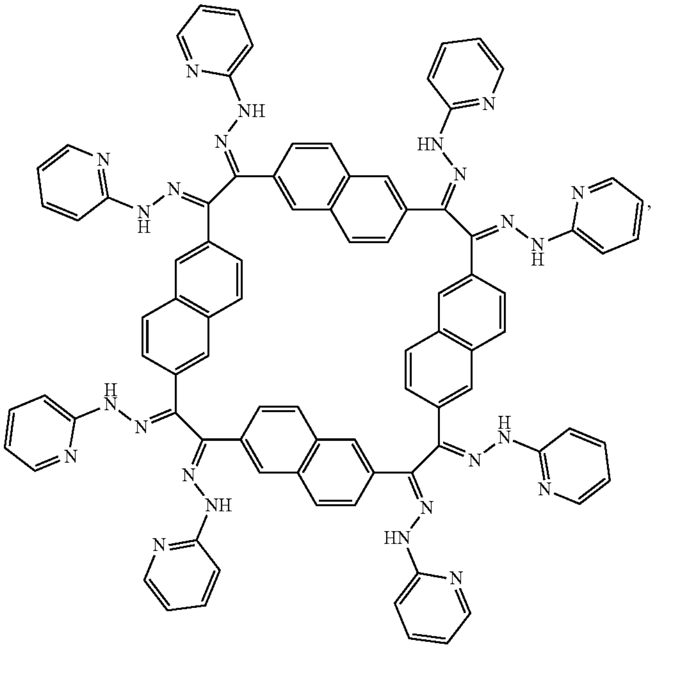

-continued
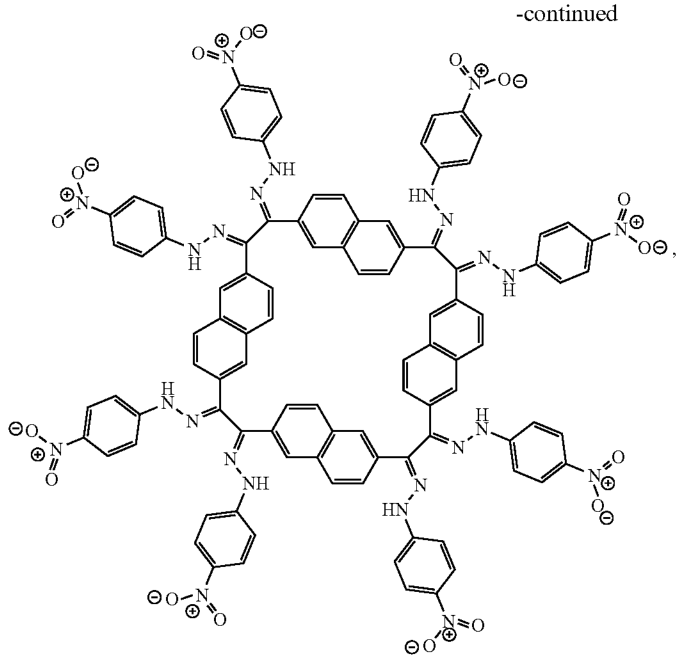
, and
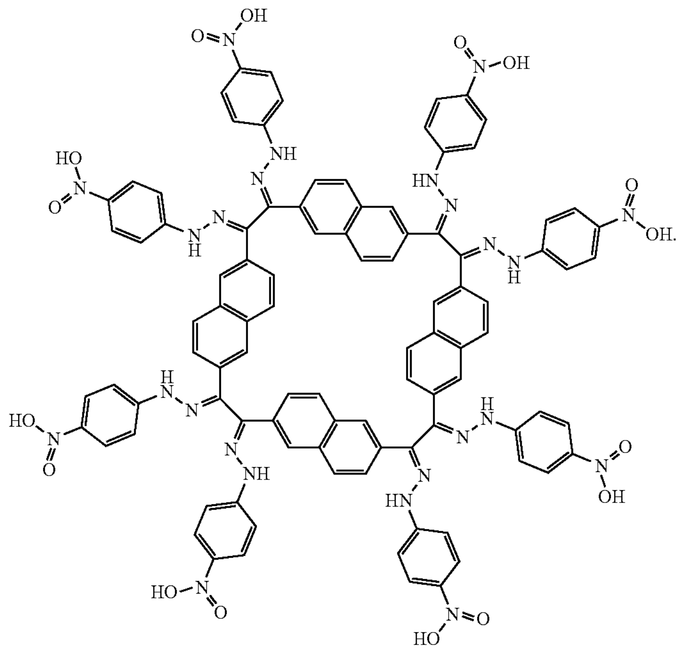
Embodiment 21B. An article of manufacture comprising a compound of embodiment 7B.
Embodiment 22B. The article of manufacture of embodiment 21B, wherein the article of manufacture is a paint, a primer, or a coating material.

Additional embodiments include those listed below:

Embodiment 1C. A compound of Formula (VI):

Formula (VI)

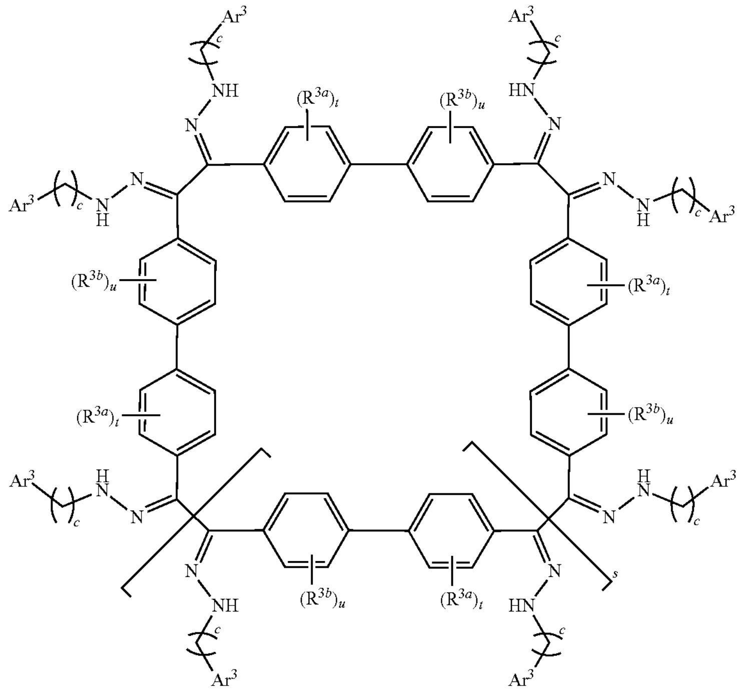

wherein:

s is 0, 1, 2, 3, or 4;

t is 0, 1, 2, 3, or 4;

u is 0, 1, 2, 3, or 4;

c is 0, 1, or 2;

$Ar^3$ is optionally substituted aryl, or optionally substituted heteroaryl;

$R^{3a}$ is an electron withdrawing group, or an electron donating group; and $R^{3b}$ is an electron withdrawing group, or an electron donating group.

Embodiment 2C. The compound of embodiment 1C, wherein $Ar^2$ is selected from the group consisting of:

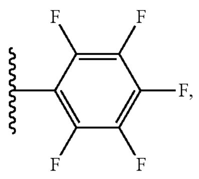 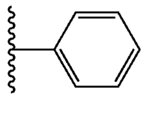, 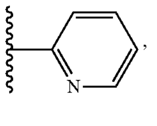,

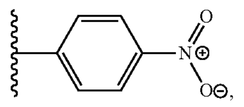, and 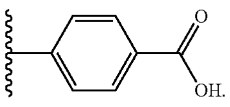

Embodiment 3C. A compound of embodiment 1C, wherein the compound is a compound of Formula (VI-a):

Formula (VI-a)

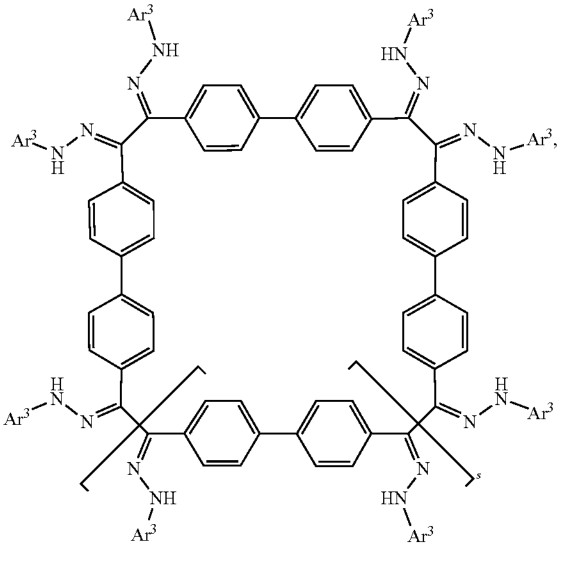

wherein:

s is 0, 1, 2, 3, or 4;

$Ar^3$ is optionally substituted aryl, or optionally substituted heteroaryl.

Embodiment 4C. The compound of embodiment 3C, wherein $Ar^2$ is selected from the group consisting of:

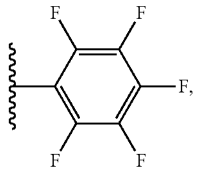 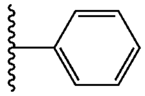, 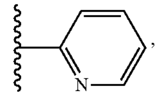,

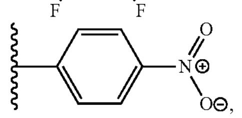 and 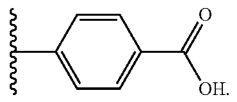

Embodiment 5C. A compound of embodiment 1C, wherein the compound is a compound of Formula (VI-b):

Formula (VI-b)

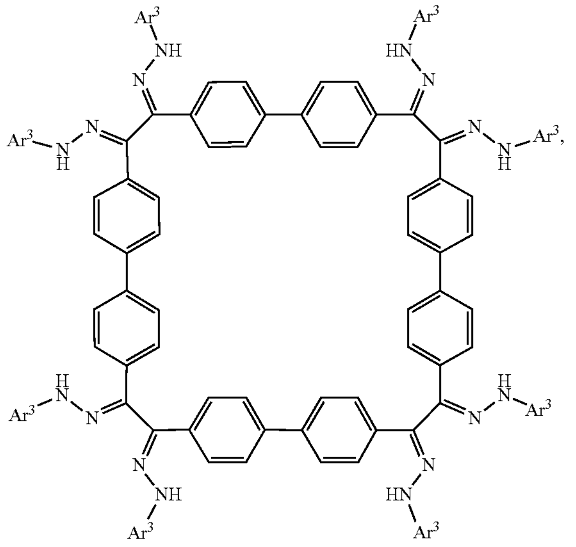

wherein:

$Ar^3$ is optionally substituted aryl, or optionally substituted heteroaryl.

Embodiment 6C. The compound of embodiment 5C, wherein $Ar^2$ is selected from the group consisting of:

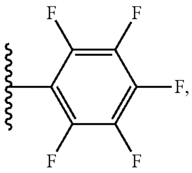 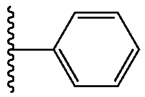, 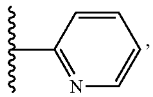,

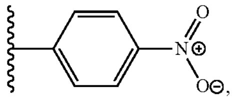 and 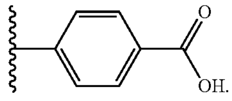

Embodiment 7C. The compound of embodiment 1C, wherein the compound of Formula (VI) is selected from the group consisting of:

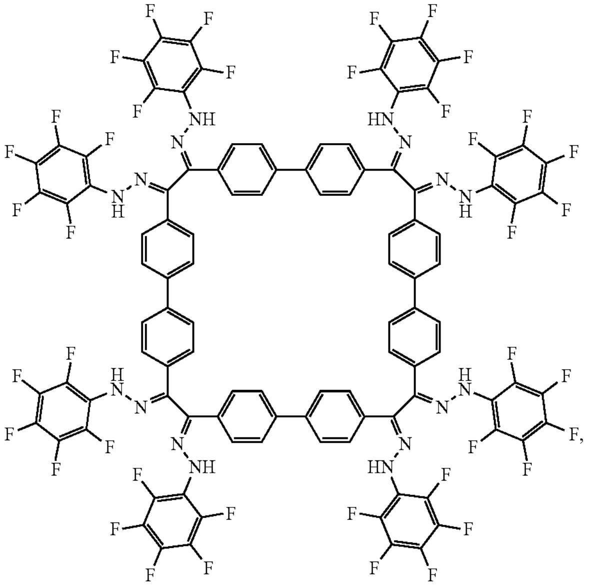,

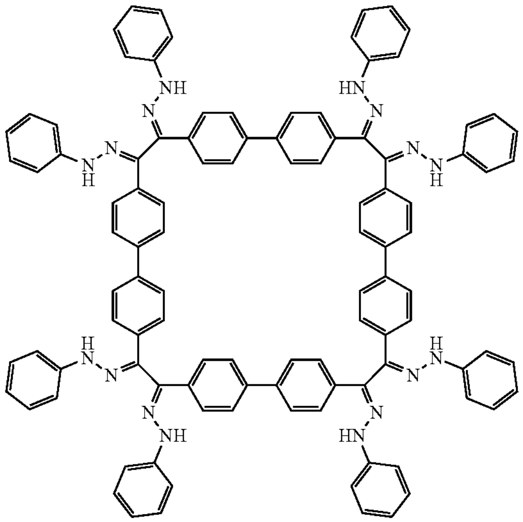,

-continued
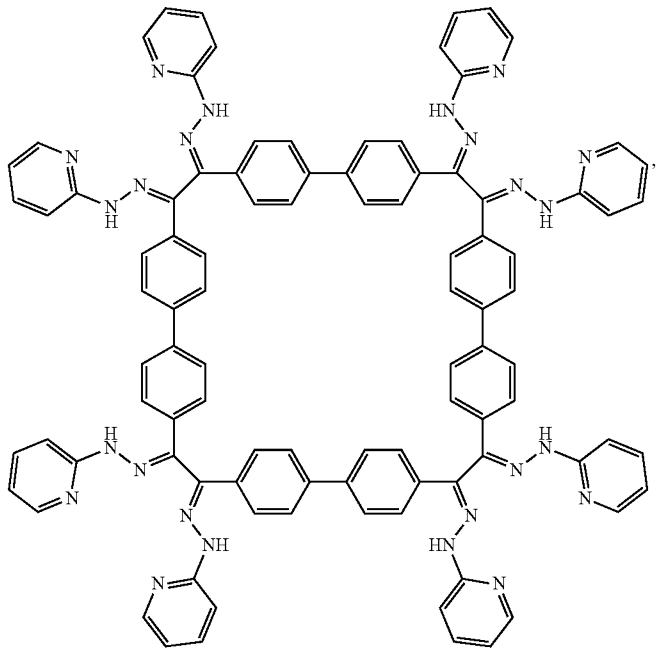
,
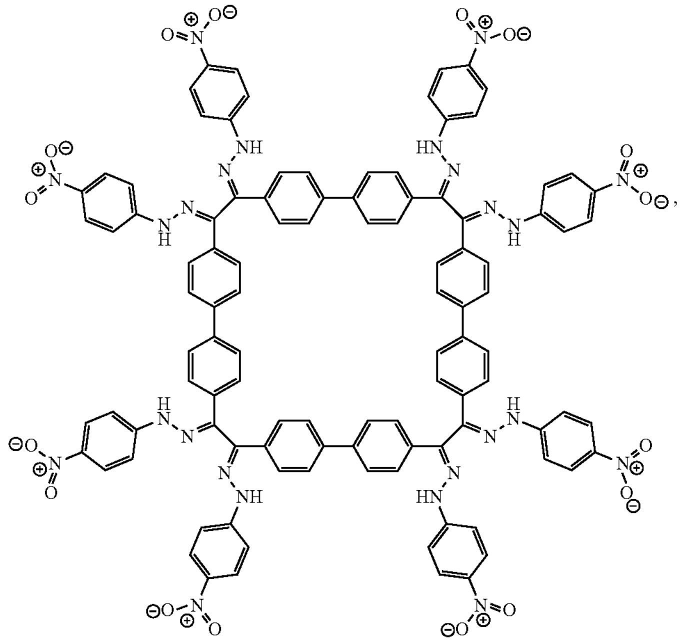
,

-continued

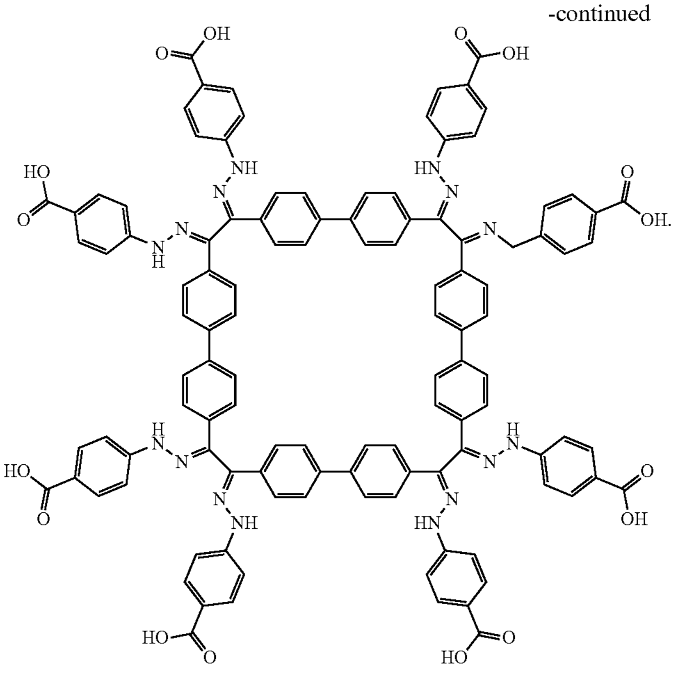

Embodiment 8C. A method for removing a material from a medium, the method comprising:

providing a medium comprising a material;

contacting the medium with a compound of embodiment 1C;

capturing the material with the compound; and removing the compound that contains the captured material from the medium.

Embodiment 9C. The method of embodiment 8C, further comprising removing the captured material from the compound.

Embodiment 10C. The method of embodiment 8C, wherein the material is non-radioactive molecular iodine ($I_2$), radioactive molecular iodine ($I_2$), or combination thereof.

Embodiment 11C. The method of embodiment 8C, wherein the medium is aqueous medium, organic medium, or combination thereof.

Embodiment 12C. A method for removing a material from a medium, the method comprising:

providing a medium comprising a material;

contacting the medium with a compound of embodiment 7C;

capturing the material with the compound; and removing the compound that contains the captured material from the medium.

Embodiment [13]C. The method of embodiment 12C, further comprising removing the captured material from the compound.

Embodiment 14C. The method of embodiment 12C, wherein the material is non-radioactive molecular iodine ($I_2$), radioactive molecular iodine ($I_2$), or combination thereof.

Embodiment 15C. The method of embodiment 12C, wherein the medium is aqueous medium, organic medium, or combination thereof.

Embodiment 16C. A method of making a compound of embodiment 1C, the method comprising:

reacting a compound of Formula (V) with a compound of Formula (IX) to obtain a compound of Formula (VI) of embodiment 1C, wherein the compound of Formula (V) is:

Formula (V)

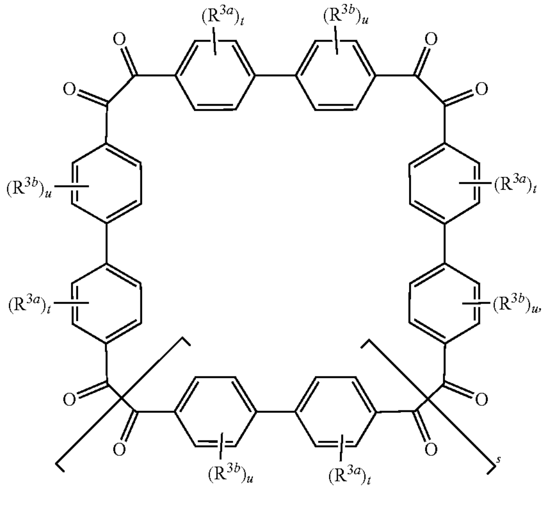

wherein:

s is 0, 1, 2, 3, or 4;

t is 0, 1, 2, 3, or 4;

u is 0, 1, 2, 3, or 4;

$Ar^2$ is optionally substituted aryl, or optionally substituted heteroaryl;

$R^{3a}$ is an electron withdrawing group, or an electron donating group; and $R^{3b}$ is an electron withdrawing group, or an electron donating group, and wherein the compound of Formula (IX) is:

Formula (IX)

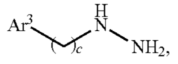

wherein, $Ar^3$ is optionally substituted aryl, or optionally substituted heteroaryl; and c is 0, 1, or 2.

Embodiment 17C. An article of manufacture comprising a compound of embodiment 1C.

Embodiment 18C. The article of manufacture of embodiment 17C, wherein the article of manufacture is a paint, a primer, a coating, or a coating material.

Embodiment 19C. A composition comprising a compound of embodiment 1C.

Embodiment 20C. The composition of embodiment 19C, wherein the compound is selected from the group consisting of:

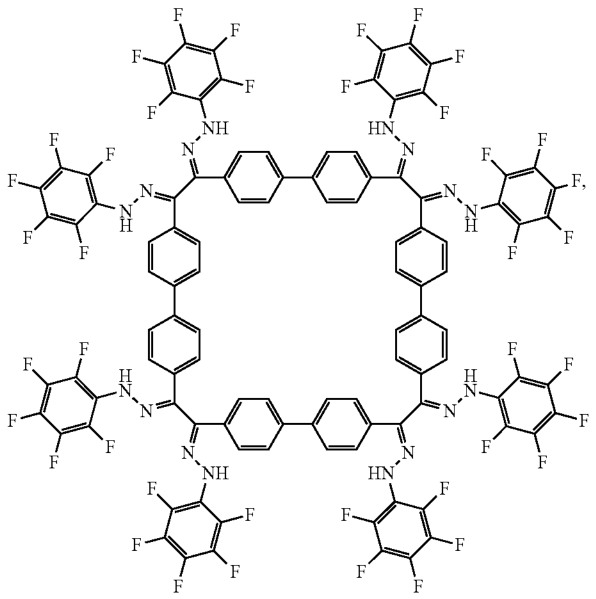

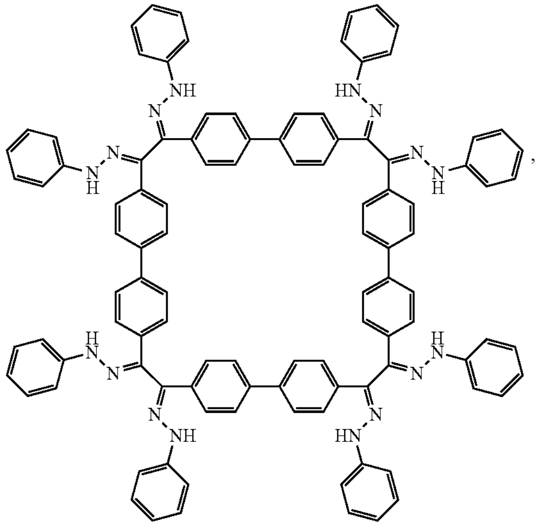

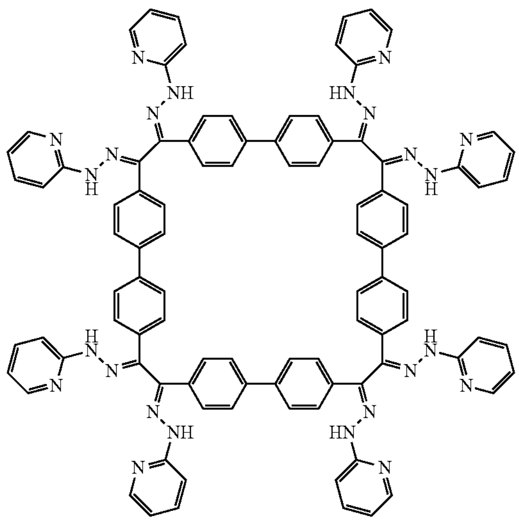

,

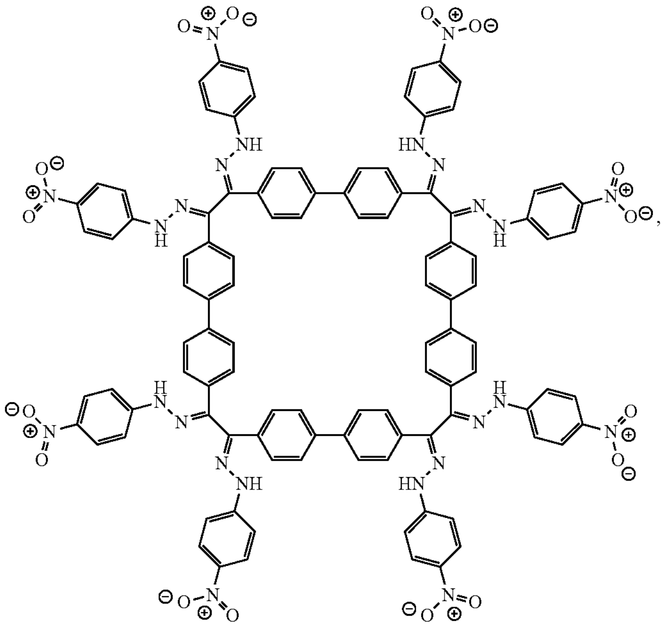 [SMILES: O=C(O)c1ccc(N/N=C2/C(=N/Nc3ccc(C(=O)O)cc3)c3ccc(cc3)-c3ccc(cc3)C(=N\Nc3ccc(C(=O)O)cc3)/C(=N/Nc3ccc(C(=O)O)cc3)c3ccc(cc3)-c3ccc(cc3)C(=N\Nc3ccc(C(=O)O)cc3)/C(=N/Nc3ccc(C(=O)O)cc3)c3ccc(cc3)-c3ccc(cc3)C(=N\Nc3ccc(C(=O)O)cc3)/C(=N/Nc3ccc(C(=O)O)cc3)c3ccc(cc3)-c3ccc2cc3)cc1]

-continued

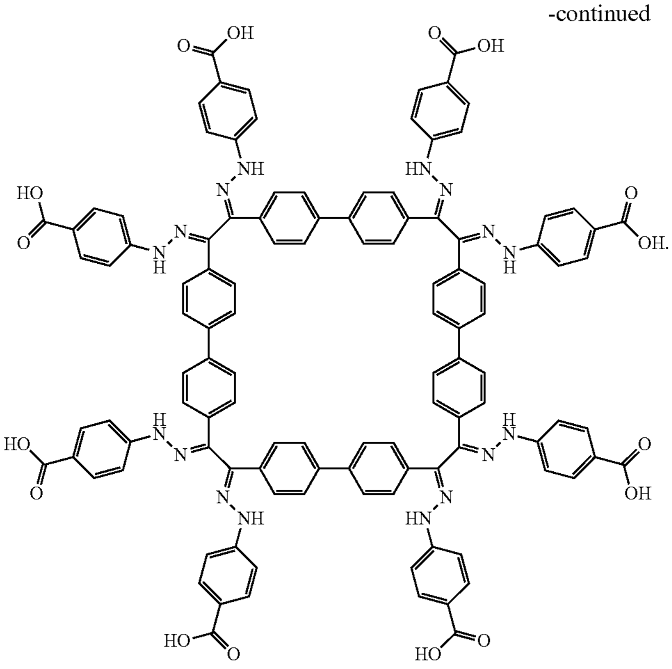

Embodiment 21C. An article of manufacture comprising a compound of embodiment 7C.

Embodiment 22C. The article of manufacture of embodiment 21C, wherein the article of manufacture is a paint, a primer, a coating, or a coating material.

Additional embodiments include those listed below:

Embodiment 1D. A composition, comprising at least one compound, wherein the at least one compound is selected from the group consisting of a compound of Formula (II), a compound of Formula (IV), and a compound of Formula (VI), and any combination thereof: wherein the compound of Formula (II) is:

Formula (II)

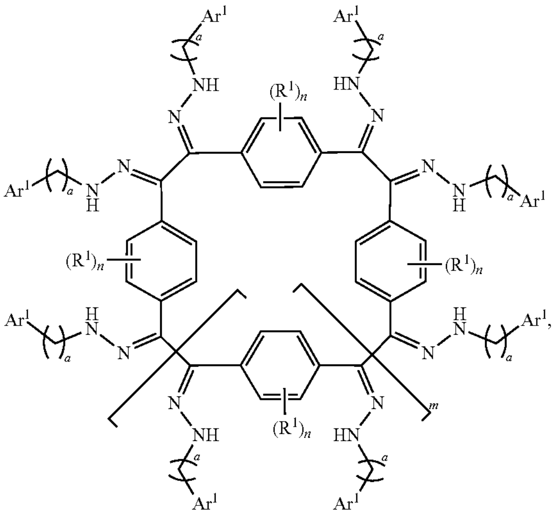

wherein:

m is 0, 1, 2, 3, or 4;

n is 0, 1, 2, 3 or 4;

a is 0, 1 or 2;

$Ar^1$ is optionally substituted aryl, or optionally substituted heteroaryl; and $R^1$ is an electron withdrawing group, or an electron donating group;

wherein the compound of Formula (IV) is:

Formula (IV)

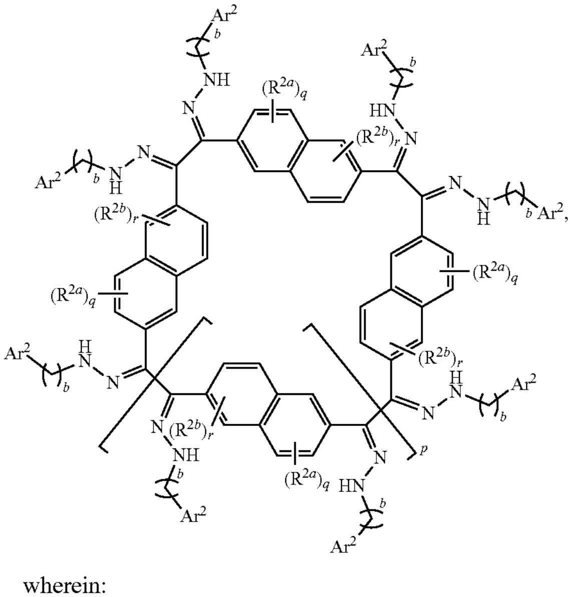

wherein:

p is 0, 1, 2, 3, or 4;

q is 0, 1, 2, or 3;

r is 0, 1, 2, or 3;

b is 0, 1, or 2;

$Ar^2$ is optionally substituted aryl, or optionally substituted heteroaryl;

$R^{2a}$ is an electron withdrawing group, or an electron donating group; and $R^{2b}$ is an electron withdrawing group, or an electron donating group; and wherein the compound of Formula (VI) is:

Formula (VI)

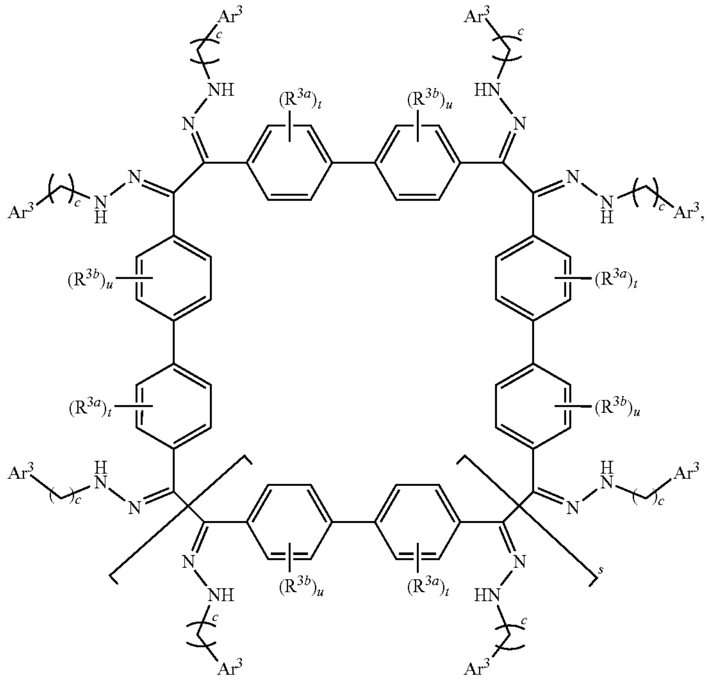

wherein:

s is 0, 1, 2, 3, or 4;

t is 0, 1, 2, 3, or 4;

u is 0, 1, 2, 3, or 4;

c is 0, 1, or 2;

$Ar^3$ is optionally substituted aryl, or optionally substituted heteroaryl;

$R^{3a}$ is an electron withdrawing group, or an electron donating group; and $R^{3b}$ is an electron withdrawing group, or an electron donating group.

Embodiment 2D: The composition of embodiment 1D, wherein the compound of Formula (II) is a compound of Formula (II-a):

Formula (II-a)

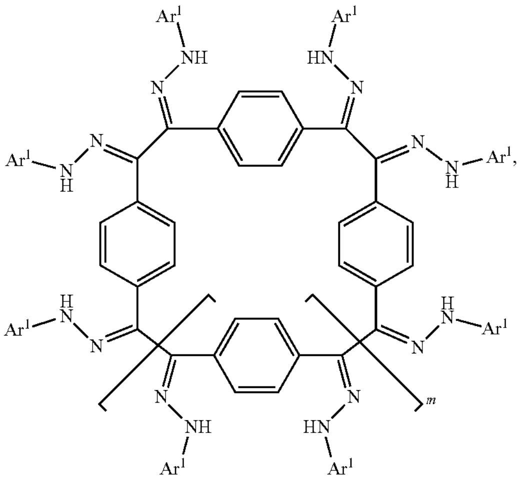

wherein:

m is 0, 1, 2, 3, or 4; and $Ar^1$ is optionally substituted aryl, or optionally substituted heteroaryl;

wherein the compound of Formula (IV) is a compound of Formula (IV-a):

Formula (IV-a)

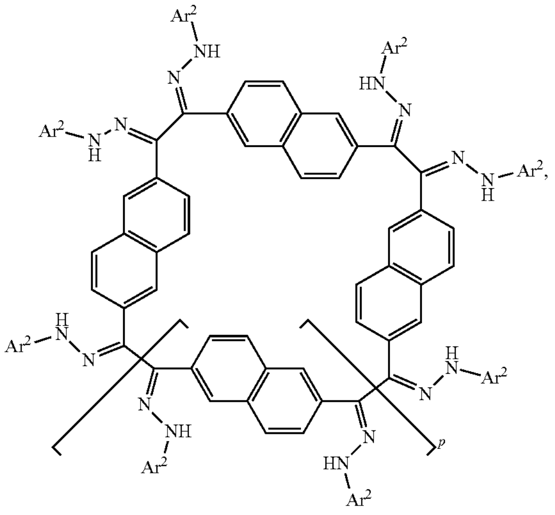

wherein:

p is 0, 1, 2, 3, or 4; and $Ar^3$ is optionally substituted aryl, or optionally substituted heteroaryl; and wherein the compound of Formula (VI) is a compound of Formula (VI-a).

Formula (VI-a)

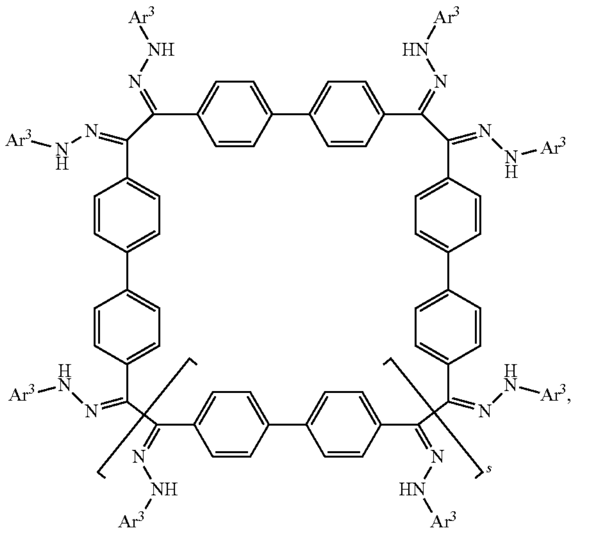

wherein:

s is 0, 1, 2, 3, or 4;

$Ar^3$ is optionally substituted aryl, or optionally substituted heteroaryl.

Embodiment 3D: The composition of embodiment 1D or embodiment 2D, wherein the compound of Formula (II) or the compound of Formula (II-a) is a compound of Formula (II-b):

Formula (II-b)

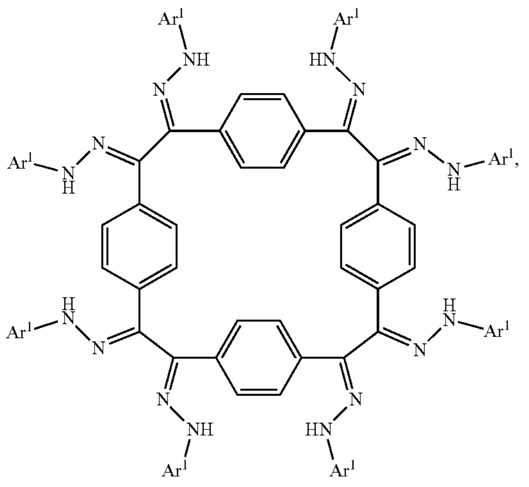

wherein: $Ar^1$ is optionally substituted aryl, or optionally substituted heteroaryl.

Embodiment 4D: The composition of embodiment 1D or embodiment 2D, wherein the compound of Formula (IV) or the compound of Formula (IV-a) is a compound of Formula (IV-b):

Formula (IV-b)

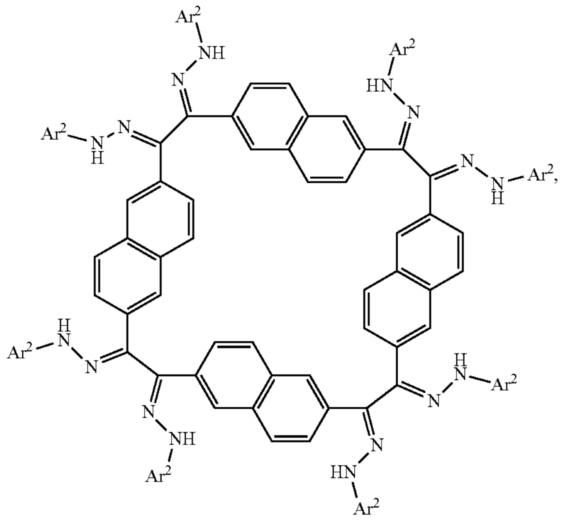

wherein:

$Ar^2$ is optionally substituted aryl, or optionally substituted heteroaryl.

Embodiment 5D. The composition of embodiment 1D or embodiment 2D, wherein the compound of Formula (VI) or the compound of Formula (VI-a) is a compound of Formula (VI-b):

Formula (VI-b)

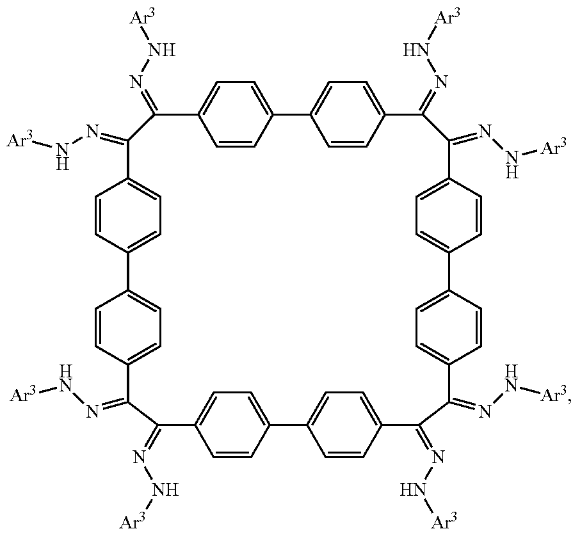

wherein:

$Ar^3$ is optionally substituted aryl, or optionally substituted heteroaryl.

Embodiment 6D: The composition of embodiment 1D, or embodiment 2D, or embodiment 3D, or embodiment 4D, or embodiment 5D, wherein $Ar^1$, $Ar^2$, or $Ar^3$ is selected from the group consisting of.

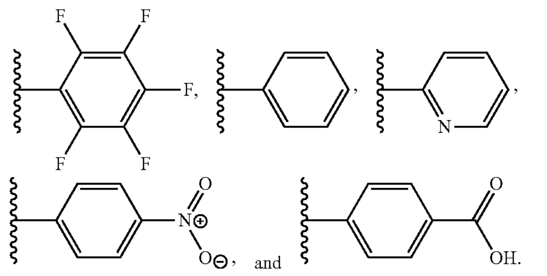
Embodiment 7D: The composition of embodiment 1D or embodiment 2D or embodiment 3D, wherein the compound of Formula (II) or the compound of Formula (II-a) or the compound of Formula (II-b) is selected from the group consisting of:
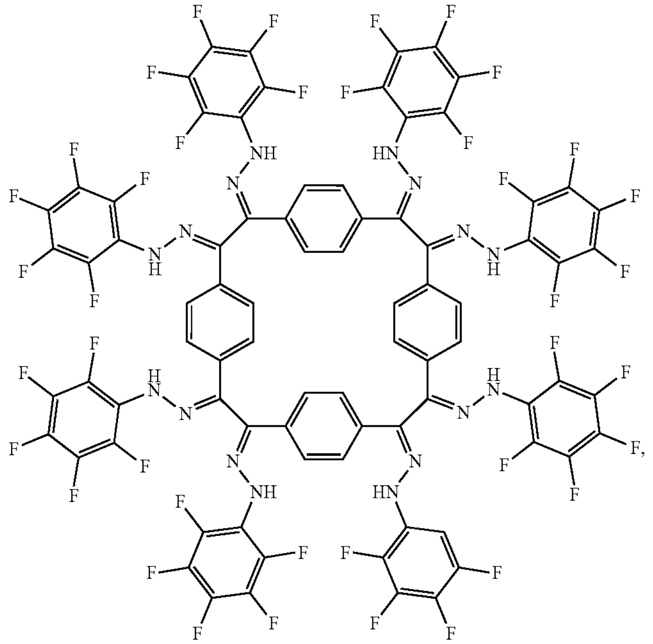
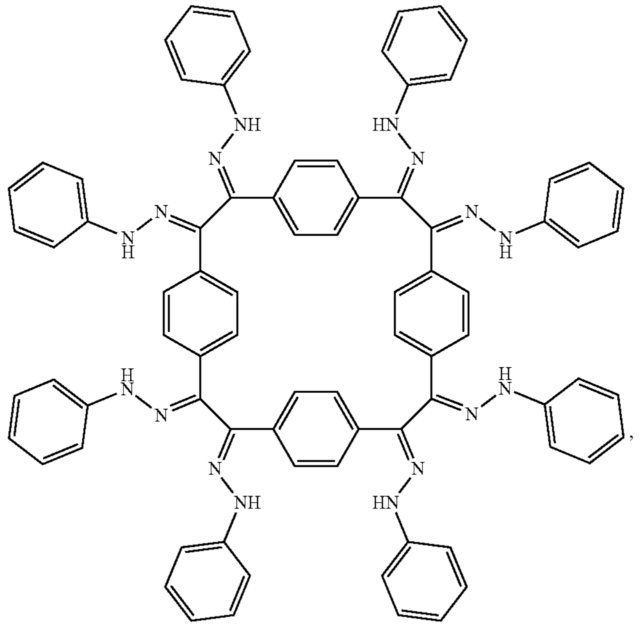

-continued
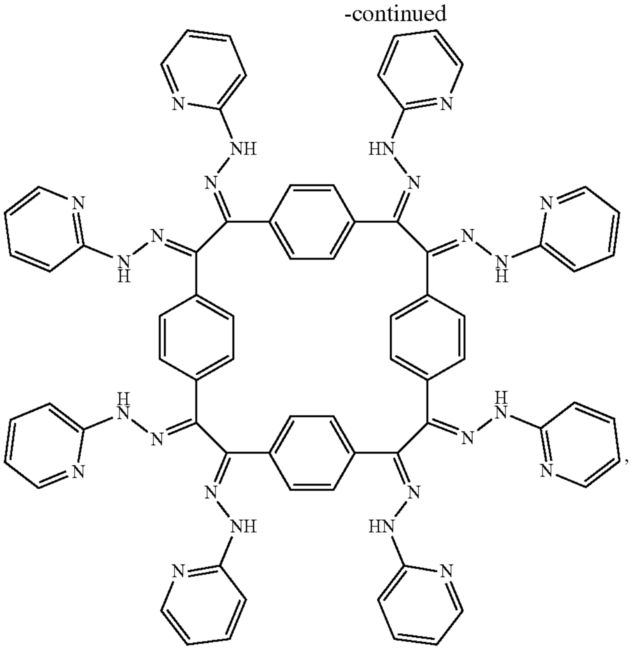
,
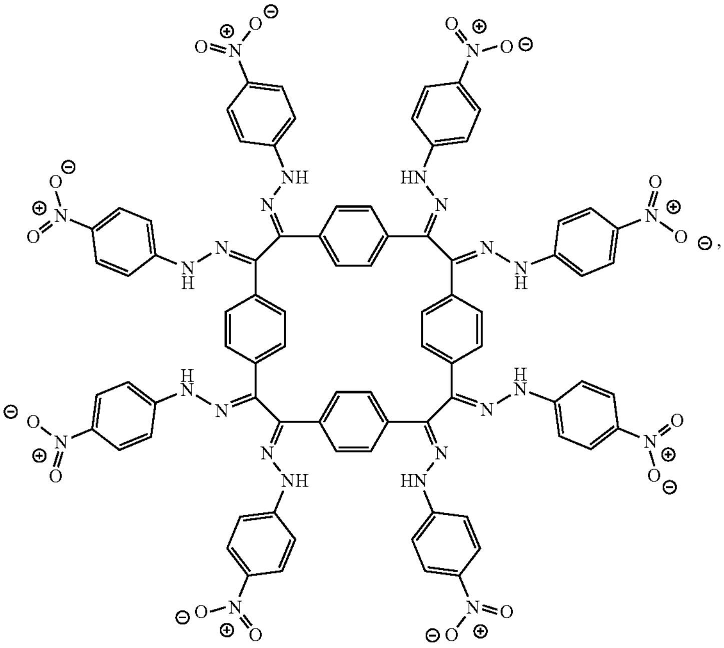
, and

-continued
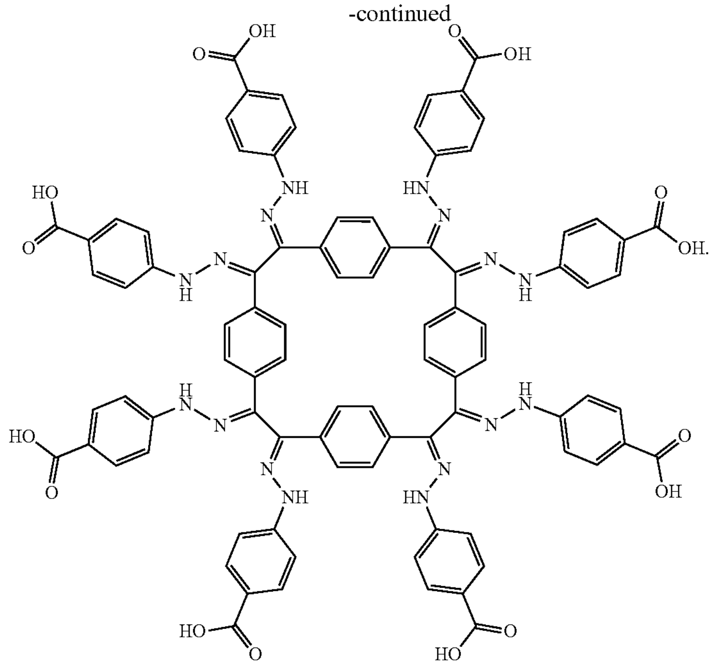
Embodiment 8D: The composition of embodiment 1D or embodiment 2D or embodiment 4D, wherein the compound of Formula (IV) or the compound of Formula (IV-a) or the compound of Formula (IV-b) is selected from the group consisting of:
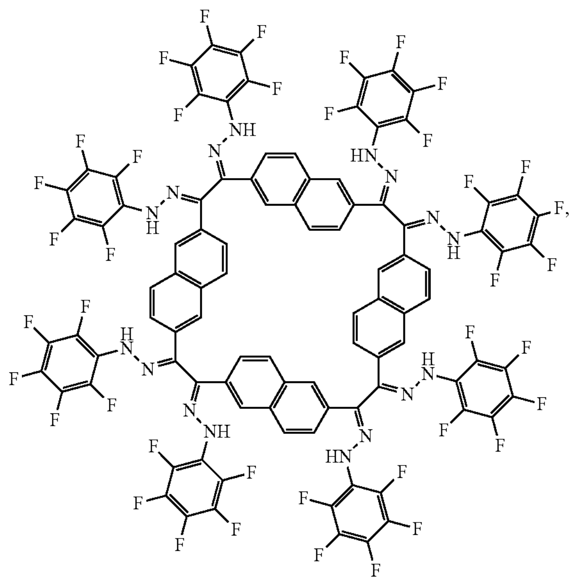
,
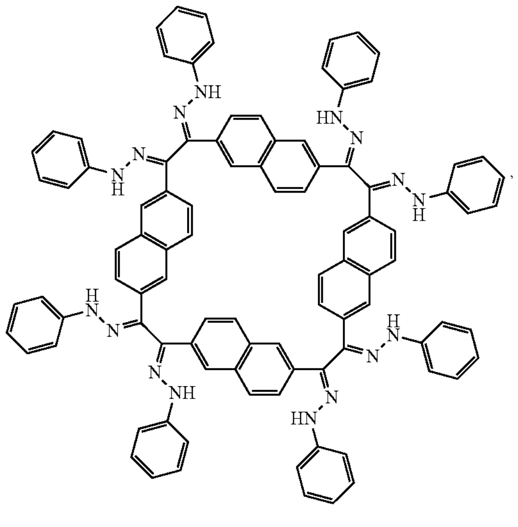
, -continued
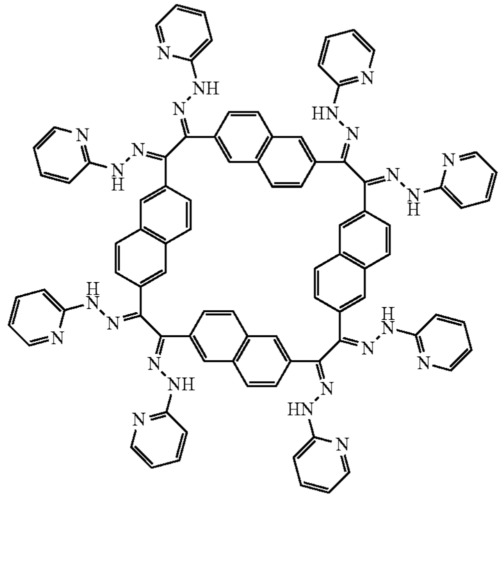
,
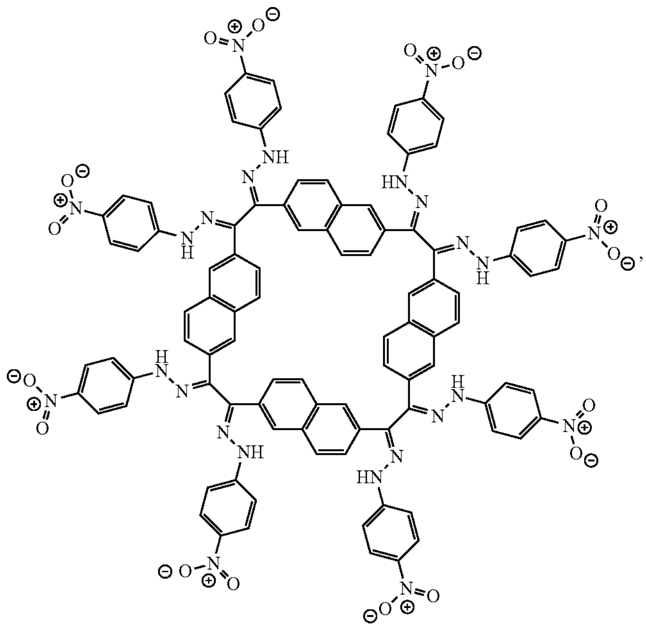
, and
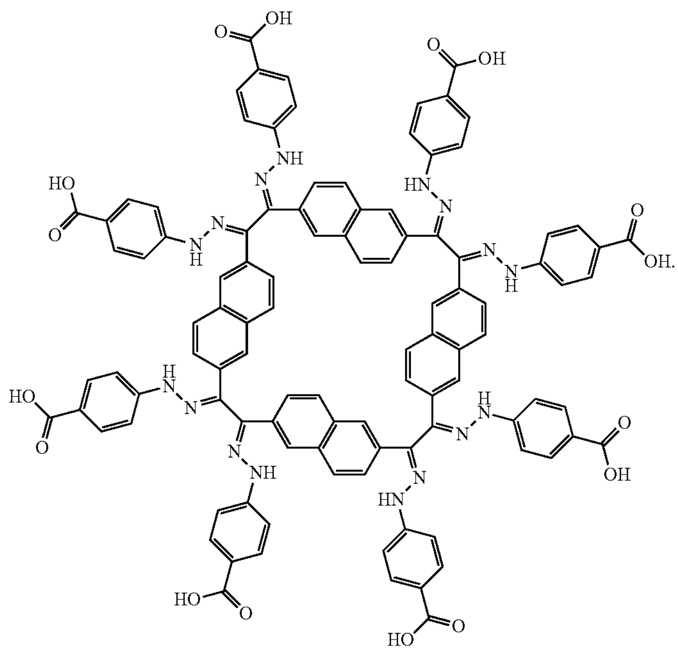 [SMILES: O=C(O)c1ccc(N/N=C2/C(=N/Nc3ccc(C(=O)O)cc3)c3ccc4cc(ccc4c3)C(=N\Nc3ccc(C(=O)O)cc3)/C(=N/Nc3ccc(C(=O)O)cc3)c3ccc4cc(ccc4c3)C(=N\Nc3ccc(C(=O)O)cc3)/C(=N/Nc3ccc(C(=O)O)cc3)c3ccc4cc(ccc4c3)C(=N\Nc3ccc(C(=O)O)cc3)/C(=N/Nc3ccc(C(=O)O)cc3)c3ccc4cc2ccc4c3)cc1]
.

Embodiment 9D: The composition of embodiment 1D or embodiment 2D or embodiment 5D, wherein the compound of Formula (VI) or the compound of Formula (VI-a) or the compound of Formula (VI-b) is selected from the group consisting of:
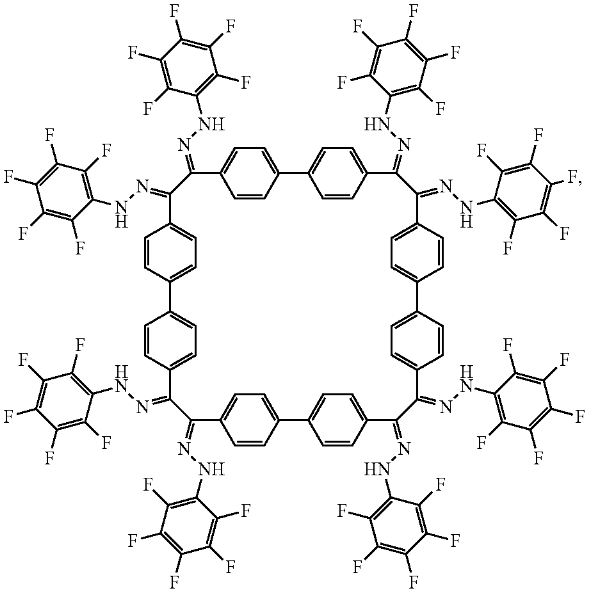
,
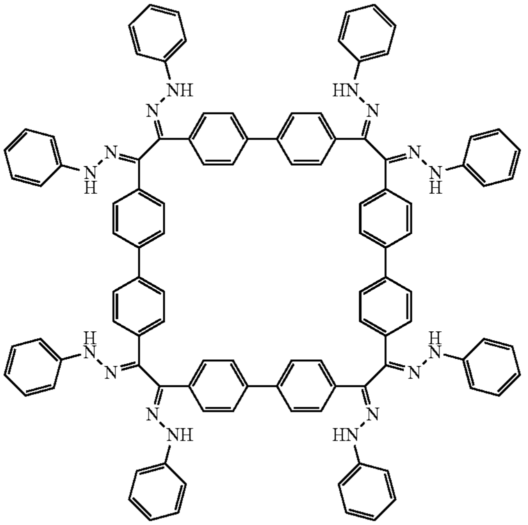
,
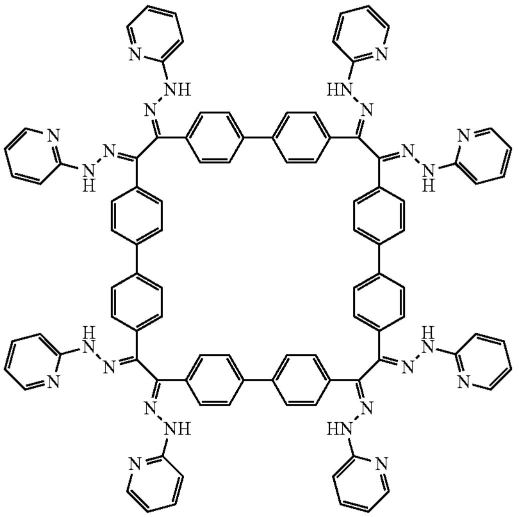
,
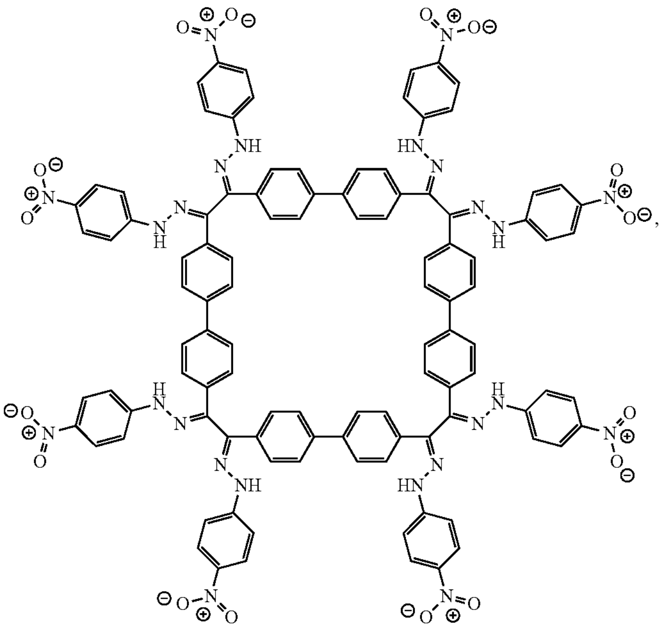 [SMILES: O=C(O)c1ccc(N/N=C2/C(=N/Nc3ccc(C(=O)O)cc3)c3ccc(cc3)-c3ccc(cc3)C(=N\Nc3ccc(C(=O)O)cc3)/C(=N/Nc3ccc(C(=O)O)cc3)c3ccc(cc3)-c3ccc(cc3)C(=N\Nc3ccc(C(=O)O)cc3)/C(=N/Nc3ccc(C(=O)O)cc3)c3ccc(cc3)-c3ccc(cc3)C(=N\Nc3ccc(C(=O)O)cc3)/C(=N/Nc3ccc(C(=O)O)cc3)c3ccc(cc3)-c3ccc2cc3)cc1]
, -continued

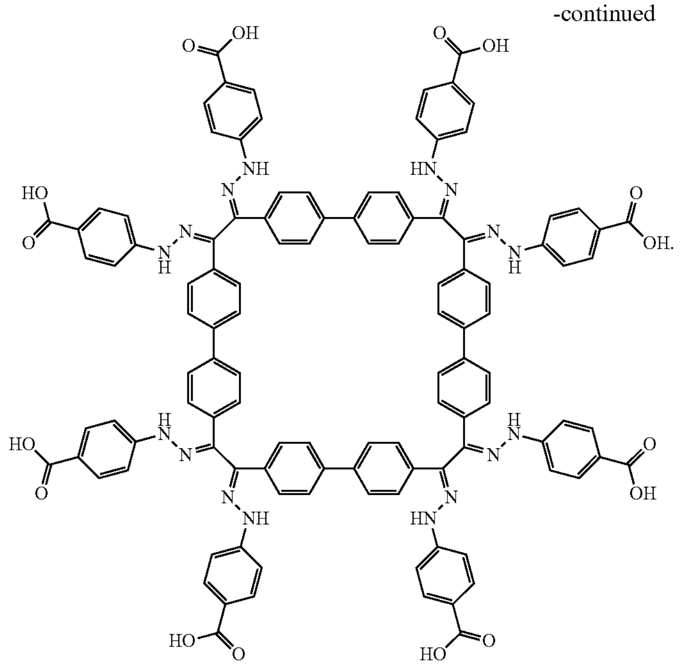

Additional embodiments include those listed below:

In some embodiments, a compound of Formula (II-a) is a compound of Formula (II). In some embodiments, a compound of Formula (II-b) is a compound of Formula (II). In some embodiments, a compound of Formula (II-b) is a compound of Formula (II-a).

In some embodiments, a compound of Formula (IV-a) is a compound of Formula (IV). In some embodiments, a compound of Formula (IV-b) is a compound of Formula (IV). In some embodiments, a compound of Formula (IV-b) is a compound of Formula (IV-a).

In some embodiments, a compound of Formula (VI-a) is a compound of Formula (VI). In some embodiments, a compound of Formula (VI-b) is a compound of Formula (VI). In some embodiments, a compound of Formula (VI-b) is a compound of Formula (VI-a).

Additional embodiments include those listed below:

In various embodiment the composition of the present invention is a paint, a primer, a coating, or a coating material.

In various embodiments, the article of manufacture of the present invention is a paint, a primer, a coating, or a coating material.

In various embodiments, the present invention is a paint, wherein the paint comprises a compound of Formula (II), a compound of Formula (II-a), a compound of Formula (II-b), a compound of Formula (IV), a compound of Formula (IV-a), a compound of Formula (IV-b), a compound of Formula (VI), a compound of Formula (VI-a), a compound of Formula (VI-b), compound 1a, compound 1b, compound 1c, compound 1d, or compound 1e, or any combination thereof. In some embodiments, the paint further comprises a carrier. In some embodiments, the carrier is a solvent. In some embodiments, the solvent is water, comprises water, or contains water; or is an organic solvent, comprises an organic solvent, or contains an organic solvent; or is a combination of water and an organic solvent, comprises a combination of water and an organic solvent, or contains a combination of water and an organic solvent.

In various embodiments, the present invention is a primer, wherein the primer comprises a compound of Formula (II), a compound of Formula (II-a), a compound of Formula (II-b), a compound of Formula (IV), a compound of Formula (IV-a), a compound of Formula (IV-b), a compound of Formula (VI), a compound of Formula (VI-a), a compound of Formula (VI-b), compound 1a, compound 1b, compound 1c, compound 1d, or compound 1e, or any combination thereof. In some embodiments, the primer further comprises a carrier. In some embodiments, the carrier is a solvent. In some embodiments, the solvent is water, comprises water, or contains water; or is an organic solvent, comprises an organic solvent, or contains an organic solvent; or is a combination of water and an organic solvent, comprises a combination of water and an organic solvent, or contains a combination of water and an organic solvent.

In various embodiments, the present invention is a coating material, wherein the coating material comprises a compound of Formula (II), a compound of Formula (II-a), a compound of Formula (II-b), a compound of Formula (IV), a compound of Formula (IV-a), a compound of Formula (IV-b), a compound of Formula (VI), a compound of Formula (VI-a), a compound of Formula (VI-b), compound 1a, compound 1b, compound 1c, compound 1d, or compound 1e, or any combination thereof. In some embodiments, the coating material further comprises a carrier. In some embodiments, the carrier is a solvent. In some embodiments, the solvent is water, comprises water, or contains water; or is an organic solvent, comprises an organic solvent, or contains an organic solvent; or is a combination of water and an organic solvent, comprises a combination of water and an organic solvent, or contains a combination of water and an organic solvent.

In various embodiments, the present invention is a coating, wherein the coating comprises a compound of Formula (II), a compound of Formula (II-a), a compound of Formula (II-b), a compound of Formula (IV), a compound of Formula (IV-a), a compound of Formula (IV-b), a compound of Formula (VI), a compound of Formula (VI-a), a compound of Formula (VI-b), compound 1a, compound 1b, compound 1c, compound 1d, or compound 1e, or any combination thereof. In some embodiments, the coating further comprises a carrier. In some embodiments, the carrier is a solvent. In some embodiments, the solvent is water, comprises water, or contains water; or is an organic solvent, comprises an organic solvent, or contains an organic solvent; or is a combination of water and an organic solvent, comprises a combination of water and an organic solvent, or contains a combination of water and an organic solvent.

Additional embodiments include those listed below:

In various embodiments, the present invention provides a composition, wherein the composition comprises a compound of Formula (II), a compound of Formula (II-a), a compound of Formula (II-b), a compound of Formula (IV), a compound of Formula (IV-a), a compound of Formula (IV-b), a compound of Formula (VI), a compound of Formula (VI-a), a compound of Formula (VI-b), compound 1a, compound 1b, compound 1c, compound 1d, or compound 1e, or any combination thereof. In some embodiments, the composition further comprises a carrier. In some embodiments, the carrier is a solvent. In some embodiments, the solvent is water, comprises water, or contains water; or is an organic solvent, comprises an organic solvent, or contains an organic solvent; or is a combination of water and an organic solvent, comprises a combination of water and an organic solvent, or contains a combination of water and an organic solvent.

In some embodiments, the composition is a coating, a coating material, a material for use as a coating, a primer, a material for use as a primer, a paint, and/or a material for use as a paint. In some embodiments the coating, the coating material, the material for use as a coating, the primer, the material for use as a primer, the paint, and/or the material for use as a paint, further comprises a carrier. In some embodiments, the carrier is a solvent. In some embodiments, the solvent is water, comprises water, or contains water, or is an organic solvent, comprises an organic solvent, or contains an organic solvent; or is a combination of water and an organic solvent, comprises a combination of water and an organic solvent, or contains a combination of water and an organic solvent. In some embodiments, the paint is a nuclear paint. In some embodiments, the primer is a nuclear primer. In some embodiments, the coating material is a nuclear coating material.

In some embodiments, the composition is a paint, a primer, or coating material for painting, priming, or coating a tank, container, vessel, or pipe, or any component thereof. In some embodiments, the composition is a paint, a primer, or coating material for coating a waste containment tank, waste containment container, or waste containment vessel. In some embodiments, the waste containment tank, waste containment container, or waste containment vessel is a nuclear waste containment tank, nuclear waste containment container, or nuclear waste containment vessel.

Additional embodiments include those listed below:

In some embodiments, a compound of Formula (I-a) is a compound of Formula (I). In some embodiments, a compound of Formula (I-b) is a compound of Formula (I). In some embodiments, a compound of Formula (I-b) is a compound of Formula (I-a).

In some embodiments, a compound of Formula (III-a) is a compound of Formula (III). In some embodiments, a compound of Formula (III-b) is a compound of Formula (III). In some embodiments, a compound of Formula (III-b) is a compound of Formula (III-a).

In some embodiments, a compound of Formula (V-a) is a compound of Formula (V). In some embodiments, a compound of Formula (V-b) is a compound of Formula (V). In some embodiments, a compound of Formula (V-b) is a compound of Formula (V-a).

EXAMPLES

The invention is further illustrated by the following examples which are intended to be purely exemplary of the invention, and which should not be construed as limiting the invention in any way. The following examples are illustrative only, and are not intended to limit, in any manner, any of the aspects described herein. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

General Methods and Materials

All syntheses were performed under nitrogen in standard oven-dried glassware. Column chromatography was performed on silica gel 60, 32-63 mesh and analytical TLC on J. T. Baker plastic-backed silica gel IB-F plates. $^{1}H$ NMR, $^{13}C$ NMR, and $^{19}F$ NMR spectra were recorded on JEOL ECA-500 or 600 MHz spectrometers with working frequencies of 500 or 600 MHz for $^{1}H$, 126 or 151 MHz for $^{13}C$, and 565 MHz for $^{19}F$ nuclei. Chemical shifts are reported in ppm (d) with the residual signals of deuterated solvents used for calibration. All $^{13}C$ NMR spectrum were recorded with simultaneous decoupling of $^{1}H$ nuclei. The $^{13}C$ NMR spectrum of compound 1a was not reported because of the extensive coupling between $^{13}C$ and $^{19}F$, which resulted in complex peaks with very low intensities. Infrared spectra were collected on a Nicolet iS10 FT-IR spectrometer.

Mass spectrometry analyses were performed by the Mass Spectrometry Facility at University of Texas-Austin. Elemental analyses were conducted at Atlantic Microlab, Norcross, GA. Melting points were measured in open capillary tubes using a Barnstead International Mel-TEMP apparatus and are uncorrected. Adsorption spectra were recorded using a PerkinElmer LAMBDA 25 UV/Vis spectrometer.

The following starting materials and solvents were purchased from commercial suppliers and used without further purification: 4-nitrophenylhydrazine hydrochloride, NaCN, PhMe, EtOH, and $CHCl_3$ from Sigma-Aldrich; pentafluorophenylhydrazine from Alfa Aesar; phenylhydrazine, 4-hydrazinobenzoic acid, p-xylene, and terephthaldehyde from TCI; benzil, TsOH, THE, n-hexane, AcOH, and $HNO_3$ from Oakwood Chemicals, and $Et_2O$ from VWR. The 4 Å molecular sieves used in the Dean Stark apparatuses were purchased from ThermoFisher and activated in a vacuum oven at 120° C. overnight. Cyclotetrabenzoin (compound 6) and cyclotetrabenzil (compound 3) were synthesized and purified following known literature methods.

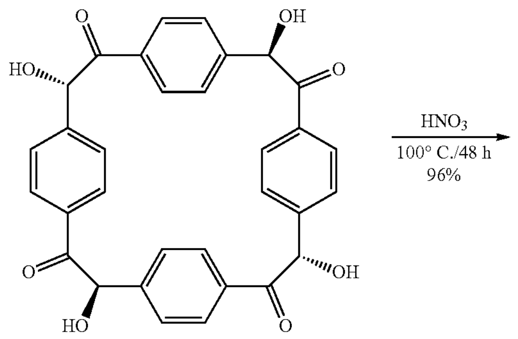

Compound 6

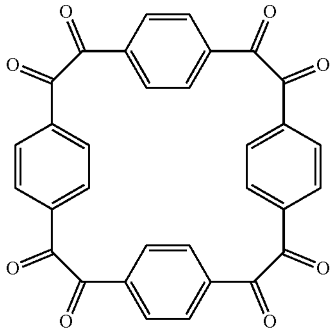

Compound 3

Example 1

Synthesis of Compound 1a

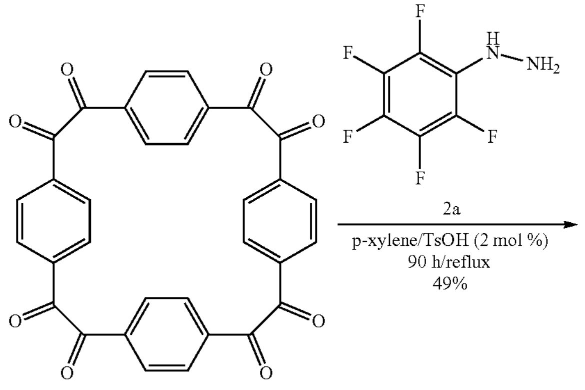

3

-continued

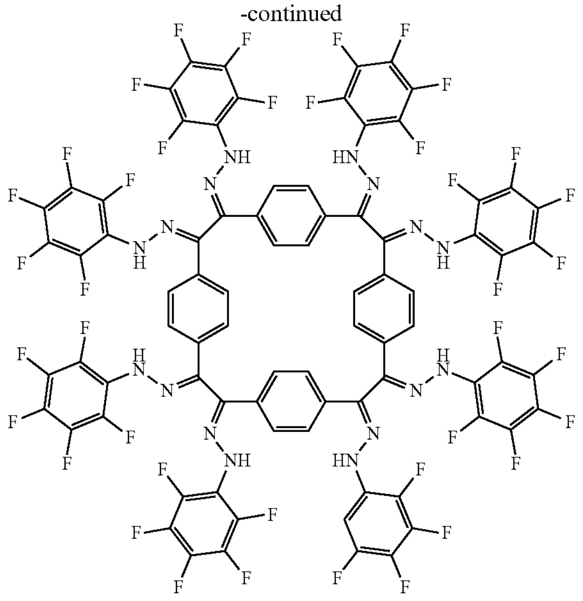

1a

Octahydrazone Compound 1a-A solution of compound 3 (0.53 g, 1.00 mmol), pentafluorohydrazine (2a, 2.38 g, 12 mmol), and p-toluenesulfonic acid (38.00 mg, 0.20 mmol) in p-xylene (50 mL) was prepared in a 100 mL round-bottom flask equipped with a magnetic stirrer and fitted with a reflux condenser and a Dean-Stark adapter. The solution was heated at reflux for 90 h, then cooled and poured into a solution of cold hexane (200 mL). The solution was allowed to come to room temperature and the yellow precipitate was collected by vacuum filtration and washed with EtOH (50 mL) and $Et_2O$ (50 mL). After filtration, the residue was dissolved in $CHCl_3$ (100 mL) and the solution passed through a 2 cm thick Celite pad, which was washed with another portion of $CHCl_3$ (100 mL). The yellow solution was concentrated in vacuo to 50 mL and was then carefully layered with hot hexane (200 mL). The round bottom flask was sealed with a septum, and after 3 d the precipitate was collected and washed with EtOH (50 mL) and $Et_2O$ (50 mL) to afford pure compound 1a as a yellow solid in 49% yield (0.98 g, 0.49 mmol).

Compound 1a: mp 154-156° C. $^{1}H$ NMR (600 MHz, $CDCl_3$) δ 8.28 (s, 16H), 7.43 (s, 8H), 6.80 (s, 16H) ppm. $^{19}F$-NMR (565 MHz, $CDCl_3$) δ −154.78 (d, J=21.7 Hz, 16F), −162.11 (t, J=19.5 Hz, 16F), −162.87 (t, J=21.7 Hz, 8F) ppm. FT-IR (neat): $\tilde{v}$=3323, 1658, 1520, 1486, 1451, 1409, 1278, 1181, 1139, 1030, 1011, 973, 849, 726, 632, 574 $cm^{-1}$. ESI-HRMS: m/z $[M+H]^+$: Calcd for $[C_{80}H_{25}F_{40}N_{16}]^+$ 1969.1804; Found 1969.1812, with correct isotope distribution.

Example 2

Synthesis of Compound 1b

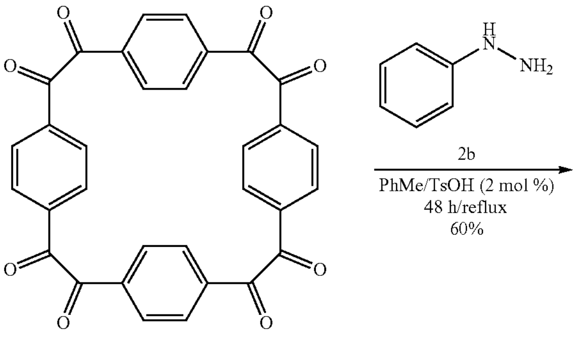

3

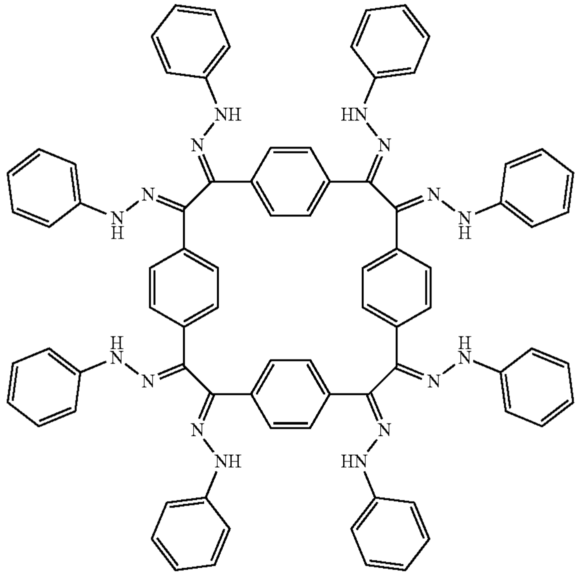

1b

Octahydrazone Compound 1b-A solution of compound 3 (0.53 g, 1.00 mmol), phenylhydrazine (2b, 1.30 g, 12 mmol), and p-toluenesulfonic acid (38 mg, 0.20 mmol) in PhMe (50 mL) was prepared in a 250 mL round bottom flask equipped with a magnetic stirrer and fitted with a reflux condenser and a Dean-Stark adapter. The solution was heated at reflux for 48 h, then cooled to room temperature, and the formed orange precipitate was collected through vacuum filtration. The residue was washed with EtOH (50 mL) and $Et_2O$ (50 mL), dissolved in $CHCl_3$ (150 mL), and the solution was passed through a 2 cm thick Celite pad, which was then washed with another portion of $CHCl_3$ (100 mL). The solvent was evaporated from the orange solution using a rotary evaporator, and the solid was recrystallized from $CHCl_3$ to afford compound 1b as a crystalline reddish-orange powder in 60% yield (0.75 g, 0.60 mmol).

Compound 1b: mp 216-219° C. $^1H$ NMR (600 MHz, $CDCl_3$) & 8.39 (s, 8H), 7.73 (d, J=6.2 Hz, 8H), 7.24 (d J=6.2 Hz, 16H), 7.12 (d, J=7.6 Hz, 16H), 6.89 (t, J=6.9 Hz, 8H), 6.71 (s, 4H) ppm. $^{13}C$ NMR (151 MHz, $CDCl_3$) δ 143.69, 134.87, 134.70, 129.40, 121.50, 113.68, 77.33, 77.12, 76.90 ppm. FT IR (neat): $\tilde{\nu}$=3312, 1599, 1566, 1497, 1245, 1141, 1002, 966, 845, 747, 688, 503 cm-1. ESI-HRMS: m/z $[M+Na]^+$: Calcd for $[C_{80}H_{64}N_{16}{}^{-}Na]^+$ 1271.5392; Found 1271.5353, with correct isotope distribution.

Example 3

Synthesis of Compound 1c

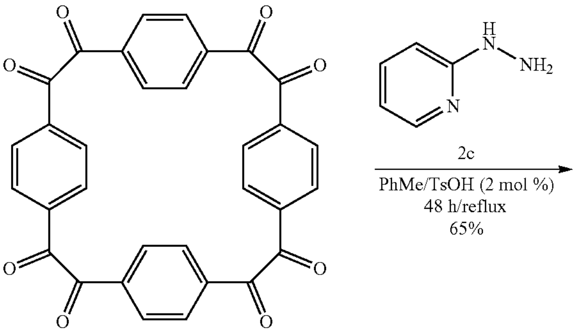

3

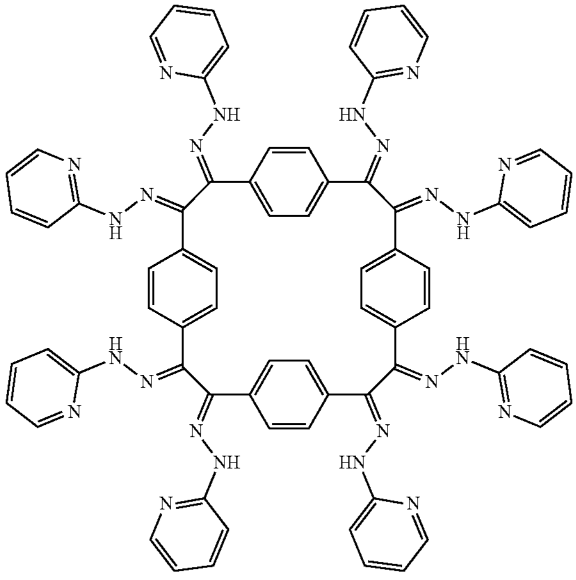

1c

Octahydrazone Compound 1c—A solution of compound 3 (0.53 g, 1.00 mmol), 2-hydrazinopyridine (2c, 4.37 g, 40 mmol), and p-toluenesulfonic acid (38 mg, 0.20 mmol) in EtOH (50 mL) was prepared in a 100 ml round bottom flask equipped with a magnetic stirrer and fitted with a reflux condenser and a Dean-Stark adapter. The solution was heated at reflux for 48 h, and then the solvent was evaporated from the reaction mixture using a rotary evaporator. The resulting solid was suspended in EtOH (100 mL) and the resulting orange precipitate was collected by vacuum filtration and washed with EtOH (50 mL). After filtration, the residue was dissolved in $CHCl_3$ (100 mL) and the solution passed through a 2 cm thick Celite pad, which was washed with an additional portion of $CHCl_3$ (100 mL). The solvent was evaporated from the orange solution using a rotary evaporator, and the resulting solid was dissolved in AcOH (50 mL) in a 250 mL round bottom flask and careful layered with hot $Et_2O$ (150 mL). The solution was capped with a septum and left for 3 d to afford compound 1c as a crystalline orange-yellow powder in 65% yield (0.82 g, 0.65 mmol).

Compound 1c: mp 268-270° C. 1H NMR (600 MHZ, $CDCl_3$) § 8.74 (s, 8H), 8.24 (s. 8H), 7.84 (s, 8H), 7.61 (d, J=6.5 Hz, 8H), 7.37 (s, 8H), 6.76 (t. J=5.5 Hz, 8H), 6.69 (s, 8H) ppm. $^{13}C$ NMR (151 MHz, $CDCl_3$) δ 156.44, 147.73, 137.92, 136.41, 134.71, 127.90, 124.96, 116.78, 108.55, 77.38, 77.12, 76.87 ppm. FT IR (neat): $\tilde{v}$=3316, 2970, 2360, 1739, 1647, 1591, 1571, 1489, 1436, 1307, 1230, 1139, 1007, 987, 844, 767, 735, 617, 513 $cm^{-1}$. ESI-HRMS: m/z $[M+2H]^{2+}$: Calcd for $[C_{72}H_{58}N_{24}]^{2+}$ 626.2633; Found 626.2656, with correct isotope distribution.

Example 4

Synthesis of Compound 1d

Octahydrazone Compound 1d-A solution of compound 3 (0.53 g, 1.00 mmol), 4-nitrophenylhydrazine hydrochloride (2d, 4.37 g, 40 mmol), and p-toluenesulfonic acid (19.00 mg, 0.10 mmol) in p-xylene (50 mL) was prepared in a 100 mL round bottom flask equipped with a magnetic stirrer and fitted with a reflux condenser and a Dean-Stark adapter. The solution was heated at reflux for 60 h, and then cooled to room temperature to produce a red precipitate, which was collected through vacuum filtration. The residue was washed with EtOH (50 mL) and $Et_{20}$ (50 mL), dissolved in THF (150 mL), and the solution was passed through a 2-cm thick Celite pad which was washed with another portion of THF (100 mL). The solvent was evaporated from the orange solution using a rotary evaporator, and the obtained solid was recrystallized from THE to afford compound 1d as a crystalline red powder in 90% yield (1.45 g, 0.90 mmol).

Compound 1d: mp 252-254° C. 1H NMR (600 MHz, DMSO-$d_6$) δ 10.72 (s, 8H), 8.32 (s, 8H), 8.09 (d, J=8.9 Hz, 16H), 7.42 (d, J=7.6 Hz, 16H), 6.67 (s, 8H) ppm. $^{13}C$ NMR (151 MHZ, $CDCl_3$) δ 151.11, 140.04, 134.90, 126.19, 113.59 ppm. FT-IR (neat): @=3628, 3262, 2952, 1590, 1541, 1520, 1495, 1409, 1318, 1304, 1257, 1135, 1105, 1027, 1002, 951, 862, 838, 768, 748, 691 cm-1. ESI-HRMS: m/z $[M-2H]^{2-}$: Calcd for $[C_{80}H_{54}N_{24}O_{16}]^{2-}$ 803.2074; Found 803.2077, with correct isotope distribution.

Example 5

Synthesis of Compound 1e

Octahydrazone Compound 1e—A solution of 3 (0.53 g, 1.00 mmol), 4-hydrazinobenzoic acid (2e, 1.83 g, 12 mmol), and p-toluenesulfonic acid (38 mg, 0.20 mmol) in PhMe (50 mL) was prepared in a 100 mL round bottom flask equipped with a magnetic stirrer and fitted with a reflux condenser and a Dean-Stark condenser. The solution was heated to reflux for 48 h, and then cooled to room temperature to produce a red precipitate, which was collected by vacuum filtration. The residue was washed with EtOH (50 mL) and $Et_2O$ (50 mL), dissolved in THF (150 mL), and the solution was passed through a 2 cm thick Celite pad and washed with another portion of THF (100 mL). The solvent was evaporated from the orange solution using a rotary evaporator, and the solid was suspended in EtOH (200 mL). The suspension was heated at reflux overnight and filtered while hot to give compound 1e as an orange-red powder in 85% yield (1.36 g, 0.85 mmol).

Compound 1e: mp 266-268° C. $^1H$ NMR (600 MHz, DMSO-$d_6$) δ 12.30 (s, 8H), 10.12 (s, 8H), 8.23 (s, 8H), 7.74 (d, J=7.6 Hz, 16H), 7.33 (d, J=7.6 Hz, 16H), 6.60 (s, 8H) ppm. $^{13}C$ NMR (151 MHz, $CDCl_3$) δ 167.79, 149.19, 137.89, 135.13, 131.27, 121.91, 113.38 ppm. FT-IR (neat): $\tilde{v}$=2996, 1677, 1599, 1515, 1404, 1310, 1237, 1157, 1093, 1026, 1004, 961, 843, 766, 695 $cm^{-1}$. ESI-HRMS: m/z $[M-2H]^{2-}$: Calcd for $[C_{88}H_{62}N_{16}O_{16}]^{2-}$ 799.2271; Found 799.2266, with correct isotope distribution.

Example 6

Synthesis of Compound 4

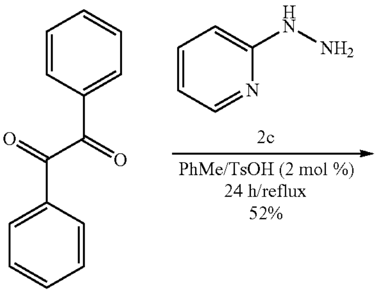

5

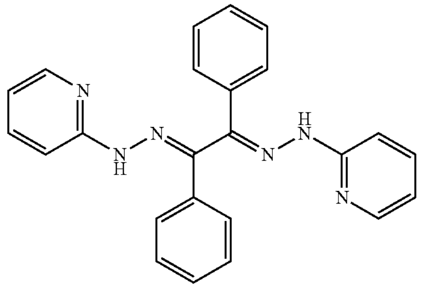

4

Benzil-bis-2-pyridinylhydrazone compound (4)—A solution of benzil 5 (0.50 g, 2.38 mmol), 2-hydrazinopyridine (2c, 2.08 g, 19 mmol), and p-toluenesulfonic acid (90.54 mg, 0.48 mmol) in PhMe (65 mL) was prepared in a 100 mL round bottom flask equipped with a magnetic stirrer and fitted with a reflux condenser and a Dean-Stark adapter. The solution was heated at reflux for 24 h, and then the solvent was evaporated from the reaction mixture using a rotary evaporator. After purification by column chromatography on silica gel using 4:1 hexanes/EA as eluent and evaporation of fractions containing the product, compound 4 was obtained as a crystalline light-yellow powder in 65% yield (0.82 g, 0.65 mmol).

Compound 4: mp 110-112° C. 1H NMR (500 MHZ, $CDCl_3$) & 8.54 (s, 2H), 7.99 (s, 2H), 7.70-7.71 (m, 4H), 7.63-7.67 (m, 2H), 7.53 (t. J=7.5 Hz, 2H), 7.34 (q, J=7.0 Hz, 6H), 6.76-6.79 (m, 2H) ppm. BC NMR (126 MHz, $CDCl_3$) δ 156.06, 147.39, 138.41, 133.99, 129.47, 129.09, 125.95, 116.73, 108.29 ppm. FT IR (neat): $\tilde{v}$=3320, 2970, 2924, 1594, 1576, 1507, 1434, 1306, 1140, 1129, 1071, 1011, 754, 688 $cm^{-1}$.

Example 7

Single Crystal Structures and Analyses

Crystals of compounds 1a-1d were obtained through a common procedure that commenced by dissolving the crude product (15 mg) in $CHCl_3$ (compound 1a, compound 1b), AcOH (compound 1c), or THF (compound 1d). The solutions were sonicated for 10 min and filtered through a PTFE syringe filter (0.22 μm, 30 mm). The resulting filtrates (0.15 mL) were added to round-bottomed 0.75 mL culture tubes, and these tubes were placed inside 2-dram scintillation vials containing hexane (compound 1a, compound 1d), $Et_2O$ (compound 1c), or EtOH (compound 1b) as the diffusion solvents. The vials were tightly capped and kept at ambient conditions without external disturbances. Single crystals suitable for X-ray diffraction analysis were harvested after 2-5 d. Crystals of compound 1e were prepared by first dissolving the pure product (15 mg) in THF. The solution was heated, allowed to cool to room temperature, and filtered through a PTFE syringe filter (0.22 μm, 30 mm). The resulting filtrate (0.75 mL) was added to a 2-dram scintillation vial and this vial was placed inside a 5-dram scintillation vial containing 5 mL of a 0.2M solution of $I_2$ in acetone as the diffusion solution. The vial was tightly capped and kept at ambient conditions in a dark place without external disturbance. Single crystals suitable for X-ray diffraction analysis were harvested after 7 d.

Single crystal X-ray measurements for compounds 1a-1e were performed on a Bruker DUO platform diffractometer equipped with a 4K CCD APEX II detector and an Incoatec 30-Watt Cu microsource with compact multilayer optics. Data were collected using a narrow-frame algorithm with scan widths of 0.5% in omega and an exposure time of 20 s/frame at 4 cm detector distance. The data were integrated using the Bruker SAINT program, with the intensities corrected for Lorentz factor, polarization, air absorption, and absorption due to variations in the path length through the detector faceplate. The data were scaled, and an absorption correction was applied using SADABS. The structures were solved with SHELXT 2014 and refined with SHELXL 2018 using full-matrix least-squares refinement. The non-H atoms were refined with anisotropic thermal parameters, and all the H atoms were calculated in idealized positions and refined riding on their parent atoms.

Example 8

Figure 8:
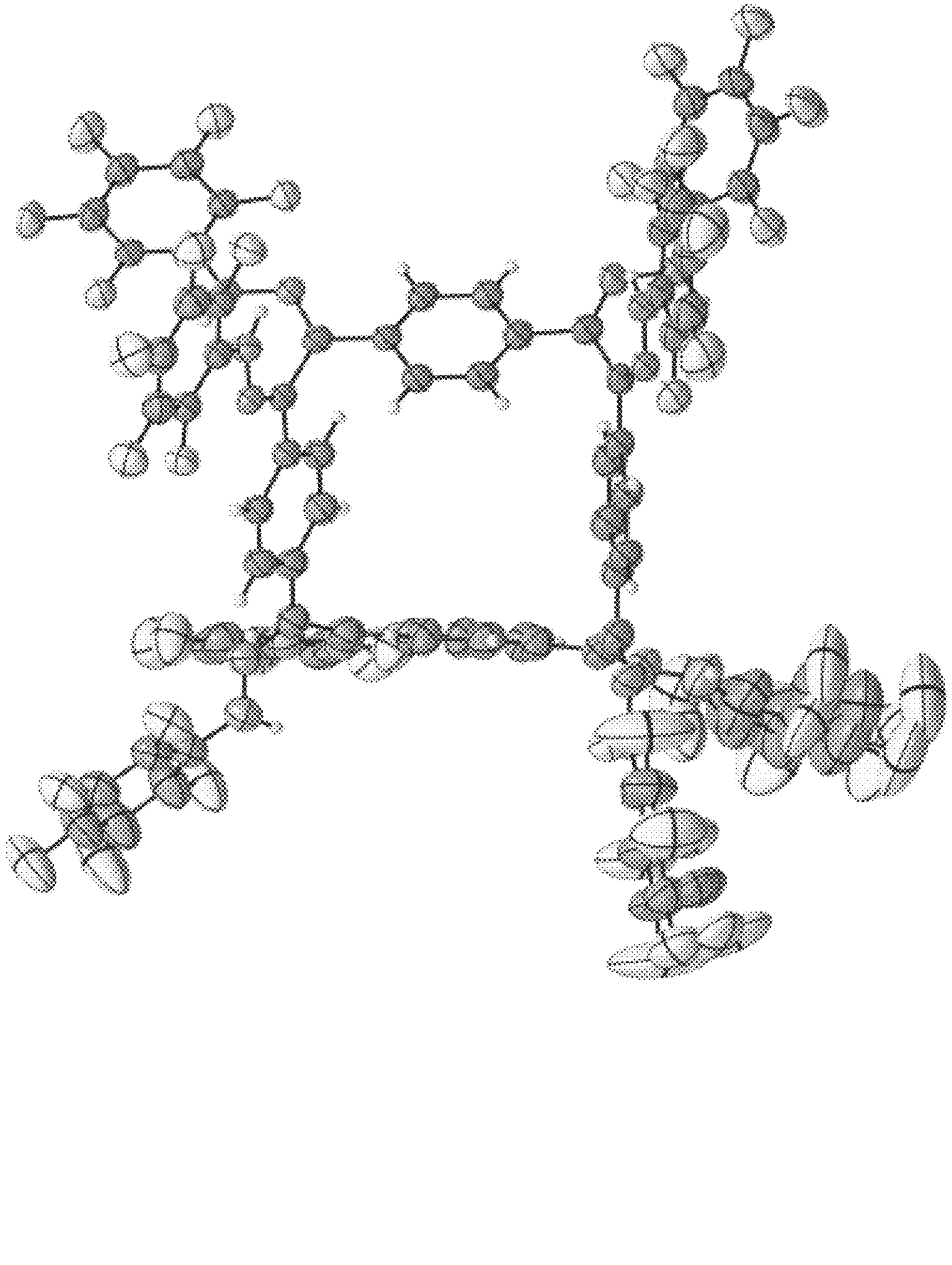
FIG. 8 depicts in accordance with various embodiments of the invention, ORTEP diagram of the single crystal structure of cyclotetra(bisarylhydrazone)benzil compound 1a. Thermal ellipsoids shown at 50% probability.

FIG. 8. ORTEP diagram of the single crystal structure of compound 1a. Thermal ellipsoids shown at 50% probability.

TABLE 3

| Crystal data and structure refinement parameters for compound 1a (CCDC code 2164803). | |
|---|---|
| Identification code | XW23NC_214EtOH_squeezed |
| Empirical formula | $C_{80}H_{46}N_{16}$ |
| Formula weight | 1249.47 |
| Temperature/K | 173(2) |
| Crystal system | monoclinic |
| Space group | P 21/n |
| a/Å | 11.2200(7) |
| b/Å | 34.722(2) |
| c/Å | 23.4803(17) |
| α/° | 90 |
| β/° | 93.868(4) |
| γ/° | 90 |
| Volume/Å$^3$ | 9126.8(10) |
| Z | 4 |
| $\rho_{calc}$ g/cm$^3$ | 0.909 |
| μ/mm$^{-1}$ | 0.438 |
| F(000) | 2624.0 |
| Crystal size/mm$^3$ | 0.56 × 0.06 × 0.02 |
| Radiation | CuKα (λ = 1.54178) |
| 2Θ range for data collection/° | 2.275 to 66.876 |

TABLE 3-continued

| Crystal data and structure refinement parameters for compound 1a (CCDC code 2164803). | |
|---|---|
| Index ranges | −13 ≤ h ≤ 13, −38 ≤ k ≤ 40, −23 ≤ l ≤ 27 |
| Reflections collected | 81271 |
| Independent reflections | 16051 [$R_{int}$ = 0.0943] |
| Data/restraints/parameters | 16051/756/865 |
| Goodness-of-fit on F2 | 1.047 |
| Final R indexes [I >= 2σ (I)] | $R_1$ = 0.0819, w$R_2$ = 0.2384 |
| Final R indexes [all data] | $R_1$ = 0.1095, w$R_2$ = 0.2571 |
| Largest diff. peak/hole/e Å$^{-3}$ | 0.251/−0.279 |

Example 9

Figure 9:
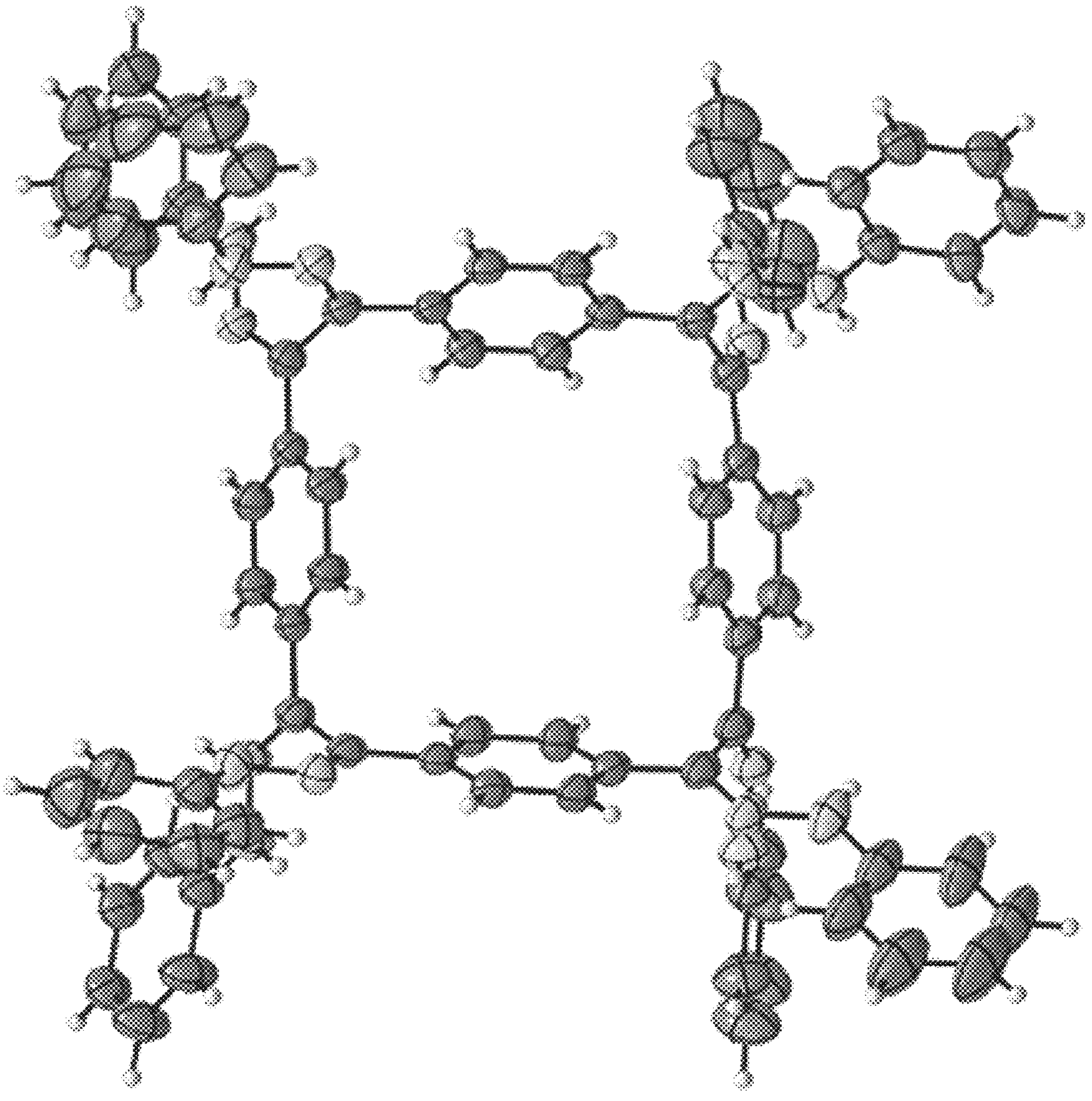
FIG. 9 depicts in accordance with various embodiments of the invention, ORTEP diagram of the single crystal structure of cyclotetra(bisarylhydrazone)benzil compound 1b. Thermal ellipsoids shown at 50% probability.

FIG. 9. ORTEP diagram of the single crystal structure of compound 1b. Thermal ellipsoids shown at 50% probability.

TABLE 4

| Crystal data and structure refinement for compound 1b (CCDC code 2164804) | |
|---|---|
| Identification code | 4-8Hex_XW168_a_sq |
| Empirical formula | $C_{80}H_{24}F_{40}N_{16}$ |
| Formula weight | 1969.15 |
| Temperature/K | 123(2) |
| Crystal system | Triclinic |
| Space group | P-1 |
| a/Å | 11.9175(4) |
| b/Å | 20.6330(7) |
| c/Å | 21.1795(6) |
| α/° | 110.459(2) |
| β/° | 91.480(2) |
| γ/° | 98.540(2) |
| Volume/Å$^3$ | 4808.3(3) |
| Z | 2 |
| $\rho_{calc}$ g/cm$^3$ | 1.360 |
| μ/mm$^{-1}$ | 1.244 |
| F(000) | 1952.0 |
| Crystal size/mm$^3$ | 0.28 × 0.16 × 0.01 |
| Radiation | CuKα (λ = 1.54178) |
| 2Θ range for data collection/° | 4.468 to 137.04 |
| Index ranges | −14 ≤ h ≤ 14, −24 ≤ k ≤ 24, −25 ≤ l ≤ 24 |
| Reflections collected | 53369 |
| Independent reflections | 17113 [$R_{int}$ = 0.0518, $R_{sigma}$ = 0.0676] |
| Data/restraints/parameters | 17113/2842/1423 |
| Goodness-of-fit on F2 | 1.124 |
| Final R indexes [I >= 2σ (I)] | $R_1$ = 0.0722, w$R_2$ = 0.2031 |
| Final R indexes [all data] | $R_1$ = 0.1048, w$R_2$ = 0.2322 |
| Largest diff. peak/hole/e Å$^{-3}$ | 0.46/−0.44 |

Example 10

Figure 10:
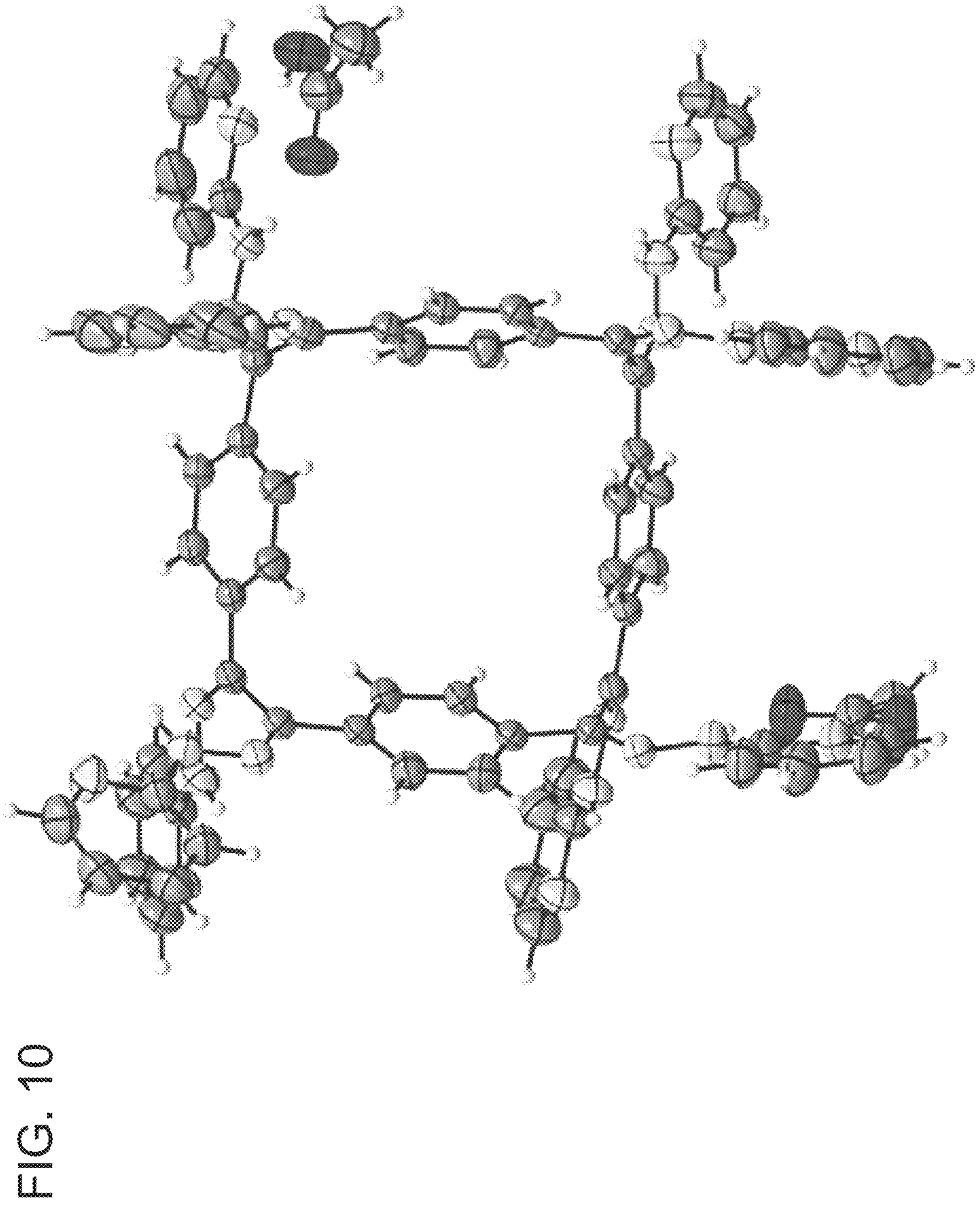
FIG. 10 depicts in accordance with various embodiments of the invention, ORTEP diagram of the single crystal structure of cyclotetra(bisarylhydrazone)benzil compound 1c. Thermal ellipsoids shown at 50% probability.

FIG. 10. ORTEP diagram of the single crystal structure of compound 1e. Thermal ellipsoids shown at 50% probability.

TABLE 5

| Crystal data and structure refinement for compound 1c (CCDC code 2164805). | |
|---|---|
| Identification code | P-HYDRA_XW305_sq |
| Empirical formula | $C_{80}H_{72}N_{24}O_8$ |
| Formula weight | 1497.61 |
| Temperature/K | 123(2) |
| Crystal system | monoclinic |
| Space group | P2/c |

TABLE 5-continued

| Crystal data and structure refinement for compound 1c (CCDC code 2164805). | |
|---|---|
| a/Å | 11.7744(3) |
| b/Å | 19.8090(5) |
| c/Å | 20.2595(5) |
| α/° | 90 |
| β/° | 98.432(2) |
| γ/° | 90 |
| Volume/$Å^3$ | 4674.2(2) |
| Z | 2 |
| $\rho_{calc}$ g/$cm^3$ | 1.064 |
| μ/$mm^{-1}$ | 0.591 |
| F(000) | 1568.0 |
| Crystal size/$mm^3$ | 0.12 × 0.04 × 0.04 |
| Radiation | CuKα (λ = 1.54178) |
| 2Θ range for data collection/° | 4.46 to 132.024 |
| Index ranges | −13 ≤ h ≤ 13, −23 ≤ k ≤ 22, −20 ≤ l ≤ 23 |
| Reflections collected | 43188 |
| Independent reflections | 7938 [$R_{int}$ = 0.0450, $R_{sigma}$ = 0.0310] |
| Data/restraints/parameters | 7938/0/507 |
| Goodness-of-fit on F2 | 1.062 |
| Final R indexes [I >= 2σ (I)] | $R_1$ = 0.0526, $wR_2$ = 0.1514 |
| Final R indexes [all data] | $R_1$= 0.0692, $wR_2$ = 0.1645 |
| Largest diff. peak/hole/e $Å^{-3}$ | 0.40/−0.21 |

Example 11

Figure 11:
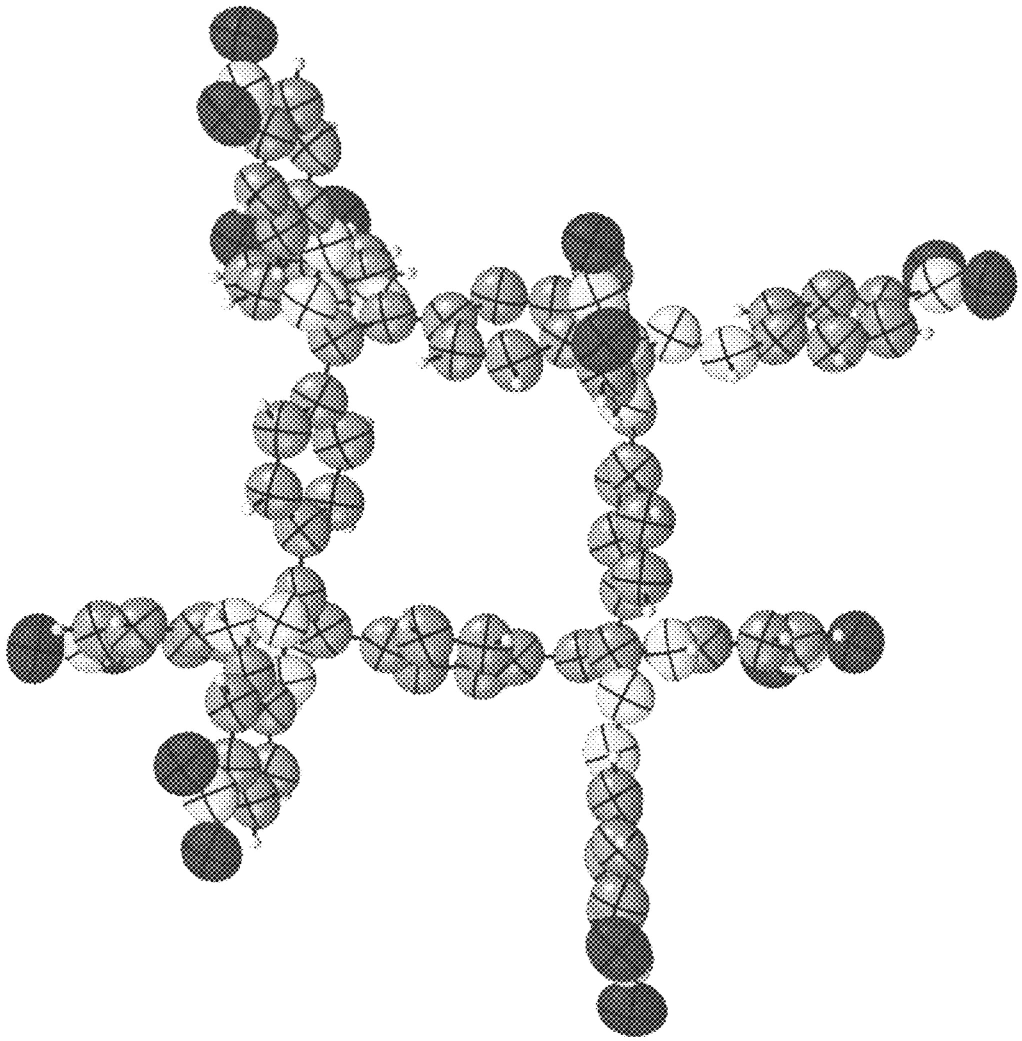
FIG. 11 depicts in accordance with various embodiments of the invention, ORTEP diagram of the single crystal structure of cyclotetra(bisarylhydrazone)benzil compound 1d. Thermal ellipsoids shown at 50% probability.

FIG. 11. ORTEP diagram of the single crystal structure of compound 1d. Thermal ellipsoids shown at 50% probability.

TABLE 6

| Crystal data and structure refinement for compound 1d (CCDC code 2164806). | |
|---|---|
| Identification code | XW341_sq |
| Empirical formula | $C_{80}H_{56}N_{24}O_{16}$ |
| Formula weight | 1609.48 |
| Temperature/K | 123(2) |
| Crystal system | tetragonal |
| Space group | P-421c |
| a/Å | 21.4622(9) |
| b/Å | 21.4622(9) |
| c/Å | 14.5938(11) |
| α/° | 90 |
| β/° | 90 |
| γ/° | 90 |
| Volume/$Å^3$ | 6722.3(8) |
| Z | 2 |
| $\rho_{calc}$ g/$cm^3$ | 0.795 |
| μ/$mm^{-1}$ | 0.483 |
| F(000) | 1664.0 |
| Crystal size/$mm^3$ | 0.36 × 0.04 × 0,04 |
| Radiation | CuKα (λ = 1.54178) |
| 2Θ range for data collection/° | 7.324 to 108.988 |
| Index ranges | −22 ≤ h ≤ 22, −19 ≤ k ≤ 22, −15 ≤ l ≤ 15 |

TABLE 6-continued

| Crystal data and structure refinement for compound 1d (CCDC code 2164806). | |
|---|---|
| Reflections collected | 24924 |
| Independent reflections | 4104 [$R_{int}$ = 0.1067, $R_{sigma}$ = 0.0695] |
| Data/restraints/parameters | 4104/222/272 |
| Goodness-of-fit on F2 | 1.040 |
| Final R indexes [I >= 2σ (I)] | $R_1$ = 0.0527, $wR_2$ = 0.1510 |
| Final R indexes [all data] | $R_1$ = 0.1005, $wR_2$ = 0.1813 |
| Largest diff. peak/hole/e $Å^{-3}$ | 0.10/−0.11 |
| Flack parameter | 0.5(6) |

Example 12

Figure 12:
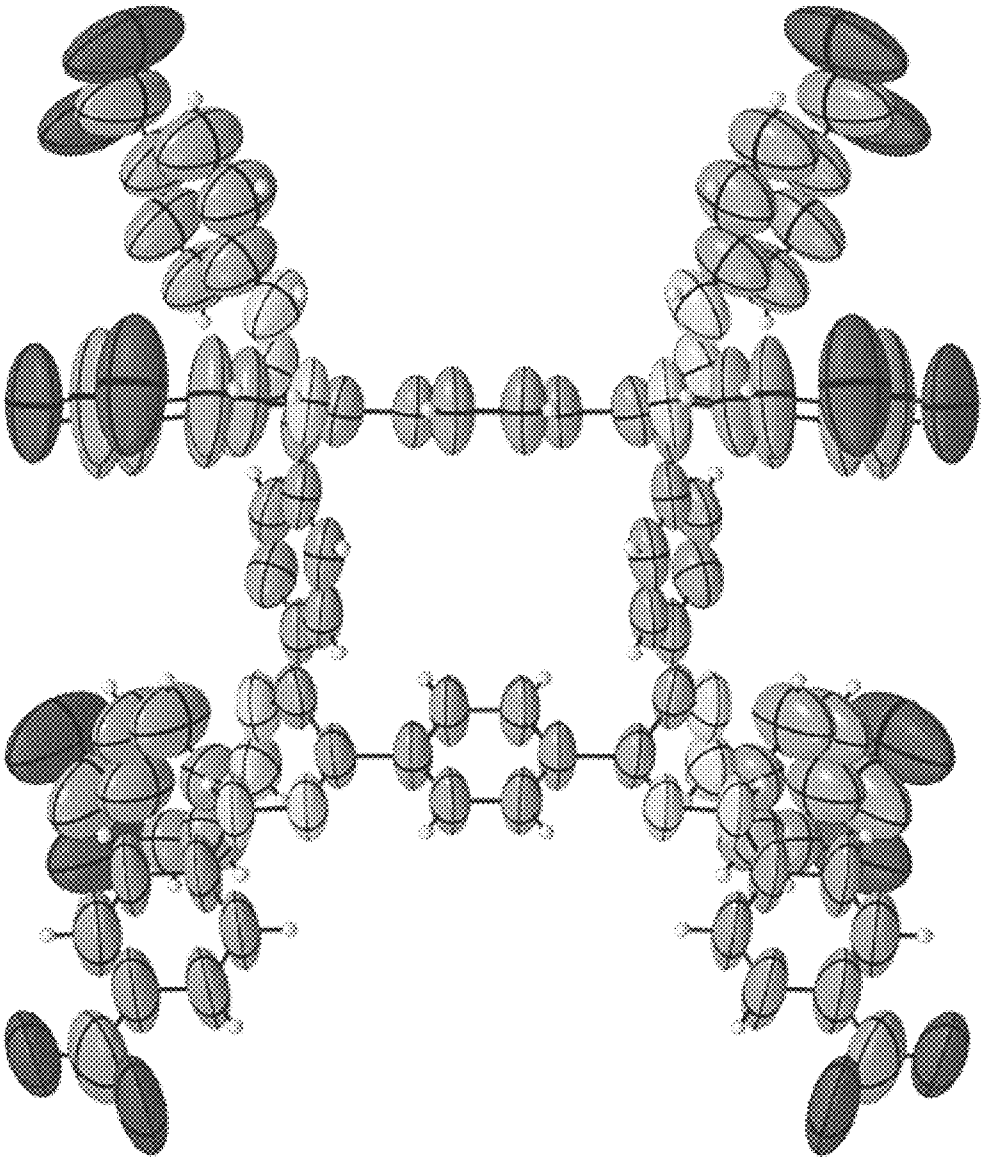
FIG. 12 depicts in accordance with various embodiments of the invention, ORTEP diagram of the single crystal structure of cyclotetra(bisarylhydrazone)benzil compound 1e. Thermal ellipsoids shown at 50% probability.
Figure 13:
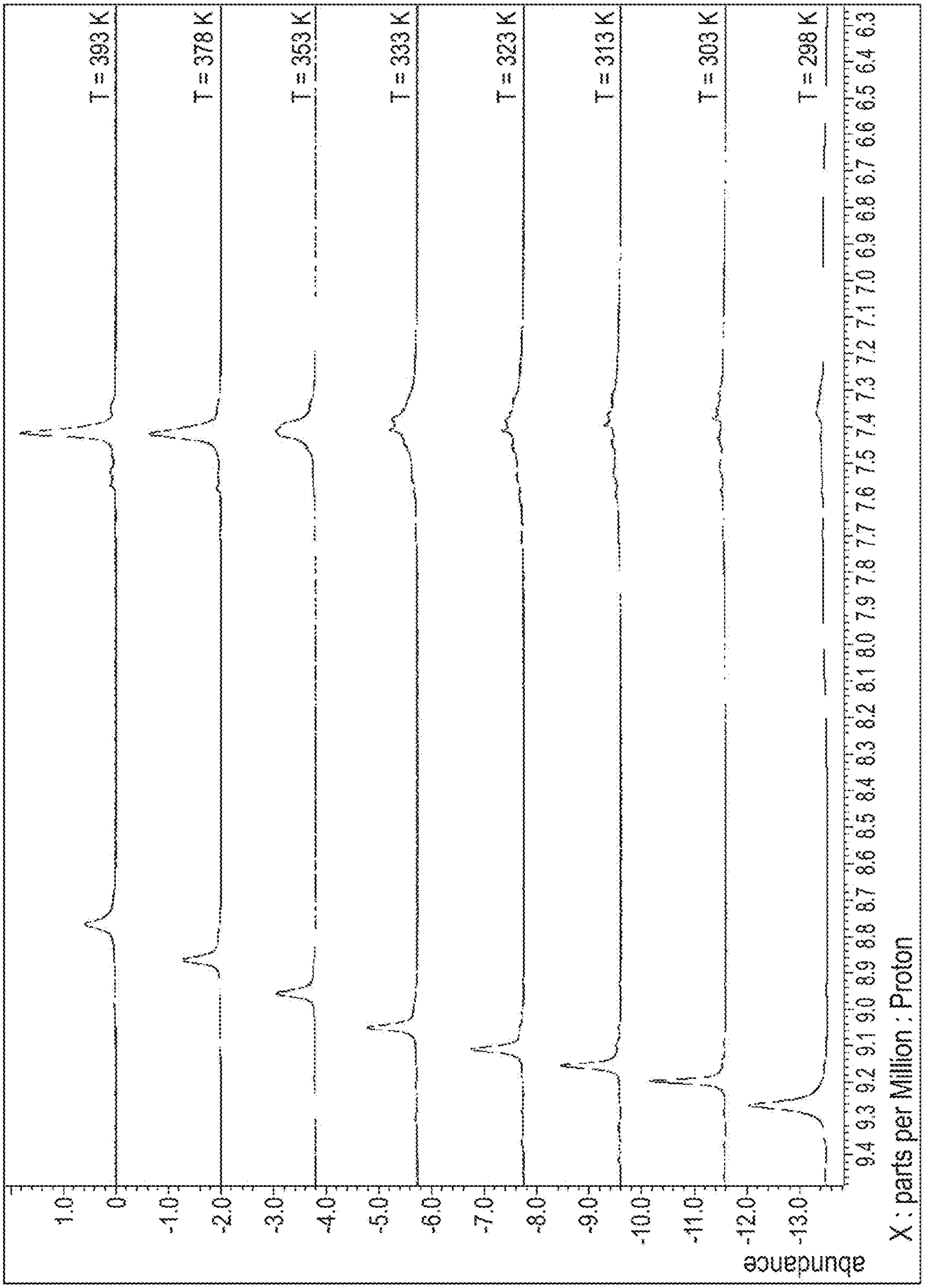
FIG. 13 depicts in accordance with various embodiments of the invention, $^{1}H$ NMR spectra of cyclotetra(bisarylhydrazone)benzil compound 1a collected at various temperatures in DMSO-$d_6$.
Figure 14:
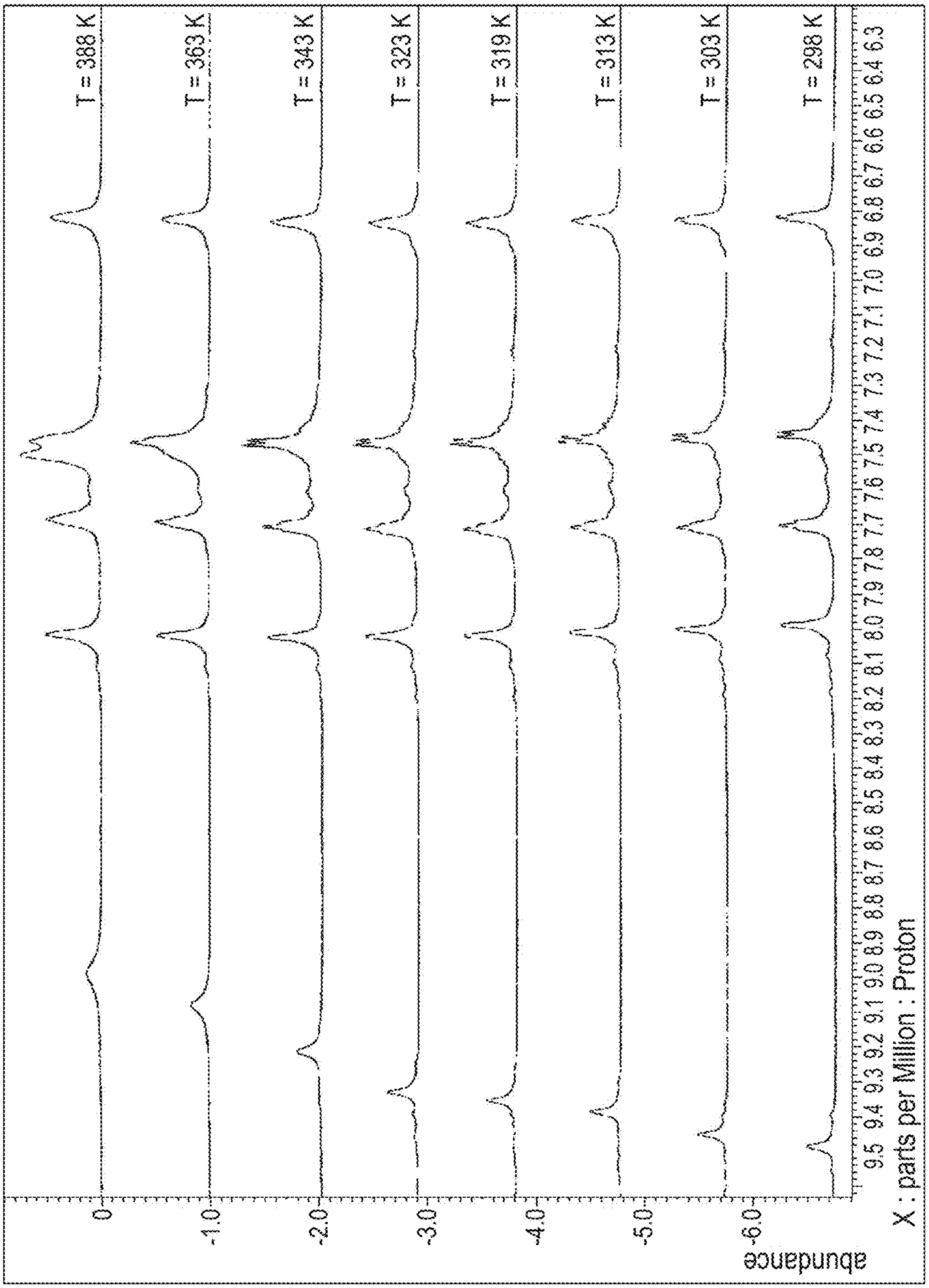
FIG. 14 depicts in accordance with various embodiments of the invention, $^{1}H$ NMR spectra of cyclotetra(bisarylhydrazone)benzil compound 1c collected at various temperatures in DMSO-$d_6$.
Figure 15:
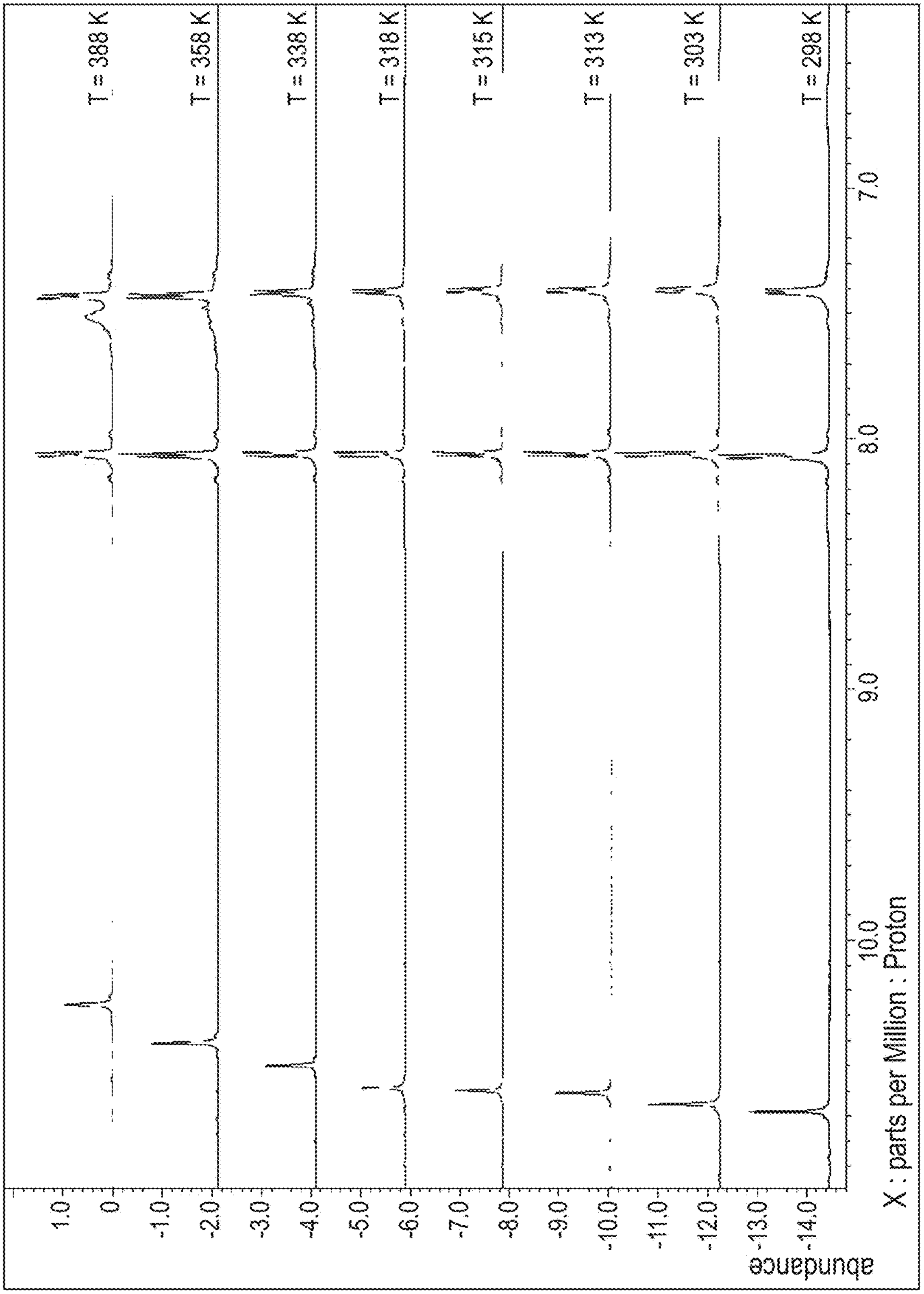
FIG. 15 depicts in accordance with various embodiments of the invention, $^{1}H$ NMR spectra of cyclotetra(bisarylhydrazone)benzil compound 1d collected at various temperatures in DMSO-$d_6$.
Figure 16:
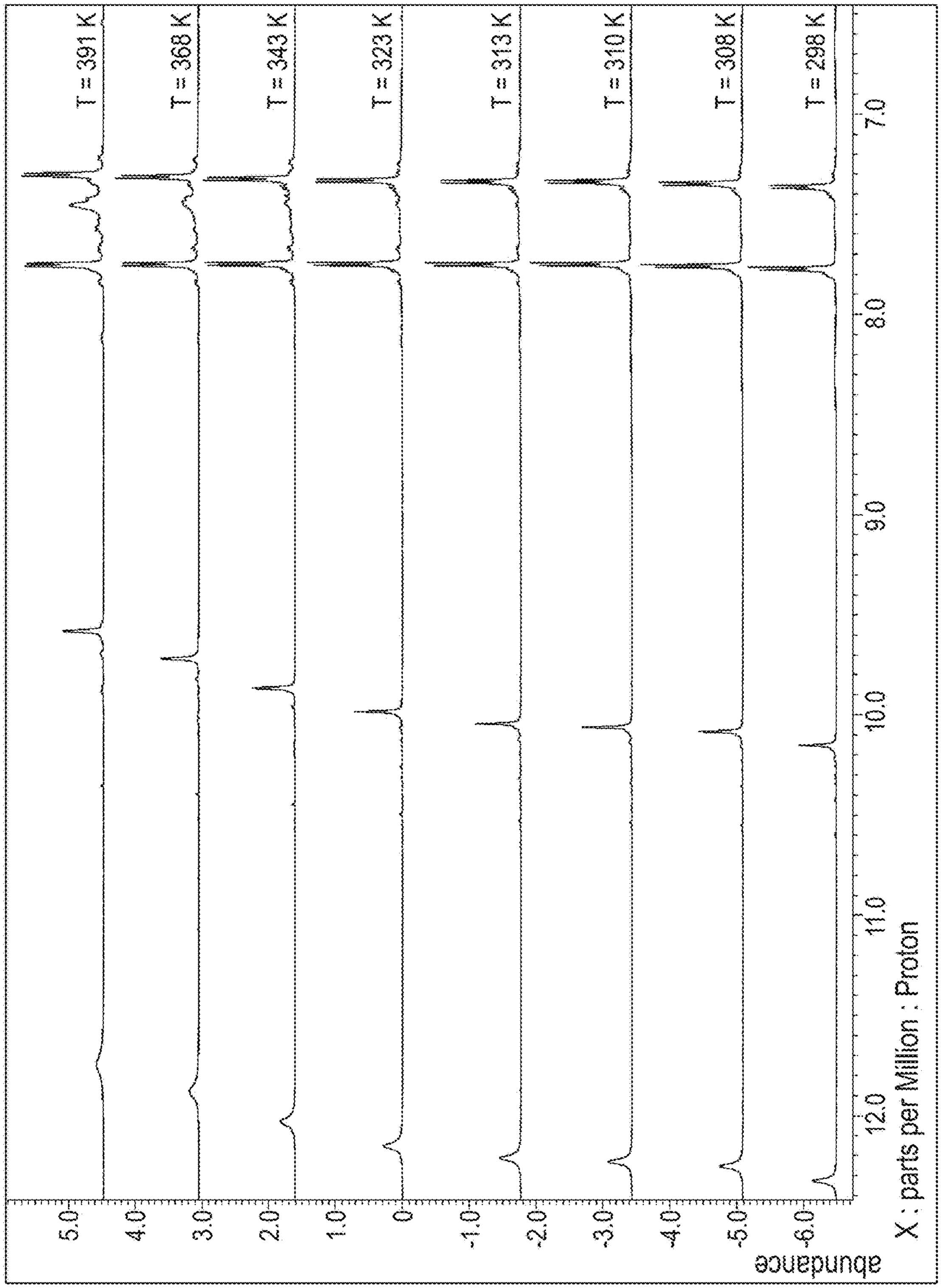
FIG. 16 depicts in accordance with various embodiments of the invention, $^{1}H$ NMR spectra of cyclotetra(bisarylhydrazone)benzil compound 1e collected at various temperatures in DMSO-$d_6$.
Figure 17:
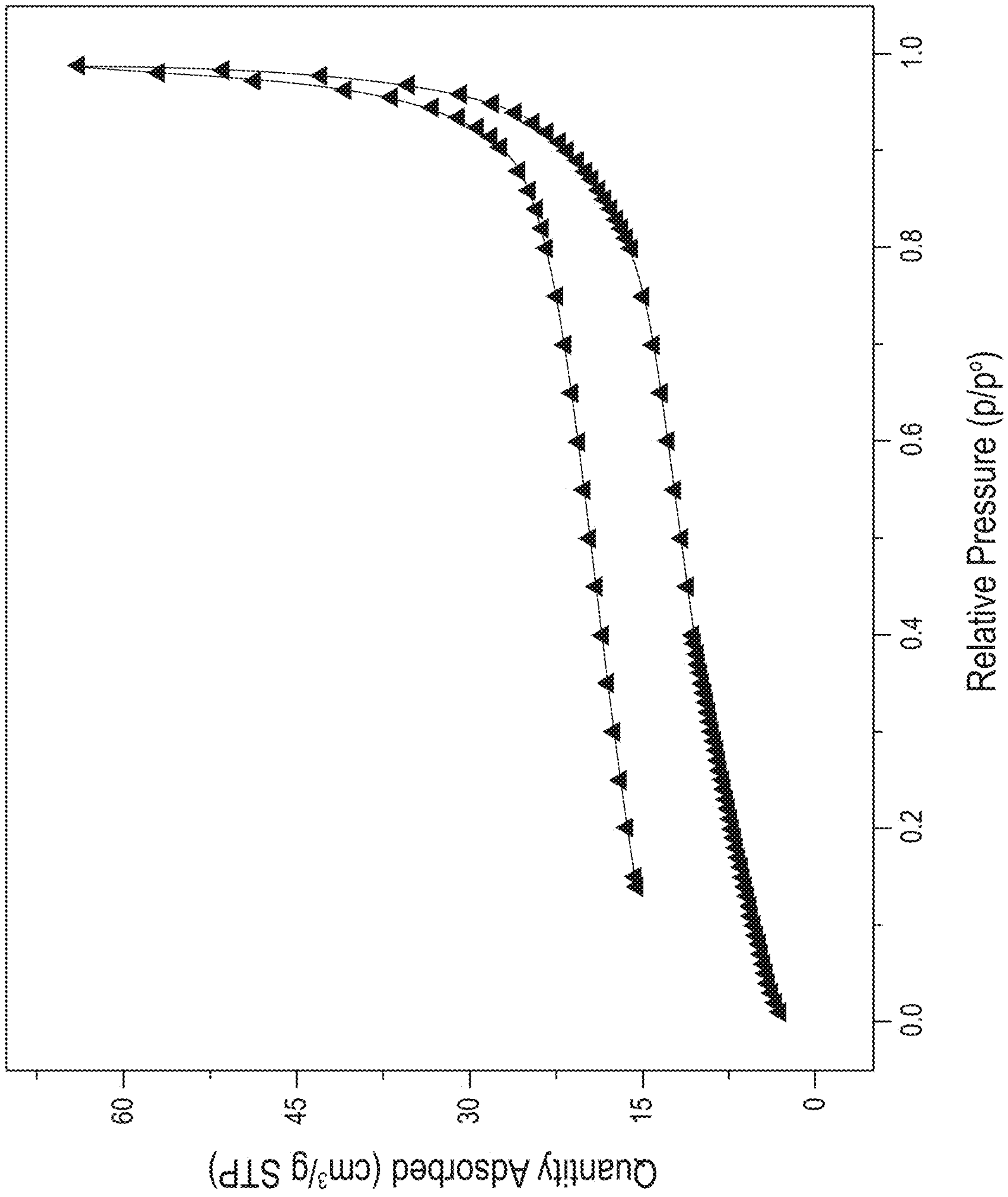
FIG. 17 depicts in accordance with various embodiments of the invention, $N_2$ adsorption/desorption isotherm for cyclotetra(bisarylhydrazone)benzil compound 1c. BET surface area is 24.14 $m^2$ $g^{-1}$.
Figure 18:
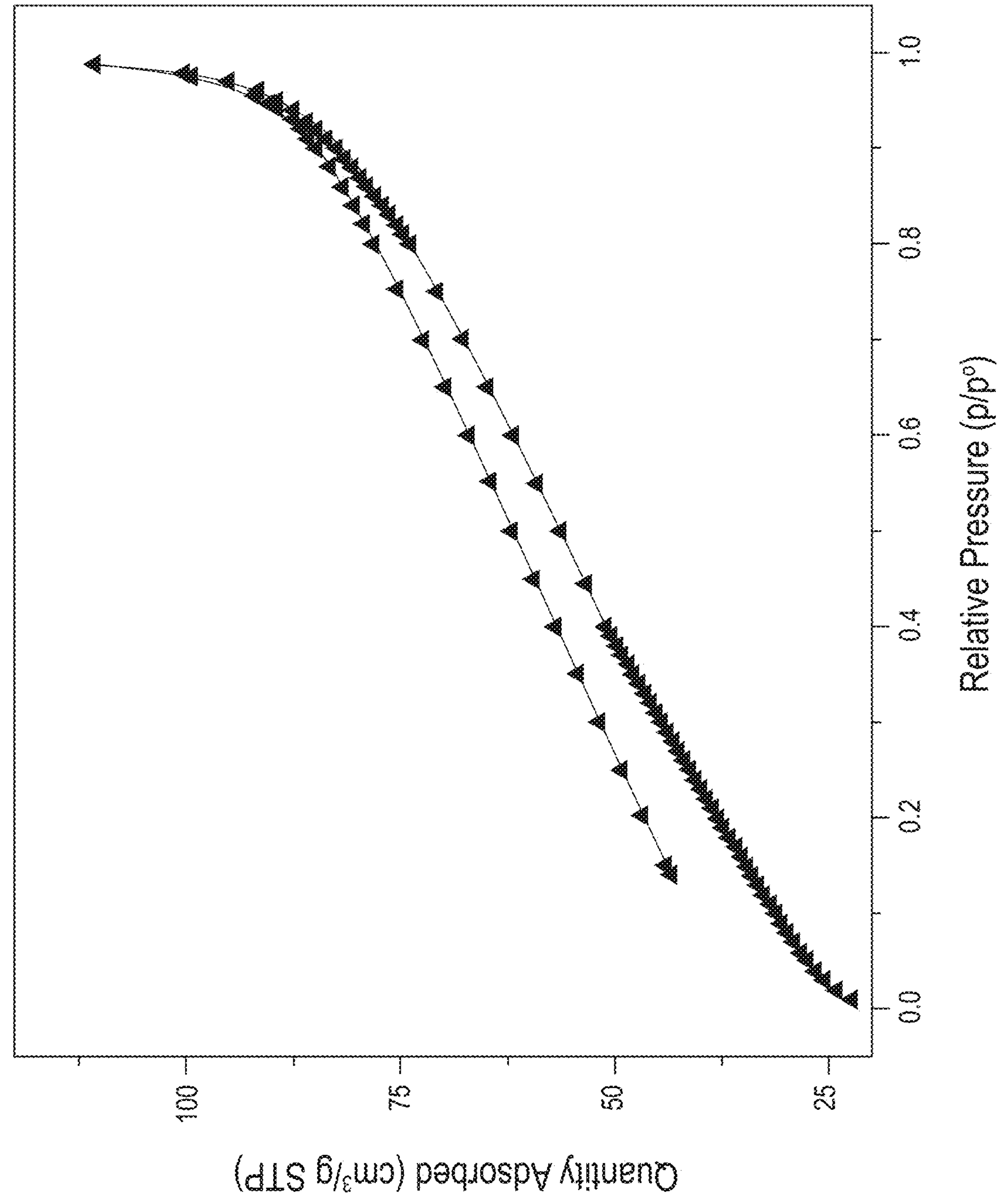
FIG. 18 depicts in accordance with various embodiments of the invention, $N_2$ adsorption/desorption isotherm for cyclotetra(bisarylhydrazone)benzil compound 1e. BET surface area is 131.47 $m^2$ $g^{-1}$.

FIG. 12. ORTEP diagram of the single crystal structure of compound 1e. Thermal ellipsoids shown at 50% probability.

TABLE 7

| Crystal data and structure refinement for compound 1e (CCDC code 2164631). | |
|---|---|
| Identification code | XW337G_sq |
| Empirical formula | $C_{88}H5_6N_{16}O_{16}$ |
| Formula weight | 1593.48 |
| Temperature/K | 123(2) |
| Crystal system | orthorhombic |
| Space group | Pmna |
| a/Å | 33.1931(11) |
| b/Å | 27.7955(11) |
| c/Å | 31.8933(13) |
| α/° | 90 |
| β/° | 90 |
| γ/° | 90 |
| Volume/$Å^3$ | 29425.4(19) |
| Z | 4 |
| $\rho_{calc}$ g/$cm^3$ | 0.360 |
| μ/$mm^{-1}$ | 0.212 |
| F(000) | 3296.0 |
| Crystal size/$mm^3$ | 0.48 × 0.32 × 0.25 |
| Radiation | CuKα (λ = 1.54178) |
| 2Θ range for data collection/° | 3.178 to 89.312 |
| Index ranges | −29 ≤ h ≤ 28, −22 ≤ k ≤ 25, −29 ≤ l ≤ 21 |
| Reflections collected | 119862 |
| Independent reflections | 11878 [$R_{int}$ = 0.0853, $R_{sigma}$ = 0.0688] |
| Data/restraints/parameters | 11878/2657/703 |
| Goodness-of-fit on F2 | 1.194 |
| Final R indexes [I >= 2σ (I)] | $R_1$ = 0.1381, $wR_2$ = 0.3388 |
| Final R indexes [all data] | $R_1$ = 0.2015, $wR_2$ = 0.3799 |
| Largest diff. peak/hole/e $Å^{-3}$ | 0.25/−0.30 |

Example 13

Physical Characteristics of the Macrocyclic Cores of the Octahydrazones

TABLE 8

Distance and angle measurements of the macrocyclic cores of compounds 1a-1e compared to the two conformers of cyclotetrabenzil compound (3).

| | Cyclobenzil (3) Conformer | | Octahydrazones | | | | |
|---|---|---|---|---|---|---|---|
| | Chair | Boat | 1a | 1b | 1c | 1d | 1e |
| Centroid-to-centroid | 7.62 | 7.39 | 7.19 | 7.38 | 7.34 | 7.32 | 7.24 |
| distances of opposing | 7.33 | 7.22 | 7.09 | 7.37 | 7.34 | 7.32 | 7.29 |
| skeletal phenyl rings [Å] | | | | | | | |
| Tilt angle between | 0.0 | 23.0 | 41.2 | 54.6 | 50.8 | 46.7 | 47.4 |
| planes of opposing | 0.0 | 40.8 | 46.1 | 56.4 | 50.8 | 46.70 | 48.2 |
| skeletal phenyl rings [°] | | | | | | | |
| Centroid-to-centroid | 9.45 | 9.31 | 9.38 | 9.35 | 9.18 | 8.83 | 9.14 |
| distances of opposing | 8.79 | 8.77 | 8.87 | 9.02 | 8.97 | 8.83 | 9.14 |
| skeletal corner | | | | | | | |
| C—C bonds [Å] | | | | | | | |
| [Ph—C—C—Ph] | −91.5 | −89.3 | −72.0 | −80.3 | −91.0 | −89.6 | −70.3 |
| torsion angles | 77.7 | 77.8 | 62.4 | 71.1 | 82.6 | 89.6 | 73.9 |
| in macrocycle | 91.5 | −89.3 | −72.8 | −85.6 | −91.6 | −89.6 | −73.9 |
| skeleton [°] | −77.7 | 77.8 | 57.0 | 76.2 | 82.6 | 89.6 | 70.3 |

Example 14

Iodine Adsorption Studies

All iodine adsorption studies were performed using new vials. Iodine vapor uptake experiments were performed by placing compound 1c (6.4 mg) in a 1-dram vial which was then placed inside a sealed 5-dram vial, sealed with Parafilm, and left undisturbed at room temperature in a dark, cool place. The inner vial was taken out for weighing daily and placed back in the same spot. The vapor experiments were conducted in triplicates and the reported values are the average of the three obtained weights. Following the uptake experiments, this powder of $I_2$@1c was used to collect FT-IR and NMR spectra, and for the $I_2$ release experiments. UV/Vis spectra were collected on 1 mM iodine solutions prepared by dissolving $I_2$ (6.4 mg) in the corresponding solvent (25 mL) or mixing 1% Lugol's $I_2$ solution (80 μL) with $H_2O$ (25 mL).

Iodine release experiments were performed by placing 12@1c powder (6.6 mg) in a 2-dram vial and submerging it in 1,4-dioxane (4 mL) for 24 h sealed. The iodine solution in 1,4-dioxane was decanted after the allotted time had passed. The weight of the vial containing the sample was recorded before and after 1,4-dioxane was added and decanted to calculate the efficiency of release.

Iodine adsorption experiments between two immiscible liquids were performed by first placing water or 4 mM aqueous $I_2$ solution (5 mL) in an 8-dram vial, layering compound 1c (20 mg) atop that first layer, and then slowly pipetting in hexane or 4 mM iodine solution in hexane. The vials were sealed and left undisturbed at room temperature in a dark, cool place.

TABLE 9

Porosity and iodine capacity of Octahydrazone compound 1c.

| Adsorbent | $S_{BET}$ [$m^2$ $g^{-1}$] | $I_2$ Capture Capacity [g $g^{-1}$] |
|---|---|---|
| Octahydrazone Compound 1c | 24 | 4.15 |

Example 15

Contact Angle Measurements

Contact angles between $H_2O$ and compound 1c, compound 3, and compound 4 were performed on thin films on glass spin-coated from $CHCl_3$ solutions using a ramé-hart model 100 contact angle goniometer equipped with a Matrix Technology Micro-Electrapette 25. The reported values are an average of three measurements taken on different areas of the same sample slide; all measurements were performed at 293 K with the pipet tip remaining in contact with the drop. The glass slides were prepared by spin-coating 5 mg of sample dissolved in 20 μL at 1000 rpm for 30 s and cured at 120° C. for 2 h.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A compound of Formula (II):

Formula (II)

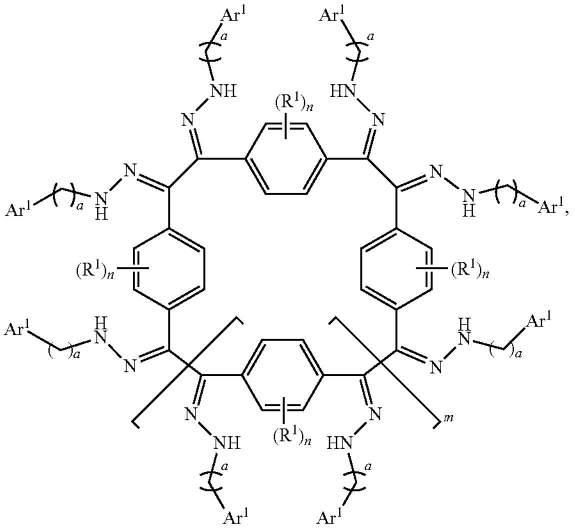

wherein:

m is 0, 1, 2, 3, or 4;

n is 0, 1, 2, 3 or 4;

a is 0, 1 or 2;

$Ar^1$ is optionally substituted aryl, or optionally substituted heteroaryl; and $R^1$ is an electron withdrawing group, or an electron donating group.

2. The compound of claim 1, wherein $Ar^1$ is selected from the group consisting of:

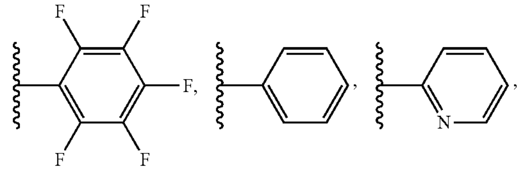

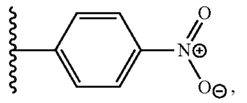

and

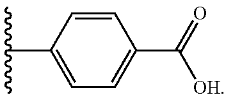

3. The compound of claim 1, wherein the compound of Formula (II) is a compound of Formula (II-a):

Formula (II-a)

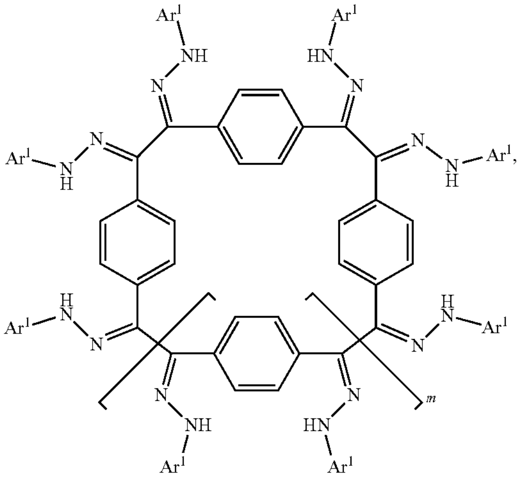

wherein:

m is 0, 1, 2, 3, or 4; and $Ar^1$ is optionally substituted aryl, or optionally substituted heteroaryl.

4. The compound of claim 3, wherein $Ar^1$ is selected from the group consisting of:

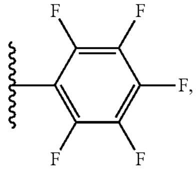, 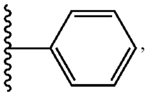, 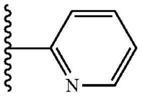,

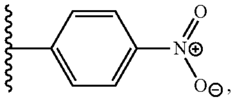, and 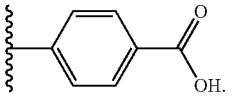

5. The compound of claim 1, wherein the compound of Formula (II) is a compound of Formula (II-b):

Formula (II-b)

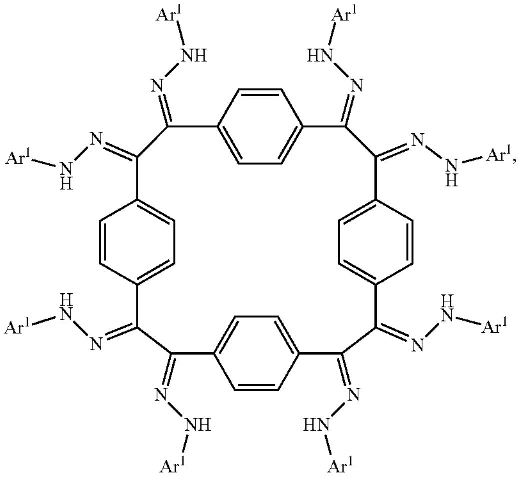

wherein:

$Ar^1$ is optionally substituted aryl, or optionally substituted heteroaryl.

6. The compound of claim 5, wherein $Ar^1$ is selected from the group consisting of:

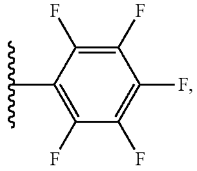, 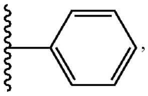, 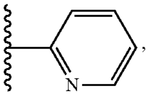,

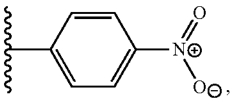, and 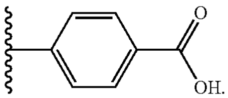

7. The compound of claim 1, wherein the compound of Formula (II) is selected from the group consisting of:

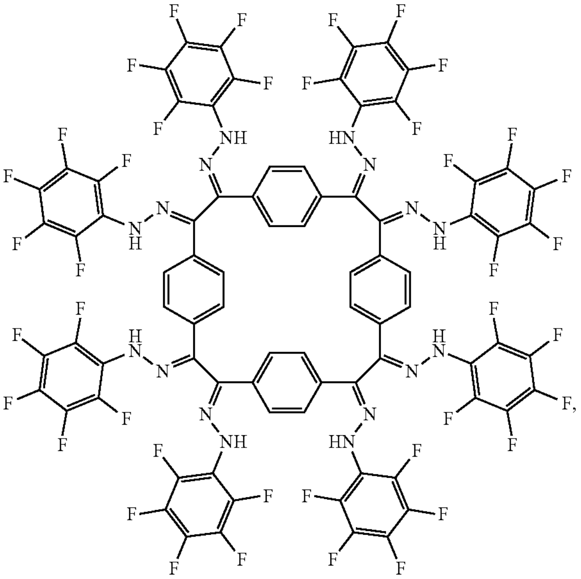,

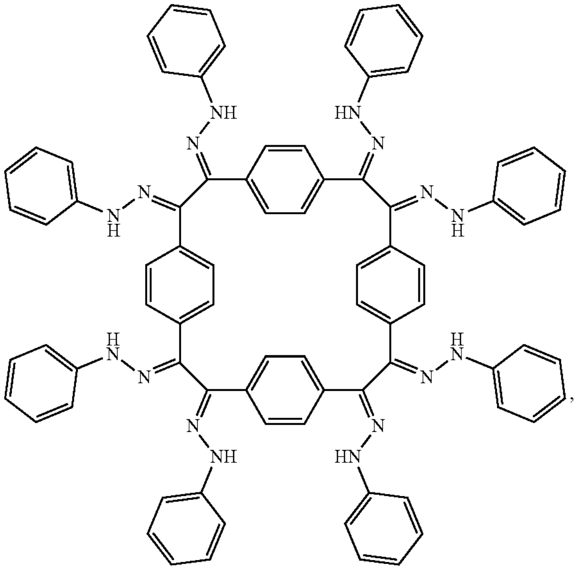,

-continued

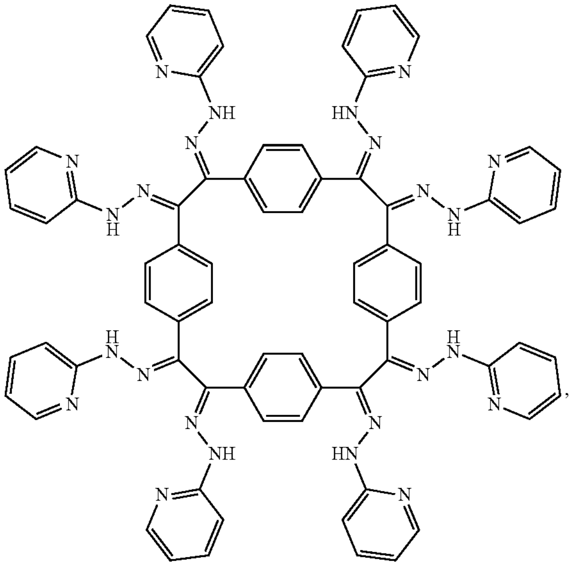

,

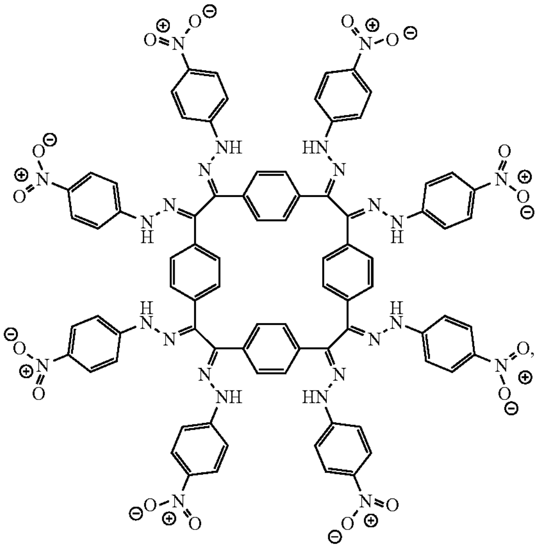

and

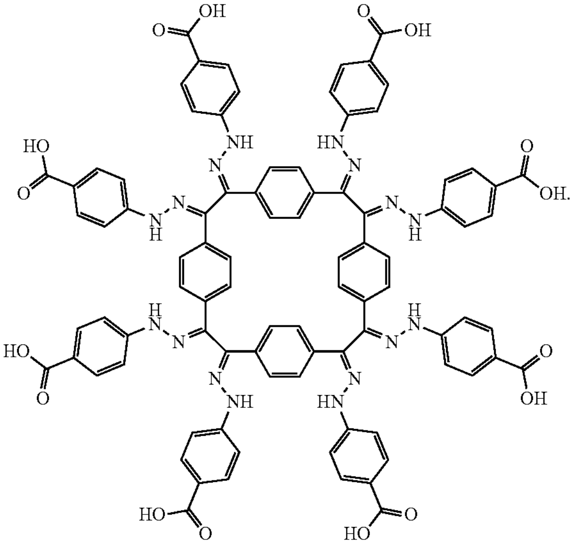

8. A method for removing a material from a medium, the method comprising:

providing a medium comprising a material;

contacting the medium with a compound of claim 1;

capturing the material with the compound; and removing the compound that contains the captured material from the medium.

9. The method of claim 8, further comprising removing the captured material from the compound.

10. The method of claim 8, wherein the material is non-radioactive molecular iodine ($I_2$), radioactive molecular iodine ($I_2$), or combination thereof.

11. The method of claim 8, wherein the medium is aqueous medium, organic medium, or combination thereof.

12. A method for removing a material from a medium, the method comprising:

providing a medium comprising a material;

contacting the medium with a compound of claim 7;

capturing the material with the compound; and removing the compound that contains the captured material from the medium.

13. The method of claim 12, further comprising removing the captured material from the compound.

14. The method of claim 12, wherein the material is non-radioactive molecular iodine ($I_2$), radioactive molecular iodine ($I_2$), or combination thereof.

15. The method of claim 12, wherein the medium is aqueous medium, organic medium, or combination thereof.

16. A method of making a compound of claim 1, the method comprising:

reacting a compound of Formula (I) with a compound of Formula (VII) to obtain a compound of Formula (II) of claim 1, wherein the compound of Formula (I) is:

Formula (I)

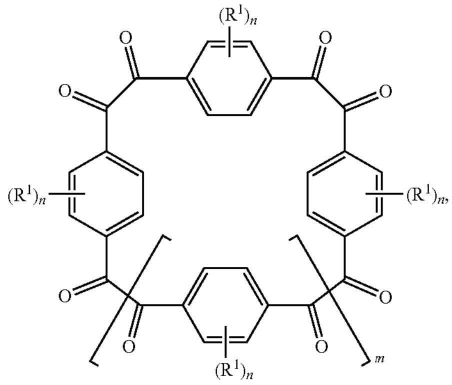

wherein:

m is 0, 1, 2, 3, or 4;

n is 0, 1, 2, 3 or 4; and $R^1$ is an electron withdrawing group, or an electron donating group; and wherein the compound of Formula (VII) is:

Formula (VII)

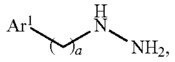

wherein, $Ar^1$ is optionally substituted aryl, or optionally substituted heteroaryl; and a is 0, 1 or 2.

17. An article of manufacture comprising a compound of claim 1.

18. The article of manufacture of claim 17, wherein the article of manufacture is a paint, a primer, a coating, or a coating material.

19. A composition comprising a compound of claim 1.

20. The composition of claim 19, wherein the compound is selected from the group consisting of:

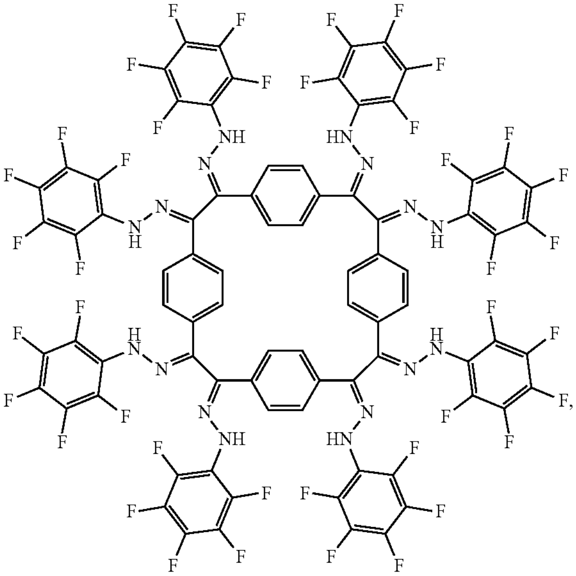

,

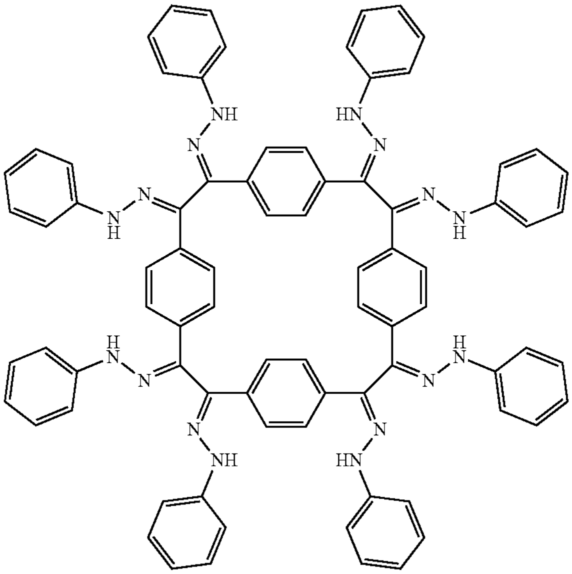

,

-continued

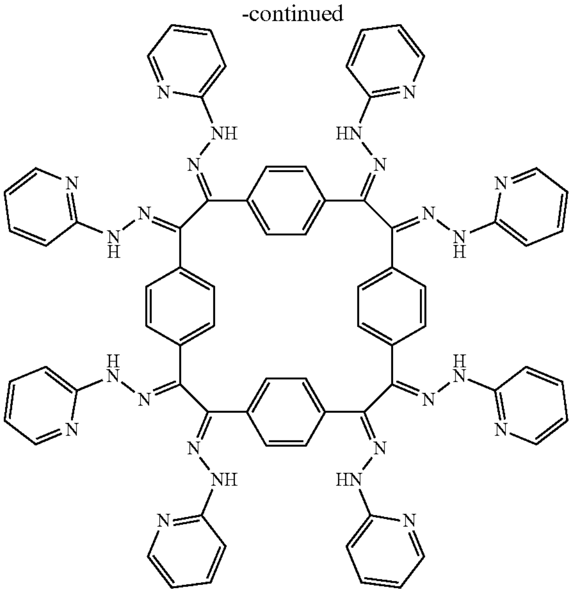

,

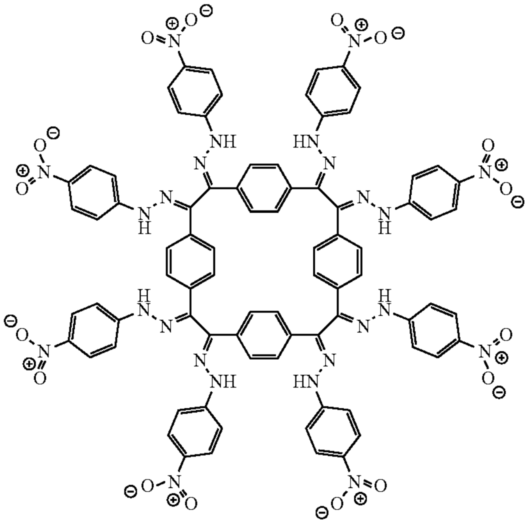

, and

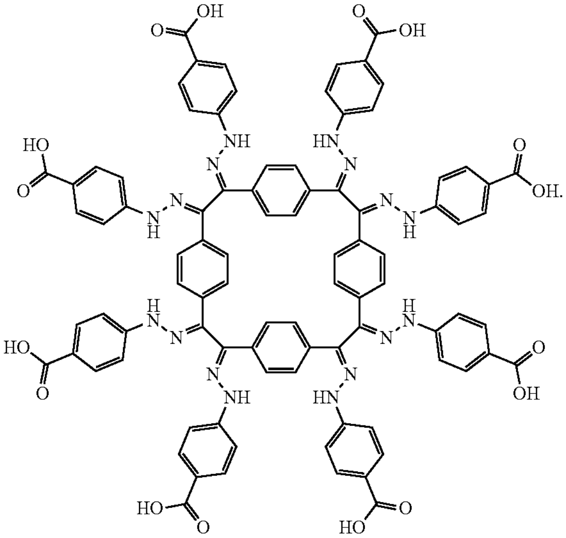

* * * * *